US008563565B2

(12) United States Patent
Norimine et al.

(10) Patent No.: US 8,563,565 B2
(45) Date of Patent: Oct. 22, 2013

(54) PYRAZOLOQUINOLINE DERIVATIVES

(71) Applicant: Eisai R&D Management Co., Ltd., Tokyo (JP)

(72) Inventors: Yoshihiko Norimine, Tsukuba (JP); Kunitoshi Takeda, Tsukuba (JP); Koji Hagiwara, Tsukuba (JP); Yuichi Suzuki, Tsukuba (JP); Yuki Ishihara, Tsukuba (JP); Nobuaki Sato, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 13/644,745

(22) Filed: Oct. 4, 2012

(65) Prior Publication Data
US 2013/0143907 A1 Jun. 6, 2013

Related U.S. Application Data

(60) Provisional application No. 61/544,860, filed on Oct. 7, 2011, provisional application No. 61/550,623, filed on Oct. 24, 2011, provisional application No. 61/558,110, filed on Nov. 10, 2011, provisional application No. 61/580,903, filed on Dec. 28, 2011.

(51) Int. Cl.
A01N 43/54 (2006.01)
A01N 43/58 (2006.01)
A01N 43/60 (2006.01)
A61K 31/505 (2006.01)
A61K 31/535 (2006.01)
C07D 413/00 (2006.01)
C07D 487/00 (2006.01)
C07D 471/00 (2006.01)
C07D 403/00 (2006.01)

(52) U.S. Cl.
USPC ............ 514/274; 514/213.01; 514/233.2; 514/250; 514/252.02; 544/117; 544/262; 544/359; 544/346

(58) Field of Classification Search
USPC ...... 514/213.01, 233.2, 250, 252.02; 544/262, 117, 359, 346
See application file for complete search history.

(56) References Cited

U.S. PATENT DOCUMENTS

2006/0035920 A1* 2/2006 Boyle et al. .................. 514/292
2010/0048556 A1 2/2010 Okada et al.
(Continued)

FOREIGN PATENT DOCUMENTS

JP 2011-516454 5/2011
WO WO2007/032466 3/2007
(Continued)

OTHER PUBLICATIONS

Bonkale et al., "Reduced nitric oxide responsive soluble guanylyl 10 cyclase activity in the superior temporal cortex of patients with Alzheimer's disease," Neurosci. Lett., 1995, 187:5-8.
Brandon and Rotella, "Potential CNS—14 Applications for Phosphodiesterase Enzyme Inhibitors," Annual Reports in Medicinal Chemistry, 2007, 42:3-12.
(Continued)

Primary Examiner — Savitha Rao
Assistant Examiner — Angela Brown-Pettigrew
(74) Attorney, Agent, or Firm — Fish & Richardson P.C.

(57) ABSTRACT

A compound and/or pharmacologically acceptable salt thereof represented by the formula (I) has PDE9 inhibitory action, so that the intracerebral cGMP concentration is anticipated to be elevated. The PDE9 inhibitory action and the increase in cGMP lead to the improvement of learning and memory behaviors, and the compound (I) has a potential use of a therapeutic agent for cognitive dysfunctions in Alzheimer's disease.

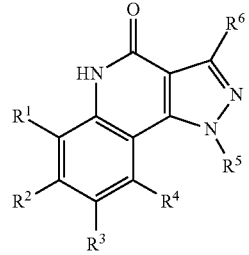

wherein $R^1$ is a hydrogen atom; $R^2$ is an aromatic ring group, etc.; $R^3$ is a hydrogen atom, etc; $R^4$ is a hydrogen atom; $R^5$ is an oxepanyl group, etc.; $R^6$ is a hydrogen atom.

15 Claims, 1 Drawing Sheet

(56) References Cited

U.S. PATENT DOCUMENTS

| | | |
|---|---|---|
| 2011/0082137 A1 | 4/2011 | Giovannini et al. |
| 2011/0131467 A1 | 6/2011 | Weathers |
| 2011/0184000 A1 | 7/2011 | Giovannini et al. |
| 2011/0319385 A1 | 12/2011 | Kaizawa et al. |

FOREIGN PATENT DOCUMENTS

| | | |
|---|---|---|
| WO | WO2008/072779 | 6/2008 |
| WO | WO2008/139293 | 11/2008 |
| WO | WO2009/121919 | 10/2009 |
| WO | WO2010/101230 | 9/2010 |
| WO | WO2012/033144 | 3/2012 |

OTHER PUBLICATIONS

Domek-Lopacinska et al., "Cyclic GMP metabolism and its role in brain physiology," *J. Physiol. Pharmacol.*, 2005, 56(Suppl. 2):15-34.

Fisher et al, "Isolation and characterization of PDE9A, a novel -8 human cGMP-specific phosphodiesterase," *J. Biol. Chem.*, 1998, 273:15559-15564.

van der Staay et al., "The novel selective PDE9 inhibitor BAY 73-6691 improves learning and memory in rodents," *Neuropharmacology*, 2008, 55:908-918.

Wang, "Cyclic GMP-dependent protein kinase and cellular signaling in the nervous system," *J. Neurochem.*, 1997, 68:443-456.

International Search Report in International Application No. PCT/JP2012/075748, mailed Nov. 20, 2012, 2 pages.

* cited by examiner

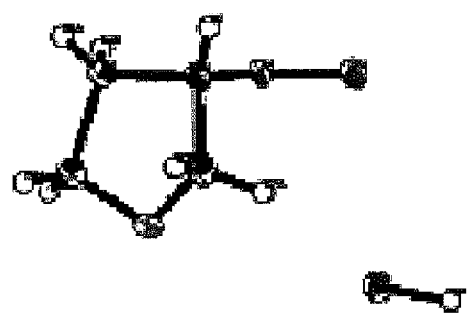

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: hPDE9-1

<400> SEQUENCE: 1
aggatgggat ccggctcctc ca                                           22

<210> SEQ ID NO 2
<211> LENGTH: 21
<212> TYPE: DNA
<213> ORGANISM: Artificial
<220> FEATURE:
<223> OTHER INFORMATION: hPDE9A-3

<400> SEQUENCE: 2
caggcacagt ctccttcact g                                            21
```

PYRAZOLOQUINOLINE DERIVATIVES

CROSS-REFERENCE TO RELATED APPLICATION

This application claims the benefit of the following applications: U.S. provisional application No. 61/544,860 filed on Oct. 7, 2011, U.S. provisional application No. 61/550,623 filed on Oct. 24, 2011, U.S. provisional application No. 61/558,110 filed on Nov. 10, 2011, and U.S. provisional application No. 61/580,903 filed on Dec. 28, 2011, the disclosures of all of which are herein incorporated by reference in their entireties.

BACKGROUND OF THE INVENTION

1. Field of the Invention

The present invention relates to pyrazoloquinoline derivatives having inhibitory activity against phosphodiesterase 9 (PDE9), and pharmacologically acceptable salts thereof, and pharmaceutical applications thereof.

2. Related Background of the Invention

Cyclic guanosine monophosphate (hereinafter, referred to as cGMP) functioning as a second messenger in cells is known to play an important role in various physiological functions including learning and memory behaviors.

On the postsynaptic site of the brain neural circuits, nitrogen monoxide (hereinafter, referred to as NO) biosynthesized by a nitrogen monoxide synthetase activates a guanylate cyclase, which is a cGMP synthetase. The activated guanylate cyclase biosynthesizes cGMP from guanosine triphosphate. The cGMP activates a cGMP-dependent protein kinase (hereinafter, referred to as PKG) to phosphorylate various proteins participating in synapse plasticity. The activation of the NO/cGMP/PKG cascade is known to participate in the induction of synapse plasticity (Long Term Potentiation; hereinafter, referred to as LTP) of the hippocampus known as a neural substrate for learning and memory behaviors (for example, see Non Patent Literature 1). A medicine activating the signal transmission of the cascade is known to improve LIP of the hippocampus and the learning behavior of animals, while a medicine inhibiting the cascade is known to exhibit the opposite action (Non Patent Literature 2). Therefore, from these findings, an increase in cGMP in the brain is anticipated to lead to an improvement of learning and memory behaviors.

cGMP is metabolized to 5'-GMP having no PKG activation action by a phosphodiesterase (hereinafter, referred to as PDE). The PDE is known to have 11 families, and PDE9 is known to metabolize specifically cGMP, and to be expressed in the brain, the spleen, the small intestine and the like (for example, see Non Patent Literature 3). That is, inhibition of PDE9 is anticipated to increase cGMP in brains. It is reported that a PDE9 inhibitor actually enhances hippocampus LTP, and improves the learning and memory behaviors in a novel-object recognition test/passive avoidance learning test or the like in animals (Non Patent Literature 4). Clinically, guanylate cyclase activity decreases and possibility of a decrease in the cGMP level is indicated in the superior temporal cortex of Alzheimer's disease patients, (Non Patent Literature 5). Therefore, the PDE9 has a possibility of having many close relations with pathologies of neurodegenerative diseases and psychiatric diseases, particularly with pathologies of cognitive dysfunctions and the like in the Alzheimer's disease, such as Alexander's disease, Alpers' disease, Alzheimer's disease, amyotrophic lateral sclerosis (ALS; known as Lou Gehrig's disease or motor neuron disease), ataxia-telangiectasia, Batten's disease (known also as Spielmeyer-Vogt-Sjogren-Batten's disease), Binswanger's dementia (subcortical angiosclerotic encephalopathy), bipolar disorder, bovine spongiform encephalopathy (BSE), Canavan's disease, chemotherapy induction dementia, Cockayne's syndrome, corticobasal degeneration, Creutzfeldt-Jakob's disease, depression, Down's syndrome, frontotemporal lobe degeneration (including frontotemporal dementia, semantic dementia and progressive nonfluent aphasia), Gerstmann-Straussler-Scheinker's disease, glaucoma, Huntington's disease (chorea), ITV related dementia, hyperkinesis, Kennedy's disease, Korsakoffs syndrome (amnesic confabulation syndrome), Krabbe's disease, Lewy-bodies dementia, progressive logopenic aphasia, Machado-Joseph's disease (spinocerebellar ataxia type 3), multiple sclerosis, multiple atrophy (olivopontocerebellar atrophy), myasthenia gravis, Parkinson's disease, Pelizaeus-Merzbacher's disease, Pick's disease, dementia presenilis (slight cognitive impairment), primary lateral sclerosis, primary progressive aphasia, radiation-induced dementia, Refsum's disease (phytanic acid storage disease), Sandhoffs disease, Schilder's disease, schizophrenia, semantic dementia, senile dementia, Shy-Drager syndrome, spinocerebellar ataxia, spinal muscle atrophy, Steele-Richardson-Olszewski's disease (progressive supranuclear palsy), and vascular amyloidosis and vascular dementia (multiple infarct dementia).

Recently, the following compound has been known which has PDE9 inhibitory activity and has a purpose of prevention or therapy of Alzheimer's disease (Patent Literature 1).

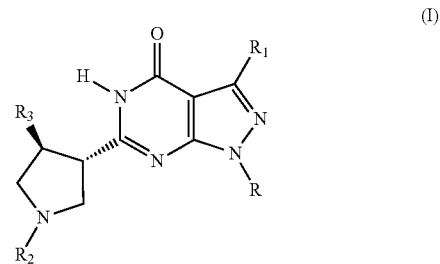

(I)

The above compound is a pyrazolopyrimidine derivative, and a compound having a structure totally different from a pyrazoloquinoline skeleton.

On the other hand, as a compound having a pyrazoloquinoline skeleton, the following compound described in Patent Literature 2 is known.

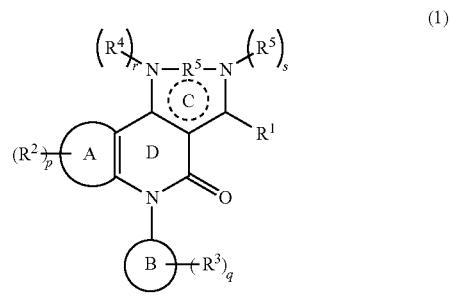

(1)

wherein a ring A is a benzene ring or the like; and $R^6$ is a direct bond or the like.

However, a ring B in the above compound denotes a benzene ring or the like. Although it is stated that the above compound has inhibitory activity against PDE4 and is used for various types of inflammatory diseases, there is no description nor implication of the inhibitory activity against PDE9, and the like.

As compounds having PDE9 inhibitory activity, the following compounds described in Patent Literature 3 and Patent Literature 4 are known.

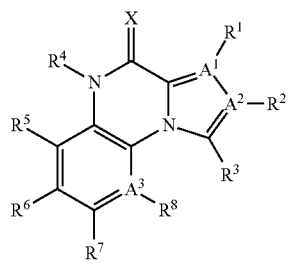

(I)

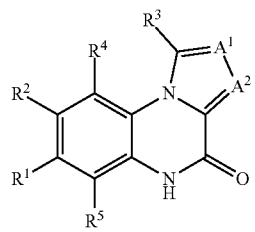

(1)

Any of the above compounds is a quinoxaline derivative, and is a compound having a structure totally different from a pyrazoloquinoline skeleton.

As a compound having a pyrazoloquinoline skeleton and having PDE9 inhibitory activity, the following compound described in Patent Literature 5 is known.

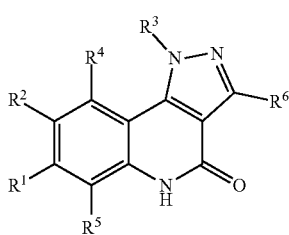

(I)

wherein either $R^1$ or $R^2$ is a group represent by the formula

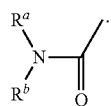

(II)

The structure of the above compound is restricted in $R^1$ and $R^2$, thus the compound is a compound having a structure totally different from the compound of the present invention.
[Patent Literature 1] WO 2008/139293
[Patent Literature 2] WO 2007/032466
[Patent Literature 3] WO 2008/072779
[Patent Literature 4] WO 2010/101230
[Patent Literature 5] WO 2012/033144
[Non Patent Literature 1] Domek-Lopacinska et al., "Cyclic GMP metabolism and its role in brain physiology", J Physiol Pharmacol., vol. 56, Suppl 2: pp. 15-34, 2005

[Non Patent Literature 2] Wang X., "Cyclic GMP-dependent protein kinase and cellular signaling in the nervous system", J. Neurocem., vol. 68, pp. 443-456, 1997
[Non Patent Literature 3] Fisher et al., "Isolation and characterization of PDE9A, a novel human cGMP-specific phosphodiesterase", J. Biol. Chem., vol. 273: pp. 15559-15564, 1998
[Non Patent Literature 4] van der Staay et al., "The novel selective PDE9 inhibitor BAY 73-6691 improves learning and memory in rodents", Neuropharmacology, vol. 55: pp. 908-918, 2008
[Non Patent Literature 5] Bonkale et al., "Reduced nitric oxide responsive soluble guanylyl cyclase activity in the superior temporal cortex of patients with Alzheimer's disease", Neurosci. Lett., vol 187, pp. 5-8, 1995

SUMMARY OF THE INVENTION

It is an object of the present invention to provide a novel compound or pharmacologically acceptable salt thereof having PDE9 inhibitory action, and a pharmaceutical composition containing the same.

As a result of exhaustive studies to solve the above-mentioned problems, the present inventors have found a novel pyrazoloquinoline derivative or pharmacologically acceptable salt thereof having PDE9 inhibitory action.

That is, the present invention relates to the following <1> to <20>.

<1> A compound and/or pharmacologically acceptable salt thereof represented by the formula (I):

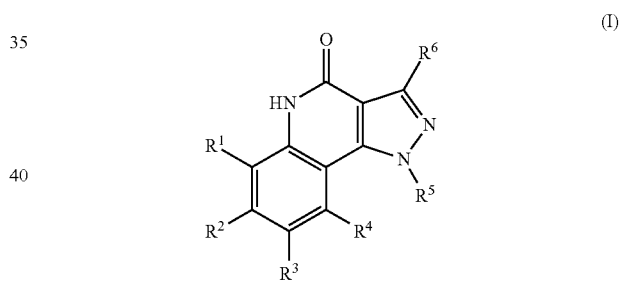

(I)

wherein
$R^1$ is a hydrogen atom;
$R^2$ is an aromatic ring group selected from the group consisting of a phenyl group, a pyridinyl group, and a pyrimidinyl group, where the two atoms on the aromatic ring which are adjacent to the carbon atom attached to the pyrazolo[4,3-c]quinoline ring each independently has a substituent selected from Group A1, and the other atoms on the aromatic ring independently optionally have a substituent selected from Group B1;
$R^3$ is a hydrogen atom, or a fluorine atom;
$R^4$ is a hydrogen atom;
$R^5$ is an oxepanyl group, a dioxepanyl group, a tetrahydropyranyl group, or a tetrahydrofuranyl group optionally having a methoxy group;
$R^6$ is a hydrogen atom;
Group A1 consists of a halogen atom, a C1-6 alkyl group optionally having 1 to 3 halogen atoms, and a C1-6 alkoxy group; and
Group B1 consists of a halogen atom, a cyano group, a C1-6 alkyl group optionally having 1 to 3 halogen atoms, a C1-6 alkoxy-C1-6 alkyl group, a C1-6 alkoxy group optionally having 1 to 3 halogen atoms, and a tetrahydropyranyl group, with the proviso that when $R^2$ is a 3-pyridinyl group, the substituent at the 4-position is a halogen atom, or a C1-6 alkyl group optionally having 1 to 3 halogen atoms.

<2> The compound and/or pharmacologically acceptable salt thereof according to <1>, wherein $R^2$ is an aromatic ring group selected from the group consisting of a phenyl group, a 3-pyridinyl group, a 4-pyridinyl group, and a 5-pyrimidinyl group, where the two atoms on the aromatic ring which are adjacent to the carbon atom attached to the pyrazolo[4,3-c]quinoline ring each independently has a substituent selected from Group A2, and the other atoms on the aromatic ring independently optionally have a substituent selected from Group B2;

$R^5$ is a 4-oxepanyl group, a 1,4-dioxepan-6-yl group, a 3,4,5,6-tetrahydro-2H-3-pyranyl group, a 3,4,5,6-tetrahydro-2H-4-pyranyl group, or a 3-tetrahydrofuranyl group;

Group A2 consists of a chlorine atom, and a methyl group optionally having 1 to 2 fluorine atoms, an ethyl group, a methoxy group, and an ethoxy group; and Group B2 consists of a fluorine atom, a chlorine atom, a cyano group, a methyl group optionally having 1 to 3 fluorine atoms, an ethyl group, a methoxymethyl group, a methoxy group optionally having 1 to 3 fluorine atoms, an ethoxy group, an isopropyloxy group, and a 3,4,5,6-tetrahydro-2H-4-pyranyl group.

<3> The compound and/or pharmacologically acceptable salt thereof according to <2>, wherein $R^3$ is a fluorine atom.

<3.1> The compound and/or pharmacologically acceptable salt thereof according to <3>, wherein $R^5$ is a 3,4,5,6-tetrahydro-2H-4-pyranyl group, or a 3-tetrahydrofuranyl group.

<4> The compound and/or pharmacologically acceptable salt thereof according to <1>, wherein $R^3$ is a hydrogen atom; and $R^5$ is a tetrahydropyranyl group, or a tetrahydrofuranyl group optionally having a methoxy group.

<5> The compound and/or pharmacologically acceptable salt thereof according to <2>, wherein $R^3$ is a hydrogen atom; and $R^5$ is a 3,4,5,6-tetrahydro-2H-3-pyranyl group, a 3,4,5,6-tetrahydro-2H-4-pyranyl group, or a 3-tetrahydrofuranyl group.

<6> The compound and/or pharmacologically acceptable salt thereof according to <1>, wherein $R^2$ is an aromatic ring group selected from the group consisting of a phenyl group, a 3-pyridinyl group, and a 4-pyridinyl group, where the two atoms on the aromatic ring which are adjacent to the carbon atom attached to the pyrazolo[4,3-c]quinoline ring each independently has a substituent selected from Group A3, and the other atoms on the aromatic ring independently optionally have a substituent selected from Group B3;

$R^3$ is a hydrogen atom;

$R^4$ is a hydrogen atom;

$R^5$ is a 3,4,5,6-tetrahydro-2H-4-pyranyl group, or a 3-tetrahydrofuranyl group;

Group A3 consists of a methyl group, and a methoxy group; and

Group B3 consists of a methyl group, a methoxy group, and a methoxymethyl group.

<7> A compound and/or pharmacologically acceptable salt thereof selected from the following group:

1) 7-(6-methoxy-2,4-dimethylpyridin-3-yl)-1-(tetrahydro-2H-pyran-4-yl)-1H-pyrazolo[4,3-c]quinolin-4(5H)-one, 2) 7-(2-methoxy-4,6-dimethylpyridin-3-yl)-1-(tetrahydro-2H-pyran-4-yl)-1H-pyrazolo[4,3-c]quinolin-4(5H)-one, 3) (S)-7-(6-isopropyloxy-2,4-dimethylpyridin-3-yl)-1-(tetrahydrofuran-3-yl)-1H-pyrazolo[4,3-c]quinolin-4(5H)-one, 4) 8-fluoro-7-(2-methoxy-4,6-dimethylpyridin-3-yl)-1-(tetrahydro-2H-pyran-4-yl)-1H-pyrazolo[4,3-c]quinolin-4(5H)-one, 5) 1-(1,4-dioxepan-6-yl)-7-(2-methoxy-3,5-dimethylpyridin-4-yl)-1H-pyrazolo[4,3-c]quinolin-4(5H)-one, 6) 1-(1,4-dioxepan-6-yl)-7-(2-methoxy-4,6-dimethylpyridin-3-yl)-1H-pyrazolo[4,3-c]quinolin-4(5H)-one, 7) (S)-8-fluoro-7-(2-methoxy-3,5-dimethylpyridin-4-yl)-1-(tetrahydrofuran-3-yl)-1H-pyrazolo[4,3-c]quinolin-4(5H)-one, 8) 7-(2-methoxy-3,5-dimethylpyridin-4-yl)-1-(tetrahydro-2H-pyran-4-yl)-1H-pyrazolo[4,3-c]quinolin-4(5H)-one, 9) (−)-7-(2-methoxy-4,6-dimethylpyridin-3-yl)-1-(tetrahydrofuran-3-yl)-1H-pyrazolo[4,3-c]quinolin-4(5H)-one, 10) (−)-7-(6-methoxy-2,4-dimethylpyridin-3-yl)-1-(tetrahydrofuran-3-yl)-1H-pyrazolo[4,3-c]quinolin-4(5H)-one, 11) (S)-8-fluoro-7-(2-methoxy-4,6-dimethylpyridin-3-yl)-1-(tetrahydrofuran-3-yl)-1H-pyrazolo[4,3-c]quinolin-4(5H)-one 12) (S)-7-(6-ethoxy-2,4-dimethylpyridin-3-yl)-1-(tetrahydrofuran-3-yl)-1H-pyrazolo[4,3-c]quinolin-4(5H)-one 13) (S)-8-fluoro-7-(6-methoxy-2,4-dimethylpyridin-3-yl)-1-(tetrahydrofuran-3-yl)-1H-pyrazolo[4,3-c]quinolin-4(5H)-one and 14) (S)-7-(2-methoxy-3,5-dimethylpyridin-4-yl)-1-(tetrahydrofuran-3-yl)-1H-pyrazolo[4,3-c]quinolin-4(5H)-one.

<8> 7-(6-isopropyloxy-2,4-dimethylpyridin-3-yl)-1-(tetrahydrofuran-3-yl)-1H-pyrazolo[4,3-c]quinolin-4(5H)-one and/or a pharmacologically acceptable salt thereof <9> (S)-7-(6-isopropyloxy-2,4-dimethylpyridin-3-yl)-1-(tetrahydrofuran-3-yl)-1H-pyrazolo[4,3-c]quinolin-4(5H)-one and/or a pharmacologically acceptable salt thereof <10> 8-fluoro-7-(2-methoxy-3,5-dimethylpyridin-4-yl)-1-(tetrahydrofuran-3-yl)-1H-pyrazolo[4,3-c]quinolin-4(5H)-one and/or a pharmacologically acceptable salt thereof <11> (S)-8-fluoro-7-(2-methoxy-3,5-dimethylpyridin-4-yl)-1-(tetrahydrofuran-3-yl)-1H-pyrazolo[4,3-c]quinolin-4(5H)-one and/or a pharmacologically acceptable salt thereof:

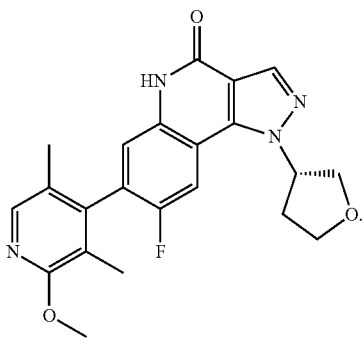 [SMILES: COc1ncc(C)c(-c2cc3[nH]c(=O)c4cnn([C@H]5CCOC5)c4c3cc2F)c1C]

<12> 7-(2-methoxy-3,5-dimethylpyridin-4-yl)-1-(tetrahydrofuran-3-yl)-1H-pyrazolo[4,3-c]quinolin-4(5H)-one and/or a pharmacologically acceptable salt thereof <13> (S)-7-(2-methoxy-3,5-dimethylpyridin-4-yl)-1-(tetrahydrofuran-3-yl)-1H-pyrazolo[4,3-c]quinolin-4(5H)-one and/or a pharmacologically acceptable salt thereof:

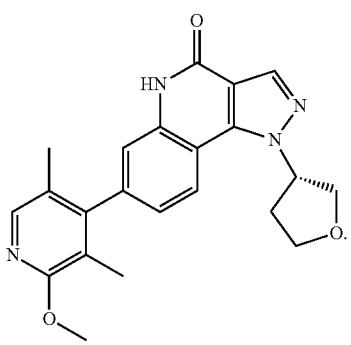 [SMILES: COc1ncc(C)c(-c2ccc3c(c2)[nH]c(=O)c2cnn([C@H]4CCOC4)c23)c1C]

<14> 1-(1,4-dioxepan-6-yl)-7-(2-methoxy-3,5-dimethylpyridin-4-yl)-1H-pyrazolo[4,3-c]quinolin-4(5H)-one and/or a pharmacologically acceptable salt thereof.

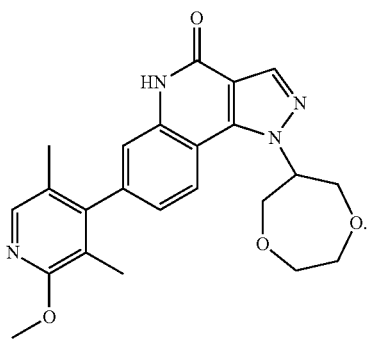 [SMILES: COc1ncc(C)c(-c2ccc3c(c2)[nH]c(=O)c2cnn(C4COCCOC4)c23)c1C]

<14.1> 8-fluoro-7-(6-methoxy-2,4-dimethylpyridin-3-yl)-1-(tetrahydrofuran-3-yl)-1H-pyrazolo[4,3-c]quinolin-4(5H)-one and/or a pharmacologically acceptable salt thereof.

<14.2> (S)-8-fluoro-7-(6-methoxy-2,4-dimethylpyridin-3-yl)-1-(tetrahydrofuran-3-yl)-1H-pyrazolo[4,3-c]quinolin-4(5H)-one and/or a pharmacologically acceptable salt thereof.

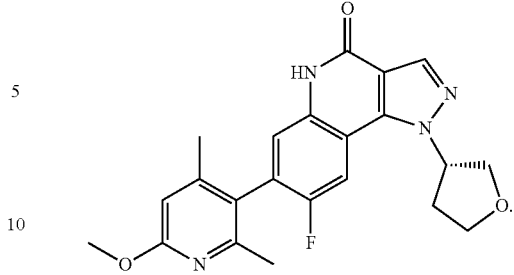

<14.3> 8-fluoro-7-(2-methoxy-4,6-dimethylpyridin-3-yl)-1-(tetrahydrofuran-3-yl)-1H-pyrazolo[4,3-c]quinolin-4(5H)-one and/or a pharmacologically acceptable salt thereof.

<14.4> (S)-8-fluoro-7-(2-methoxy-4,6-dimethylpyridin-3-yl)-1-(tetrahydrofuran-3-yl)-1H-pyrazolo[4,3-c]quinolin-4(5H)-one and/or a pharmacologically acceptable salt thereof

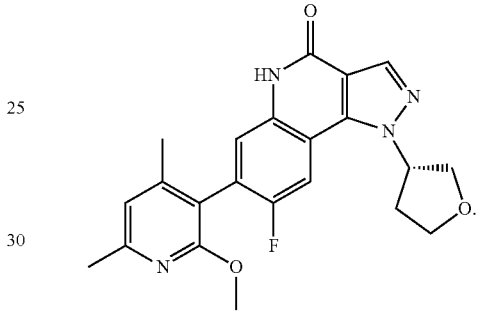

<14.5> 7-(6-ethoxy-2,4-dimethylpyridin-3-yl)-1-(tetrahydrofuran-3-yl)-1H-pyrazolo[4,3-c]quinolin-4(5H)-one and/or a pharmacologically acceptable salt thereof <14.6> (S)-7-(6-ethoxy-2,4-dimethylpyridin-3-yl)-1-(tetrahydrofuran-3-yl)-1H-pyrazolo[4,3-c]quinolin-4(5H)-one and/or a pharmacologically acceptable salt thereof:

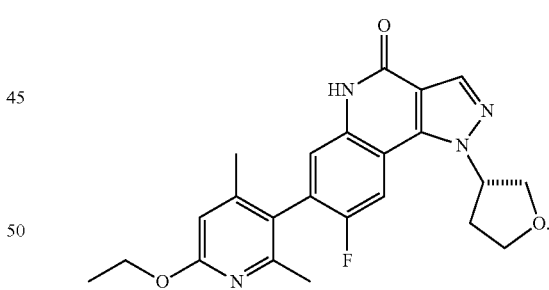

<15> A pharmaceutical composition comprising the compound and/or pharmacologically acceptable salt thereof according to <1> as an active ingredient.

<16> The pharmaceutical composition according to <15> which is a PDE9 inhibitor.

<17> The pharmaceutical composition according to <15> for increasing the intracerebral cGMP concentration.

<18> A cognitive impairment improving agent in Alzheimer's disease, comprising the compound and/or pharmacologically acceptable salt thereof according to <1>.

<19> A method for improving cognitive impairment in Alzheimer's disease, comprising administering the compound and/or pharmacologically acceptable salt thereof according to <1> to a patient <20> The compound or pharmacologically acceptable salt thereof according to <1> for use for improving cognitive impairment in Alzheimer's disease.

The pyrazoloquinoline derivative (hereinafter, referred to as a compound (I)) represented by the formula (I) or pharmacologically acceptable salt thereof according to the present invention has PDE9 inhibitory action as shown in activity data in Pharmacological Test Example described later. The compound (I) according to the present invention mostly exhibits an $IC_{50}$ value of 1,000 nM or below as the PDE9 inhibitory action, and a compound exhibiting an $IC_{50}$ value of 100 nM or below is preferable.

The compound (I) according to the present invention has PDE9 inhibitory action, so that the intracerebral cGMP concentration is anticipated to be elevated. The PDE9 inhibitory action and the increase in cGMP lead to the improvement of learning and memory behaviors, and the compound (I) has a potential use of a therapeutic agent for cognitive dysfunctions and the like in Alzheimer's disease.

BRIEF DESCRIPTION OF THE DRAWINGS

FIG. 1 is a view showing a three-dimensional structure obtained by X-ray diffraction of the compound obtained in Preparation Example 53.

DESCRIPTION OF THE PREFERRED EMBODIMENTS

Hereinafter, the content of the present invention will be described in detail.

Throughout the present specification, the structural formulas for the compounds will show only one specific isomer for convenience, but the invention includes all isomers such as geometric isomers, optical isomers, stereoisomers and tautomers implied by the compound structures, as well as their isomer mixtures, and the compounds may therefore be any of the isomers or mixtures thereof in any desired proportion, without being limited to the formulas that are shown for convenience. Thus, for example, the compounds of the invention may exist as optically active forms or racemic mixtures, all of which are included without limitations according to the invention, and whether racemic mixtures or optically active forms, they may be used as mixtures with the optically active forms in any desired proportion. It will be understood, however, that some isomers or racemates or other mixtures of isomers may exhibit more activity than others.

Polymorphic crystals may also exist, and there may be used any crystal form or a mixture thereof without any restrictions, as well as amorphous forms, and the compounds of the invention also include both anhydrate and solvate (especially hydrate).

Compounds of the compound (I) labeled with isotopes are also included in the present invention. A compound labeled with an isotope is the same as the compound (I), except that one or more atoms are replaced by atoms having atomic masses or mass numbers different from those usually found in the natural world. Isotopes which can be incorporated in the compound according to the present invention are isotopes of, for example, hydrogen, carbon, nitrogen, oxygen, fluorine, phosphorus, sulfur, iodine, and chlorine, and include $^{2}H$, $^{3}H$, $^{11}C$, $^{14}C$, $^{15}N$, $^{18}O$, $^{18}P$, $^{32}P$, $^{35}S$, $^{123}I$ and $^{125}I$.

The above isotope-labeled compounds, for example, compounds in which radioisotopes such as $^{3}H$, and/or $^{14}C$ are incorporated, are useful for the tissue distribution assay of medicines and/or substrates. $^{3}H$ and $^{14}C$ are considered to be useful for ease of the preparation and detection thereof. Isotopes $^{11}C$ and $^{18}F$ are considered to be useful for PET (positron-emission tomography); and an isotopes $^{125}I$ is considered to be useful for SPECT (single photon emission computed tomography); and all are useful for brain imaging. The replacement by a heavier isotope such as $^{2}H$ causes some type of therapeutic advantages including an increase in the in-vivo half-life period or a decrease in the necessary dose due to higher metabolic stability, and therefore, is considered to be useful under some situation. The above isotope-labeled compounds can be similarly prepared by carrying out procedures disclosed in the following Examples by using reagents labeled with isotopes easily utilizable in place of reagents not labeled with an isotope.

Hereinafter, the meanings of terms, symbols and the like described in the present specification will be described, and the present invention will be described in detail.

A "halogen atom" in the present specification means a fluorine atom, a chlorine atom, a bromine atom or an iodine atom. Suitable examples of the "halogen atom" include a fluorine atom and a chlorine atom.

A "C1-6 alkyl group" in the present specification means a straight-chain or branched-chain alkyl group having 1 to 6 carbon atoms, and specific examples include a methyl group, an ethyl group, a 1-propyl group, a isopropyl group, a 2-methyl-1-propyl group, a 2-methyl-2-propyl group, a 1-butyl group, a 2-butyl group, a 1-pentyl group, a 2-pentyl group, a 3-pentyl group, a 1-hexyl group, a 2-hexyl group and a 3-hexyl group.

A "C1-6 alkoxy group" in the present specification means an oxygen atom to which a "C1-6 alkyl group" defined in the above is attached, and specific examples include a methoxy group, an ethoxy group, a isopropyloxy group, a 1-pentyloxy group and a 1-hexyloxy group.

A "C1-6 alkoxy-C1-6 alkyl group" in the present specification means a "C1-6 alkyl group" defined in the above to which a "C1-6 alkoxy group" defined in the above is attached, and specific examples include a methoxymethyl group, a 1-methoxyethyl group, a 2-methoxyethyl group, a 1-methoxypropyl group, a 2-methoxypropyl group, a 3-methoxypropyl group, a 2-methoxy-2-propyl group, a (1-propyloxy)methyl group, an (isopropyloxy)methyl group, a 1-(1-propyloxy)ethyl group, a 2-(1-propyloxy)ethyl group, a 1-(isopropyloxy)ethyl group, a 2-(isopropyloxy)ethyl group, a 1-(1-propyloxy)propyl group, a 2-(1-propyloxy)propyl group, a 3-(1-propyloxy)propyl group, a 2-(1-propyloxy)-2-propyl group, a 1-(isopropyloxy)propyl group, a 2-(isopropyloxy)propyl group, a 3-(isopropyloxy)propyl group, and a 2-(isopropyloxy)-2-propyl group.

In the definition of $R^2$, "an aromatic ring group selected from the group consisting of a phenyl group, a pyridinyl group, and a pyrimidinyl group, where the two atoms on the aromatic ring which are adjacent to the carbon atom attached to the pyrazolo[4,3-c]quinoline ring each independently has a substituent selected from Group A1, and the other atoms on the aromatic ring independently optionally have a substituent selected from Group B1" means:

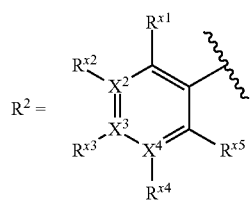

wherein $X^2$ to $X^4$ is a carbon atom or a nitrogen atom to form a phenyl group, a pyridinyl group, or a pyrimidinyl group;

when $X^n$ (n=2 to 4) is a nitrogen atom, $R^{xn}$ is not present; and when $X^n$ (n=2 to 4) is a carbon atom, $R^{xn}$ is a hydrogen atom or a substituent selected from Group B1, and $R^{x1}$ and $R^{x5}$ is independently a substituent selected from Group A1.

The definitions of $R^1$ to $R^6$ of the compound represented by the formula (I), and preferable examples will be described hereinafter.

$R^1$ is a hydrogen atom.

$R^2$ is an aromatic ring group selected from the group consisting of a phenyl group, a pyridinyl group, and a pyrimidinyl group, where the two atoms on the aromatic ring which are adjacent to the carbon atom attached to the pyrazolo[4,3-c]quinoline ring each independently has a substituent selected from Group A1, and the other atoms on the aromatic ring independently optionally have a substituent selected from Group B1.

$R^2$ is preferably an aromatic ring group selected from the group consisting of a phenyl group, a 3-pyridinyl group, a 4-pyridinyl group, and a 5-pyrimidinyl group, where the two atoms on the aromatic ring which are adjacent to the carbon atom attached to the pyrazolo[4,3-c]quinoline ring each independently has a substituent selected from Group A2, and the other atoms on the aromatic ring independently optionally have a substituent selected from Group B2

$R^2$ is more preferably an aromatic ring group selected from the group consisting of a phenyl group, a 3-pyridinyl group, and a 4-pyridinyl group, where the two atoms on the aromatic ring which are adjacent to the carbon atom attached to the pyrazolo[4,3-c]quinoline ring each independently has a substituent selected from Group A3, and the other atoms on the aromatic ring independently optionally have a substituent selected from Group B3.

$R^3$ is a hydrogen atom, or a fluorine atom.

$R^4$ is a hydrogen atom.

$R^5$ is an oxepanyl group, a dioxepanyl group, a tetrahydropyranyl group, or a tetrahydrofuranyl group optionally having a methoxy group.

$R^5$ is preferably a 4-oxepanyl group, a 1,4-dioxepan-6-yl group, a 3,4,5,6-tetrahydro-2H-3-pyranyl group, a 3,4,5,6-tetrahydro-2H-4-pyranyl group, or a 3-tetrahydrofuranyl group, and more preferably is a 3,4,5,6-tetrahydro-2H-4-pyranyl group, or a 3-tetrahydrofuranyl group.

$R^6$ is a hydrogen atom.

Group A1 consists of a halogen atom, a C1-6 alkyl group optionally having 1 to 3 halogen atoms, and a C1-6 alkoxy group.

Group B1 consists of a halogen atom, a cyano group, a C1-6 alkyl group optionally having 1 to 3 halogen atoms, a C1-6 alkoxy-C1-6 alkyl group, a C1-6 alkoxy group optionally having 1 to 3 halogen atoms, and a tetrahydropyranyl group.

Group A2 consists of a chlorine atom, and a methyl group optionally having 1 to 2 fluorine atoms, an ethyl group, a methoxy group, and an ethoxy group.

Group B2 consists of a fluorine atom, a chlorine atom, a cyano group, a methyl group optionally having 1 to 3 fluorine atoms, an ethyl group, a methoxymethyl group, a methoxy group optionally having 1 to 3 fluorine atoms, an ethoxy group, an isopropyloxy group, and a 3,4,5,6-tetrahydro-2H-4-pyranyl group.

Group A3 consists of a methyl group, and a methoxy group.

Group B3 consists of a methyl group, a methoxy group, and a methoxymethyl group.

A "pharmacologically acceptable salt" in the present specification is not especially limited as long as a salt formed with the compound according to the present invention, and specific examples include inorganic acid salts, organic acid salts, inorganic base salts, organic base salts, and acidic or basic amino acid salts.

If only a "pharmacologically acceptable salt" in the present specification is a salt formed in a suitable ratio unless there is any especially limiting description, the number of acid molecules per one molecule of the compound in a formed salt, although being not especially limited, is preferably about 0.1 to about 5 molecules, more preferably about 0.5 to about 2 molecules, and still more preferably about 0.5, about 1 or about 2 molecules, per one molecule of the compound.

Preferable examples of inorganic acid salts include hydrochlorides, hydrobromides, sulfates, nitrates and phosphates, and preferable examples of organic acid salts include acetates, succinates, fumarates, maleates, tartrates, citrates, lactates, stearates, benzoates, methanesulfonates, p-toluenesulfonates and benzenesulfonates.

Preferable examples of inorganic base salts include alkaline metal salts such as sodium salts and potassium salts, alkaline earth metal salts such as calcium salts and magnesium salts, aluminum salts, and ammonium salts, and preferable examples of organic base salts include diethylamine salts, diethanolamine salts, meglumine salts and N,N-dibenzylethylenediamine salts.

Preferable examples of acidic amino acid salts include aspartates and glutamates, and preferable examples of basic amino acid salts include arginine salts, lysine salts and ornithine salts.

[General Production Methods]

The compound according to the present invention can be produced by methods described in the below. However, production methods of the compound according to the present invention are not limited thereto.

The compound (I) according to the present invention can be produced by the following production methods A, B. C and D.

<Production Method A>

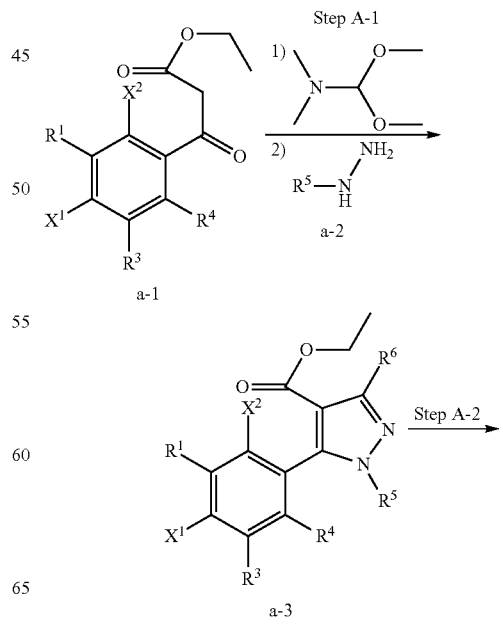

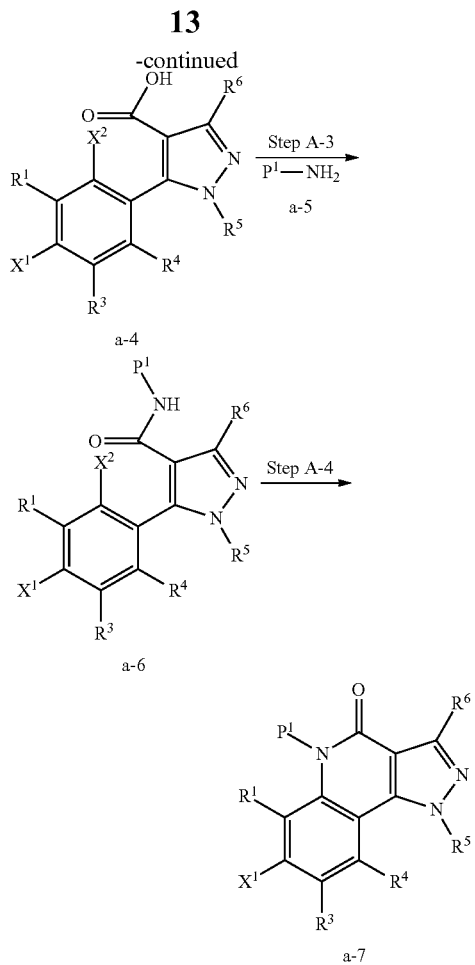

wherein $R^1$, $R^3$, $R^4$, $R^5$ and $R^6$ each have the same definitions as the above definitions; $P^1$ means a protecting group of an NH group, such as 2,4-dimethoxybenzyl group; and $X^1$ and $X^2$ denote a halogen atom.

Step A-1

This step is a step of condensation reaction of a compound represented by the formula a-1 (referred to as a compound a-1 in some cases; hereinafter, the same applies) with DMF-DMA, and thereafter allowing the resultant to react with a hydrazine derivative a-2 to structure a pyrazole ring to thereby obtain a compound a-3, by a well-known method. The present reaction may be carried out in a gas flow or an atmosphere of an inert gas such as nitrogen or argon.

The compound a-1 can be synthesized according to a well-known method (for example, the description in Reuman, Michael et al., "Journal of Medicinal Chemistry", 1995, vol. 38, p. 2531-2540, or Wentland Mark P et al., "Journal of Medicinal Chemistry", 1993, vol. 36, p. 1580-1596).

This step can be carried out specifically with reference to the reaction condition, post-reaction operation, purifying method and the like described in Preparation Examples 1, 2, 3, 4, 5, 6, 10 and 11 described later and the like.

As the compound a-2, a commercially available one as it is may be used, or may be synthesized by means well-known by those skilled in the art. The compound can be produced by converting a corresponding ketone derivative to a hydrazide-imine, and reducing the hydrazideimine using borane, sodium cyanoborohydride or the like. The compound a-2 may also be used in a form a salt such as a hydrochloride.

With respect to a solvent used in the present reaction, in the condensation reaction of the compound a-1 with DMF-DMA, the DMF-DMA can be used in 5 to 20 times molar equivalent as a reaction agent and concurrently solvent. A solvent used in the successive pyrazole ring formation reaction with the hydrazine derivative a-2 is not especially limited as long as it is a solvent which dissolves reaction starting raw materials to some degree, and does not inhibit the reaction, but is suitably methanol, ethanol, n-butanol, t-butanol, THF, 1,4-dioxane, water or a mixed solvent thereof and more suitably ethanol.

The reaction temperature usually depends on starting raw materials, solvents to be used, and other reagents and the like used in the reaction. In the condensation reaction of the compound a-1 with DMF-DMA, the reaction temperature is suitably 0° C. to a reflux temperature of the solvent (internal temperature of a reaction vessel), and more suitably room temperature. In the successive pyrazole ring formation reaction with the hydrazine derivative a-2, the reaction temperature is suitably room temperature to a reflux temperature of the solvent (internal temperature of a reaction vessel), and more suitably 70° C. to a reflux temperature of the solvent.

The reaction time usually depends on starting raw materials, solvents to be used, and other reagents and the like used in the reaction. In the condensation reaction of the compound a-1 with DMF-DMA, the reaction time is suitably 0.5 to 24 hours, and more suitably 1 to 3 hours, at the above temperature after the addition of the reagents. In the successive pyrazole ring formation reaction with the hydrazine derivative a-2, the reaction time is suitably 0.5 to 24 hours, and more suitably 1 to 8 hours, at the above temperature after the addition of the reagents.

Step A-2

This step is a step of hydrolyzing the compound a-3 in the presence of a base to thereby obtain a compound a-4.

A solvent used in the present reaction is not especially limited as long as it is a solvent which dissolves starling raw materials to some degree, and does not inhibit the reaction, but suitably includes methanol, ethanol, n-butanol, t-butanol, THF, 1,4-dioxane, water or mixed solvents thereof.

The base depends on starting raw materials, solvents to be used and the like, and is not especially limited, but examples thereof include sodium hydroxide, lithium hydroxide, potassium hydroxide, lithium carbonate, sodium carbonate, potassium carbonate, sodium hydrogencarbonate, potassium carbonate, cesium carbonate, lithium tetramethylsilyl oxide (TMSOLi). A base can be used in 1 to 10 times molar equivalent with respect to the a-3.

The reaction temperature usually depends on starting raw materials, solvents to be used, and other reagents and the like used in the reaction, and is suitably 0° C. to a reflux temperature of the solvent (internal temperature of a reaction vessel), and more suitably room temperature to 50° C.

The reaction time usually depends on starting raw materials, solvents to be used, and other reagents and the like used in the reaction, and is suitably 1 to 48 hours, and more suitably 2 to 12 hours, at the above temperature after the addition of the reagents.

Step A-3

This step is a step of allowing the compound a-4 to react with an amine derivative a-5 by using a condensing agent to thereby obtain a compound a-6. The present reaction may be carried out also in a gas flow or an atmosphere of an inert gas such as nitrogen or argon.

This step can be carried out specifically with reference to the reaction condition, post-reaction operation, purifying method and the like described in Preparation Example 1, 2, 4 and 5 described later and the like.

The condensing agent depends on starting raw materials, solvents to be used and the like, and is not especially limited, but DCC, EDC, PYBOP, CDI and the like can be used. A condensing agent can be used in 1 to 5 times molar equivalent, and suitably 1 to 2 times molar equivalent, with respect to the compound a-4.

A solvent used in the present reaction is not especially limited as long as it is a solvent which dissolves starting raw materials to some degree, and does not inhibit the reaction, but suitably includes THF, dichloromethane, DMF or mixed solvents thereof.

The amine derivative a-5 can be used in 1 to 10 times molar equivalent, and is suitably in 1 to 2 times molar equivalent, with respect to the compound a-4.

The reaction temperature usually depends on starting raw materials, solvents to be used, and other reagents and the like used in the reaction, and is suitably 0° C. to a reflux temperature of the solvent (internal temperature of a reaction vessel), and more suitably 0° C. to room temperature.

The reaction time usually depends on starting raw materials, solvents to be used, and other reagents and the like used in the reaction. After the addition of the condensing agent to the compound a-4, the reaction is carried out suitably for 1 to 48 hours; and more suitably 1 to 3 hours, at the above temperature, and thereafter the amine derivative a-5 is added and the reaction is carried out at the above temperature for 1 to 48 hours, and more suitably for 8 to 15 hours.

Step A-4

This step is a step of intramolecularly cyclizing the compound a-6 in the presence of a base to thereby obtain a compound a-7. The present reaction may be carried out also in a gas flow or an atmosphere of an inert gas such as nitrogen or argon.

This step can be carried out specifically with reference to the reaction condition, post-reaction operation, purifying method and the like described in Preparation Example 1, 2, 4 and 5 described later and the like.

A solvent used in the present reaction is not especially limited as long as it is a solvent which dissolves starting raw materials to some degree, and does not inhibit the reaction, but suitably includes THF, DMF or mixed solvents thereof.

The base, in the case of being used in the reaction, depends on starting raw materials, solvents to be used and the like, and is not especially limited, but examples thereof include bases such as sodium hydroxide, KTB, LDA, LHMDS, sodium hydride and potassium hydride; but preferable is sodium hydroxide, KTB, sodium hydride or the like. A base can be used in 1 to 5 times molar equivalent, and preferably 1 to 3 times molar equivalent, with respect to the compound a-6.

The reaction temperature usually depends on starting raw materials, solvents to be used, and other reagents and the like used in the reaction, and is suitably −78° C. to a reflux temperature of the solvent (internal temperature of a reaction vessel), and more suitably −20° C. to room temperature.

The reaction time usually depends on starting raw materials, solvents to be used, and other reagents and the like used in the reaction, and is suitably 1 to 48 hours, and more suitably 1 to 5 hours, at the above temperature.

<Production Method B>

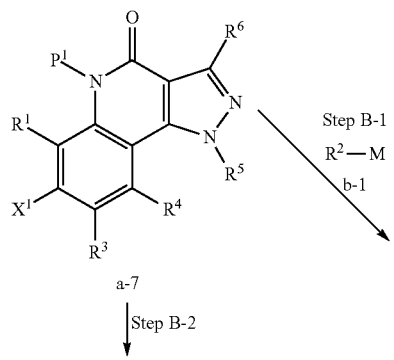

a-7

Step B-2

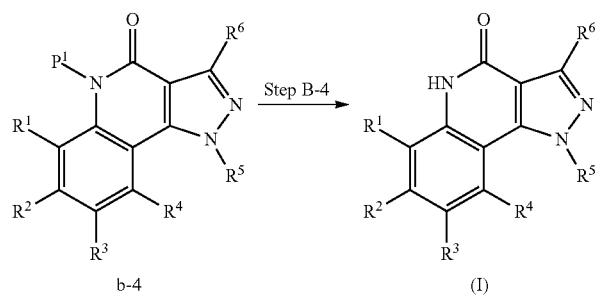

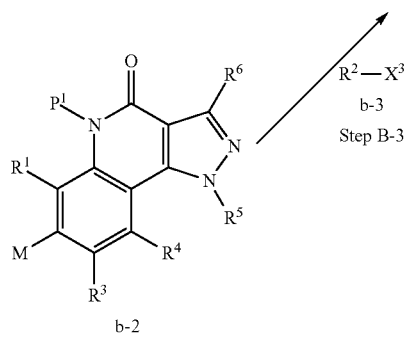

wherein $R^1$, $R^2$, $R^3$, $R^4$, $R^5$, $R^6$, and $P^1$ each have the same definitions as the above definitions; $X^1$ and $X^3$ means a halogen atom and M means —$BF_3^-K^+$, —$B(OH)_2$, a group represented by the formula:

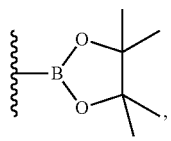

—$Sn(n-Bu)_3$, —ZnBr, —ZnCl, or the like.

Step B-1

This step is a step of subjecting a compound a-7 and a compound b-1 to a coupling reaction using a transition metal catalyst to thereby convert them to a compound b-4.

This step can be carried out specifically with reference to the reaction condition, post-reaction operation, purifying method and the like described in Examples 1, 2 and 3 described later and the like.

The compound a-7 can be obtained by <Production Method A> or the like.

The present reaction may be carried out also in a gas flow or an atmosphere of an inert gas such as nitrogen or argon.

A solvent used in the present reaction is not especially limited as long as it is a solvent which dissolves starting raw materials to some degree, and does not inhibit the reaction; but examples thereof include alcoholic solvents such as methanol or ethanol, etheric solvents such as THF, DME, MTBE, 1,4-dioxane, cyclopentyl methyl ether, diethyl ether, diisopropyl ether, dibutyl ether and dicyclopentyl ether, aromatic hydrocarbon-based solvents such as benzene, toluene, xylene and mesitylene, amide-based solvents such as DMF and NMP, aliphatic hydrocarbon-based solvents such as heptane and hexane, water, or mixed solvents thereof; suitable is an aromatic hydrocarbon-based solvent, an amide-based solvent such as DMF or NMP, an etheric solvent such as 1,4-dioxane, water, or a mixture thereof, and more suitable is a mixed solvent of DMF, NMP or 1,4-dioxane with water.

The base depends on starting raw materials, solvents to be used and the like, and is not especially limited, but examples thereof include inorganic bases such as lithium hydroxide, sodium hydroxide, potassium hydroxide, lithium carbonate, sodium carbonate, potassium carbonate, sodium hydrogencarbonate, potassium hydrogencarbonate, tripotassium phosphate n-hydrate, cesium carbonate, cesium fluoride and potassium fluoride, and organic bases such as imidazole, pyridine, TEA and DIPEA; and preferable are TEA, cesium carbonate and the like. Potassium hydrogenfluoride may also be added.

The transition metal catalyst depends on starting raw materials, solvents to be used and the like, and is not especially limited as long as not inhibiting the reaction, but suitably includes $Pd(PPh_3)_4$, $PdCl_2(PPh_3)_2$, palladium (II) acetate/triphenylphosphine, palladium (II) acetate/2-dicyclohexylphosphino-2',4',6'-triisopropylbiphenyl, palladium (II) acetate/bis[2-(diphenylphosphino)phenyl]ether, palladium (1) chloride, $Pd_2(dba)_3$/tri-t-butylphosphine, $Pd_2(dba)_3$, $Pd(t-Bu_3P)_2$, $[(t-Bu)_2P(OH)]_2PdCl_2$, and 1,1'-bis(diphenylphosphino)ferrocene dichloropalladium (II). Depending on a transition metal catalyst to be used, use of a copper (II) iodide, lithium chloride or the like in combination thereof gives good results such as an improvement in the yield and a reduction in the reaction time in some cases.

The reaction temperature usually depends on starting raw materials, solvents, and other reagents used in the reaction, and is suitably 0° C. to a reflux temperature of the solvent (internal temperature of a reaction vessel), and more suitably 60 to 150° C. Use of a microwave reaction apparatus gives good results such as an improvement in the yield and a reduction in the reaction time in some cases.

The reaction time usually depends on starting raw materials, solvents, other reagents used in the reaction, and the reaction temperature, and is suitably 1 to 48 hours, and more suitably 1 to 6 hours, at the above temperature after the addition of the reagents.

The compound b-1 can be used in 1 to 5 times molar equivalent, and is suitably in 1 to 3 times molar equivalent, with respect to the compound a-7.

The base can be used in 1 to 10 times molar equivalent, and is suitably in 2 to 5 times molar equivalent, with respect to the compound a-7.

The transition metal catalyst can be used in 0.05 to 1 time molar equivalent, and is suitably in 0.05 to 0.1 times molar equivalent, with respect to the compound a-7.

Step B-2

This step is a step of converting a compound a-7 and bis(pinacolato)diboron or the like to a compound b-2 by coupling reaction using a transition metal catalyst.

Specifically, this step can be performed with reference to the reaction conditions, the post-reaction operation, the purification method and the like described in the later-described Preparation Examples 1, 3, 4, 5 and 6 and the like.

The compound a-7 can be obtained by the <Preparation Method A> or the like.

This reaction can also be performed in a stream or atmosphere of an inert gas such as nitrogen or argon.

The solvent used in this reaction is not particularly limited unless it can dissolve the starting material to a certain extent and does not inhibit the reaction. Examples include ether solvents such as THF, DME, MTBE, 1,4-dioxane, cyclopentyl methyl ether, diethyl ether, diisopropyl ether, dibutyl ether and dicyclopentyl ether, aromatic hydrocarbon solvents such as benzene, toluene, xylene and mesitylene, amide solvents such as DMF and NMP, and aliphatic hydrocarbon solvents such as heptane and hexane. Aromatic hydrocarbon solvents, amide solvents such as DMF and NMP, or ether solvents such as DME and 1,4-dioxane, or mixed solvents thereof are preferred, and DMF, NMP or 1,4-dioxane, or mixed solvents thereof are more preferred.

The base varies according to the starting material, the solvent used and the like and is not particularly limited. Examples include inorganic bases such as potassium acetate, lithium hydroxide, sodium hydroxide, potassium hydroxide, lithium carbonate, sodium carbonate, potassium carbonate, sodium bicarbonate, potassium bicarbonate, cesium carbonate, cesium fluoride and potassium fluoride, and organic bases such as imidazole, pyridine, TEA and DIPEA. Potassium acetate or the like is preferred.

The transition metal catalyst varies according to the starting material, the solvent used and the like and is not particularly limited unless it does not inhibit the reaction. Preferred examples include Pd(PPh$_3$)$_4$, palladium(II) acetate/triphenylphosphine, palladium(II) acetate/2-dicyclohexylphosphino-2',4',6'-triisopropylbiphenyl, palladium(II) chloride, Pd$_2$(dba)$_3$1-tri-t-butylphosphine, Pd$_2$(dba)$_3$, Pd(t-Bu$_3$P)$_2$ and 1,1'-bis(diphenylphosphino)ferrocenedichloropalladium(II). More preferred examples include 1,1'-bis(diphenylphosphino)ferrocenedichloropalladium(II).

The reaction temperature usually varies according to the starting material, the solvent, and furthermore the reagent used in the reaction, and is preferably 0° C. to the reflux temperature of the solvent (the internal temperature in the reaction vessel), more preferably 60 to 150° C. Use of a microwave reaction apparatus gives good results such as an improvement in the yield and a reduction in the reaction time in some cases.

The reaction time usually varies according to the starting material, the solvent, and furthermore the reagent used in the reaction and the reaction temperature, and is preferably 1 to 48 hours, more preferably 1 to 6 hours, at the above temperature after adding the reagent Bis(pinacolato)diboron can be used in an amount of 1 to 5 molar equivalents based on the compound a-7. The amount is preferably 1 to 3 molar equivalents.

The base can be used in an amount of 1 to 10 molar equivalents based on the compound a-7. The amount is preferably 2 to 5 molar equivalents.

The transition metal catalyst can be used in an amount of 0.05 to 1 molar equivalent based on the compound a-7. The amount is preferably 0.05 to 0.1 molar equivalent.

Step B-3

This step is a step of converting a compound b-3 and the compound b-2 to a compound b-4 by coupling reaction using a transition metal catalyst.

This step can be performed under the same conditions as in Step B-1. Specifically, this step can be performed with reference to the reaction conditions, the post-reaction operation, the purification method and the like described in the later-described Examples 4, 6, and 25 and the like.

Step B-4

This step is a step of removing a protecting group P$^1$ of the compound b-4 to thereby obtain the compound (I). The deprotection of a protecting group is described in many well-known literatures, for example, T. Greene et al., "Protective Groups in Organic Synthesis" (John Wiley & sons. Inc., New York, 1999)(hereinafter, referred to as Synthesis Reference Literature 1). The deprotection reaction of an amino group depends on the kind of a protecting group, and is not especially limited, but for example, in the case of a 2,4-dimethoxybenzyl group or the like, the deprotection can be carried out under an acidic condition.

In the case where the protecting group P$^1$ is a 2,4-dimethoxybenzyl group, a solvent used in the present reaction may be any one as long as it dissolves starting raw materials to some degree and does not inhibit the reaction. The solvent is not especially limited, but examples thereof include alcoholic solvents such as methanol and ethanol, etheric solvents such as THF, DME, MTBE, cyclopentyl methyl ether, diethyl ether, diisopropyl ether, dibutyl ether and dicyclopentyl ether, halogenated hydrocarbon-based solvents such as dichloromethane and chloroform, acetic acid, or mixed solvents thereof. An acid may be used as a solvent.

As the acid, for example, trifluoroacetic acid (TFA), hydrochloric acid and sulfuric acid can be used. Preferable is TFA. An acid can be used in a 1 to 100 times volume with respect to the compound b-4.

The reaction temperature usually depends on starting raw materials, solvents, and other reagents used in the reaction, and is suitably 0° C. to a reflux temperature of the solvent (internal temperature of a reaction vessel), and more suitably 40 to 60° C.

The reaction time usually depends on starting raw materials, solvents, other reagents used in the reaction, and the reaction temperature, and is suitably 0.5 to 24 hours, and more suitably 1 to 12 hours, at the above temperature after the addition of the reagents.

<Preparation Method C>

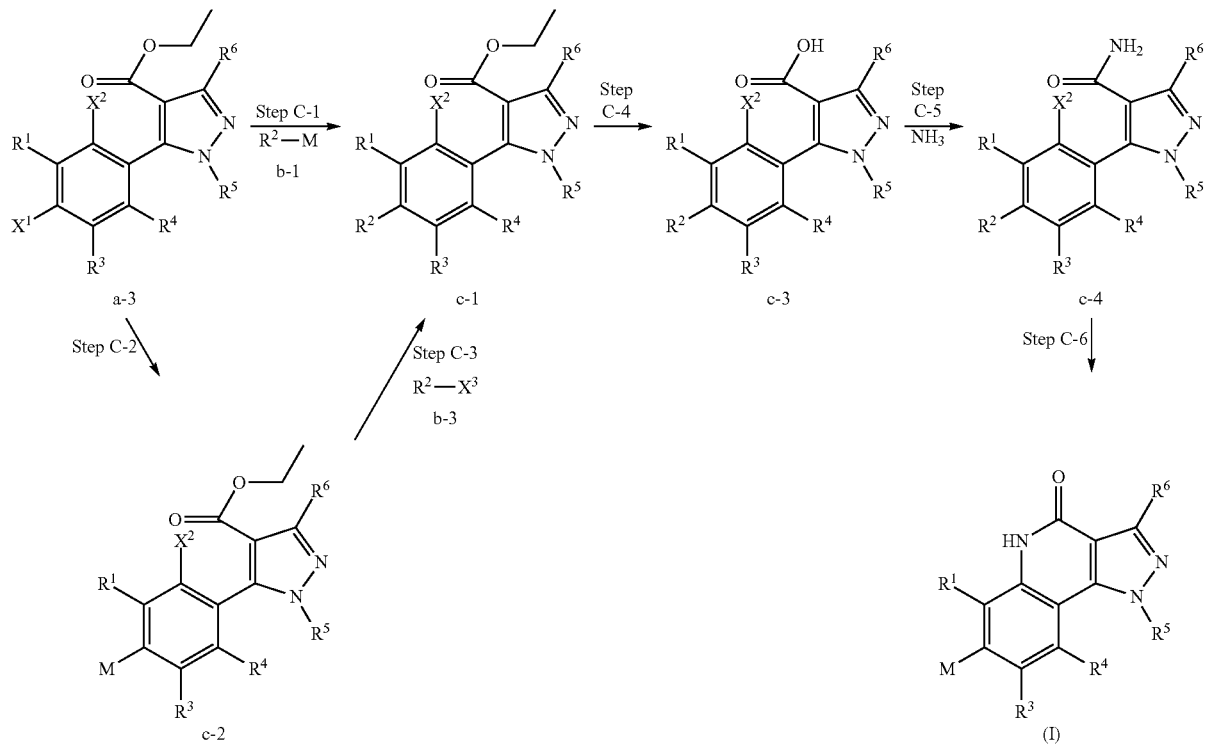

In the formulas, $R^2$, $R^3$, $R^4$, $R^5$, $R^6$ and M are as defined above, respectively, and $X^1$, $X^2$ and $X^3$ each represent a halogen atom.

Step C-1

This step is a step of converting a compound b-1 and a compound a-3 to a compound c-1 by coupling reaction using a transition metal catalyst.

This step can be performed under the same conditions as in Step B-1 of the <Preparation Method B>. Specifically, this step can be performed with reference to the reaction conditions, the post-reaction operation, the purification method and the like described in the later-described Example 52 and the like.

Step C-2

This step is a step of converting a compound a-3 and bis(pinacolato)diboron or the like to a compound c-2 by coupling reaction using a transition metal catalyst This step can be performed under the same conditions as in Step B-2 of the <Preparation Method B>. Specifically, this step can be performed with reference to the reaction conditions, the post-reaction operation, the purification method and the like described in the later-described Preparation Examples 3 and 6 and the like.

Step C-3

This step is a step of converting a compound b-3 and the compound c-2 to a compound c-1 by coupling reaction using a transition metal catalyst This step can be performed under the same conditions as in Step B-3 of the <Preparation Method B>. Specifically, this step can be performed with reference to the reaction conditions, the post-reaction operation, the purification method and the like described in the later-described Example 26 and the like.

Step C-4

This step is a step of obtaining a compound c-3 by hydrolyzing the compound c-1 in the presence of a base.

This step can be performed under the same conditions as in Step A-2 of the <Preparation Method A>. Specifically, this step can be performed with reference to the reaction conditions, the post-reaction operation, the purification method and the like described in the later-described Example 26 and the like.

Step C-5

This step is a step of obtaining a compound c-4 by reacting the compound c-3 with aqueous ammonia using a condensing agent This reaction can also be performed in a stream or atmosphere of an inert gas such as nitrogen or argon.

This step can be performed under the same conditions as in Step A-3 of the <Preparation Method A>. Specifically, this step can be performed with reference to the reaction conditions, the post-reaction operation, the purification method and the like described in the later-described Examples 5, 26, 52, 53, 54 and 55 and the like.

Step C-6

This step can be performed under the same conditions as in Step A-4 of the <Preparation Method A>. Specifically, this step can be performed with reference to the reaction conditions, the post-reaction operation, the purification method and the like described in the later-described Examples 5, 26, 52, 53, 54 and 55 and the like.

<Preparation Method D>

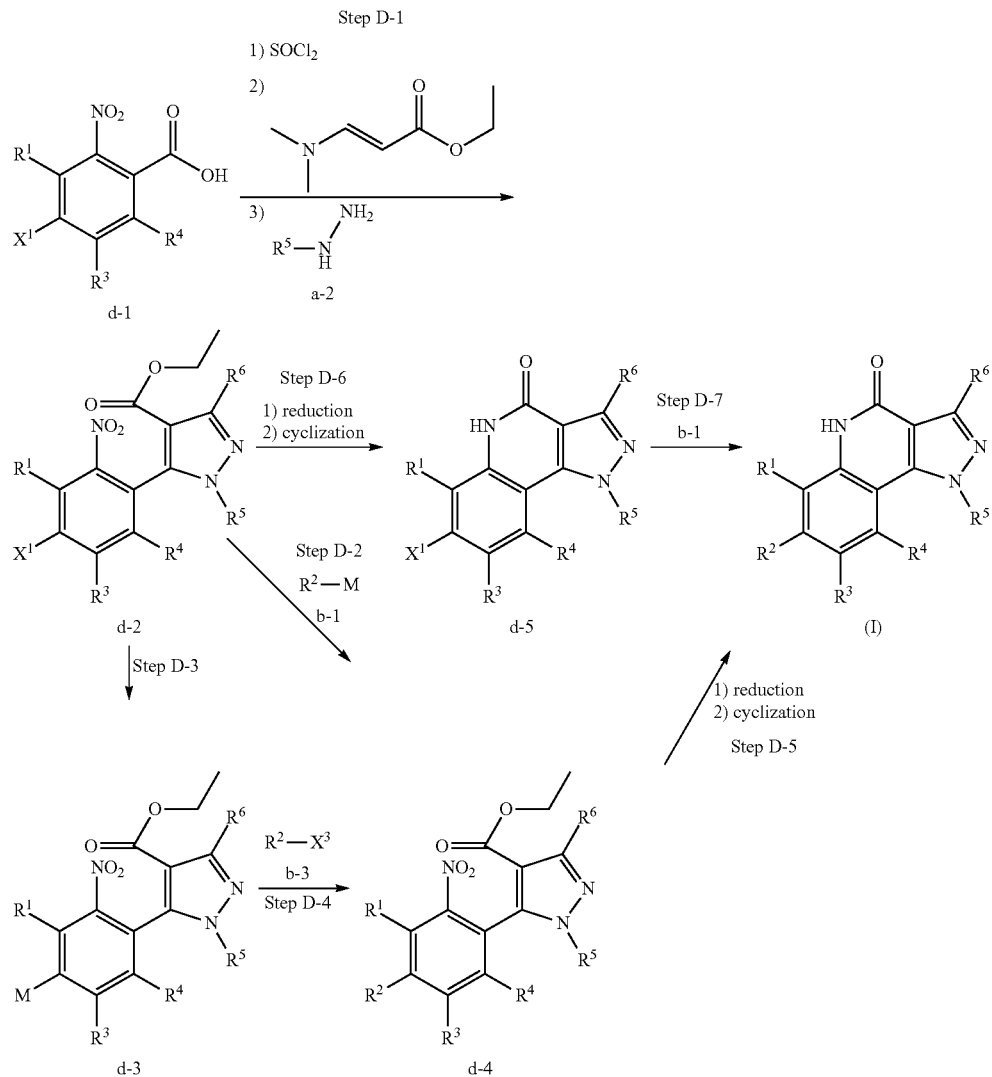

In the formulas, $R^1$, $R^2$, $R^3$, $R^4$, $R^5$, $R^6$ and M are as defined above, respectively, and $X^1$ and $X^3$ each represent a halogen atom.

Step D-1

This step is a step of obtaining a compound d-2 by a known method by reacting a compound d-1 with thionyl chloride to convert it to a corresponding acid chloride derivative, and then performing condensation reaction with ethyl dimethylaminoacrylate and subsequently reacting with a hydrazine derivative a-2 to form a pyrazole ring. This reaction can also be performed in a stream or atmosphere of an inert gas such as nitrogen or argon.

Specifically, this step can be performed with reference to the reaction conditions, the post-reaction operation, the purification method and the like described in the later-described Preparation Example 7 and the like.

The compound a-2 can be a commercially available product used as is, and can also be synthesized by a means known to a person skilled in the art. The compound can be prepared by converting a corresponding ketone derivative to a hydrazide imine and reducing using borane, sodium cyanoborohydride or the like. The compound a-2 can also be used as a salt such as hydrochloride.

The solvent used in the step of reacting a compound d-1 with thionyl chloride to convert it to a corresponding acid chloride derivative in this reaction is not particularly limited unless the solvent can dissolve the reaction starting material to a certain extent and does not inhibit the reaction. The solvent is preferably THF, acetonitrile, DMF or DMA, more preferably acetonitrile. The solvent used in the next condensation reaction with ethyl dimethylaminoacrylate is not particularly limited unless it can dissolve the reaction starting material to a certain extent and does not inhibit the reaction. The solvent is preferably TI-IF, acetonitrile, DMF or DMA, more preferably acetonitrile. The solvent used in the subsequent pyrazole ring-forming reaction with a hydrazine derivative a-2 is not particularly limited unless it can dissolve the reaction starting material to a certain extent and does not inhibit the reaction. The solvent is preferably methanol, ethanol, n-butanol, t-butanol, THF, 1,4-dioxane, acetonitrile, water or a mixed solvent thereof, more preferably a mixed solvent of acetonitrile and water.

The reaction temperature usually varies according to the starting material, the solvent used, and furthermore the reagent used in the reaction. The reaction temperature in the step of obtaining a corresponding acid chloride from a compound d-1 and thionyl chloride is preferably 0° C. to the reflux temperature of the solvent (the internal temperature in the reaction vessel), more preferably 50° C. to 80° C. The reaction temperature in the next condensation reaction with ethyl dimethylaminoacrylate is preferably 0° C. to the reflux temperature of the solvent (the internal temperature in the reaction vessel), more preferably 20° C. to 80° C. The reaction temperature in the subsequent pyrazole ring-forming reaction with a hydrazine derivative a-2 is preferably room temperature to the reflux temperature of the solvent (the internal temperature in the reaction vessel), more preferably 50° C. to the reflux temperature of the solvent.

The reaction time usually varies according to the starting material, the solvent used, and furthermore the reagent used in the reaction. The reaction time in the step of obtaining a corresponding acid chloride by reaction of a compound d-1 with thionyl chloride is preferably 0.5 to 24 hours, more preferably 1 to 3 hours, at the above temperature after adding the reagent. The reaction time in the next condensation reaction with ethyl dimethylaminoacrylate is preferably 0.5 to 24 hours, more preferably 1 to 3 hours, at the above temperature after adding the reagent. The reaction time in the subsequent pyrazole ring-forming reaction with a hydrazine derivative a-2 is preferably 0.5 to 60 hours, more preferably 12 to 24 hours, at the above temperature after adding the reagent.

Step D-2

This step is a step of converting a compound b-1 and the compound d-2 to a compound d-4 by coupling reaction using a transition metal catalyst.

This step can be performed under the same conditions as in Step B-1 of the <Preparation Method B>. Specifically, this step can be performed with reference to the reaction conditions, the post-reaction operation, the purification method and the like described in the later-described Examples 27, and 43 and the like.

Step D-3

This step is a step of converting the compound d-2 and bis(pinacolato)diboron or the like to a compound d-3 by coupling reaction using a transition metal catalyst.

This step can be performed under the same conditions as in Step B-2 of the <Preparation Method B>. Specifically, this step can be performed with reference to the reaction conditions, the post-reaction operation, the purification method and the like described in the later-described Preparation Examples 7 and 9 and the like.

Step D-4

This step is a step of converting a compound b-3 and the compound d-3 to a compound d-4 by coupling reaction using a transition metal catalyst.

This step can be performed under the same conditions as in Step B-3 of the <Preparation Method B>. Specifically, this step can be performed with reference to the reaction conditions, the post-reaction operation, the purification method and the like described in the later-described Examples 45 and 51 and the like.

Step D-5

This step is a step of obtaining a compound (I) by a known method by converting the nitro group of the compound d-4 to an amino group using a reducing agent, and then condensing the amino group with the ester to perform intramolecular cyclization reaction. This reaction can also be performed in a stream or atmosphere of an inert gas such as nitrogen or argon. Specifically, this step can be performed with reference to the reaction conditions, the post-reaction operation, the purification method and the like described in the later-described Examples 27, 41, 43, 45, 51, and 62 and the like.

Examples of the reducing agent in this step include iron, tin(II) chloride and sodium hydrosulfite. Iron and tin(II) chloride are preferred, and iron is more preferred. The intramolecular cyclization reaction proceeds by heating without using a reagent in particular.

The solvent used in the step of converting the nitro group of the compound d-4 to an amino group using a reducing agent in this reaction is not particularly limited unless the solvent can dissolve the reaction starting material to a certain extent and does not inhibit the reaction. The solvent is methanol, ethanol, n-butanol, t-butanol, ethyl acetate or a mixed solvent thereof, more preferably methanol or ethanol. The solvent used in the subsequent intramolecular cyclization reaction is not particularly limited unless it can dissolve the reaction starting material to a certain extent and does not inhibit the reaction. The solvent is acetic acid, ethanol, n-butanol, t-butanol, THF or 1,4-dioxane, preferably acetic acid, ethanol, n-butanol or t-butanol, more preferably acetic acid.

The reaction temperature usually varies according to the starting material, the solvent used, and furthermore the reagent used in the reaction. The reaction temperature in the step of converting the nitro group of the compound d-4 to an amino group using a reducing agent is preferably 0° C. to the reflux temperature of the solvent (the internal temperature in the reaction vessel), more preferably 80° C. to the reflux temperature of the solvent (the internal temperature in the reaction vessel). The reaction temperature in the subsequent intramolecular cyclization reaction is preferably 0° C. to the reflux temperature of the solvent (the internal temperature in the reaction vessel), more preferably 50° C. to the reflux temperature of the solvent (the internal temperature in the reaction vessel).

The reaction time usually varies according to the starting material, the solvent used, and furthermore the reagent used in the reaction. The reaction time in the step of converting the nitro group of the compound d-4 to an amino group using a reducing agent is preferably 0.5 to 24 hours, more preferably 1 to 3 hours, at the above temperature after adding the reagent. The reaction time in the subsequent intramolecular cyclization reaction is preferably 0.5 to 24 hours, more preferably 1 to 3 hours, at the above temperature after adding the reagent.

Step D-6

This step is a step of obtaining a compound d-5 by a known method by converting the nitro group of the compound d-2 to an amino group using a reducing agent, and then condensing the amino group with the ester to perform intramolecular cyclization reaction.

This step can be performed under the same conditions as in Step D-5 of the <Preparation Method D>. Specifically, this step can be performed with reference to the reaction conditions, the post-reaction operation, the purification method and the like described in the later-described Example 63 and the like.

Step D-7

This step is a step of converting a compound represented by compound b-1 and the compound d-5 to a compound (I) by coupling reaction using a transition metal catalyst.

This step can be performed under the same conditions as in Step B-1 of the <Preparation Method B>. Specifically, this step can be performed with reference to the reaction conditions, the post-reaction operation, the purification method and the like described in the later-described Example 63 and the like.

After the completion of the reaction in each method and each step described above, a target compound for each step can be collected from a reaction mixture according to a conventional method.

For example, in the case where the reaction mixture is wholly a liquid, the reaction mixture, as desired, is returned to room temperature or cooled with ice; an acid, an alkali, an oxidizing agent or a reducing agent is suitably neutralized; an organic solvent immiscible like water and ethyl acetate and not reacting with a target compound is added; and a layer containing the target compound is separated. Then, a solvent immiscible with the obtained layer and not reacting with the target compound is added to wash the layer containing the target compound, and the layer is separated. Additionally, if the layer is an organic layer, by drying the layer using a desiccant such as anhydrous magnesium sulfate or anhydrous sodium sulfate, and distilling out the solvent, the target compound can be collected. If the layer is a water layer, by electrically desalting the layer, and thereafter lyophilizing the layer, the target compound can be collected.

If the reaction mixture is wholly a liquid, and if possible, only by distilling out substances (for example, a solvent and reagents) other than a target compound under normal pressure or reduced pressure, the target compound can be collected.

Further in the case where a target compound alone deposits as a solid, or in the case where the reaction mixture is wholly a liquid and only a target compound precipitates as a solid in the procedure of collection, by first filter-collecting the target compound by a filtration method, washing the filter-collected target compound with a proper organic or inorganic solvent, and drying the target compound, the target compound can be collected, and by treating the mother liquid similarly to the case where the reaction mixture is wholly a liquid, the target compound can further be collected.

Further in the case where only a reagent or a catalyst is present as a solid, or in the case where the reaction mixture is wholly a liquid, where a reagent or a catalyst alone precipitates as a solid in the procedure of collection, and where a target compound is dissolved in a solution, by first filtrating out the reagent or the catalyst by a filtration method, washing the filtered-out reagent or catalyst with a proper organic or inorganic solvent, combining the obtained washed liquid with the mother liquid, and treating the obtained mixed liquid similarly to the case where the reaction mixture is wholly a liquid, the target compound can be collected.

Particularly in the case where substances other than a target compound contained in the reaction mixture do not inhibit a reaction of a next step, the reaction mixture as it is may be used in the next step without particularly isolating the target compound.

In order to improve the purity of the target compound collected in the above method, a recrystallization method, various types of chromatographies and a distillation method can be carried out suitably.

In the case where a collected target compound is a solid, the purity of the target compound can usually be improved by a recrystallization method. In the recrystallization method, a single solvent or a mixed solvent of a plurality of solvents which does not react with the target compound can be used. Specifically, a target compound is first dissolved at room temperature or under heating in a single solvent or a mixed solvent of a plurality of solvents which does not react with the target compound. By cooling the obtained mixed liquid with ice water or the like or leaving it at room temperature, the target compound can be crystallized from the mixed liquid.

In the case where a collected target compound is a liquid, the purity of the target compound can be improved by various types of chromatographies. Weakly acidic silica gels such as Silica Gel 60 (70-230 mesh or 340-400 mesh) made by Merck or BW-300 (300 mesh) made by Fuji Silysia Chemical Ltd. can generally be used. In the case where a target compound has a basicity and exhibits too intense adsorption by the above silica gels, or in other cases, a propylamine-coated silica gel (200-350 mesh) made by Fuji Silysia Chemical Ltd. or the like may be used. In the case where a target compound has a bipolarity, in the case where the elution by a highly polar solvent such as methanol is necessary, or in other cases, NAM-200H or NAM-300H made by NAM Laboratory may be used. A target compound improved in purity can be obtained by eluting the target compound with a single solvent or a plurality of solvents which do not react with the target compound by using these silica gels, and distilling out the solvent(s).

In the case where a collected target compound is a liquid, the purity of the target compound can be improved also by a distillation method. In the distillation method, by depressurizing a target compound at room temperature or under heating, the target compound can be distilled out.

Although the above are typical examples of production methods of the compound (I) according to the present invention, raw material compounds and various types of reagents in production of the compound according to the present invention may form salts, hydrates or solvates, and any compounds and reagents thereof depend on starting raw materials, solvents to be used and the like, and are not especially limited as long as not inhibiting the reactions. Also a solvent to be used depends on starting raw materials, reagents and the like, and is not of course especially limited as long as not inhibiting the reactions and dissolving starting substances to some degree. In the case where the compound (I) according to the present invention is obtained as a free body, the compound (I) can be converted to the state of a salt which the compound (I) may form or a hydrate thereof by a conventional method.

In the case where the compound (I) according to the present invention is obtained as a salt of the compound (I) or a hydrate of the compound (I), the salt and the hydrate can be converted to a free body of the compound (I) by a conventional method.

Various types of isomers (for example, geometric isomers, optical isomers, rotational isomers, stereoisomers and tautomers) obtained for the compound (I) according to the present invention can be purified and isolated by using usual separation means, for example, recrystallization, a diastereomeric salt method, an enzymatic resolution method, and various types of chromatographies (for example, thin-layer chromatography, column chromatography and gas chromatography).

[Pharmaceutical preparation] A compound of the formula (I) according to the present invention and/or a pharmaceutically acceptable salt thereof can be pharmaceutically prepared by a conventional method, and the dosage form can be made, for example, an oral preparation, (tablet, granule, powder, capsule, syrup, or the like), an injection (for intravenous administration, for intramuscular administration, for subcutaneous administration, for intraperitoneal administration, and for others), and an external preparation (endermic preparation (ointment, patch, and the like), eyedrops, nasal drops, suppository, and the like).

In the case of producing an oral solid preparation, to a compound of the formula (I) and/or a pharmaceutically acceptable salt thereof, as required, an excipient, a binder, a disintegrant, a lubricant, a colorant and the like are added, and a tablet, a granule, a powder and a capsule can be produced by conventional methods. The tablet, granule, powder, capsule and the like, as required, may be film-coated.

Examples of the excipient include lactose, cornstarch and crystalline cellulose; examples of the binder include hydroxypropyl cellulose and hydroxypropyl methyl cellulose; examples of the disintegrant include carboxymethyl cellulose calcium and croscarmellose sodium; examples of the lubricant include magnesium stearate and calcium stearate; examples of the colorant include titanium oxide; and examples of the film coating agent include hydroxypropyl cellulose, hydroxypropyl methyl cellulose and methyl cellulose, but these additives are of course not limited to these examples.

These solid preparations such as tablets, capsules, granules and powders can each contain usually 0.001 to 99.5% by weight, preferably 0.01 to 90% by weight or the like, of a compound of the formula (I) and/or a pharmaceutically acceptable salt thereof.

In the case of producing an injection (for intravenous administration, for intramuscular administration, for subcutaneous administration, for intraperitoneal administration, and for others), to a compound of the formula (I) and/or a pharmaceutically acceptable salt thereof, as required, a pH regulator, a buffer agent, a suspending agent, a solubilizer, an antioxidant, a preservative (antiseptic), an isotonic agent, and the like are added, and an injection can be produced by a conventional method. The preparations may be lyophilized to be made extemporaneous dissolution-type lyophilized preparations.

Examples of the pH regulator and the buffer agent include organic acids or inorganic acids and/or salts thereof; examples of the suspending agent include methyl cellulose, Polysorbate 80 and carboxymethyl cellulose sodium; examples of the solubilizer include Polysorbate 80 and polyoxyethylene sorbitan monolaurate; examples of the antioxidant include α-tocopherol; examples of the preservative include methyl paraoxybenzoate and ethyl paraoxybenzoate; and examples of the isotonic agent include glucose, sodium chloride and mannitol, but these additives are of course not limited to these examples.

These injections can each contain usually 0.000001 to 99.5% by weight, preferably 0.00001 to 90% by weight or the like, of a compound of the formula (I) and/or a pharmaceutically acceptable salt thereof.

In the case of producing an external preparation, a basis raw material is added to a compound of the formula (I) or a pharmaceutically acceptable salt thereof, and as required, for example, the preservative, a stabilizer, the pH regulator, the antioxidant, the colorant and the like are added, and for example, an endemic preparation (ointment, patch, and the like), eyedrops, nasal drops, suppository, and the like can be produced by conventional methods.

As basis raw materials to be used, various raw materials usually used, for example, for medicines, quasi-drugs and cosmetics can be used. Specific examples thereof include raw materials such as animal and vegetable oils, mineral oils, ester oils, waxes, emulsifiers, higher alcohols, fatty acids, silicon oils, surfactants, phospholipids, alcohols, polyhydric alcohols, water-soluble polymers, clay minerals and purified water.

These external preparations can each contain usually 0.000001 to 99.5% by weight, preferably 0.00001 to 90% by weight or the like, of a compound of the formula (I) or a pharmaceutically acceptable salt thereof.

The compound according to the present invention can be made a chemical probe to trap a target protein of a physiologically active low-molecular compound. That is, the compound according to the present invention can be converted to an affinity chromatography probe, a photoaffinity probe and the like by introducing a labeling group, a linker or the like to a moiety different from a structural moiety essential to develop the activity of the compound, by the technique described in J. Mass Spectrum. Soc. Jpn., Vol. 51, No. 5, 2003, p. 492-498, WO2007/139149, or the like.

Examples of the labeling group, the linker or the like used in a chemical probe include groups shown in the group consisting of the following (1) to (5):

(1) protein labeling groups such as photoaffinity labeling groups (for example, a benzoyl group, a benzophenone group, an azido group, a carbonyl azido group, a diaziridine group, an enone group, a diazo group and a nitro group), and chemoaffinity groups (for example, ketone groups whose alpha-carbon atom is replaced by a halogen atom, a carbamoyl group, an ester group, an alkylthio group, an α,β-unsaturated ketone, a Michael receptor of an ester or the like, and an oxirane group);

(2) cleavable linkers such as —S—S—, —O—Si—O—, monosaccharides (a glucose group, a galactose group, and the like), and disaccharides (lactose and the like), and oligopeptide linkers cleavable by an enzymatic reaction;

(3) biotin and fishing tag groups such as a 3-(4,4-difluoro-5,7-dimethyl-4H-3a,4a-diaza-4-bora-s-indacen-3-yl)propionyl group;

(4) radioactive labeling groups of $^{125}$I, $^{32}$P, $^{3}$H, $^{14}$C or the like; fluorescent labeling groups such as fluorescein, rhodamine, dansyl, umbelliferone, 7-nitrofurazanyl, and 3-(4,4-difluoro-5,7-dimethyl-4H-3a,4a-diaza-4-bora-s-indecen-3-yl)propionyl group; chemiluminescent groups such as luciferin and luminol; and markers capable of detecting heavy metal ions such as lanthanide metal ions and radium ions; and (5) groups attached to solid carriers such as glass beads, glass beds, microliter plates, agarose bends, agarose beds, polystyrene beads, polystyrene beds, nylon beads and nylon beds.

Probes prepared by introducing labeling groups selected from the group consisting of the above (1) to (5), or the like, to the compound according to the present invention by methods described in the above literatures or the like can be used as chemical probes to identify labeled proteins useful for search and the like of new drug discovery targets.

The compound (I) according to the present invention can be produced, for example, by methods described in the following Examples, and the effects of the compound can be verified by methods described in the following Test Examples. However, these are only exemplifications, and the present invention is not limited to the following specific examples in any case, and changes and modifications may be made without departing from the scope of the present invention.

It is indicated that compounds for which literature names or the like are described were produced according to the literatures or the like.

Abbreviations used in the present specification are common ones well-known by those skilled in the art. The following abbreviations will be used in the present specification.

Ac: acetyl
BAST: bis(2-methoxyethyl)aminosulfur trifluoride
Bn: benzyl
Boc: tert-butoxycarbonyl
BOP: benzotriazol-1-yloxy-tris(dimethylamino)phosphonium hexafluorophosphate.
Bu: butyl
CAN: cerium ammonium nitrate
CDI: 1,1'-carbonyldiimidazole
DAST: diethylaminosulfur trifluoride DBU: 1,8-diazabicyclo[5.4.0]undec-7-ene
DCC: 1,3-dicyclohexylcarbodiimide
DCM: dichloromethane
DDQ: 2,3-dichloro-5,6-dicyano-1,4-benzoquinone
DEAD: diethyl azodicarboxylate
DIAD: diisopropyl azodicarboxylate
DIBAL-H: diisobutylaluminium hydride
DIPEA: N,N-diisopropylethylamine
DMAP: 4-(dimethylamino)pyridine
DME: 1,2-dimethoxyethane
DMF: N,N-dimethylformamide
DMF-DMA: N,N-dimethylformamide dimethyl acetal
DMSO: dimethylsulfoxide
DTT: dithiothreitol
EDC: 1-ethyl-3-(3-dimethylaminopropyl)carbodiimide hydrochloride
EGTA: glycol ether diamine tetraacetic acid
HATU: O-(7-azabenzotriazol-1-yl)-N,N,N',N'-tetramethyluronium hexafluorophosphate
HBTU: O-benzotriazole-N,N,N',N'-tetramethyluronium hexafluorophosphate
HOBT: 1-hydroxybenzotriazole
IPA: isopropyl alcohol
KHMDS: potassium bis(trimethylsilyl)amide
KTB: potassium tert-butoxide
LAH: lithium aluminum hydride
LDA: lithium diisopropylamide
LHMDS: lithium bis(trimethylsilyl) amide
mCPBA: 3-chloroperbenzoic acid
m-: meta
MTBE: t-butylmethylether
n-: normal
NaBH(OAc)$_3$: sodium triacetoxyborohydride
NaHMDS: sodium bis(trimethylsilyl)amide
NBS: N-bromosuccinimide
NCS: N-chlorosuccinimide
NIS: N-iodosuccinimide
NMP: N-methyl-2-pyrrolizinone
o-: ortho
p-: para
Pd(t-Bu$_3$P)$_2$: bis(tri-t-butylphosphine)palladium
Pd$_2$(dba)$_3$: tris(dibenzylideneacetone)dipalladium
Pd(dppf)Cl$_2$ DCM complex: [1,1-bis(diphenylphosphine)ferrocene]dichloropalladium(II) DCM complex
Pd(PPh$_3$)$_4$: tetrakis(triphenylphosphine)palladium(0)
PdCl$_2$(PPh$_3$)$_2$: bis(triphenylphosphine)palladium(II)dichloride
PYBOP: benzotriazol-1-yloxytris(pyridino)phosphonium hexafluorophosphate
t-: tertiary
TBAF: tetrabutylammonium fluoride
TEA: triethylamine
Tf: trifluoromethanesulfonyl
TFA: trifluoroacetic acid
TFAA: trifluoroacetic acid anhydride
THF: tetrahydrofuran
THP: tetrahydropyran.
TMEDA: N,N,N',N'-tetramethylethylenediamine
TMS: trimethylsilyl
Tris: trishydroxymethylaminomethane
Ts: paratoluenesulfonyl
$^1$H-NMR: proton nuclear magnetic resonance spectrometry
LC-MS: liquid chromatography-mass spectrometry
Xantphos: 4,5-bis(diphenylphosphino)-9,9-dimethylxanthine
Z: benzyloxycarbonyl "Room temperature" in the following Examples and Preparation Examples usually indicates about 10° C. to about 35° C. % indicates weight percent unless otherwise specified.

The chemical shift of the proton nuclear magnetic resonance spectrum is recorded in δ units (ppm) from tetramethylsilane; and the coupling constant is recorded in hertz (Hz). The abbreviations of splitting patterns are as follows: s: singlet, d: doublet, t triplet, q: quartet, m: multiplet, brs: broad singlet and brd: broad doublet.

In a reaction using a microwave reaction apparatus in the following Examples and Preparation Examples, Emrys™ Liberator made by Personal chemistry was used.

For the optical resolution of a compound, Parallex Flex™, made by Biotage, (column: one of CHIRALPAK® AD-H, IA, B3 and IC made by Daicel Corp., and CHIRALCEL® OD-H and OJ-H made by Daicel Corp.; column size 2 cm Φ×25 cm) was used. The retention time in the tables in the examples means a value when one of CHIRALPAK® AD-H, IA, 113 and IC made by Daicel Corp., and CHIRALCEL® OD-H and OJ-H made by Daicel Corp. (column size: 0.46 cm Φ×15 cm or 0.46 cm Φ×25 cm) was used and the flow rate was set at 1.00 ml/min. The optical rotation (+/−) was measured by an OR-2090 chiral detector (Hg—Xe lamp, 150 W) made by JASCO.

With respect to the chromatography, in the case where there is a description as silica gel column chromatography, was used a Parallel Prep, made by Yamazen Corp., (column: Hi-Flash™ Column (Silicagel), made by Yamazen Corp., size: one of S (16×60 mm), M (20×75 mm), L (26×100 mm), 2 L (26×150 mm), and 3 L (46×130 mm)) or spherical shape silica gel for chromatography PSQ60B™ made by Fuji Silysia Chemical Ltd., silica gel for chromatography BW-300™ made by Fuji Silysia Chemical Ltd., Wakogel® C-200 made by Wako Pure Chemical Industries, Ltd. or Silica Gel 60® (70-230 mesh) made by Merck Ltd. Japan. In the case where there is a description as NH silica gel column chromatography, was used a Parallel Prep, made by Yamazen Corp., (column: Hi-Flash™ Column (Amino), made by Yamazen Corp., size: one of S (16×60 mm), M (20×75 mm), L (26×100 mm), 2 L (26×150 mm), and 3 L (46×130 mm)) or NH silica gel (200-350 mesh) made by Fuji Silysia Chemical Ltd.

(±)-indicates a racemate, and (+)- and (−)-indicate the (+) type and the (−) type of an enantiomer, respectively.

The names of following compounds were used as those indicated in "E notebook" ver. 12 (Perkin Elmer) except commonly used reagents.

Preparation Example 1

Synthesis of [5-(2,4-dimethoxybenzyl)-4-oxo-1-(tetrahydro-2H-pyran-4-yl)-4,5-dihydro-1H-pyrazolo[4,3-c]quinolin-7-yl]boronic acid

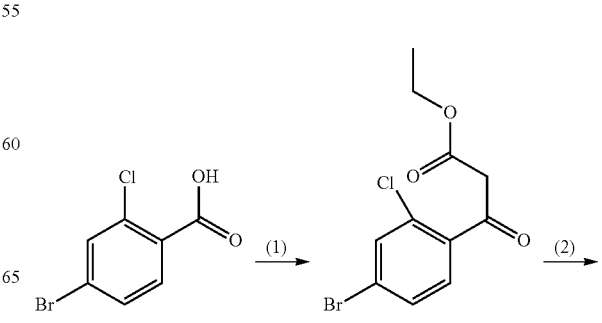

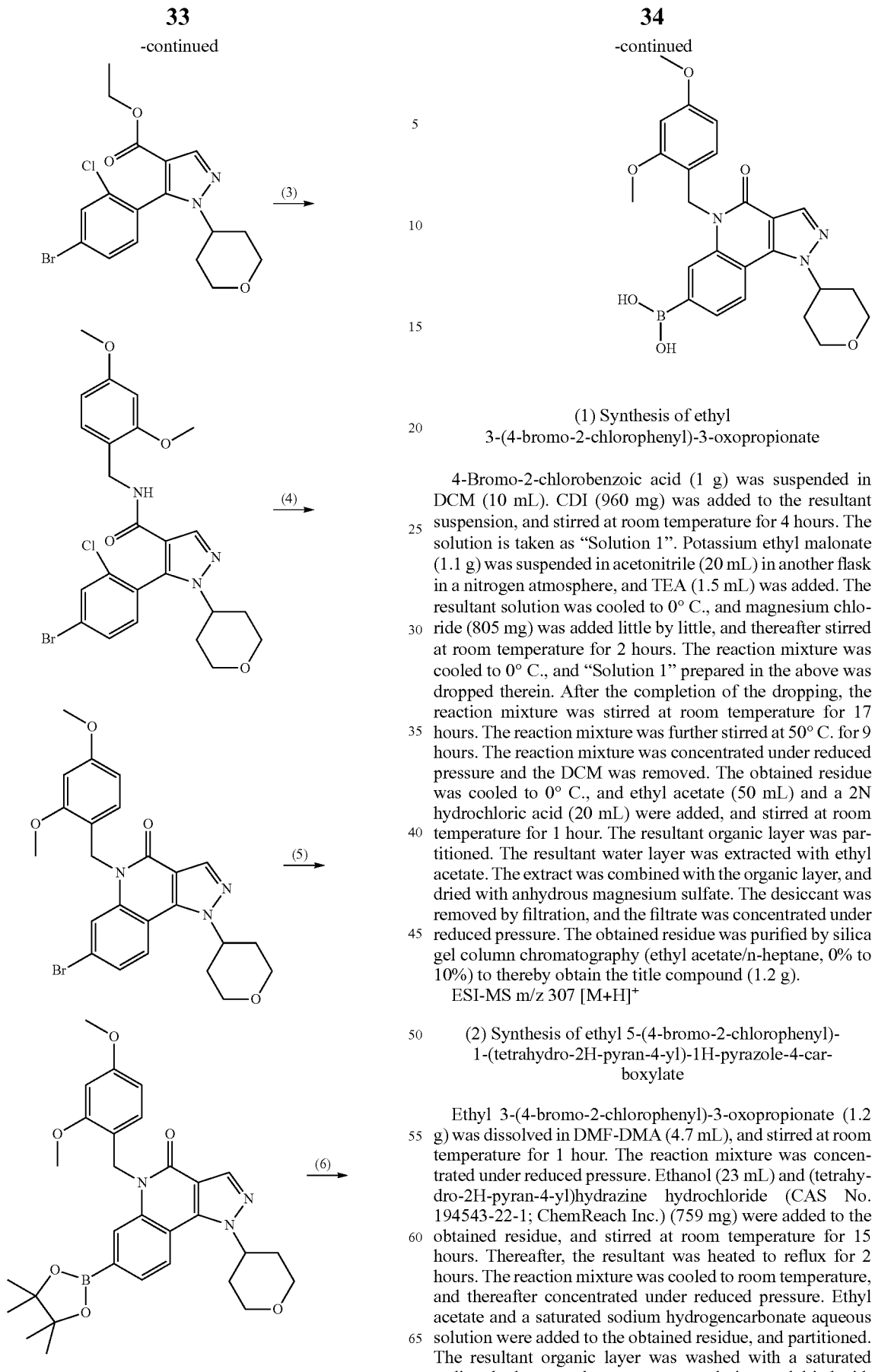

(1) Synthesis of ethyl 3-(4-bromo-2-chlorophenyl)-3-oxopropionate

4-Bromo-2-chlorobenzoic acid (1 g) was suspended in DCM (10 mL). CDI (960 mg) was added to the resultant suspension, and stirred at room temperature for 4 hours. The solution is taken as "Solution 1". Potassium ethyl malonate (1.1 g) was suspended in acetonitrile (20 mL) in another flask in a nitrogen atmosphere, and TEA (1.5 mL) was added. The resultant solution was cooled to 0° C., and magnesium chloride (805 mg) was added little by little, and thereafter stirred at room temperature for 2 hours. The reaction mixture was cooled to 0° C., and "Solution 1" prepared in the above was dropped therein. After the completion of the dropping, the reaction mixture was stirred at room temperature for 17 hours. The reaction mixture was further stirred at 50° C. for 9 hours. The reaction mixture was concentrated under reduced pressure and the DCM was removed. The obtained residue was cooled to 0° C., and ethyl acetate (50 mL) and a 2N hydrochloric acid (20 mL) were added, and stirred at room temperature for 1 hour. The resultant organic layer was partitioned. The resultant water layer was extracted with ethyl acetate. The extract was combined with the organic layer, and dried with anhydrous magnesium sulfate. The desiccant was removed by filtration, and the filtrate was concentrated under reduced pressure. The obtained residue was purified by silica gel column chromatography (ethyl acetate/n-heptane, 0% to 10%) to thereby obtain the title compound (1.2 g).
ESI-MS m/z 307 [M+H]$^+$ (2) Synthesis of ethyl 5-(4-bromo-2-chlorophenyl)-1-(tetrahydro-2H-pyran-4-yl)-1H-pyrazole-4-carboxylate Ethyl 3-(4-bromo-2-chlorophenyl)-3-oxopropionate (1.2 g) was dissolved in DMF-DMA (4.7 mL), and stirred at room temperature for 1 hour. The reaction mixture was concentrated under reduced pressure. Ethanol (23 mL) and (tetrahydro-2H-pyran-4-yl)hydrazine hydrochloride (CAS No. 194543-22-1; ChemReach Inc.) (759 mg) were added to the obtained residue, and stirred at room temperature for 15 hours. Thereafter, the resultant was heated to reflux for 2 hours. The reaction mixture was cooled to room temperature, and thereafter concentrated under reduced pressure. Ethyl acetate and a saturated sodium hydrogencarbonate aqueous solution were added to the obtained residue, and partitioned. The resultant organic layer was washed with a saturated sodium hydrogencarbonate aqueous solution, and dried with anhydrous magnesium sulfate. The desiccant was removed by filtration, and the filtrate was concentrated under reduced pressure. The resultant residue was purified by silica gel column chromatography (ethyl acetate/n-heptane, 10% to 30% to 50%) to thereby obtain the title compound (1.5 g).

$^1$H-NMR (400 MHz, CDCl$_3$) δ (ppm): 1.15 (t, J=7.2 Hz, 3H), 1.63-1.73 (m, 1H), 1.83-191 (m, 1H), 2.22-2.45 (m, 2H), 3.29-3.41 (m, 2H), 3.83-3.93 (m, 1H), 3.99-4.10 (m, 2H), 4.09-4.15 (m, 2H), 7.16 (d, J=8.2 Hz, 1H), 7.54 (dd, J=8.2 Hz, 2.0 Hz, 1H), 7.73 (d, J=2.0 Hz, 1H), 8.05 (s, 1H).

ESI-MS m/z 415 [M+H]

(3) Synthesis of 5-(4-bromo-2-chlorophenyl)-N-(2,4-dimethoxybenzyl)-1-(tetrahydro-2H-pyran-4-yl)-1H-pyrazole-4-carboxamide Ethyl 5-(4-bromo-2-chlorophenyl)-1-(tetrahydro-2H-pyran-4-yl)-1H-pyrazole-4-carboxylate (1.5 g) was added to ethanol (28 mL), and heated to 60° C. to be dissolved. A 5N sodium hydroxide aqueous solution (2.1 mL) was added to the resultant solution, and stirred at 50° C. for 2 and a half hours. The reaction mixture was cooled to room temperature, and thereafter, CHCl$_3$ (100 mL), a 5N hydrochloric acid (12 mL) and a saturated saline solution were added, and partitioned. The resultant organic layer was dried with anhydrous magnesium sulfate. The desiccant was removed by filtration, and the filtrate was concentrated under reduced pressure. The obtained residue was suspended in DCM (31 mL); and CDI (825 mg) was added, and stirred at room temperature. After 30 min, 2,4-dimethoxybenzylamine (1.0 mL) was added to the resultant solution, and stirred at room temperature for 1 hour. A saturated sodium hydrogencarbonate aqueous solution was added to the reaction mixture, and partitioned. The resultant water layer was extracted with ethyl acetate. The extract was combined with the resultant organic layer, and washed with a saturated sodium hydrogencarbonate aqueous solution. The resultant organic layer was dried with anhydrous magnesium sulfate. The desiccant was removed by filtration, and the filtrate was concentrated under reduced pressure. The obtained residue was purified by silica gel column chromatography (ethyl acetate/n-heptane, 50% to 80%) to thereby obtain the title compound (1.6 g).

$^1$H-NMR (400 MHz, CDCl$_3$) δ (ppm): 1.57-1.64 (m, 1H), 1.83-1.90 (m, 1H), 2.18-2.29 (m, 1H), 2.33-2.44 (m, 1H), 327-3.39 (m, 2H), 3.75 (s, 3H), 3.80 (s, 3H), 3.97-4.09 (m, 2H), 4.33-4.26 (m, 2H), 5.72-5.81 (m, 1H), 6.37-6.44 (m, 3H), 7.08 (d, J=82 Hz, 1H), 7.17 (d, J=8.4 Hz, 1H), 7.49 (dd, J=8.2 Hz, 2.0 Hz, 1H), 7.70 (d, J=2.0 Hz, 1H), 7.92 (s, 1H).

ESI-MS m/z 536 [M+H]$^+$

(4) Synthesis of 7-bromo-5-(2,4-dimethoxybenzyl)-1-(tetrahydro-2H-pyran-4-yl)-1H-dihydropyrazolo[4,3-e]quinolin-4(5H)-one 5-(4-Bromo-2-chlorophenyl)-N-(2,4-dimethoxybenzyl)-1-(tetrahydro-2H-pyran-4-yl)-1H-pyrazole-4-carboxamide (1.6 g) was dissolved in THF (29 mL). The solution was cooled to 0° C., and KTB (434 g) was added. The mixture was stirred at room temperature for 26 hours. A saturated ammonium chloride aqueous solution and methanol were added to the reaction mixture, which was extracted with CHCl$_3$. The resultant organic layer was dried with anhydrous magnesium sulfate. The desiccant was removed by filtration, and the filtrate was concentrated under reduced pressure. DMF and water were added to the obtained residue. The precipitated solid was filter-collected to thereby obtain the title compound (1.1 g).

$^1$H-NMR (400 MHz, CDCl$_3$) δ (ppm): 2.10-2.20 (m, 2H), 2.42-2.55 (m, 2H), 3.67 (t, J=11.0 Hz, 2H), 3.68 (s, 3H), 4.02 (s, 3H), 4.19-4.25 (m, 2H), 4.90-5.00 (m, 1H), 5.50 (s, 2H), 6.36 (dd, J=8.2 Hz, 4.2 Hz, 1H), 6.52 (d, J=4.2 Hz, 1H), 7.00 (d, J=8.2 Hz, 1H), 7.39 (d, J=8.4 Hz, 1H), 7.81 (d, J=8.4 Hz, 1H), 7.82 (s, 1H), 832 (s, 1H). ESI-MS m/z 500 [M+H]$^+$

(5) Synthesis of 5-(2,4-dimethoxybenzyl)-1-(tetrahydro-2H-pyran-4-yl)-7-(4,4,5,5-tetramethyl-1,3,2-dioxaborolan-2-yl)-1H-dihydropyrazolo[4,3-c]quinolin-4(5H)-one 7-Bromo-5-(2,4-dimethoxybenzyl)-1-(tetrahydro-2H-pyran-4-yl)-1H-dihydropyrazolo[4,3-c]quinolin-4(5H)-one (200 mg) was dissolved in 1,4-diozane (10 mL). Bis(pinacolato)diboron (132 mg), Pd(dppf)Cl$_2$ DCM complex (15 mg) and potassium acetate (118 mg) were added to the resultant solution, and allowed to react at 130° C. for 2 hours using a microwave reaction apparatus. The reaction mixture was returned to room temperature, and thereafter concentrated under reduced pressure. The obtained residue was purified by silica gel column chromatography (ethyl acetate/n-heptane, 30% to 100%) to thereby obtain the title compound (175 mg).

$^1$H-NMR (400 MHz, CDCl$_3$) δ (ppm): 1.24 (s, 6H), 1.34 (s, 6H), 2.13-222 (m, 2H), 2.42-2.55 (m, 2H), 3.63-3.77 (m, 2H), 3.74 (s, 3H), 4.02 (s, 3H), 4.19-4.25 (m, 2H), 4.97-5.07 (m, 1H), 5.62 (s, 2H), 6.32 (dd, J=8.2 Hz, 4.2 Hz, 1H), 6.50 (d, J=4.2 Hz, 1H), 7.03 (d, J=8.2 Hz, 1H), 7.68 (d, J=10.0 Hz, 1H), 7.95 (d, J=10.0 Hz, 1H), 8.02 (s, 1H), 8.34 (s, 1H).

ESI-MS m/z 546 [M+H]$^+$

(6) Synthesis of [5-(2,4-dimethoxybenzyl)-4-oxo-1-(tetrahydro-2H-pyran-4-yl)-4,5-dihydro-1H-pyrazolo[4,3-c]quinolin-7-yl]boronic acid Synthesized 5-(2,4-dimethoxybenzyl)-1-(tetrahydro-2H-pyran-4-yl)-7-(4,4,5,5-tetramethyl-1,3,2-dioxaborolan-2-yl)-1H-dihydropyrazolo[4,3-c]quinolin-4(5H)-one (150 mg) was dissolved in 1,4-dioxane (10 mL). 2 N HCl (1 mL) was added to the solution, and the mixture was stirred at room temperature. After 30 minutes, the precipitated solid was collected by filtration. The resulting solid was dried under reduced pressure to give the title compound (104 mg).

$^1$H-NMR (400 MHz, CDCl$_3$) δ (ppm): 2.13-2.25 (m, 2H), 2.42-2.60 (m, 2H), 3.71 (s, 3H), 3.72 (s, 3H), 3.81 (s, 2H), 4.17-4.29 (m, 2H), 4.98-5.09 (m, 1H), 5.62 (s, 2H), 6.32 (dd, J=8.2 Hz, 4.2 Hz, 1H), 6.46 (d, J=4.2 Hz, 1H), 6.94 (d, J=82 Hz, 1H), 7.36 (d, J=10.0 Hz, 1H), 7.73 (s, 1H), 8.03 (d, J=10.0 Hz, 1H), 8.36 (s, 1H).

ESI-MS m/z 464 [M+H]$^+$

Preparation Example 2

Synthesis of 7-chloro-5-(2,4-dimethoxybenzyl)-1-(tetrahydro-2H-pyran-4-yl)-1H-pyrazolo[4,3-c]quinolin-4(5H)-one

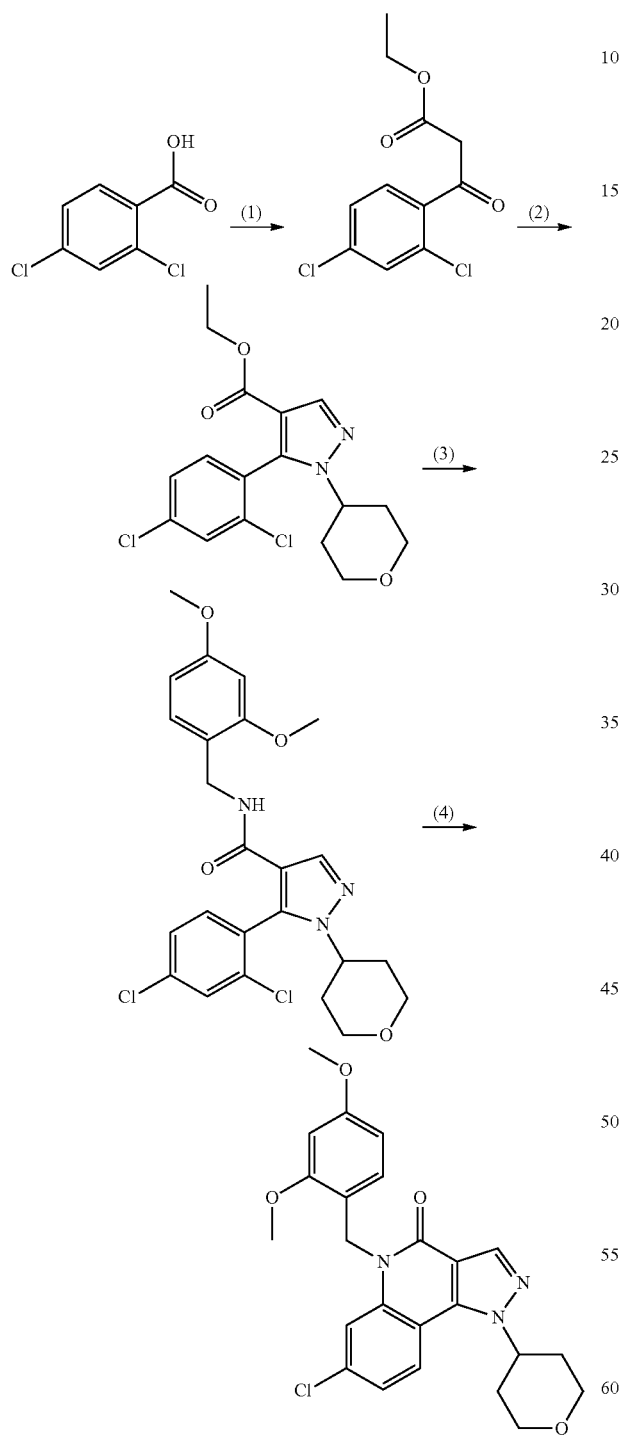

The title compound was obtained by performing the reactions (1) to (4) in accordance with Preparation Example 1 using 2,4-dichlorobenzoic acid and (tetrahydro-2H-pyran-4-yl)hydrazine hydrochloride as raw materials.

$^1$H-NMR (400 MHz, DMSO-$d_6$) δ (ppm): 2.00-2.09 (m, 2H), 2.10-224 (m, 2H), 3.62-3.76 (m, 2H), 3.69 (s, 3H), 3.94 (s, 3H), 3.95-4.04 (m, 2H), 5.18-5.27 (m, 1H), 5.36 (brs, 2H), 6.34-6.37 (m, 1H), 6.63-6.65 (m, 2H), 7.37-7.42 (m, 2H), 8.27-8.29 (m, 2H).

ESI-MS m/z 454 [M+H]$^+$

Preparation Example 3

Synthesis of ethyl 5-(2-fluoro-4-(4,4,5,5-tetramethyl-1,3,2-dioxaborolan-2-yl)phenyl)-1-(tetrahydro-2H-pyran-4-yl)-1H-pyrazole-4-carboxylate

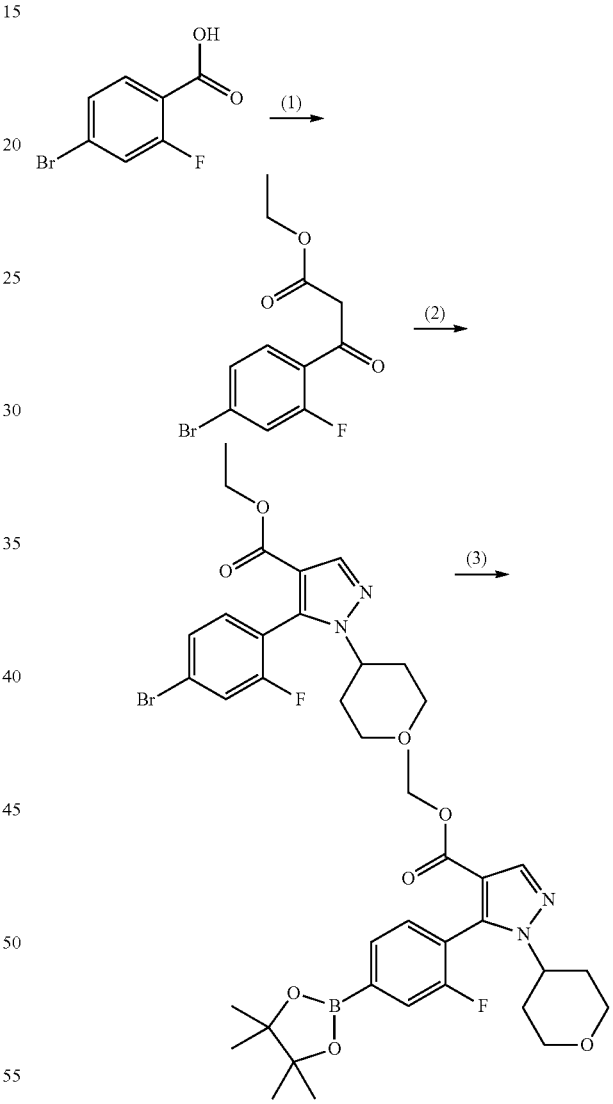

(1) Synthesis of ethyl 3-(4-bromo-2-fluorophenyl)-3-oxopropanoate

CDI (8.88 g) was added to a suspension of 4-bromo-2-fluorobenzoic acid (CAS No. 112704-79-7) (10 g) in DCM (97 mL), and the mixture was stirred at room temperature for 3.5 hours. This solution is called "solution 1."

In another flask, TEA (15.9 mL) and magnesium chloride (10.9 g) were sequentially added to a suspension of potassium ethylmalonate (15.5 g) in acetonitrile (303 mL), and the mixture was stirred at room temperature for three hours and 10 minutes. The "solution 1" prepared above was added dropwise to the reaction mixture over 25 minutes, and then the reaction mixture was stirred at mom temperature overnight. The reaction mixture was concentrated to half volume under reduced pressure. The resulting residue was diluted with ethyl acetate (500 mL), and 5 N hydrochloric acid (250 mL) was added under ice-cooling, followed by stirring at room temperature for one hour. The organic layer was separated. The organic layer was washed with brine, dried over anhydrous magnesium sulfate, filtered and concentrated under reduced pressure. The resulting residue was purified by silica gel column chromatography (ethyl acetate/n-heptane, 5% to 20%) to give the title compound (12.8 g).

ESI-MS m/z 291 [M+H]+

(2) Synthesis of ethyl 5-(4-bromo-2-fluorophenyl)-1-(tetrahydro-2H-pyran-4-yl)-1H-pyrazole-4-carboxylate A solution of ethyl 3-(4-bromo-2-fluorophenyl)-3-oxopropanoate (25.6 g) in DMF-DMA (129 mL) was stirred at room temperature for four hours. The reaction mixture was concentrated under reduced pressure. Toluene (250 mL) was added to the residue. The solution was concentrated under reduced pressure. Ethanol (550 mL) was added to the residue. The solution was cooled in an ice bath. (Tetrahydro-2H-pyran-4-yl)hydrazine hydrochloride (15.4 g) was added to the solution. The mixture was warmed to room temperature over one hour and then heated under reflux for two hours. The reaction mixture was stirred at room temperature overnight and then concentrated under reduced pressure. The residue was partitioned by adding ethyl acetate (400 mL) and brine (200 mL). The organic layer was washed with brine (200 mL), dried over anhydrous magnesium sulfate and filtered, and the filtrate was concentrated under reduced pressure. The residue was purified by silica gel column chromatography (ethyl acetate/n-heptane, 10% to 25%). The resulting crude purified product was suspended in a mixed solution of MTBE (30 mL) and n-heptane (50 mL), followed by stirring at room temperature overnight. The precipitated solid was collected by filtration. The resulting solid was suspended in a mixed solution of MTBE (30 mL) and n-heptane (50 mL), followed by stirring at room temperature overnight The precipitated solid was collected by filtration. Alter drying, the title compound (22.8 g) was obtained.

$^1$H-NMR (400 MHz, CDCl$_3$) δ (ppm): 1.13-1.23 (m, 3H), 1.63-1.73 (m, 1H), 1.77-1.87 (m, 1H), 2.27-2.44 (m, 2H), 3.29-3.44 (m, 2H), 3.91-4.11 (m, 3H), 4.11-4.20 (m, 2H), 7.16-7.24 (m, 1H), 7.39-7.49 (m, 2H), 8.05 (d, J=0.59 Hz, 1H).

ESI-MS m/z 419 [M+Na]+

(3) Synthesis of ethyl 5-[2-fluoro-4-(4,4,5,5-tetramethyl-1,3,2-dioxaborolan-2-yl)phenyl)-1-(tetrahydro-2H-pyran-4-yl)-1H-pyrazole-4-carboxylate A mixture of ethyl 5-(4-bromo-2-fluorophenyl)-1-(tetrahydro-2H-pyran-4-yl)-1H-pyrazole-4-carboxylate (2 g), bis(pinacolato)diboron (1.53 g), Pd(dppf)Cl$_2$-DCM complex (0.18 g) and potassium acetate (1.48 g) was dried under reduced pressure using a vacuum pump for one hour. DMF (20 mL) was added to the dried residue, and the mixture was stirred at 85° C. for six hours. The reaction mixture was returned to room temperature and then filtered through Celite™. The filtrate was concentrated under reduced pressure. The residue was partitioned by adding ethyl acetate (100 mL) and water (100 mL). The aqueous layer was extracted with ethyl acetate (20 mL×2). The combined organic layers were dried over anhydrous magnesium sulfate and filtered, and the filtrate was concentrated under reduced pressure. The residue was purified by silica gel column chromatography (ethyl acetate/n-heptane, 10% to 20%) to give the title compound (2.18 g). $^1$H-NMR (400 MHz, CDCl$_3$) δ (ppm): 1.12-1.17 (m, 3H), 1.37 (s, 12H), 1.64-1.72 (m, 1H), 1.81-1.85 (m, 1H), 2.30-2.39 (m, 2H), 3.28-3.36 (m, 2H), 3.94-4.08 (m, 3H), 4.13 (q, J=7.0 Hz, 2H), 7.29-7.32 (m, 1H), 7.61-7.64 (m, 1H), 7.68-7.70 (m, 1H), 8.05 (s, 1H).

Preparation Example 4

Synthesis of (±)-5-(2,4-dimethoxybenzyl)-1-(tetrahydro-2H-pyran-3-yl)-7-(4,4,5,5-tetramethyl-1,3,2-dioxaborolan-2-yl)-1H-pyrazolo[4,3-c]quinolin-4(5H)-one

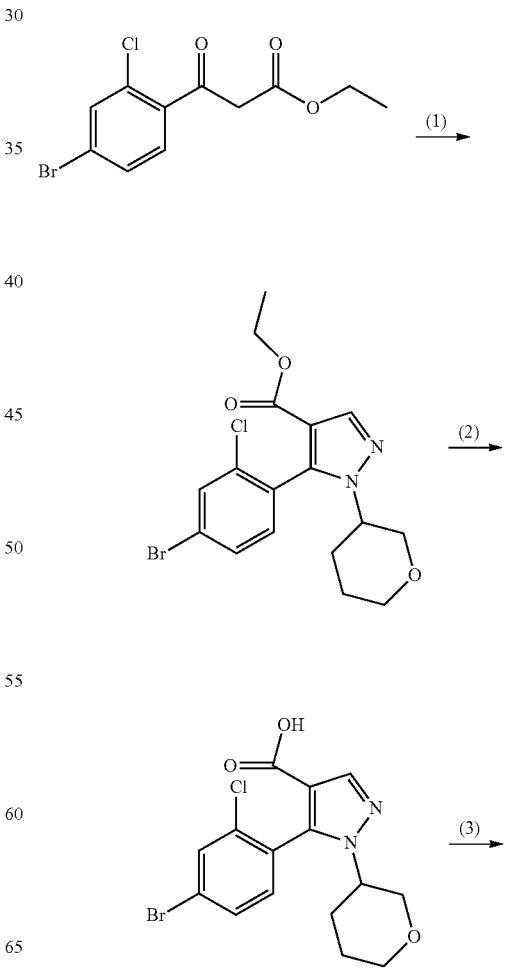

Preparation Example 5

Synthesis of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one

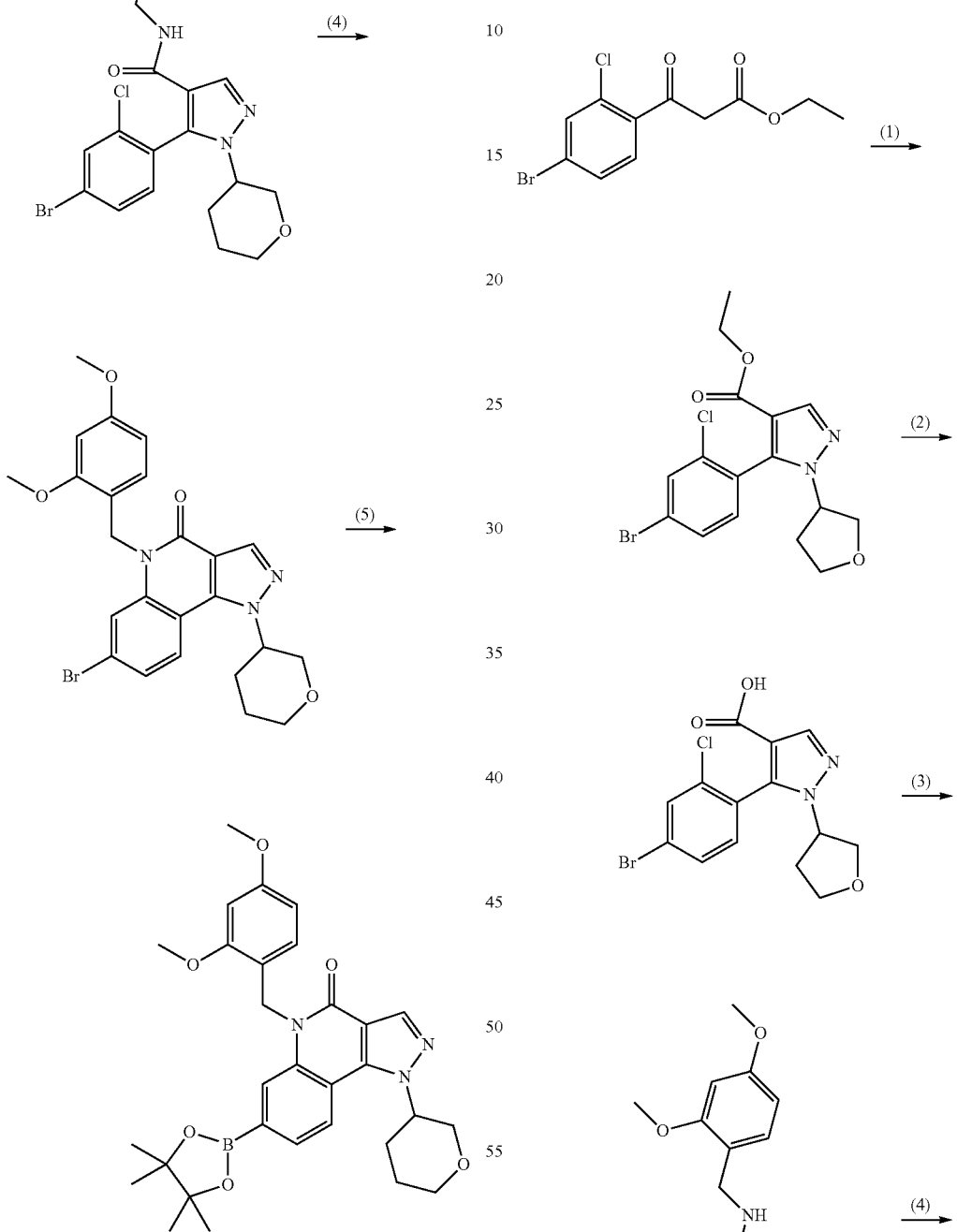

The title compound was obtained by performing the reactions (1) to (5) in accordance with Preparation Example 1 using ethyl 3-(4-bromo-2-chlorophenyl)-3-oxopropanoate obtained in Preparation Example 1 and (±)-(tetrahydro-2H-pyran-3-yl)hydrazine hydrochloride obtained in Preparation Example 17 as raw materials.

ESI-MS m/z 546 [M+H]$^+$

-continued

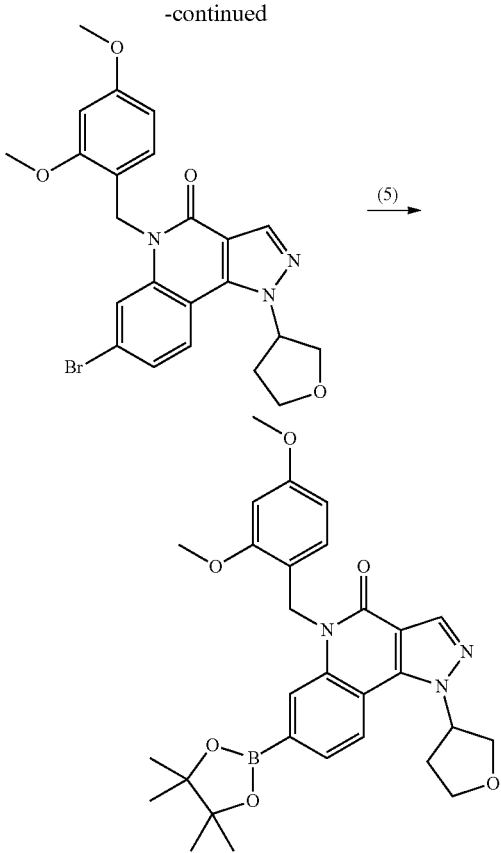

(1) Synthesis of (±)-ethyl 5-(4-bromo-2-chlorophenyl)-1-(tetrahydrofuran-3-yl)-1H-pyrazole-4-carboxylate Ethyl 3-(4-bromo-2-chlorophenyl)-3-oxopropanoate obtained in Preparation Example 1(1) (2.00 g) was dissolved in DMF-DMA (6.96 mL), and the reaction mixture was Mined at room temperature for 1.5 hours. The reaction mixture was concentrated under reduced pressure, and the residue was dissolved in ethanol (40 mL). (±)-(Tetrahydrofuran-3-yl)hydrazine hydrochloride (998 mg) was added to the solution, and the mixture was heated under reflux for two hours. The reaction mixture was cooled to room temperature and then concentrated under reduced pressure. The residue was extracted with ethyl acetate, and the organic layer was purified by silica gel column chromatography (ethyl acetate/n-heptane, 10% to 30%) to give the title compound (1.05 g).
ESI-MS m/z 401 [M+H]$^+$ (2) Synthesis of (±)-5-(4-bromo-2-chlorophenyl)-1-(tetrahydrofuran-3-yl)-1H-pyrazole-4-carboxylic acid A mixture of (±)-ethyl 5-(4-bromo-2-chlorophenyl)-1-(tetrahydrofuran-3-yl)-1H-pyrazole-4-carboxylate (1.05 g) and a 5 M aqueous sodium hydroxide solution (1.58 mL) was stirred in a mixed solvent of ethanol (20 mL) and water (5 mL) at 60° C. for three hours. The reaction mixture was cooled to room temperature and then concentrated under reduced pressure. 5 M hydrochloric acid was added to the residue, followed by extraction with ethyl acetate. The organic layer was dried over anhydrous magnesium sulfate, and the desiccant was filtered off. The filtrate was concentrated under reduced pressure to give the title compound (1 g).
ESI-MS m/z 371 [M+H]$^+$ (3) Synthesis of (±)-5-(4-bromo-2-chlorophenyl)-N-(2,4-dimethoxybenzyl)-1-(tetrahydrofuran-3-yl)-1H-pyrazole-4-carboxamide (±)-5-(4-bromo-2-chlorophenyl)-1-(tetrahydrofuran-3-yl)-1H-pyrazole-4-carboxylic acid (1 g) was dissolved in DCM (20 mL), and CDI (611 mg) was added, followed by stirring at room temperature for one hour. 2,4-dimethoxybenzylamine (0.809 mL) was added to the reaction mixture, and the mixture was stirred at room temperature for two hours. A saturated aqueous sodium bicarbonate solution was added to the reaction mixture, followed by extraction with DCM. The organic layer was concentrated under reduced pressure, and the residue was purified by silica gel column chromatography (ethyl acetate/n-heptane, 10% to 40%) to give the title compound (1.26 g).
ESI-MS m/z 522 [M+H]$^+$ (4) Synthesis of (±)-7-bromo-5-(2,4-dimethoxybenzyl)-1-(tetrahydrofuran-3-yl)-1H-pyrazolo[4,3-c]quinolin-4(5H)-one (±)-5-(4-bromo-2-chlorophenyl)-N-(2,4-dimethoxybenzyl)-1-(tetrahydrofuran-3-yl)-1H-pyrazole-4-carboxamide (1.26 g) was dissolved in THF (25 mL), and KTB (597 mg) was added at 0° C. The mixture was stirred for 12 hours while gradually warming to room temperature. The reaction mixture was cooled to 0° C., and water was added, followed by filtration. The filtration residue was separately stored. The filtrate was extracted with ethyl acetate, and the organic layer was concentrated under reduced pressure. The residue was purified by silica gel column chromatography (ethyl acetate/n-heptane, 10% to 70%). The resulting fraction and the filtration residue obtained above were combined and concentrated to give the title compound (488 mg).
$^1$H-NMR (400 MHz, CDCl$_3$) δ (ppm): 2.50-2.62 (m, 1H), 2.72-2.82 (m, 1H), 3.76 (s, 3H), 4.02 (s, 3H), 4.07-4.15 (m, 1H), 4.19-4.32 (m, 2H), 4.35-4.42 (m, 1H), 5.46-5.57 (m, 3H), 634 (dd, J=8.6 Hz, 2.2 Hz, 1H), 6.52 (d, J=2.2 Hz, 1H), 6.99 (d, J=8.6 Hz, 1H), 7.38 (dd, J=8.6 Hz, 1.8 Hz, 1H), 7.82 (d, J=1.8 Hz, 1H), 7.89 (d, J=8.6 Hz, 1H), 8.32 (s, 1H).
ESI-MS m/z 506 [M+Na]$^+$ (5) Synthesis of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one A mixture of (±)-7-bromo-5-(2,4-dimethoxybenzyl)-1-(tetrahydrofuran-3-yl)-1H-pyrazolo[4,3-c]quinolin-4(5H)-one (300 mg), bis(pinacolato)diboron (204 mg), Pd(dppf)Cl$_2$-DCM complex (13.6 mg) and potassium acetate (182 mg) was reacted in a mixed solvent of 1,4-dioxane (15 mL) and DMSO (1 mL) using a microwave reactor at 130° C. for three hours. The reaction mixture was cooled to room temperature and then concentrated under reduced pressure. The residue was extracted with ethyl acetate, and the organic layer was concentrated under reduced pressure. The residue was subjected to a silica gel pad and eluted with ethyl acetate to give the title compound (428 mg) as a crude purified product.
ESI-MS m/z 532 [M+H]$^+$

Preparation Example 6

Synthesis of ethyl 5-[2-fluoro-4-(4,4,5,5-tetramethyl-1,3,2-dioxaborolan-2-yl)phenyl]-1-[(S)-tetrahydrofuran-3-yl]-1H-pyrazole-4-carboxylate

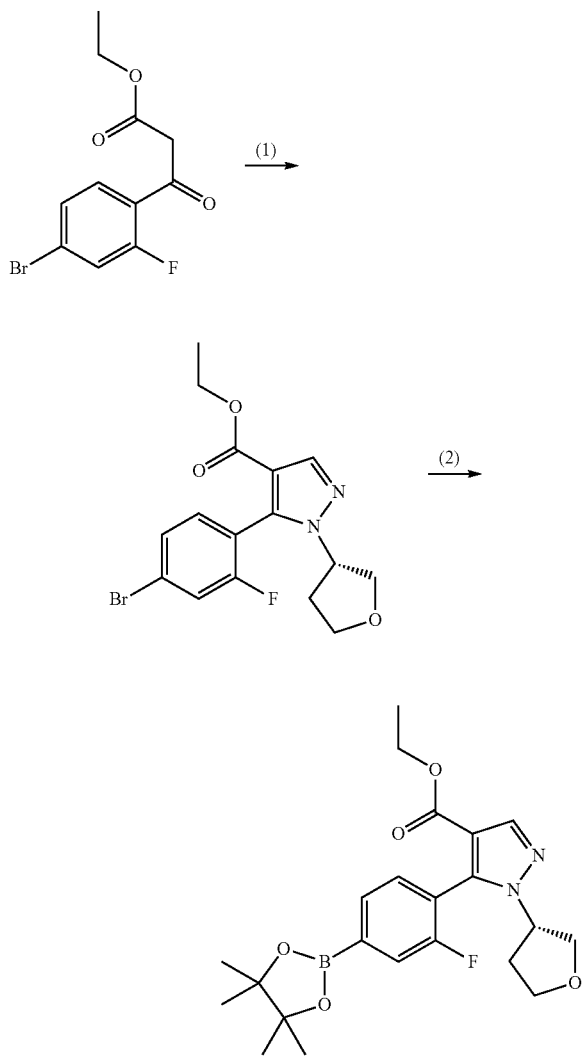

(1) Synthesis of ethyl 5-(4-bromo-2-fluorophenyl)-1-[(S)-tetrahydrofuran-3-yl]-1H-pyrazole-4-carboxylate A solution of ethyl 3-(4-bromo-2-fluorophenyl)-3-oxopropanoate obtained in Preparation Example 3(1) (45 g) in DMF-DMA (165 mL) was stirred at 50° C. for two hours and 15 minutes. The reaction mixture was concentrated under reduced pressure. Toluene (200 mL) was added to the residue, and the mixture was concentrated again under reduced pressure. Ethanol (950 mL) was added to the residue, and the mixture was warmed to 50° C. A solution of (S)-(tetrahydrofuran-3-yl)hydrazine hydrochloride (21.6 g) in water (60 mL) was added dropwise to the solution over 35 minutes. The resulting reaction mixture was stirred at 50° C. for two hours and 10 minutes. The reaction mixture was cooled to room temperature and then concentrated to half volume under reduced pressure. Water (200 mL) was added to the residue, and ethanol was distilled off under reduced pressure. Ethyl acetate (500 mL) was added to the resulting residue, and the organic layer was separated. The aqueous layer was extracted with ethyl acetate (100 mL). The combined organic layers were washed with brine, dried over anhydrous magnesium sulfate, filtered and concentrated under reduced pressure. The residue was purified by silica gel column chromatography (ethyl acetate/n-heptane, 10% to 15%) and then purified by short path NH silica gel column chromatography (ethyl acetate/n-heptane, 33%) to give the title compound (43.1 g).

$^1$H-NMR (400 MHz, CDCl$_3$) δ (ppm): 1.19 (t, J=7.2 Hz, 3H), 2.19-2.49 (m, 2H), 3.87-4.07 (m, 3H), 4.11-4.25 (m, 3H), 4.58-4.65 (m, 1H), 7.17-7.26 (m, 1H), 7.39-7.47 (m, 2H), 8.06 (s, 1H).

ESI-MS m/z 407 [M+Na]$^+$ (2) Synthesis of ethyl 5-[2-fluoro-4-(4,4,5,5-tetramethyl-1,3,2-dioxaborolan-2-yl)phenyl]-1-[(S)-tetrahydrofuran-3-yl]-1H-pyrazole-4-carboxylate A mixture of ethyl 5-(4-bromo-2-fluorophenyl)-1-[(S)-tetrahydrofuran-3-yl]-1H-pyrazole-4-carboxylate (43.1 g), bis(pinacolato)diboron (34.3 g), Pd(dppf)Cl$_2$-DCM complex (4.59 g) and potassium acetate (33.1 g) was dried under reduced pressure using a vacuum pump for one hour. A solution of dried residue in DMF (430 mL) was stirred at 80° C. for three hours and 10 minutes. The reaction mixture was returned to room temperature and then filtered through Celite™. The filtrate was concentrated under reduced pressure. Ethyl acetate (430 mL) and brine (200 mL) were added to the residue, followed by stirring for five minutes. The insoluble matter was filtered off through Celite™. The organic layer was separated from the filtrate. The aqueous layer was re-extracted with ethyl acetate (50 mL). The combined organic layers were dried over anhydrous magnesium sulfate and filtered, and the filtrate was concentrated under reduced pressure. The residue was purified by silica gel column chromatography (ethyl acetate/n-heptane, 10% to 15%) to give the title compound (51.9 g).

$^1$H-NMR (400 MHz, CDCl$_3$) δ (ppm): 1.16 (t, J=7.2 Hz, 3H), 1.37 (s, 12H), 2.15-2.49 (m, 2H), 3.85-4.06 (m, 3H), 4.14 (q, 0.1-7.2 Hz, 2H), 4.20 (dd, J=15.6, 8.4 Hz, 1H), 4.57-4.66 (m, 1H), 7.30 (t, J=7.2 Hz, 0.5H), 7.35 (t, J=7.2 Hz, 0.5H), 7.63 (dd, J=5.6, 2.0 Hz, 1H), 7.70 (dd, J=7.2, 2.0 Hz, 1H), 8.06 (s, 1H).

Preparation Example 7

Synthesis of ethyl 5-[2-nitro-4-(4,4,5,5-tetramethyl-1,3,2-dioxaborolan-2-yl)phenyl]-1-[(S)-tetrahydrofuran-3-yl]-1H-pyrazole-4-carboxylate

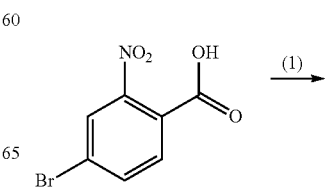

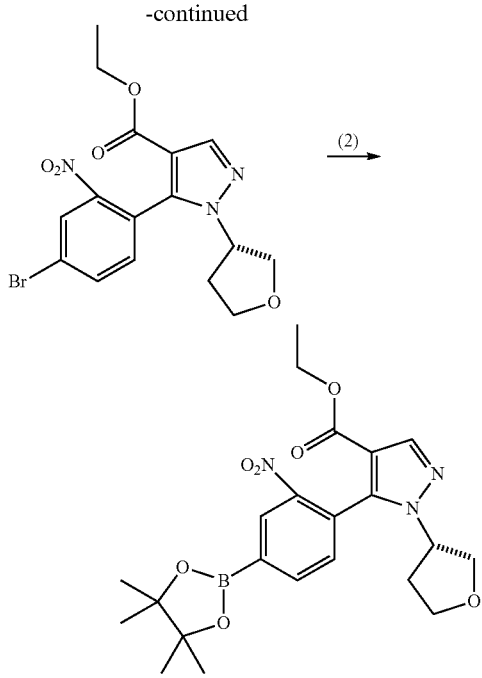

(1) Synthesis of ethyl 5-(4-bromo-2-nitrophenyl)-1-[(S)-tetrahydrofuran-3-yl]-1H-pyrazole-4-carboxylate 4-bromo-2-nitrobenzoic acid (10 g) was dissolved in acetonitrile (50 mL). Thionyl chloride (32 mL) was added to the solution, and the mixture was stirred for three hours with heating under reflux. The reaction mixture was cooled with ice water, and triethylamine (11.3 mL) was added dropwise. Ethyl 3-dimethylamineacrylate (6.4 mL) was further added dropwise. After stirring at room temperature for three hours, (S)-(tetrahydrofuran-3-yl)hydrazine hydrochloride (6.2 g) was dissolved in water (10 mL), and the aqueous solution was added dropwise to the reaction mixture. Thereafter, the mixture was stirred at room temperature for 60 hours. The reaction mixture was partitioned by adding water (50 mL) and ethyl acetate (200 mL). The organic layer was washed with a 2 N aqueous sodium hydroxide solution (100 mL) and brine (50 mL) and dried over anhydrous magnesium sulfate. The desiccant was removed by filtration, and the filtrate was concentrated under reduced pressure. Ethyl acetate (5 mL) was added to the resulting residue which was dissolved with heating under reflux. The solution was cooled with ice water. After one hour, the precipitated solid was collected by filtration to give the crude purified product (7.5 g). Further, the filtrate was concentrated under reduced pressure. MTBE (10 mL) was added to the resulting residue, and the precipitated solid was collected by filtration to give the title compound (1.5 g).

$^1$H-NMR (400 MHz, CDCl$_3$) δ (ppm): 1.13 (td, J=7.2 Hz, 1.6 Hz, 3H), 2.15-2.34 (m, 1H), 2.39-2.55 (m, 1H), 3.85-4.14 (m, 5H), 4.21 (q, J=7.7 Hz, 1H), 4.47-4.62 (m, 1H), 7.21 (d, J=8.2 Hz, 0.5H), 7.26 (d, J=8.2 Hz, 0.5H), 7.88 (t, J=2.2 Hz, 0.5H), 7.88 (I, J=2.2 Hz, 0.5H), 8.02 (s, 1H), 8.35 (d, J=2.2 Hz, 0.5H) 8.37 (d, J=2.2 Hz, 0.5H).

ESI-MS m/z 410 [M+H]$^+$ (2) Synthesis of ethyl 5-[2-nitro-4-(4,4,5,5-tetramethyl-1,3,2-dioxaborolan-2-yl)phenyl]-1-[(S)-tetrahydrofuran-3-yl]-1H-pyrazole-4-carboxylate A mixture of ethyl 5-(4-bromo-2-nitrophenyl)-1-[(S)-tetrahydrofuran-3-yl]-1H-pyrazole-4-carboxylate (650 mg), bis(pinacolato)diboron (483 mg), Pd(dppf)Cl$_2$-DCM complex (64.7 mg) and potassium acetate (467 mg) was dried under reduced pressure using a vacuum pump for one hour. DMF (6.5 mL) was added to the dried residue, and the mixture was stirred at 80° C. for four hours. The reaction mixture was returned to room temperature and then filtered through Celite™. The filtrate was concentrated under reduced pressure. Water was added to the residue, followed by extraction with ethyl acetate. The organic layer was dried over anhydrous magnesium sulfate, filtered and concentrated under reduced pressure. The residue was purified by silica gel column chromatography (ethyl acetate/n-heptane, 50% to 100%) to give the title compound (417 mg).

$^1$H-NMR (400 MHz, CDCl$_3$) δ (ppm): 1.07-1.11 (m, 3H), 1.38 (s, 12H), 2.14-2.31 (m, 1H), 2.41-2.53 (m, 1H), 3.85-4.11 (m, 5H), 4.12-4.24 (m, 1H), 4.49-4.57 (m, 1H), 7.29-7.40 (m, 1H), 8.02-8.03 (m, 1H), 8.13-8.16 (m, 1H), 8.58-8.60 (m, 1H).

Preparation Example 8

Synthesis of (±)-ethyl 5-(4-bromo-2-nitrophenyl)-1-(oxepan-4-yl)-1H-pyrazole-4-caroylate

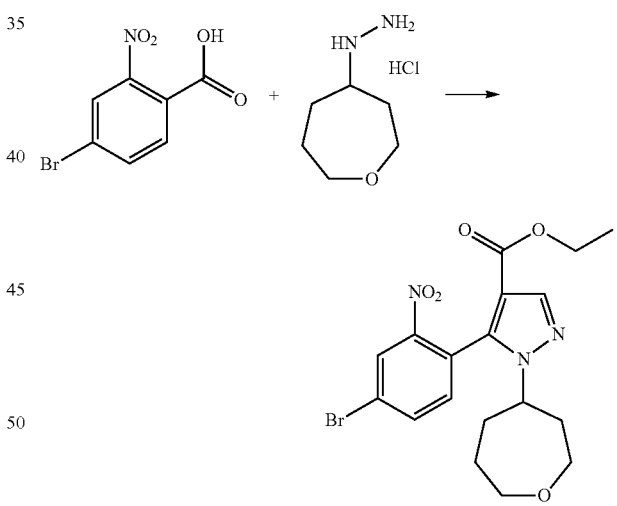

The title compound (369 mg) was obtained by the same method as in Preparation Example 7 from 4-bromo-2-nitrobenzoic acid (2.5 g) and (±)-oxepan-4-ylhydrazine hydrochloride obtained in Preparation Example 15 (1.69 g).

$^1$H-NMR (400 MHz, CDCl$_3$) δ (ppm): 1.13 (t, J=7.2 Hz, 3H), 1.48-1.65 (m, 1H), 1.76-1.91 (m, 1H), 1.95-2.21 (m, 2H), 227-2.51 (m, 2H), 3.54-3.73 (m, 2H), 3.78-3.88 (m, 2H), 4.02-4.13 (m, 3H), 7.20 (d, J=8.0 Hz, 0.5H), 7.21 (d, J=8.0 Hz, 0.5H), 7.87 (dd, J=8.0, 2.0 Hz, 0.5H), 7, 88 (dd, J=8.0, 2.0 Hz, 0.5H), 8.00 (s, 0.5H), 8.01 (s, 0.5H), 8.35 (d, J=2.0 Hz, 0.5H), 8.36 (d, J=2.0 Hz, 0.5H).

ESI-MS m/z 462 [M+Na]$^+$

Preparation Example 9

Synthesis of ethyl 1-(1,4-dioxepan-6-yl)-5-[2-nitro-4-(4,4,5,5-tetramethyl-1,3,2-dioxaborolan-2-yl)phenyl]-1H-pyrazole-4-carboxylate

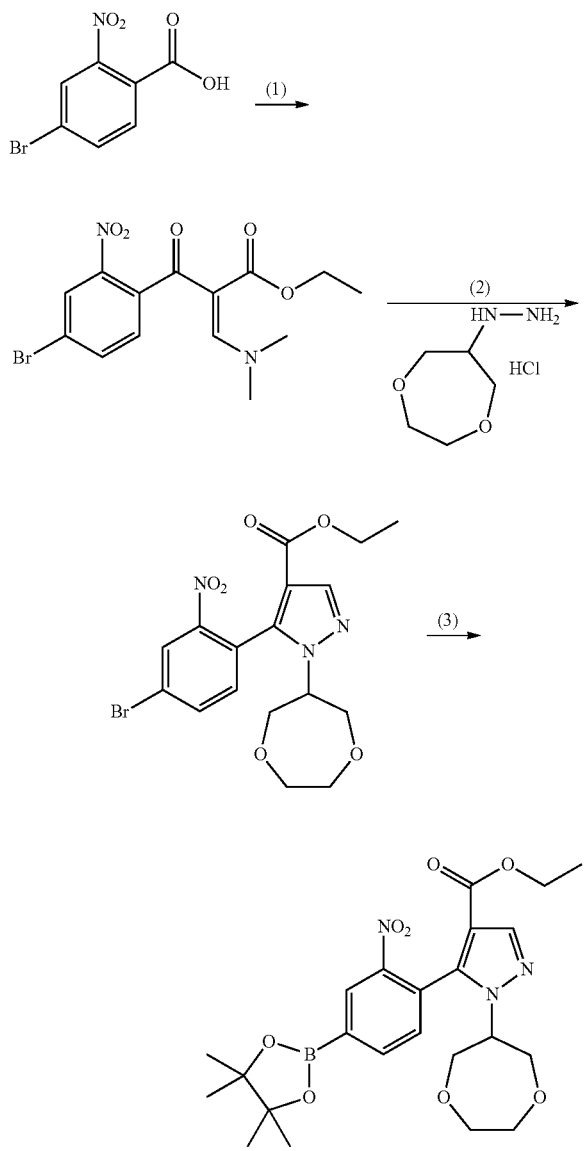

(1) Synthesis of (Z)-ethyl 2-(4-bromo-2-nitrobenzoyl)-3-(dimethylamino)acrylate A solution of 4-bromo-2-nitrobenzoic acid (2.5 g) in thionyl chloride (2.93 mL) was stirred at 80° C. for 3 hours. The reaction mixture was concentrated under reduced pressure. Toluene (3 mL) was added to the residue and the mixture was concentrated again under reduced pressure. A solution of the resulting acid chloride in acetonitrile (8 mL) was added dropwise to a solution of ethyl 3-dimethylaminoacrylate (1.46 g) and TEA (2.83 mL) in acetonitrile (30 mL) at room temperature over 6 minutes. The resulting reaction mixture was stirred at room temperature overnight. The reaction mixture was partitioned by adding ethyl acetate and water. The aqueous layer was extracted again with ethyl acetate. The combined organic layers were washed with brine, dried over anhydrous magnesium sulfate, filtered and concentrated under reduced pressure. The residue was purified by silica gel column chromatography (ethyl acetate/heptane, 33 to 66%) to give the title compound (2.55 g).

$^{1}$H-NMR (400 MHz, CDCl$_{3}$) δ (ppm): 0.91 (t, J=7.2 Hz, 3H), 3.11 (s, 3H), 3.39 (s, 3H), 3.89 (q, J=7.2 Hz, 2H), 7.25 (d, J=8.0 Hz, 1H), 7.74 (d, J=8.0, 1.6 Hz, 1H), 8.00 (s, 1H), 8.19 (d, J=1.6 Hz, 1H).

ESI-MS m/z 393 [M+Na]$^{+}$

(2) Synthesis of ethyl 5-(4-bromo-2-nitrophenyl)-1-(1,4-dioxepan-6-yl)-1H-pyrazole-4-carboxylate To a solution of (Z)-ethyl 2-(4-bromo-2-nitrobenzoyl)-3-(dimethylamino)acrylate (642 mg) in acetonitrile (8 mL) was added a solution of (1,4-dioxepan-6-yl)hydrazine hydrochloride (341 mg) obtained in Preparation Example 16 in water (2 mL) at room temperature. The reaction mixture was stirred at room temperature overnight and further stirred at 50° C. for 9.5 hours. The reaction mixture was returned to room temperature and partitioned by adding ethyl acetate and water. The aqueous layer was extracted again with ethyl acetate. The combined organic layers were sequentially washed with the saturated aqueous sodium bicarbonate solution and brine, and dried over anhydrous magnesium sulfate, filtered and concentrated under reduced pressure. The resulting residue was purified by silica gel column chromatography (ethyl acetate/heptane, 20 to 33%) to give the title compound (408 mg).

$^{1}$H-NMR (400 MHz, CDCl$_{3}$) δ (ppm): 1.12 (t, J=72 Hz, 3H), 3.70-3.83 (m, 2H), 3.87-4.11 (m, 6H), 4.20-4.39 (m, 3H), 7.17 (d, J=8.0 Hz, 1H), 7.88 (dd, J=8.0, 2.0 Hz, 1H), 8.05 (s, 1H), 8.35 (d, J=2.0 Hz, 1H).

ESI-MS m/z 464 [M+Na]$^{+}$

(3) Synthesis of ethyl 1-(1,4-dioxepan-6-yl)-5-[2-nitro-4-(4,4,5,5-tetramethyl-1,3,2-dioxaborolan-2-yl)phenyl]-1H-pyrazole-4-carboxylate A mixture of ethyl 5-(4-bromo-2-nitrophenyl)-1-(1,4-dioxepan-6-yl)-1H-pyrazole-4-carboxyrate (200 mg), bis(pinacolato)diboron (138 mg), Pd(dppf)Cl$_{2}$-DCM complex (19 mg) and potassium acetate (134 mg) was dried under reduced pressure using a vacuum pump for 50 minutes. A solution of the resulting residue in DMF (3 mL) was stirred at 80° C. for 2 hours and 20 minutes. After Pd(dppf)Cl$_{2}$-DCM complex (19 mg) was added to the reaction mixture, the reaction mixture was stirred at 80° C. for 3 hours. The reaction mixture was concentrated under reduced pressure. Brine and ethyl acetate were added to the resulting residue, and the mixture was stirred at room temperature for 5 minutes. The organic layer was separated. The aqueous layer was extracted again with ethyl acetate. The combined organic layers were dried over anhydrous magnesium sulfate, filtered and concentrated under reduced pressure. The resulting residue was purified by silica gel column chromatography (ethyl acetate/heptane, 33 to 50%) to give the title compound (183 mg).

$^{1}$H-NMR (400 MHz, CDCl$_{3}$) δ (ppm): 1.08 (t, J=6.8 Hz, 3H), 1.38 (s, 12H), 3.69-3.81 (m, 2H), 3.85-4.10 (m, 6H), 4.22-4.38 (m, 3H), 7.28 (d, J=7.6 Hz, 1H), 8.05 (s, 1H), 8.13 (dd, J=7.6, 1.2 Hz, 1H), 8.57 (d, J=1.2 Hz, 1H).

Preparation Example 10

Synthesis of ethyl 5-(4-bromo-2,5-difluorophenyl)-1-(tetrahydro-2H-pyran-4-yl)-1H-pyrazole-4-carboxylate

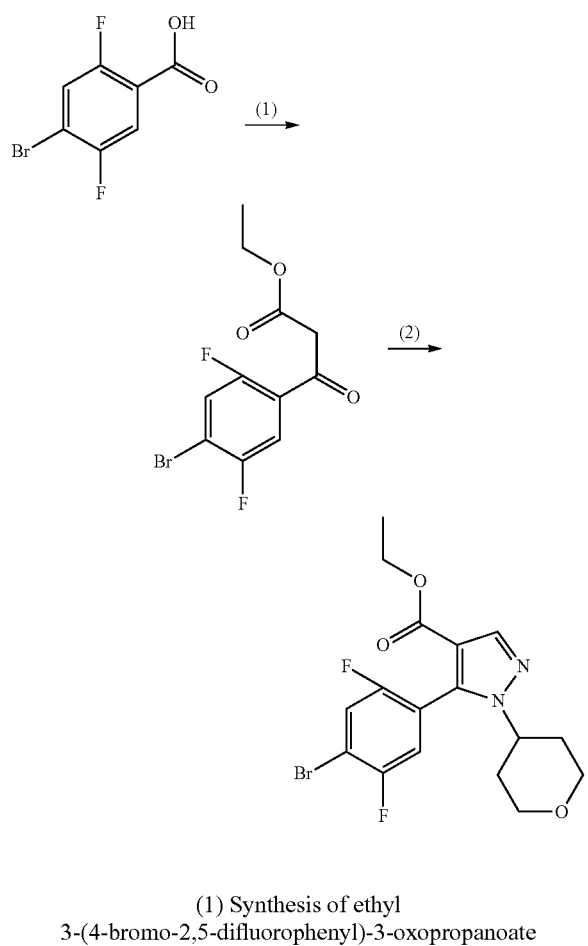

(1) Synthesis of ethyl 3-(4-bromo-2,5-difluorophenyl)-3-oxopropanoate 4-bromo-2,5-difluorobenzoic acid (395 mg) was suspended in DCM (3.6 mL). CDI (378 mg) was added to the solution, and the mixture was stirred at room temperature for about three hours. This solution is called "solution 1." In another flask, potassium ethylmalonate (567 mg) was suspended in acetonitrile (11 mL) in a nitrogen atmosphere, TEA (0.58 mL) and magnesium chloride (397 mg) were sequentially added, and the mixture was then stirred at room temperature for about three hours. The "solution 1" prepared above was added dropwise to the reaction mixture. After completion of the dropwise addition, the mixture was stirred at room temperature for about 20 hours. Ethyl acetate (50 mL) was added to the reaction mixture which was cooled to 0° C. 5 N hydrochloric acid (25 mL) was added and the mixture was stirred at room temperature for one hour. The organic layer was separated. The organic layer was washed with brine and dried over anhydrous magnesium sulfate. The desiccant was removed by filtration, and the filtrate was concentrated under reduced pressure. The resulting residue was subjected to silica gel column chromatography (ethyl acetate/n-heptane, 0% to 7%) to give the title compound (420 mg).
ESI-MS m/z 329, 331 [M+Na]$^+$

(2) Synthesis of ethyl 5-(4-bromo-2,5-d fluorophenyl)-1-(tetrahydro-2H-pyran-4-yl)-1H-pyrazole-4-carboxylate Ethyl 3-(4-bromo-2,5-difluorophenyl)-3-oxopropanoate (420 mg) was dissolved in DMF-DMA (2 mL). The reaction mixture was stirred at room temperature for about 1.5 hours and further stirred at 45° C. for 30 minutes. The reaction mixture was concentrated under reduced pressure. Ethanol (6 mL) and (tetrahydro-2H-pyran-4-yl)hydrazine hydrochloride (250 mg) were added to the resulting residue, and the mixture was stirred at 90° C. for 40 minutes. The reaction mixture was concentrated under reduced pressure. The resulting residue was partitioned by adding ethyl acetate and brine. The organic layer was washed with brine and dried over anhydrous magnesium sulfate. The desiccant was removed by filtration, and the filtrate was concentrated under reduced pressure. The residue was subjected to silica gel column chromatography (ethyl acetate/n-heptane, 14% to 35% to 52%) to give the title compound (400 mg).
$^1$H-NMR (400 MHz, CDCl$_3$) δ (ppm): 1.21 (t, J=7.1 Hz, 3H), 1.63-1.73 (m, 1H), 1.78-1.87 (m, 1H), 2.27-2.44 (m, 2H), 3.33-3.43 (m, 2H), 3.92-4.22 (m, 5H), 7.09-7.14 (m, 1H), 7.44-7.50 (m, 1H), 8.05 (s, 1H).

Preparation Example 11-1

Synthesis of ethyl 5-(4-bromo-2,5-difluorophenyl)-1-[(S)-tetrahydrofuran-3-yl]-1H-pyrazole-4-carboxylate

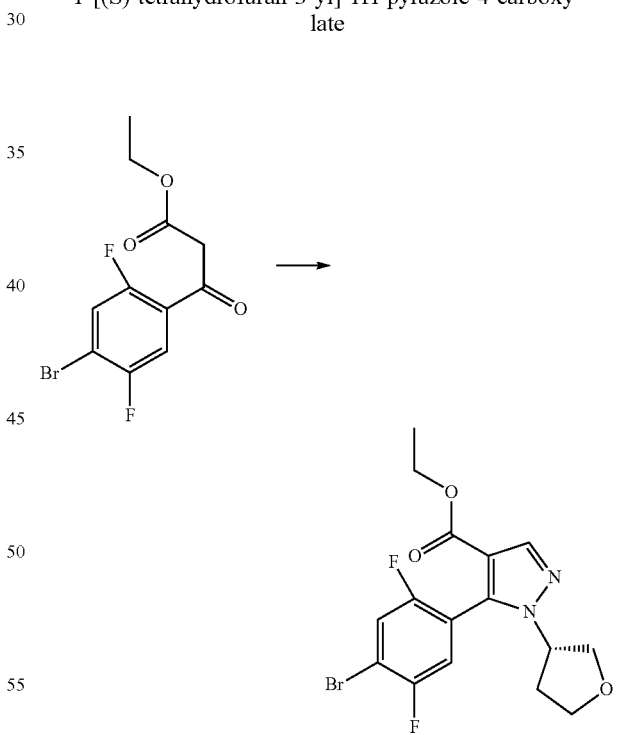

Ethyl 3-(4-bromo-2,5-difluorophenyl)-3-oxopropanoate obtained in Preparation Example 10(1) (4 g) was dissolved in DMF-DMA (18 mL), and the reaction mixture was stirred at room temperature overnight. The reaction mixture was concentrated under reduced pressure, and ethanol (80 mL) was added to the resulting residue (5.9 g), followed by warming to 60° C. A solution of (S)-(tetrahydrofuran-3-yl)hydrazine hydrochloride (2.17 g) in water (4.5 mL) was added to the solution over two minutes, and the mixture was stirred at 60°

C. for two hours. The reaction mixture was cooled to mom temperature and then concentrated under reduced pressure. The resulting residue was partitioned by adding ethyl acetate and brine. The organic layer was washed with brine and dried over anhydrous magnesium sulfate. The desiccant was removed by filtration, and the filtrate was concentrated under reduced pressure. The residue was subjected to NH silica gel column chromatography (first time: ethyl acetate/n-heptane, 10% to 30%, second time: ethyl acetate/n-heptane, 40%) to give the title compound (4.31 g). ESI-MS m/z 423 [M+Na]+

Preparation Example 11-2

Synthesis of ethyl 5-(4-bromo-2,5-difluorophenyl)-1-((R)-tetrahydrofuran-3-yl)-1H-pyrazole-4-carboxylate

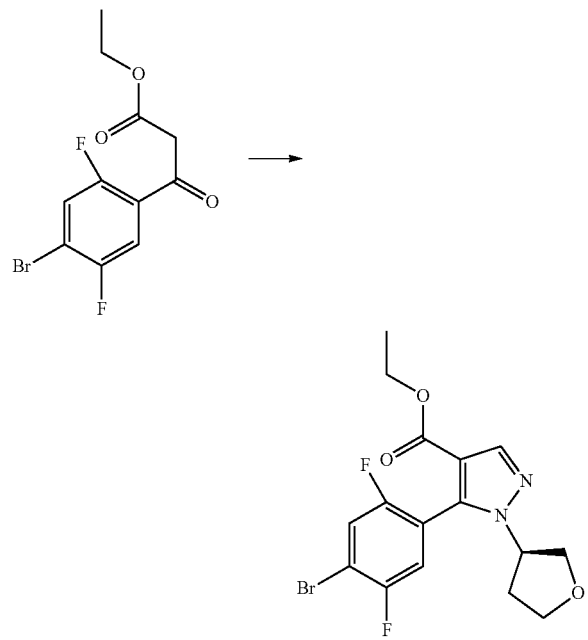

The title compound was synthesized in accordance with Preparation Example 11-1 from (R)-(tetrahydrofuran-3-yl)hydrazine hydrochloride.

ESI-MS m/z 423 [M+Na]+

Preparation Example 12

Synthesis of (±)-(tetrahydrofuran-3-yl)hydrazine hydrochloride (Method A)

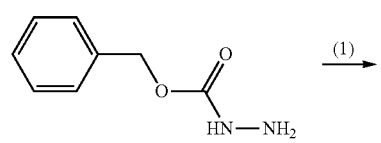

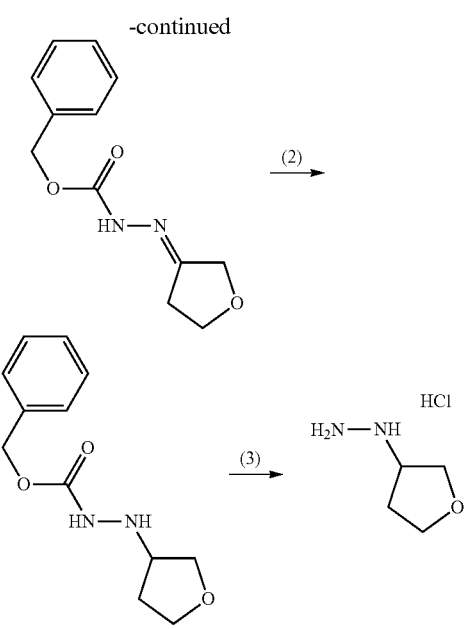

(1) Synthesis of benzyl 2-[dihydrofuran-3(2H)-ylidene]hydrazinecarboxylate 3-oxotetrahydrofuran (5.70 g) was dissolved in methanol (150 mL), and benzyl carbazate (10 g) was added to the solution. The mixture was stirred at room temperature for 12 hours. The reaction mixture was concentrated. 14.8 g of a residue was obtained as a crude purified product. This was used for the next reaction without further purification.

(2) Synthesis of (±)-benzyl 2-(tetrahydrofuran-3-yl)hydrazinecarboxylate

Benzyl 2-[dihydrofuran-3(2H)-ylidene]hydrazinecarboxylate (14.8 g) was suspended in water (96 mL). Acetic acid (42.1 mL) was added to the suspension at room temperature. The mixture was stirred at room temperature for one hour. The suspension turned into a solution. Sodium cyanoborohydride (4.0 g) was added to the solution in small portions. The mixed solution was stirred at room temperature for two hours. The reaction mixture was cooled to 0° C. The reaction mixture was neutralized by adding a 5 N aqueous sodium hydroxide solution. The mixture was extracted with chloroform. The organic layer was dried over anhydrous magnesium sulfate and then filtered. The filtrate was concentrated under reduced pressure. The residue was purified by silica gel column chromatography (methanol/ethyl acetate, 5%). The title compound (13.9 g) was obtained.

1H-NMR (400 MHz, CDCl3) δ (ppm): 1.73-1.80 (m, 1H), 1.92-2.06 (m, 1H), 3.66-3.82 (m, 3H), 3.82-4.03 (m, 2H), 5.14 (s, 2H), 7.31-7.40 (m, 5H).

It was found that the title compound can be optically resolved using chiral HPLC under the following condition. Optical resolution condition [CHIRALPAC® OD-H manufactured by Daicel Corporation, 10% ethanol/n-hexane, Retention Time=12.39 min, 13.5 min]

(3) Synthesis of (±)-(tetrahydrofuran-3-yl)hydrazine hydrochloride

Benzyl 2-(tetrahydrofuran-3-yl)hydrazinecarboxylate (32.3 mg) was dissolved in methanol (3 mL). 10% palladium carbon (50% wet) (17 mg) was added to the solution, and the mixture was stirred at room temperature for two hours in a hydrogen atmosphere. The reaction mixture was filtered. The filtrate was concentrated under reduced pressure. The residue was dissolved in methanol (1 mL). A 4 N hydrogen chloride-1,4-dioxane solution (3 mL) was added to the solution. The mixture was stirred at room temperature for three hours. The reaction mixture was concentrated under reduced pressure to give the title compound (4.9 mg).

$^1$H-NMR (400 MHz, CD$_3$OD) δ (ppm): 1.90-2.10 (m, 1H), 2.19-2.32 (m, 1H), 3.53-4.35 (m, 5H).

Preparation Example 13

Synthesis of (±)-(tetrahydrofuran-3-yl)hydrazine hydrochloride (Method B)

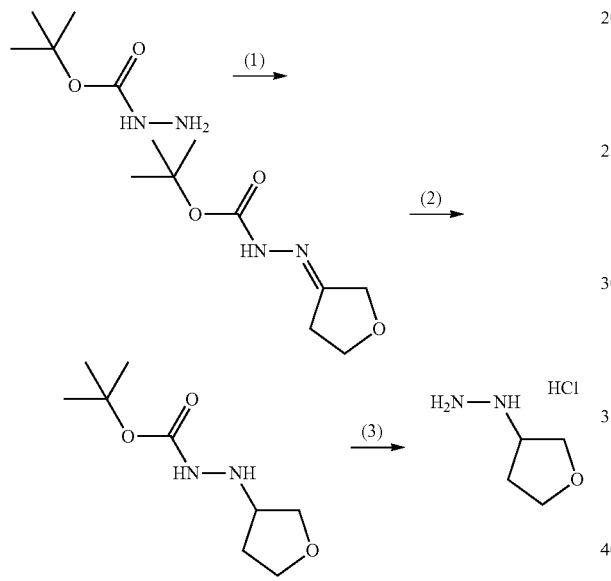

(1) Synthesis of t-butyl 2-[dihydrofuran-3(2H)-ylidene]hydrazinecarboxylate 3-oxotetrahydrofuran (10.38 g) was dissolved in methanol (200 mL), and t-butyl carbazate (17.53 g) was added to the solution. The mixture was stirred at room temperature for 12 hours. The reaction mixture was concentrated to give the title compound (27.3 g). $^1$H-NMR (400 MHz, CDCl$_3$) δ (ppm): 1.52 (s, 9H), 2.46 (t, J=6.9 Hz, al), 4.10 (t, J=6.9 Hz, 2H), 4.33 (s, 2H).

(2) Synthesis of (±)-t-butyl 2-(tetrahydrofuran-3-yl) hydrazinecarboxylate t-butyl 2-[dihydrofuran-3(2H)-ylidene]hydrazinecarboxylate (17.26 g) was suspended in water (130 mL). Acetic acid (57.2 mL) was added to the suspension at room temperature. The mixture was stirred at room temperature for one hour. Sodium cyanoborohydride (5.36 g) was added to the solution in small portions. The mixed solution was stirred at room temperature for two hours. The reaction mixture was cooled to 0° C. The reaction mixture was neutralized by adding a 5 N aqueous sodium hydroxide solution. The mixture was extracted with chloroform. The organic layer was dried over anhydrous magnesium sulfate and then filtered. The filtrate was concentrated under reduced pressure. The residue was purified by silica gel column chromatography (5% methanol/ ethyl acetate). The title compound (15.3 g) was obtained.

(3) Synthesis of (±)-(tetrahydrofuran-3-yl)hydrazine hydrochloride (±)-t-butyl 2-(tetrahydrofuran-3-yl)hydrazinecarboxylate (5 g) was dissolved in methanol (40 mL). A 4 N hydrogen chloride-1,4-dioxane solution (40 mL) was added to the solution. The mixture was stirred at room temperature overnight. The reaction mixture was concentrated under reduced pressure. The residue was triturated with ethyl acetate, water and methanol. The precipitated solid was collected by filtration to give the title compound (2.09 g).

$^1$H-NMR (400 MHz, CD$_3$OD) δ (ppm): 1.92-2.02 (m, 1H), 2.19-2.30 (m, 1H), 3.70-3.84 (m, 3H).

Preparation Example 14

Synthesis of (S)-(tetrahydrofuran-3-yl)hydrazine hydrochloride

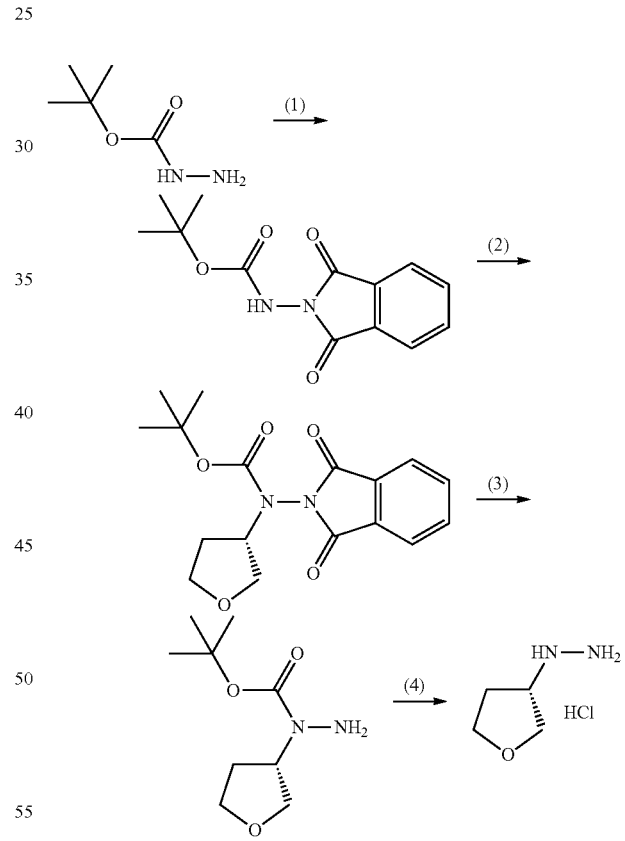

(1) Synthesis of t-butyl (1,3-dioxoisoindolin-2-yl)carbamate

A suspension of phthalic anhydride (30.0 g) and t-butyl carbazate (CAS No. 870-46-2) (26.8 g) in toluene (600 mL) was azeotropically refluxed using a Dean-Stark trap for 3.25 hours. The insoluble matter was removed by hot filtration. The filtrate was concentrated to about one-third volume under reduced pressure and then ice-cooled. The precipitated solid was collected by filtration. The resulting solid was dissolved in ethyl acetate (750 mL) and purified by short path NH silica gel column chromatography (100% ethyl acetate). The target fraction was concentrated, and the residue was then triturated with ethyl acetate (20 mL). The resulting solid was collected by filtration and dried under reduced pressure to give the title compound (16.4 g).

$^1$H-NMR (400 MHz, CDCl$_3$) δ (ppm): 1.52 (s, 9H), 6.55 (brs, 1H), 7.79 (dd, J=5.6, 3.2 Hz, 2H), 7.91 (dd, J=5.6, 3.2 Hz, 2H).

(2) Synthesis of (S)-t-butyl (1,3-dioxoisoindolin-2-yl)(tetrahydrofuran-3-yl)carbamate DEAD (11.5 mL) was added dropwise to a solution of (R)-(−)-3-hydroxytetrahydrofuran (CAS No. 86087-24-3) (4.84 g), t-butyl (1,3-dioxoisoindolin-2-yl)carbamate (12 g) and triphenylphosphine (18.0 g) in THF (160 mL) under ice-cooling over five minutes. The reaction mixture was stirred at 0° C. for three minutes and then at room temperature for seven hours and 40 minutes. The reaction mixture was concentrated under reduced pressure. The resulting residue was purified by silica gel column chromatography (ethyl acetate/n-heptane, 20%) to give the title compound (12.4 g).

$^1$H-NMR (400 MHz, CDCl$_3$) δ (ppm): 1.29 (s, 6H), 1.53 (s, 3H), 2.12-2.33 (m, 2H), 3.63-3.97 (m, 4H), 4.84-4.94 (m, 0.33H), 5.04-5.14 (m, 0.67H), 7.75-7.84 (m, 2H), 7.87-7.94 (m, 2H).

ESI-MS m/z 355 [M+Na]$^+$

Optical purity analysis >98% ee [IC, 10% ethanol/n-hexane, Retention Time=9.7 min]

(3) Synthesis of (S)-t-butyl 1-(tetrahydrofuran-3-yl)hydrazinecarboxylate

Methylhydrazine (3.94 mL) was added dropwise to a solution of (S)-t-butyl (1,3-dioxoisoindolin-2-yl)(tetrahydrofuran-3-yl)carbamate (12.3 g) in THF (125 mL) under ice-cooling over two minutes. The reaction mixture was stirred at 0° C. for 30 minutes, at room temperature for three days and then at 50° C. for four hours. The reaction mixture was ice-cooled, and the insoluble matter was then removed from the reaction mixture by filtration. The filtrate was concentrated under reduced pressure. The resulting residue was purified by silica gel column chromatography (ethyl acetate/n-heptane, 10% to 14%) to give the title compound (7.04 g).

$^1$H-NMR (400 MHz, CDCl$_3$) δ (ppm): 1.48 (s, 9H), 2.00-2.11 (m, 2H), 3.67-3.82 (m, 4H), 3.87 (dd, J=8.8, 72 Hz, 1H), 3.97 (dd, J=15.2, 7.2 Hz, 1H), 4.67-4.80 (m, 1H).

ESI-MS m/z 225 [M+Na]$^+$

(4) Synthesis of (S)-(tetrahydrofuran-3-yl)hydrazine hydrochloride (S)-t-butyl (tetrahydrofuran-3-yl)hydrazinecarboxylate (7.04 g) was dissolved in a 4 N hydrogen chloride-1,4-dioxane solution (60 mL). The resulting reaction mixture was stirred at room temperature for 25 minutes and then at 50° C. for two hours. The reaction mixture was concentrated under reduced pressure. The residue was triturated with MTBE and ethanol. The suspension was concentrated under reduced pressure to give the title compound (4.85 g).

$^1$H-NMR (400 MHz, CD$_3$OD) δ (ppm): 1.90-2.04 (m, 1H), 2.19-2.32 (m, 1H), 3.70-3.84 (m, 3H), 3.86-4.02 (m, 2H).

Preparation Example 15

Synthesis of (±)-oxepan-4-ylhydrazine hydrochloride

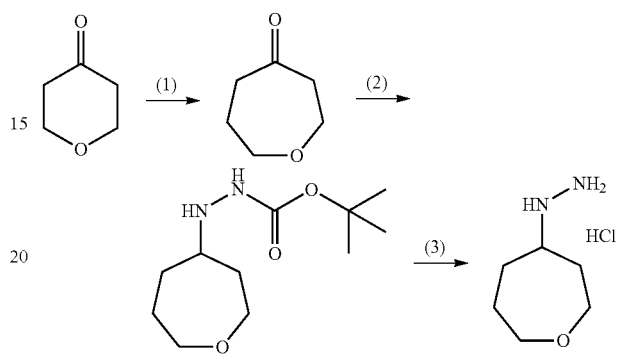

(1) Synthesis of oxepan-4-one

Boron trifluoride-diethyl ether complex (13.8 mL) was added to a solution of tetrahydro-4H-pyran-4-one (CAS No. 2994342-8) (10.0 g) in DCM (400 mL) at room temperature. The reaction mixture was cooled to −25° C. Trimethylsilyl diazomethane (2 M solution in n-hexane, 55 mL) was added dropwise to the reaction mixture over 40 minutes, and the mixture was then stirred at the same temperature for 2.5 hours. Water (40 mL) was added to the reaction mixture, followed by stirring at room temperature. The organic layer was separated. The organic layer was washed with a saturated aqueous ammonium chloride solution: 28% aqueous ammonia=10:1 (55 mL), dried over anhydrous magnesium sulfate, filtered and concentrated under reduced pressure. The resulting residue was purified by silica gel column chromatography (ethyl acetate/n-heptane, 10% to 14%) to give the title compound (3.80 g).

$^1$H-NMR (400 MHz, CDCl$_3$) δ (ppm): 1.82-1.89 (m, 2H), 2.65-2.72 (m, 4H), 3.85-3.94 (m, 4H).

(2) Synthesis of (±)-t-butyl 2-(oxepan-4-yl)hydrazinecarboxylate

The title compound (4.60 g) was obtained by the same method as in Preparation Examples 13-(1) and 13-(2) from oxepan-4-one (3.80 g) and t-butyl carbazate (3.61 g).

ESI-MS m/z 253 [M+H]$^+$

(3) Synthesis of (±)-oxepan-4-ylhydrazine hydrochloride

The title compound (3.72 g) was obtained by the same method as in Preparation Example 13-(3) from (±)-t-butyl 2-(oxepan-4-yl)hydrazinecarboxylate (4.60 g). $^1$H-NMR (400 MHz, DMSO-d$_6$) δ (ppm): 1.50-1.82 (m, 4H), 2.02-2.34 (m, 2H), 3.08-3.18 (m, 1H), 3.47-3.57 (m, 2H), 3.61-3.74 (m, 2H).

Preparation Example 16

Synthesis of (1,4-dioxepan-6-yl)hydrazine hydrochloride

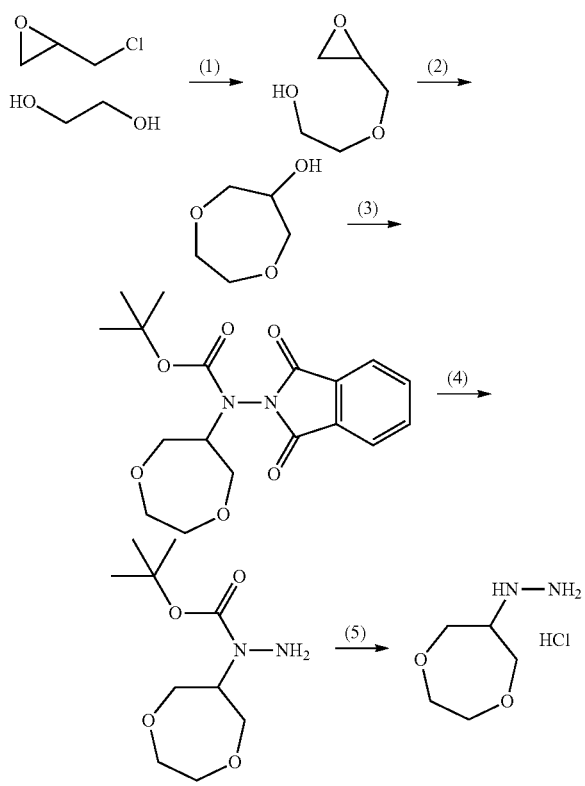

(1) Synthesis of 2-(oxiran-2-ylmethoxy)ethanol

Epichlorohydrin (31 g) was added dropwise to a mixture of ethylene glycol (20.8 g) and boron trifluoride-diethyl ether complex (0.255 mL) under ice-cooling over one hour. The reaction mixture was stirred at room temperature for one hour and 10 minutes and then at 80° C. for one hour. The reaction mixture was returned to room temperature. The reaction mixture was added dropwise to a solution of ice-cooled potassium hydroxide powder (20.7 g) in 1,4-dioxane (110 mL) over 45 minutes. The resulting reaction mixture was stirred at room temperature for 30 minutes. The insoluble matter in the reaction mixture was removed by filtration. The filtrate was concentrated under reduced pressure. The residue was purified by distillation to give a fraction having a boiling point of 58 to 62° C. at 0.3 mmHg. The product was purified by silica gel column chromatography (ethyl acetate/n-heptane, 50% to 75%) to give the title compound (3.11 g).

$^1$H-NMR (400 MHz, CDCl$_3$) δ (ppm): 2.10 (t, J=6.4 Hz, 1H), 2.65 (dd, J=4.8, 2.8 Hz, 1H), 2.82 (t, J=4.8 Hz, 1H), 3.16-3, 21 (m, 1H), 3.46 (dd, J=12.0, 6.0 Hz, 1H), 3.57-3.78 (m, 3H), 3.81-3.89 (m, 2H).

(2) Synthesis of 1,4-dioxepan-6-ol

A solution of 2-(oxiran-2-ylmethoxy)ethanol (3.11 g) in 1,4-dioxane (200 mL) was added dropwise over four hours and 20 minutes to a solution of lithium tetrafluoroborate (415 mg) and lithium hydroxide (69 mg) in 1,4-dioxane (200 mL) warmed at 55° C. The reaction mixture was stirred at 50° C. for 50 minutes and then at room temperature for 10 minutes. The insoluble matter in the reaction mixture was removed by filtration. The filtrate was concentrated under reduced pressure. The residue was purified by silica gel column chromatography (ethyl acetate/n-heptane, 40% to 50%). It was then purified again by silica gel column chromatography (diethyl ether/n-hexane 50% to 100%) to give the title compound (56 mg).

Further, the fraction containing impurities was purified again by silica gel column chromatography (diethyl ether, 100%) to give the title compound (212 mg). $^1$H-NMR (400 MHz, CDCl$_3$) δ (ppm): 2.57 (brd, J=8.8 Hz, 1H), 3.70-3.77 (m, 2H), 3.82-3.91 (m, 6H), 3.96 (brs, 1H).

(3) Synthesis of t-butyl 1,4-dioxepan-6-yl(1,3-dioxoisoindolin-2-yl)carbamate DEAD (2.2 M in toluen, 1.55 mL) was added dropwise to a solution of 1,4-dioxepan-6-ol (265 mg), t-butyl (1,3-dioxoisoindolin-2-yl)carbamate (560 mg) obtained in preparation example 14-(1) and triphenylphosphine (840 mg) in THF (10 mL) under ice-cooling over 3 minutes. The reaction mixture was stirred at 0° C. for 6 minutes, and further stirred at room temperature overnight The reaction mixture was concentrated under reduced pressure. After toluene (2.5 mL) was added to the resulting residue, the precipitated solid was removed by filtration. The filtrate was purified by silica gel column chromatography (ethyl acetate/n-heptane, 20%) to give the title compound (713 mg).

$^1$H-NMR (400 MHz, CDCl$_3$) δ (ppm): 1.28 (s, 5.4H), 1.50 (s, 3.6H), 3.60-3.72 (m, 4H), 4.02-4.11 (m, 2H), 4.13-4.21 (m, 2H), 4.64-4.71 (m, 0.4H), 4.83-4.92 (m, 0.6H), 7.77-7.83 (m, 2H), 7.89-7.96 (m, 2H).

ESI-MS m/z 385 [M+Na]$^+$

(4) Synthesis of t-butyl 1-(1,4-dioxepan-6-yl)hydrazinecarboxylate

Methylhydrazine (0.21 mL) was added dropwise to a solution of t-butyl 1,4-dioxepan-6-yl(1,3-dioxoisoindolin-2-yl)carbamate (710 mg) in THF (7 mL) over 1 minute. The reaction mixture was stirred at room temperature for 3 days and further stirred at 50° C. for 11 hours. After the reaction mixture was returned to room temperature, the insoluble matter was removed from the reaction mixture by filtration. The filtrate was concentrated under reduced pressure. After toluene was added to the residue, precipitated solid was removed by filtration, The filtrate was purified by silica gel column chromatography (ethyl acetate/n-heptane, 15% to 25%) to give the title compound (393 mg).

$^1$H-NMR (400 MHz, CDCl$_3$) δ (ppm): 1.47 (s, 9H), 3.67-3.88 (m, 6H), 3.94 (d, J=6.8 Hz, 4H), 4.40-4.60 (m, 1H).

ESI-MS m/z 255 [M+Na]$^+$

(5) Synthesis of (1,4-dioxepan-6-yl)hydrazine hydrochloride

A 4 M hydrogen chloride-1,4-dioxane solution (3 mL) was added to a solution of t-butyl 1-(1,4-dioxepan-6-yl)hydrazinecarboxylate (392 mg) in dioxane (3 mL). The reaction mixture was stirred at room temperature overnight and further stirred at 50° C. for 1 hour. The reaction mixture was concentrated under reduced pressure to give the title compound (341 mg).

$^1$H-NMR (400 MHz, DMSO-$d_6$) δ (ppm): 3.38 (quint, J=4.4 Hz, 1H), 3.62-3.74 (m, 4H), 3.80 (dd, J=12.8, 4.4 Hz, 2H), 3.86 (dd, J=12.8, 4.4 Hz, 2H).

Preparation Example 17

Synthesis of (±)-(tetrahydro-2H-pyran-3-yl)hydrazine hydrochloride

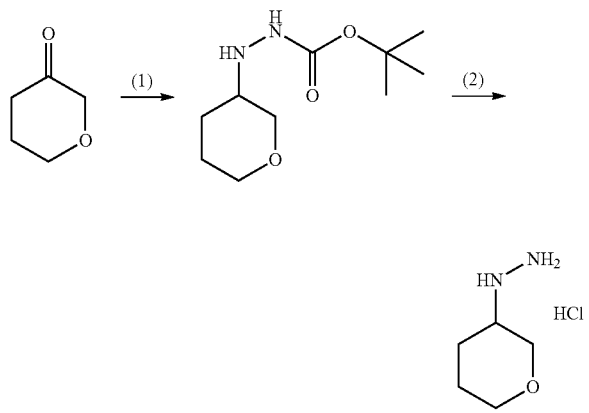

The title compound was obtained by performing the reactions (1) to (2) in accordance with Preparation Example 13 using dihydro-pyran-3-one as a raw material. $^1$H-NMR (400 MHz, CD$_3$OD) δ (ppm): 1.53-1.64 (m, 1H), 1.72-1.87 (m, 2H), 1.98-2.09 (m, 1H), 3.06-3.15 (m, 1H), 3.59-3.72 (m, 3H), 3.81-3.90 (m, 1H).

Preparation Example 18

Synthesis of (3SR,4RS)-4-hydrazinyltetrahydrofuran-3-ol hydrochloride

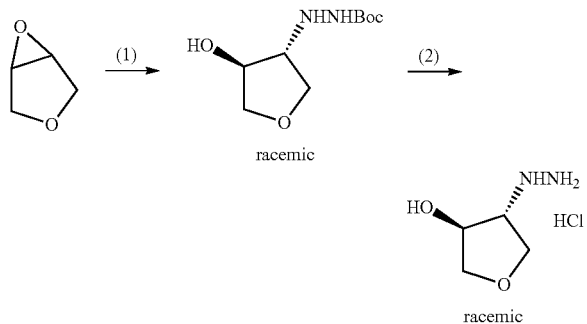

(1) Synthesis of t-butyl 2-[(3RS,4SR)-4-hydroxytetrahydrofuran-3-yl]hydrazinecarboxylate 3,4-epoxytetrahydrofuran (3.33 mL) and t-butyl carbazate (6.14 g) were dissolved in 2-propanol (15 mL), and the solution was heated to 90° C. After three days, t-butyl carbazate (6.3 g) was further added. After heating with stirring for further two days, the reaction mixture was cooled to room temperature and concentrated under reduced pressure. Xylene was added to the residue, and the mixture was concentrated again under reduced pressure. The residue was partitioned by adding chloroform and brine. The organic layer was dried over anhydrous magnesium sulfate. The desiccant was removed by filtration, and the filtrate was concentrated under reduced pressure. The residue was purified by NH silica gel column chromatography (ethyl acetate/n-heptane, 50% to 100%) to give the title compound (5.78 g).

ESI-MS m/z 241 [M+Na]$^+$ (2) Synthesis of (3SR,4RS)-4-hydrazinyltetrahydrofuran-3-ol hydrochloride A 4 M hydrogen chloride-1,4-dioxane solution (50 mL) was added to a solution of t-butyl 2-((3RS,4SR)-4-hydroxytetrahydrofuran-3-yl)hydrazinecarboxylate (5.78 g) in methanol (30 mL) under ice-cooling, and the mixture was then warmed to room temperature and stirred overnight. The reaction mixture was concentrated to give the title compound (5 g).

$^1$H-NMR (400 MHz, CD$_3$OD) δ (ppm): 3.49-3.54 (m, 1H), 3.57-3.63 (m, 1H), 3.65 (dd, J=9.67, 2.64 Hz, 1H), 3.70-3.76 (m, 1H), 3.96-4.08 (m, 2H), 4.28-4.32 (m, 1H).

Preparation Example 19

Synthesis of (2,4,6-trimethylpyridin-3-yl)boronic acid

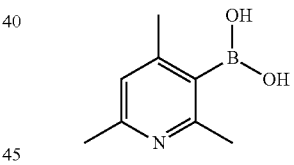

3-bromo-2,4,6-trimethylpyridine (CAS No. 23079-73-4; Prasenjit Mal etc., Journal of Organic Chemistry, 68(9), pp. 3446-3453) (1 g) was added to THF (20 mL). The solution was cooled to −78° C., and n-butyllithium (1.63 M solution in n-hexane, 3.37 mL) was added, followed by stirring at the same temperature for 30 minutes. Trimethyl borate (0.78 mL) was added to the reaction mixture, and the mixture was stirred at −78° C. for 10 minutes and at room temperature for 50 minutes. A saturated aqueous ammonium chloride solution was added to the reaction mixture, and the reaction mixture was concentrated under reduced pressure. The resulting residue was partitioned between oil and water by adding water and DCM. The aqueous layer was concentrated under reduced pressure. DCM and ethanol were added to the resulting residue. The insoluble matter was filtered, and the filtrate was concentrated under reduced pressure to give the title compound (242 mg). $^1$H-NMR (400 MHz, DMSO-$d_6$) δ (ppm): 2.50 (s, 3H), 2.63 (s, 3H), 2.67 (s, 3H), 7.52 (s, 1H).

Preparation Example 20

Synthesis of 2-bromo-5-(methoxymethyl)-1,3-dimethylbenzene

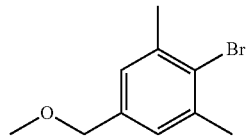

2-bromomesitylene (5.00 g) was dissolved in carbon tetrachloride (50 mL). NBS (4.45 g) and benzoyl peroxide (182 mg) were added to the solution, and the mixture was stirred at 80° C. for three hours. The reaction mixture was returned to room temperature and filtered. The solid collected by filtration was washed with n-heptane. The filtrate was concentrated under reduced pressure, and the residue was purified by silica gel column chromatography (n-heptane). The resulting fraction was concentrated under reduced pressure. The residue was dissolved in THF (120 mL). Sodium methoxide (28% solution in methanol, 9.35 mL) was added to the solution, and the mixture was stirred at 80° C. for four hours. The reaction mixture was returned to room temperature and concentrated under reduced pressure. Water was added to the residue, followed by extraction with DCM. The organic layer was concentrated under reduced pressure. The residue was purified by silica gel column chromatography (ethyl acetate/n-heptane, 0% to 5%). The resulting fraction was concentrated under reduced pressure, and the residue was purified again by NH silica gel column chromatography (n-heptane) to give the title compound (880 mg).

$^1$H-NMR (400 MHz, CDCl$_3$) δ (ppm): 2.41 (s, 6H), 3.38 (s, 3H), 4.35 (s, 2H), 7.05 (s, 2H).

Preparation Example 21

Synthesis of 3-bromo-6-chloro-2,4-dimethylpyridine

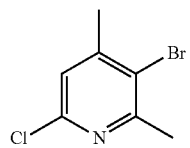

5-bromo-4,6-dimethylpyridin-2-amine (CAS No. 89856-44-0; Aldrich) (4.00 g) was added to a mixed solution of concentrated hydrochloric acid (24 mL) and water (24 mL). The solution was cooled to 0° C., and sodium nitrite (3.57 g) was added, followed by stirring at the same temperature for 10 minutes. Copper(I) chloride (5.91 g) was added to the solution, and the mixture was stirred at 0° C. for five minutes and at room temperature for four hours and 15 minutes. The reaction mixture was cooled to 0° C., and a 5 N aqueous sodium hydroxide solution was added to make the reaction mixture basic. Ethyl acetate was added to the reaction mixture, followed by filtration. The organic layer in the filtrate was separated, and the aqueous layer was extracted with ethyl acetate. The combined organic layers were concentrated under reduced pressure. The residue was purified by silica gel column chromatography (ethyl acetate/n-heptane, 5%) to give the title compound (1.79 g).

$^1$H-NMR (400 MHz, CDCl$_3$) δ (ppm): 2.39 (s, 3H), 2.65 (s, 3H), 7.06 (s, 1H).

Preparation Example 22

Synthesis of 3-bromo-6-methoxy-2,4-dimethylpyridine

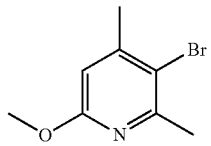

3-bromo-6-chloro-2,4-dimethylpyridine obtained in Preparation Example 21 (200 mg) was added to DMF (1 mL). Sodium methoxide (28% solution in methanol, 0.741 mL) was added to the solution, and the mixture was stirred at 60° C. for 15 hours. Water was added to the reaction mixture, followed by extraction with diethyl ether. The organic layer was concentrated under reduced pressure. The residue was purified by silica gel column chromatography (ethyl acetate/n-heptane, 0% to 10%) to give the title compound (172 mg).

$^1$H-NMR (400 MHz, CDCl$_3$) δ (ppm): 2.34 (s, 3H), 2.57 (s, 3H), 3.88 (s, 3H), 6.46 (s, 1H).

Preparation Example 23

Synthesis of 3-bromo-6-methoxy-2,4-dimethylpyridine

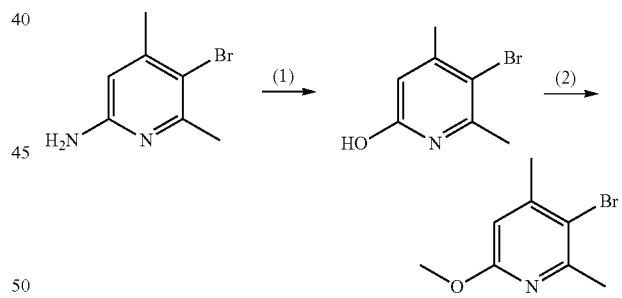

(1) Synthesis of 5-bromo-4,6-dimethylpyridin-2-ol 2-amino-5-bromo-4,6-dimethylpyridine (15 g) was dissolved in a mixed solution of sulfuric acid (14.2 mL) and water (212 mL). A solution of sodium nitrite (6.18 g) in water (31 mL) was added to the solution at 0° C. The reaction mixture was stirred at mom temperature for one hour, followed by extraction with chloroform. The organic layer was dried over anhydrous magnesium sulfate, and the desiccant was filtered off. The filtrate was concentrated under reduced pressure. MTBE was added to the residue to precipitate the solid, followed by filtration. The filtration residue was washed with MTBE to give the title compound (13.7 g).

ESI-MS m/z 204 [M+H]$^+$

(2) Synthesis of 3-bromo-6-methoxy-2,4-dimethylpyridine

A mixture of 5-bromo-4,6-dimethylpyridin-2-ol (7 g), methyl iodide (21.6 mL) and silver carbonate (19.1 g) was stirred in a chloroform solvent (140 mL) at room temperature for 36 hours. The reaction mixture was subjected to silica gel pad and eluted with a mixed solvent of (ethyl acetate:n-heptane=2:8). The resulting solution was concentrated under reduced pressure to give the title compound (6.98 g).

$^1$H-NMR (400 MHz, CDCl$_3$) δ (ppm): 2.32-2.35 (m, 3H), 2.56-2.58 (m, 3H), 3.88 (s, 3H), 6.43-6.48 (m, 1H).

ESI-MS m/z 216 [M+H]$^+$

Preparation Example 24

Synthesis of (6-methoxy-2,4-dimethylpyridin-3-yl)boronic acid

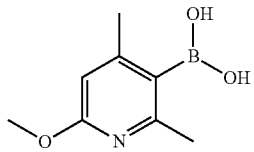

3-bromo-6-methoxy-2,4-dimethylpyridine (150 mg) was added to THF (3 mL). The solution was cooled to −78° C., and n-butyllithium (1.63 M solution in n-hexane, 0.468 mL) was added, followed by stirring at the same temperature for 30 minutes. Trimethyl borate (0.108 mL) was added to the reaction mixture, and the mixture was stirred at −78° C. for 10 minutes and at room temperature for 50 minutes. A saturated aqueous ammonium chloride solution was added to the reaction mixture, and the reaction mixture was concentrated under reduced pressure. THF was distilled off. The resulting residue was filtered. The solid collected by filtration was washed with water and n-heptane to give the title compound (41 mg).

$^1$H-NMR (400 MHz, CDCl$_3$) δ (ppm): 2.31 (s, 3H), 2.48 (s, 3H), 3.89 (s, 3H), 4.77 (brs, 2H), 6.35 (s, 1H).

Preparation Example 25

Synthesis of 3-chloro-2-methoxy-4,6-dimethylpyridine

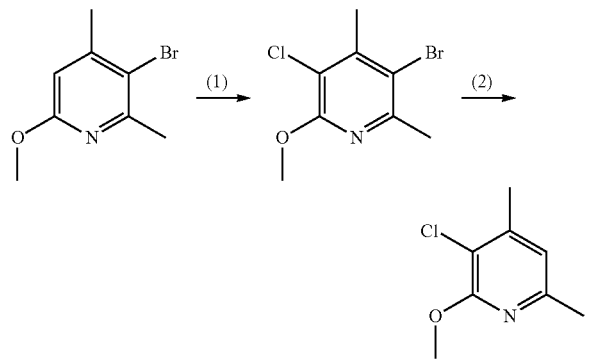

(1) Synthesis of 3-bromo-5-chloro-6-methoxy-2,4-dimethylpyridine 3-bromo-6-methoxy-2,4-dimethylpyridine obtained in Preparation Example 22 (800 mg) was added to DMF (4 mL). NCS (494 mg) was added to the solution, and the mixture was stirred at 80° C. for 14 hours. The reaction mixture was concentrated under reduced pressure. The resulting residue was purified by silica gel column chromatography (ethyl acetate/n-heptane, 5% to 30%). The title compound (930 mg) was obtained.

$^1$H-NMR (400 MHz, CDCl$_3$) δ (ppm): 2.51 (s, 3H), 2.56 (s, 3H), 3.98 (s, 3H).

(2) Synthesis of 3-chloro-2-methoxy-4,6-dimethylpyridine 3-bromo-5-chloro-6-methoxy-2,4-dimethylpyridine (930 mg) was added to THF (10 mL). The solution was cooled to −78° C., and n-butyllithium (2.6 M solution in n-hexane, 1.428 mL) was added, followed by stirring at the same temperature for one hour. A saturated aqueous ammonium chloride solution was added to the reaction mixture, followed by extraction with DCM. The organic layer was washed with brine and dried over sodium sulfate. The desiccant was removed by filtration, and the filtrate was concentrated under reduced pressure. The resulting residue was purified by silica gel column chromatography (ethyl acetate/n-heptane, 5% to 30%) to give the title compound (300 mg).

$^1$H-NMR (400 MHz, CDCl$_3$) δ (ppm): 2.31 (s, 3H), 2.38 (s, 3H), 3.99 (s, 3H), 6.62 (s, 1H).

Preparation Example 26

Synthesis of 3-bromo-2-methoxy-4,6-dimethylpyridine

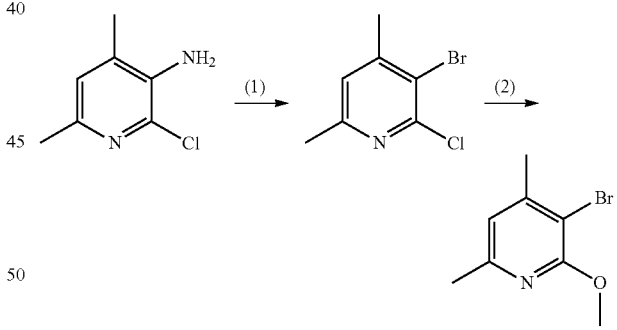

(1) Synthesis of 3-bromo-2-chloro-4,6-dimethylpyridine 2-chloro-4,6-dimethylpyridin-3-amine (2.85 g) was dissolved in hydrobromic acid (15 mL, 48% aqueous solution), and the solution was cooled to 0° C. A solution of sodium nitrite (1.51 g) in water (2 mL) was slowly added dropwise to the solution, and the mixture was stirred at 0° C. for 15 minutes. A suspension of copper(I) bromide (4.18 g) in hydrobromic acid (5 mL, 48% aqueous solution) was added dropwise to the solution, and the mixture was stirred at 0° C. for 10 minutes and then at 60° C. for one hour. The reaction mixture was cooled to room temperature, followed by extraction with ethyl acetate. The organic layer was directly subjected to an NH-silica gel pad and eluted with ethyl acetate. The resulting solution was concentrated under reduced pressure, and the residue was purified by NH silica gel column chromatography (ethyl acetate/n-heptane, 0% to 30%) to give the title compound (2.97 g).
ESI-MS m/z 220 [M+H]+

(2) Synthesis of
3-bromo-2-methoxy-4,6-dimethylpyridine

A mixture of 3-bromo-2-chloro-4,6-dimethylpyridine (2.97 g) and sodium methoxide (11.0 mL, 28% solution in methanol) was stirred in a DMF solvent (30 mL) at 80° C. for 36 hours. Water was added to the reaction mixture, followed by extraction with diethyl ether. The organic layer was concentrated under reduced pressure, and the residue was purified by silica gel column chromatography (ethyl acetate/n-heptane, 0% to 10%) to give the title compound (2.33 g).
$^1$H-NMR (400 MHz, CDCl$_3$) δ (ppm): 2.33-2.34 (m, 3H), 2.36-2.38 (m, 3H), 3.98 (s, 3H), 6.61-6.64 (m, 1H).
ESI-MS m/z 216 [M+H]+

Preparation Example 27

Synthesis of
(2-methoxy-4,6-dimethylpyridin-3-yl)boronic acid

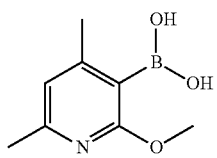

The title compound was synthesized in accordance with Preparation Example 24 using 3-bromo-2-methoxy-4,6-dimethylpyridine.
$^1$H-NMR (400 MHz, CDCl$_3$) δ (ppm): 2.37-2.42 (s, 3H), 2.47-2.52 (s, 3H), 3.99 (s, 3H), 5.91 (s, 2H), 6.60-6.67 (s, 1H).

Preparation Example 28

Synthesis of
4-bromo-2-methoxy-3,5-dimethylpyridine

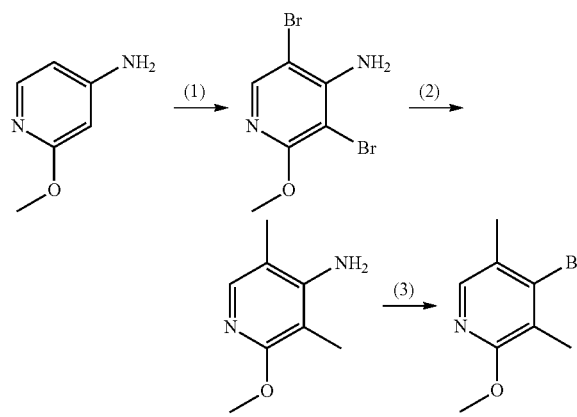

(1) Synthesis of
3,5-dibromo-2-methoxypyridin-4-amine

A mixture of 2-methoxy-pyridin-4-ylamine (15 g) and NBS (47.3 g) was stirred in an acetic acid solvent (150 mL) at room temperature for three hours. The reaction mixture was concentrated under reduced pressure, and a 5 M aqueous sodium hydroxide solution (200 mL) was added to the residue at 0° C., followed by extraction with diethyl ether. The organic layer was directly purified by a silica gel pad (ethyl acetate/n-heptane, 10%) to give the title compound (32.4 g).
ESI-MS m/z 283 [M+H]+

(2) Synthesis of
2-methoxy-3,5-dimethylpyridin-4-amine

A mixture of 3,5-dibromo-2-methoxypyridine-4-amine (16 g), trimethylboroxin (19.8 mL), Pd(dppf)Cl$_2$-DCM complex (4.15 g) and potassium carbonate (23.5 g) was heated under reflux in a mixed solvent of 1,4-dioxane (320 mL) and water (32 mL) for 12 hours. The reaction mixture was cooled to room temperature and then concentrated under reduced pressure. Water and ethyl acetate were added to the residue, followed by filtration through Celite™. The filtrate was extracted with ethyl acetate, and the organic layer was subjected to a silica gel pad (NH-silica gel) and eluted with ethyl acetate. NH-silica gel (30 g) was added to the resulting solution, and the mixture was concentrated under reduced pressure. The residue was purified by NH silica gel column chromatography (ethyl acetate/n-heptane, 0% to 30%) to give the title compound (4.43 g).
ESI-MS m/z 153 [M+H]+

(3) Synthesis of
4-bromo-2-methoxy-3,5-dimethylpyridine

A mixture of copper(I) bromide (12.1 g) and t-butyl nitrite (7.07 mL) was stirred in an acetonitrile solvent (80 mL) at 70° C. for 10 minutes. A solution of 2-methoxy-3,5-dimethylpyridin-4-amine (3.9 g) in acetonitrile (40 mL) was added dropwise to the reaction mixture at the same temperature, and the mixture was stirred at 70° C. for one hour. The reaction mixture was cooled to room temperature and then concentrated under reduced pressure. Ethyl acetate and a saturated aqueous sodium bicarbonate solution were added to the residue, and the mixture was stirred at room temperature for 30 minutes. The reaction mixture was filtered through Celite™, and the filtrate was extracted with ethyl acetate. The organic layer was concentrated under reduced pressure, and the residue was purified by NH silica gel column chromatography (n-heptane, 100%, then NH-silica gel pad, n-heptane, 100%) to give the title compound (4.3 g).
$^1$H-NMR (400 MHz, CDCl$_3$) δ (ppm): 2.28-2.29 (m, 3H), 2.29-2.31 (m, 3H), 3.93 (s, 3H), 7.77-7.84 (m, 1H).
ESI-MS m/z 216 [M+H]+

Preparation Example 29

Synthesis of (2-methoxy-3,5-dimethylpyridin-4-yl)boronic acid

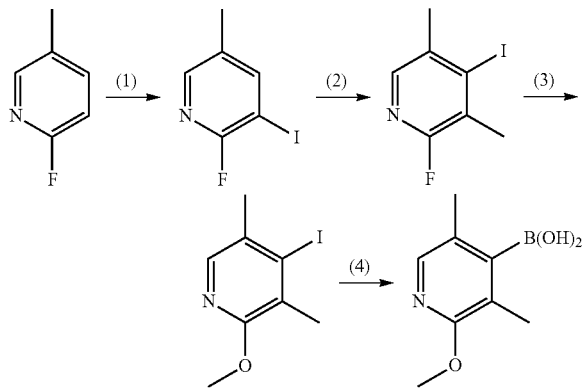

(1) Synthesis of 2-fluoro-3-iodo-5-methylpyridine

Diisopropylamine (92 mL) was added to THF (1.2 L), and the mixture was cooled to −18° C. in a nitrogen atmosphere. A 2.69 M solution of n-butyllithium in hexane (224 mL) was added dropwise to the solution. After completion of the dropwise addition, the mixture was warmed to −5° C. with stirring over 20 minutes. The reaction mixture was cooled to −73° C. A solution of 2-fluoro-5-methylpyridine (61 g) in THF (240 mL) was added dropwise to the reaction mixture. The reaction mixture was stirred at −75° C. for 3.5 hours. A solution of iodine (139 g) in THF (24 mL) was added dropwise to the reaction mixture. The reaction mixture was stirred at −75° C. for one hour and 55 minutes. After completion of the reaction, water (220 mL) was added to the reaction mixture at the same temperature. The mixture was stirred at the same temperature for five minutes. The reaction mixture was returned to room temperature, and water (1.2 L) was then added. A solution of sodium thiosulfate pentahydrate (136 g) in water (300 mL), and water (300 mL) were added to the mixture, followed by stirring for 10 minutes. The mixture was extracted with MTBE (1.2 L). The organic layer was washed with brine (500 mL). The combined aqueous layers were extracted with MTBE (1 L). The combined organic layers were dried over anhydrous magnesium sulfate. The desiccant was removed by filtration, and the filtrate was concentrated under reduced pressure. n-heptane was added to the residue, followed by cooling. The precipitated solid was collected by filtration. The residue was washed with n-heptane. The filtrate was cooled, and the precipitated solid was collected by filtration. This operation was repeated five times to give the title compound (109.69 g).

$^1$H-NMR (400 MHz, CDCl$_3$) δ (ppm): 2.29-2.31 (m, 3H), 7.93-8.14 (m, 214).

ESI-MS m/z 238 [M+H]$^+$

(2) Synthesis of 2-fluoro-4-iodo-3,5-dimethylpyridine

Diisopropylamine (88 mL) was added to THF (1.2 L), and the mixture was cooled to −18° C. in a nitrogen atmosphere. A 2.69 M solution of n-butyllithium in hexane (215 mL) was added dropwise to the solution. After completion of the dropwise addition, the mixture was warmed to −5° C. with stirring over 30 minutes. The reaction mixture was cooled to −72° C. A solution of 2-fluoro-3-iodo-5-methylpyridine (109.69 g) in TIE (240 mL) was added dropwise to the reaction mixture. The reaction mixture was stirred at −74° C. for 1.5 hours. A solution of methyl iodide (36 mL) in THF (160 mL) was added dropwise to the reaction mixture. The reaction mixture was stirred at −70° C. to −74° C. for two hours. After completion of the reaction, water (200 mL) was added to the reaction mixture at the same temperature. The mixture was stirred at the same temperature for two minutes. The reaction mixture was returned to room temperature, and water (1.2 L) was then added. The mixed solution was stirred for three minutes. Water (300 mL) was further added. The mixture was extracted with MTBE (1.2 L). The organic layer was washed with brine (500 mL). The combined aqueous layers were extracted with MTBE (1 L). The combined organic layers were dried over anhydrous magnesium sulfate. The desiccant was removed by filtration, and the filtrate was concentrated under reduced pressure. n-heptane (100 mL) was added to the residue, followed by cooling. The precipitated solid was collected by filtration. The residue was washed with n-heptane. The filtrate was cooled, and the precipitated solid was collected by filtration. This operation was repeated twice to give the title compound (86.9 g).

$^1$H-NMR (400 MHz, CDCl$_3$) δ (ppm): 2.39-2.40 (m, 6H), 7.80-7.82 (m, 1H).

ESI-MS m/z 252 [M+H]$^+$

(3) Synthesis of 4-iodo-2-methoxy-3,5-dimethylpyridine

A 28% solution of sodium methoxide in methanol (185 mL) was added to 2-fluoro-4-iodo-3,5-dimethylpyridine (97.4 g) in THF (954 mL) at 20° C. The mixture was stirred at 55° C. to 65° C. for two hours. The reaction mixture was cooled and then partitioned by adding MTBE (1 L) and water (1 L). The organic layer was washed with brine. The combined aqueous layers were extracted with MTBE (500 mL×2). The combined organic layers were dried over anhydrous magnesium sulfate. The desiccant was removed by filtration, and the filtrate was concentrated under reduced pressure. n-heptane (50 mL) was added to the residue, and the mixture was stirred at 0° C. for one hour. The precipitated solid was collected by filtration. The solid was washed with cooled n-heptane (10 mL). The title compound (42.6 g) was obtained. The filtrate was concentrated under reduced pressure. n-heptane (5 mL) was added to the residue, and the mixture was stirred at 0° C. for 30 minutes. The precipitated solid was collected by filtration. The solid was washed with cooled n-heptane (2 mL) The title compound (20.2 g) was obtained. The filtrate was concentrated under reduced pressure. n-heptane (5 mL) was added to the residue, and the mixture was stirred at 0° C. for 30 minutes. The precipitated solid was collected by filtration. The solid was washed with cooled n-heptane (2 mL). The title compound (10.7 g) was obtained. The combined title compound (73.5 g) was obtained.

$^1$H-NMR (400 MHz, CDCl$_3$) δ (ppm): 2.33-2.34 (m, 3H), 2.36-2.38 (m, 3H), 3.92 (s, 3H), 7.76 (s, 1H).

ESI-MS m/z 264 [M+H]$^+$

(4) Synthesis of (2-methoxy-3,5-dimethylpyridin-4-yl)boronic acid 4-iodo-2-methoxy-3,5-dimethylpyridine (2.0 g) in THF (40 mL) was cooled to −78° C. A 2.69 M solution of n-butyllithium in hexane (6.5 mL) was added dropwise to the solution over 10 minutes. The mixture was stirred at −78° C. for 20 minutes. Triisopropyl borate (5.26 mL) was added dropwise to the mixture over five minutes. The mixture was stirred with warming to 20° C. over 1.5 hours. Water was added to the reaction mixture, followed by extraction with ethyl acetate. The aqueous layer was neutralized with citric acid. The aqueous layer was extracted with ethyl acetate. The combined organic layers were dried over anhydrous magnesium sulfate. The desiccant was removed by filtration, and the filtrate was then concentrated under reduced pressure. The residue was triturated by adding MTBE. The precipitated solid was collected by filtration. This solid is called first crop. The filtrate was concentrated under reduced pressure. The residue was triturated by adding MTBE. The precipitated title compound (551 mg) was collected by filtration. The first crop were suspended in ethyl acetate. Trituration was performed by adding a small amount of MTBE. The precipitated title compound (553.3 mg) was collected by filtration. The filtrate was concentrated under reduced pressure. The residue was triturated by adding MTBE. The precipitated title compound (121:1 mg) was collected by filtration. The combined title compound (1.23 g) was obtained.

$^1$H-NMR. (400 MHz, CDCl$_3$) δ (ppm): 2.19-2.20 (m, 3H), 2.23-224 (m, 3H), 3.91 (s, 3H), 494 (brs, 2H), 7.74 (s, 1H).

ESI-MS m/z 182 [M+H]$^+$

Preparation Example 30

Synthesis of
3-bromo-6-(difluoromethyl)-2,4-dimethylpyridine

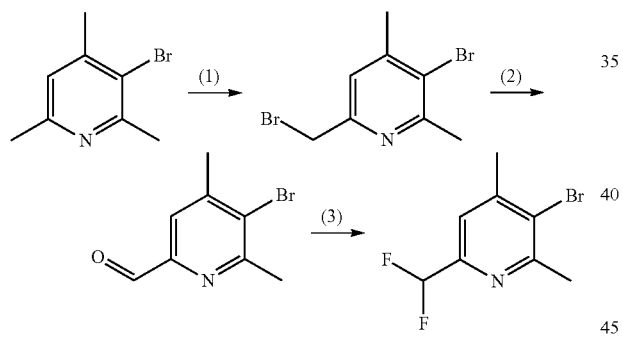

(1) Synthesis of
3-bromo-6-(bromomethyl)-2,4-dimethylpyridine

A mixture of 3-bromo-2,4,6-trimethylpyridine (15.6 g), NBS (13.9 g) and benzoyl peroxide (567 mg) was heated under reflux in a carbon tetrachloride solvent (300 mL) for two hours. The reaction mixture was cooled to room temperature and then filtered, and the filtration residue was washed with carbon tetrachloride. The resulting filtrate was concentrated under reduced pressure, and the residue was purified by silica gel column chromatography (ethyl acetate/n-heptane, 0% to 10%) to give the title compound (8.00 g).

$^1$H-NMR (400 MHz, CDCl$_3$) δ (ppm): 239-2.42 (m, 3H), 2.66-2.69 (m, 3H), 4.44 (s, 2H), 7.15 (s, 1H).

(2) Synthesis of
5-bromo-4,6-dimethylpicolinaldehyde

Sodium methoxide (1.16 g) was added to a solution of 2-nitropropane (1.96 mL) in methanol (40 mL) at mom temperature, and the mixture was stirred at the same temperature for 20 minutes. 3-bromo-6-(bromomethyl)-2,4-dimethylpyridine (2.00 g) was added to the reaction mixture, and the mixture was stirred at 50° C. for five hours. The reaction mixture was concentrated under reduced pressure, and water was added to the residue, followed by extraction with ethyl acetate. The organic layer was concentrated under reduced pressure, and the residue was purified by silica gel column chromatography (ethyl acetate/n-heptane, 0% to 50%) to give the title compound (565 mg).

$^1$H-NMR (400 MHz, CDCl$_3$) δ (ppm): 2.42-2.55 (m, 3H), 2.72-2.85 (m, 3H), 7.60-7.70 (m, 1H), 10.00 (s, 1H).

(3) Synthesis of
3-bromo-6-(difluoromethyl)-2,4-dimethylpyridine

BAST (1.07 mL) was added to a solution of 5-bromo-4,6-dimethylpicolinealdehyde (565 mg) in DCM (10 mL) at 0° C., and the mixture was stirred while gradually warming to room temperature for 12 hours. A saturated aqueous sodium bicarbonate solution was added to the reaction mixture, followed by extraction with DCM. The organic layer was concentrated under reduced pressure, and the residue was purified by silica gel column chromatography (ethyl acetate/n-heptane, 0% to 50%) to give the title compound (415 mg).

$^1$H-NMR (400 MHz, CDCl$_3$) δ (ppm): 2.47 (s, 3H), 2.71 (s, 3H), 6.39-6.70 (m, 1H), 7.33 (s, 1H).

Preparation Example 31

Synthesis of 3-bromo-(6-fluoromethyl)-2-methoxy-4-methylpyridine

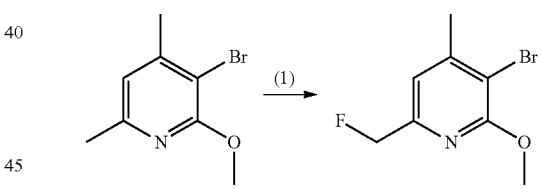

(1) Synthesis of 3-bromo-(6-fluoromethyl)-2-methoxy-4-methylpyridine

A mixture of 3-bromo-2-methoxy-4,6-dimethylpyridine obtained in Preparation Example 26(2) (300 mg), NBS (247 mg) and benzoyl peroxide (10.1 mg) was heated under reflux in a carbon tetrachloride solvent (6 mL) for two hours. The reaction mixture was cooled to room temperature and then filtered. The resulting filtrate was concentrated under reduced pressure. The residue was dissolved in TBAF (5.55 mL, 1 M solution in THF), and the mixture was stirred at room temperature for two hours. The reaction mixture was concentrated under reduced pressure, and the residue was purified by silica gel column chromatography (ethyl acetate/n-heptane, 0% to 5%) and subsequently by NH silica gel column chromatography (ethyl acetate/n-heptane, 0% to 5%) to give the title compound (136 mg).

ESI-MS m/z 234 [M+H]$^+$

Preparation Example 32

Synthesis of 3-bromo-6-(fluoromethyl)-2,4-dimethylpyridine

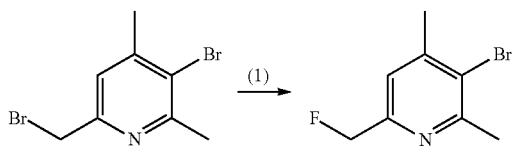

(1) Synthesis of 3-bromo-6-(fluoromethyl)-2,4-dimethylpyridine

A mixture of 3-bromo-6-(bromomethyl)-2,4-dimethylpyridine obtained in Preparation Example 30(1) (2.00 g) and TBAF (35.8 mL, 1 M solution in THF) was stirred at room temperature for two hours. The reaction mixture was concentrated under reduced pressure, and the residue was purified by silica gel column chromatography (ethyl acetate/n-heptane, 0% to 50%) to give the title compound (572 mg). $^{1}$H-NMR (400 MHz, CDCl$_3$) δ (ppm): 2.44 (s, 3H), 2.67 (s, 3H), 5.28-5.47 (m, 2H), 7.14-7.19 (m, 1H).

Preparation Example 33

Synthesis of 3-bromo-2-(fluoromethyl)-4,6-dimethylpyridine

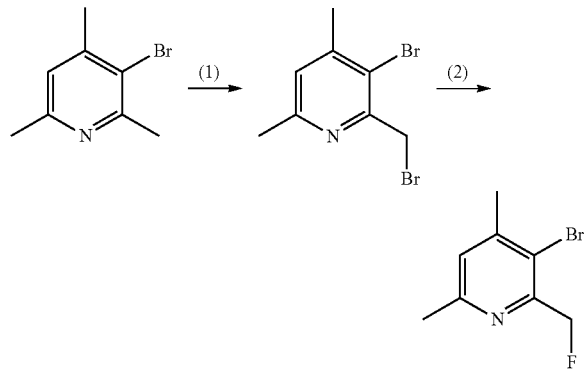

(1) Synthesis of 3-bromo-2-(bromomethyl)-4,6-dimethylpyridine

A mixture of 3-bromo-2,4,6-trimethylpyridine (15.6 g), NBS (13.9 g) and benzoyl peroxide (567 mg) was heated under reflux in a carbon tetrachloride solvent (300 mL) for two hours. The reaction mixture was cooled to room temperature and then filtered, and the filtration residue was washed with carbon tetrachloride. The resulting filtrate was concentrated under reduced pressure, and the residue was purified by silica gel column chromatography (ethyl acetate/n-heptane, 0% to 10%) to give the title compound (3.51 g).

$^{1}$H-NMR (400 MHz, CDCl$_3$) δ (ppm): 2.37-2.41 (m, 3H), 2.47 (s, 3H), 4.72 (s, 2H), 6.97 (s, 1H).

(2) Synthesis of 3-bromo-2-(fluoromethyl)-4,6-dimethylpyridine

A mixture of 3-bromo-2-(bromomethyl)-4,6-dimethylpyridine (1.00 g) and TBAF (17.9 mL, 1 M solution in THF) was stirred at room temperature for two hours. The reaction mixture was concentrated under reduced pressure, and the residue was purified by silica gel column chromatography (ethyl acetate/n-heptane, 0% to 30%) to give the title compound (651 mg).

$^{1}$H-NMR (400 MHz, CDCl$_3$) δ (ppm): 2.40 (s, 3H), 2.51 (s, 3H), 5.49-5.67 (m, 2H), 7.05 (s, 1H).

Preparation Example 34

Synthesis of 3-bromo-2-(difluoromethyl)-4,6-dimethylpyridine

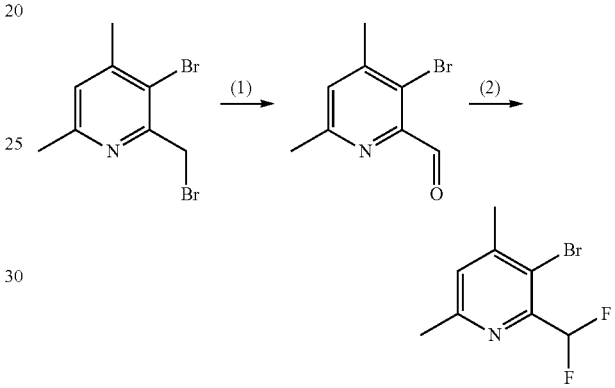

(1) Synthesis of 3-bromo-4,6-dimethylpicolinaldehyde

Sodium methoxide (581 mg) was added to a solution of 2-nitropropane (0.982 mL) in methanol (20 mL) at room temperature, and the mixture was stirred at the same temperature for 20 minutes. 3-bromo-2-(bromomethyl)-4,6-dimethylpyridine obtained in Preparation Example 33(1) (1.00 g) was added to the reaction mixture, and the mixture was stirred at 50° C. for five hours. The reaction mixture was concentrated under reduced pressure, and water was added to the residue, followed by extraction with ethyl acetate. The organic layer was concentrated under reduced pressure, and the residue was purified by silica gel column chromatography (ethyl acetate/n-heptane, 0% to 50%) to give the title compound (467 mg).

$^{1}$H-NMR (400 MHz, CDCl$_3$) δ (ppm): 2.45-2.48 (m, 3H), 2.58 (s, 3H), 7.23-7.25 (m, 1H), 10.32 (s, 1H).

(2) Synthesis of 3-bromo-2-(difluoromethyl)-4,6-dimethylpyridine

BAST (0.884 mL) was added to a solution of 3-bromo-4,6-dimethylpicolinealdehyde (467 mg) in DCM (10 mL) at 0° C., and the mixture was stirred while gradually warming to room temperature for 12 hours. A saturated aqueous sodium bicarbonate solution was added to the reaction mixture, followed by extraction with DCM. The organic layer was concentrated under reduced pressure, and the residue was purified by silica gel column chromatography (ethyl acetate/n-heptane, 0% to 50%) to give the title compound (362 mg).

$^1$H-NMR (400 MHz, CDCl$_3$) δ (ppm): 2.43 (s, 3H), 2.54 (s, 3H), 6.81-7.10 (m, 1H), 7.16 (s, 1H).

Preparation Example 35

Synthesis of 3-bromo-2-(fluoromethyl)-6-methoxy-4-methylpyridine

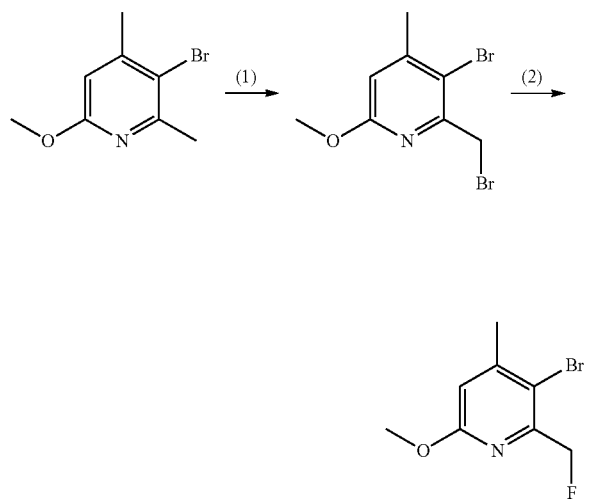

(1) Synthesis of 3-bromo-2-(bromomethyl)-6-methoxy-4-methylpyridine

A mixture of 3-bromo-6-methoxy-2,4-dimethylpyridine obtained in Preparation Example 22 (200 mg), NBS (165 mg) and benzoyl peroxide (6.73 mg) was heated under reflux in a carbon tetrachloride solvent (4 mL) for two hours. The reaction mixture was cooled to room temperature and then filtered. The resulting filtrate was concentrated under reduced pressure, and the residue was purified by silica gel column chromatography (ethyl acetate/n-heptane, 0% to 5%) to give the title compound (126 mg).

ESI-MS m/z 296 [M+H]$^+$ (2) Synthesis of 3-bromo-2-(fluoromethyl)-6-methoxy-4-methylpyridine A mixture of 3-bromo-2-(bromomethyl)-6-methoxy-4-methylpyridine (126 mg) and TBAF (1.71 mL, 1 M solution in THF) was stirred at room temperature for two hours. The reaction mixture was concentrated under reduced pressure, and the resulting residue was purified by silica gel column chromatography (ethyl acetate/n-heptane, 0% to 10%) to give the title compound (37 mg).

$^1$H-NMR (400 MHz, CDCl$_3$) δ (ppm): 2.35-2.42 (m, 3H), 3.89-3.97 (m, 3H), 5.42-5.59 (m, 2H), 6.65 (s, 1H). ESI-MS m/z 234 [M+H]$^+$ Preparation Example 36

Synthesis of 3-bromo-4-(fluoromethyl)-6-methoxy-2-methylpyridine

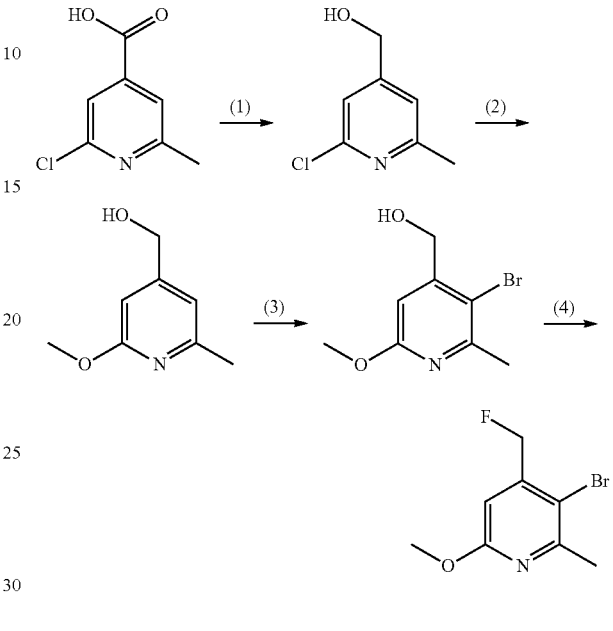

(1) Synthesis of (2-chloro-6-methylpyridin-4-yl)methanol

Borane-THF complex (16.5 mL, 1.06 M solution in THF) was added to a solution of 2-chloro-6-methylpyridine-4-carboxylic acid (2 g) in THF (10 mL), and the mixture was heated under reflux for 12 hours. 5 M hydrochloric acid was added to the reaction mixture, and the mixture was stirred at room temperature for 30 minutes. The reaction mixture was neutralized by adding a saturated aqueous sodium bicarbonate solution, followed by extraction with ethyl acetate. The organic layer was concentrated under reduced pressure, and the residue was purified by silica gel column chromatography (ethyl acetate/n-heptane, 10% to 50%) to give the title compound (1.75 g).

ESI-MS m/z 158 [M+H]$^+$ (2) Synthesis of (2-methoxy-6-methylpyridin-4-yl)methanol Sodium methoxide (11.3 mL, 28% solution in methanol) was added to a solution of (2-chloro-6-methylpyridin-4-yl)methanol (1.75 g) in DMF (18 mL), and the mixture was stirred at 80° C. for 12 hours. Subsequently, the reaction mixture was stirred at 120° C. for seven hours. The reaction mixture was concentrated under reduced pressure, and a saturated aqueous ammonium chloride solution was added to the residue, followed by extraction with ethyl acetate. The organic layer was concentrated under reduced pressure, and the residue was purified by silica gel column chromatography (ethyl acetate/n-heptane, 10% to 70%) to give the title compound (1.1 g).

¹H-NMR (400 MHz, CDCl₃) δ (ppm): 1.76 (t, J=6.1 Hz, 1H), 2.45 (s, 3H), 3.92 (s, 3H), 4.64 (d, J=6.1 Hz, 2H), 6.50-6.56 (m, 1H), 6.68-6.73 (m, 1H).

(3) Synthesis of (3-bromo-6-methoxy-2-methylpyridin-4-yl)methanol

A mixture of (2-methoxy-6-methylpyridin-4-yl)methanol (1.1 g) and NBS (1.34 g) was stirred in an acetic acid solvent (22 mL) at room temperature for 12 hours. A 5 M aqueous sodium hydroxide solution was added to the reaction mixture, followed by extraction with ethyl acetate. The organic layer was concentrated under reduced pressure, and the residue was purified by silica gel column chromatography (ethyl acetate/n-heptane, 10% to 50%) to give the title compound (1.32 g).
ESI-MS m/z 234 [M+H]⁺

(4) Synthesis of 3-bromo-4-(fluoromethyl)-6-methoxy-2-methylpyridine

BAST (0.89 mL) was added to a solution of (3-bromo-6-methoxy-2-methylpyridin-4-yl)methanol (800 mg) in DCM (16 mL) at −60° C., and the mixture was stirred while gradually warming to room temperature for two hours and stirred at room temperature for further one hour. A saturated aqueous sodium bicarbonate solution was added to the reaction mixture, followed by extraction with DCM. The organic layer was concentrated under reduced pressure, and the residue was purified by silica gel column chromatography (ethyl acetate/n-heptane, 0% to 10%, then NH-silica gel, ethyl acetate/n-heptane, 0% to 5%) to give the title compound (632 mg).
¹H-NMR (400 MHz, CDCl₃) δ (ppm): 2.57 (s, 3H), 3.91 (s, 3H), 5.29-5.47 (m, 2H), 6.70 (s, 1H).
ESI-MS m/z 234 [M+H]⁺

Preparation Example 37

Synthesis of 3-bromo-5-chloro-2-methoxy-4-methylpyridine

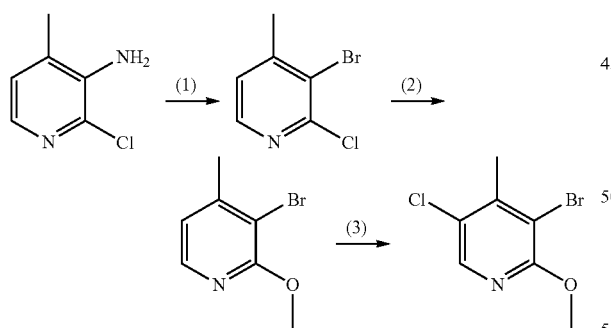

(1) Synthesis of 3-bromo-2-chloro-4-methylpyridine 3-amino-2-chloro-4-methylpyridine (2 g) was added to a mixed solvent of a 48% aqueous hydrogen bromide solution (17 mL) and water (12 mL). Sodium nitrite (2.5 g) was added to the solution at 0° C. Further, bromine (22 mL) was added. The reaction mixture was warmed to room temperature and stirred for 12 hours. The reaction mixture was partitioned by adding a 5 N aqueous sodium hydroxide solution and ethyl acetate. The organic layer was washed with brine and then dried over anhydrous magnesium sulfate. The desiccant was removed by filtration. The filtrate was concentrated under reduced pressure to give the title compound (1.7 g).
¹H-NMR (400 MHz, CDCl₃) δ (ppm): 2.51 (s, 3H), 7.01-7.24 (m, 1H), 8.06-8.35 (m, 1H).

(2) Synthesis of 3-bromo-2-methoxy-4-methylpyridine 3-bromo-2-chloro-4-methylpyridine (1 g) was added to DMF (5.6 mL). Sodium methoxide (28% solution in methanol, 4.6 mL) was added to the solution, and the mixture was stirred at 100° C. for 12 hours. The reaction mixture was partitioned by adding ethyl acetate and water. The organic layer was dried over anhydrous magnesium sulfate. The desiccant was removed by filtration, and the filtrate was concentrated under reduced pressure. The resulting residue was purified by silica gel column chromatography (ethyl acetate/n-heptane, 5% to 30%) to give the title compound (1.1 g).
¹H-NMR (400 MHz, CDCl₃) δ (ppm): 2.40 (s, 3H), 4.00 (s, 3H), 6.77 (d, J=5.1 Hz, 1H), 7.94 (d, Hz, 1H).

(3) Synthesis of 3-bromo-5-chloro-2-methoxy-4-methylpyridine 3-bromo-2-methoxy-4-methylpyridine (100 mg) was added to DMF (575 μL). NCS (72.5 mg) was added to the solution, and the mixture was stirred at 80° C. for three hours. The reaction mixture was concentrated under reduced pressure. The resulting residue was purified by silica gel column chromatography (ethyl acetate/n-heptane, 5% to 30%) to give the title compound (100 mg).
¹H-NMR (400 MHz, CDCl₃) δ (ppm): 2.51 (s, 3H), 3.98 (s, 3H), 8.02 (s, 1H).

Preparation Example 38

Synthesis of 3-bromo-6-fluoro-2,4-dimethylpyridine

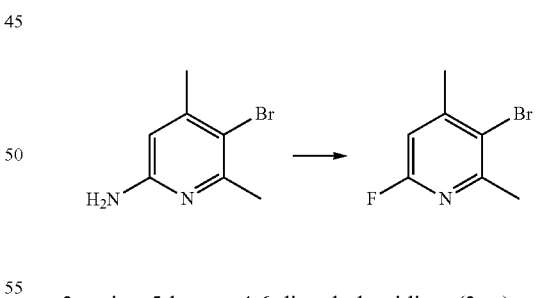

2-amino-5-bromo-4,6-dimethylpyridine (2 g) was suspended in fluoroboric acid (48% aqueous solution, 7.5 mL). Sodium nitrite (890 mg) dissolved in water (3 mL) was added to the solution at 0° C. The reaction mixture was stirred at 0° C. for 10 minutes. The precipitated solid was collected by filtration and suspended in n-heptane (100 mL). The solution was stirred with heating under reflux for two hours. After cooling to room temperature, the precipitated solid was collected by filtration. The resulting solid was dried under reduced pressure to give the title compound (500 mg).
¹H-NMR (400 MHz, CDCl₃) δ (ppm): 2.43 (s, 3H), 2.62 (s, 3H), 6.67 (s, 1H).

Preparation Example 39

Synthesis of 3-bromo-4-chloro-2,6-dimethylpyridine

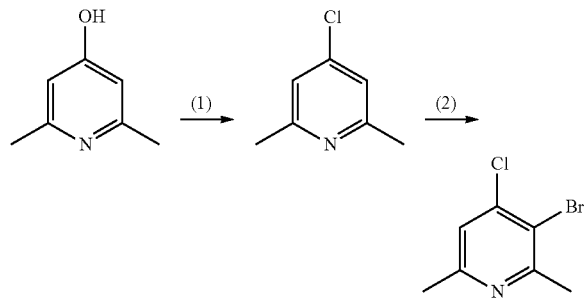

(1) Synthesis of 4-chloro-2,6-dimethylpyridine 2,6-dimethyl-4-hydroxypyridine (1 g) was added to phosphoryl chloride (5 mL). The solution was stirred at 100° C. for six hours. The reaction mixture was partitioned by adding water, a 5 N aqueous sodium hydroxide solution and ethyl acetate. The organic layer was washed with brine and then dried over anhydrous magnesium sulfate. The desiccant was removed by filtration. The filtrate was concentrated under reduced pressure to give the title compound (1.15 g).
$^1$H-NMR (400 MHz, CDCl$_3$) δ (ppm): 2.51 (s, 6H), 6.99 (s, 2H).

(2) Synthesis of 3-bromo-4-chloro-2,6-dimethylpyridine 4-chloro-2,6-dimethylpyridine (1.5 g) was added to a mixed solvent of trifluoroacetic acid (3 mL) and concentrated sulfuric acid (6 mL). NBS (22 g) was added to the solution, and the mixture was stirred at room temperature for 12 hours. A 5 N aqueous sodium hydroxide solution was added to the reaction mixture, followed by separation with ethyl acetate. The organic layer was washed with brine and then dried over anhydrous magnesium sulfate. The desiccant was removed by filtration, and the filtrate was concentrated under reduced pressure. The resulting residue was purified by silica gel column chromatography (ethyl acetate/n-heptane, 5% to 30%) to give the title compound (500 mg).
$^1$H-NMR (400 MHz, CDCl$_3$) δ (ppm): 2.46 (s, 3H), 2.49 (s, 3H), 7.11 (s, 1H).
ESI-MS m/z 222 [M+H]$^+$

Preparation Example 40

Synthesis of 3-bromo-5-chloro-2-methoxy-4,6-dimethylpyridine

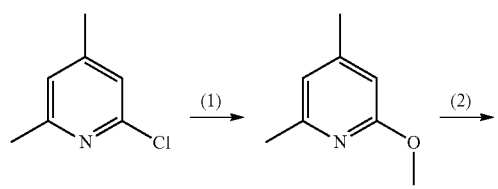

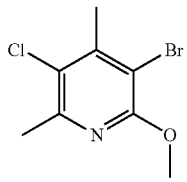

(1) Synthesis of 2-methoxy-4,6-dimethylpyridine 2-chloro-4,6-dimethylpyridine (CAS number: 30838-93-8) (400 mg) was added to DMF (3.3 mL). Sodium methoxide (28% solution in methanol, 2.6 mL) was added to the solution, and the mixture was stirred at 100° C. for 12 hours. The reaction mixture was partitioned by adding ethyl acetate and water. The organic layer was dried over anhydrous magnesium sulfate. The desiccant was removed by filtration. The filtrate was concentrated under reduced pressure to give the title compound (380 mg) as a 50% solution in DMF.
$^1$H-NMR (400 MHz, CDCl$_3$) δ (ppm): 2.24 (s, 3H), 2.40 (s, 3H), 3.89 (s, 3H), 6.35 (s, 1H), 6.56 (s, 1H).

(2) Synthesis of 3-bromo-5-chloro-2-methoxy-4,6-dimethylpyridine 2-methoxy-4,6-dimethylpyridine (380 mg) was added to DMF (3 mL). NCS (407 mg) was added to the solution, and the mixture was stirred at 80° C. for one hour. Thereafter, NBS (542 mg) was added to the solution, followed by stirring for one hour. The reaction mixture was concentrated under reduced pressure. The resulting residue was purified by silica gel column chromatography (ethyl acetate/n-heptane, 5% to 30%) to give the title compound (600 mg).
$^1$H-NMR (400 MHz, CDCl$_3$) δ (ppm): 2.50 (s, 3H), 2.51 (s, 3H), 3.97 (s, 3H).
ESI-MS m/z 252 [M+H]$^+$

Preparation Example 41

Synthesis of 3-bromo-5-fluoro-2-methoxy-4-methylpyridine

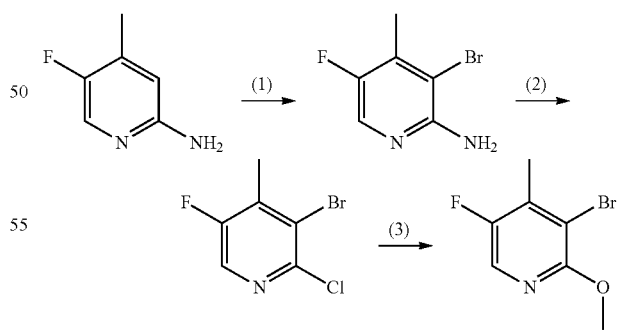

(1) Synthesis of 3-bromo-5-fluoro-4-methylpyridyl-2-amine 5-fluoro-4-methylpyridyl-2-amine (2 g) was added to acetonitrile (14 mL). NBS (3.1 g) was added to the solution. The reaction mixture was stirred at room temperature for five hours. The reaction mixture was concentrated under reduced pressure, and the resulting residue was purified by silica gel column chromatography (ethyl acetate/n-heptane, 5% to 30%) to give the title compound (2.4 g).
$^1$H-NMR (400 MHz, CDCl$_3$) δ (ppm): 2.33 (s, 3H), 4.82 (brs, 2H), 7.84 (s, 1H).
ESI-MS m/z 207 [M+H]$^+$ (2) Synthesis of 3-bromo-2-chloro-5-fluoro-4-methylpyridine 3-bromo-5-fluoro-4-methylpyridyl-2-amine (2.4 g) was added to a mixed solvent of concentrated hydrochloric acid (11 mL) and water (11 mL). Sodium nitrite (2.1 g) and copper (I) chloride (3.5 g) were added to the solution, and the mixture was stirred at room temperature for 12 hours. A 5 N aqueous sodium hydroxide solution and ethyl acetate were added to the reaction mixture, and the insoluble matter was removed by filtration through a glass filter. The filtrate was separated. The organic layer was washed with brine and dried over anhydrous magnesium sulfate. The desiccant was removed by filtration, and the filtrate was concentrated under reduced pressure. The resulting residue was purified by silica gel column chromatography (ethyl acetate/n-heptane, 5% to 30%) to give the title compound (340 mg).
$^1$H-NMR (400 MHz, CDCl$_3$) δ (ppm): 2.44 (s, 3H), 8.16 (s, 1H).
ESI-MS m/z 226 [M+H]$^+$ (3) Synthesis of 3-bromo-5-fluoro-2-methoxy-4-methylpyridine 3-bromo-2-chloro-5-fluoro-4-methylpyridine (340 mg) was added to DMF (1.8 mL). Sodium methoxide (28% solution in methanol, 5.4 mL) was added to the solution, and the mixture was stirred at 80° C. for two hours. Water was added to the reaction mixture. The precipitated solid was collected by filtration to give the title compound (240 mg).
$^1$H-NMR (400 MHz, CDCl$_3$) δ (ppm): 2.38 (s, 3H), 3.92 (s, 3H), 7.86 (s, 1H).
ESI-MS m/z 222 [M+H]$^+$ Preparation Example 42

Synthesis of 5-bromo-4,6-dimethylpicolinonitrile

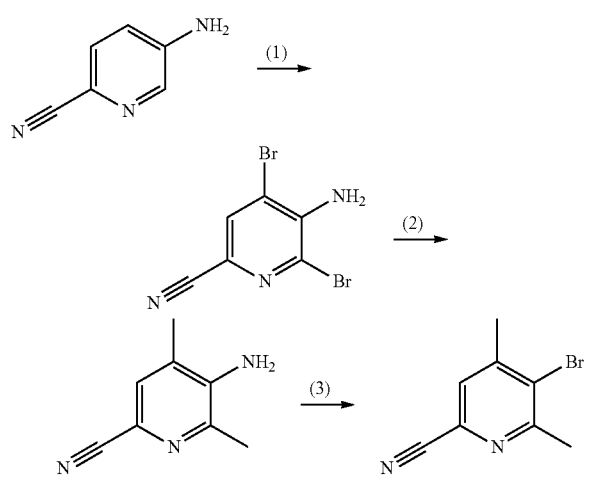

(1) Synthesis of 5-amino-4,6-dibromopicolinonitrile 5-amino-2-cyanopyridine (2 g) was added to a 48% aqueous hydrogen bromide solution (14 mL). Bromine (2.2 mL) was added to the solution at 0° C. The reaction mixture was warmed to room temperature and stirred for six hours. The precipitated solid was collected by filtration to give the title compound (4.5 g).
$^1$H-NMR (400 MHz, CDCl$_3$) δ (ppm): 5.09 (brs, 2H), 7.69 (s, 1H).
ESI-MS m/z 278 [M+H]$^+$ (2) Synthesis of 5-amino-4,6-dimethylpicolinonitrile 4,6-dibromo-5-amino-2-cyanopyridine (1 g) was dissolved in a mixed solvent of 1,4-dioxane (10 mL) and water (1 mL). Trimethylboroxin (1.3 g), Pd(dppf)Cl$_2$-DCM complex (264 mg) and potassium carbonate (1.5 mg) were added to the solution, and the mixture was reacted using a microwave reactor at 140° C. for four hours. The reaction mixture was returned to room temperature and then partitioned by adding ethyl acetate and water. The organic layer was washed with brine and dried over anhydrous magnesium sulfate. The desiccant was removed by filtration, and the filtrate was concentrated under reduced pressure. The resulting residue was purified by silica gel column chromatography (ethyl acetate/n-heptane, 0% to 100%) to give the title compound (390 mg).
$^1$H-NMR (400 MHz, CDCl$_3$) δ (ppm): 2.18 (s, 3H), 2.44 (s, 3H), 4.05 (brs, 2H), 7.28 (s, 1H).

(3) Synthesis of 5-bromo-4,6-dimethylpicolinonitrile 5-amino-4,6-dimethylpicolinonitrile (390 mg) was added to aqueous hydrogen bromide (2.9 mL). Bromine (164 µl) and sodium nitrite (467 mg) were added to the solution at 0° C. The solution was warmed to room temperature and stirred for four hours. A 5 N aqueous sodium hydroxide solution was added to the reaction mixture, followed by separation with ethyl acetate. The organic layer was washed with brine and then dried using magnesium sulfate. The desiccant was removed by filtration, and the filtrate was concentrated under reduced pressure. The resulting residue was purified by silica gel column chromatography (ethyl acetate/n-heptane, 0% to 30%) to give the title compound (300 mg).
$^1$H-NMR (400 MHz, CDCl$_3$) (ppm): 2.47 (s, 3H), 2.72 (s, 3H), 7.40 (s, 1H).
ESI-MS m/z 213 [M+H]$^+$ Preparation Example 43

Synthesis of 3-bromo-6-(difluoromethoxy)-2,4-dimethylpyridine

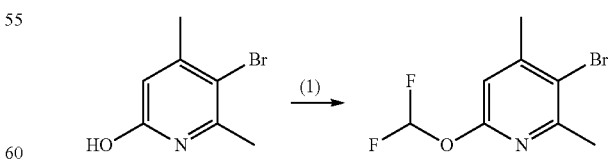

(1) Synthesis of 3-bromo-6-(difluoromethoxy)-2,4-dimethylpyridine

A mixture of 5-bromo-4,6-dimethylpyridin-2-ol obtained in Preparation Example 23(1) (500 mg), 2-(fluorosulfonyl)

difluoroacetic acid (0.307 mL) and sodium sulfate (70.3 mg) was stirred in an acetonitrile solvent (10 mL) at room temperature for 3.5 hours. A saturated aqueous sodium bicarbonate solution was added to the reaction mixture, and the mixture was then concentrated under reduced pressure. The residue was extracted with ethyl acetate, and the organic layer was concentrated under reduced pressure. The residue was purified by silica gel column chromatography (ethyl acetate/n-heptane, 0% to 10%) to give the title compound (68.6 mg).

$^1$H-NMR (400 MHz, CDCl$_3$) δ (ppm): 2.38-2.41 (m, 3H), 2.57-2.60 (m, 3H), 6.61-6.64 (m, 1H), 7.25-7.63 (m, 1H).

ESI-MS m/z 252 [M+H]$^+$

Preparation Example 44

Synthesis of 3-bromo-2-ethoxy-4-methylpyridine

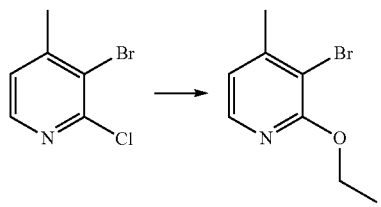

3-bromo-2-chloro-4-methylpyridine obtained in Preparation Example 37(1) (1 g) was added to a mixed solvent of ethanol (2 mL) and DMF (5.6 mL). Sodium hydride (60% oil dispersion, 58 mg) was added to the solution, and the mixture was stirred at 100° C. for five hours. The reaction mixture was partitioned by adding ethyl acetate and water. The organic layer was dried over anhydrous magnesium sulfate. The desiccant was removed by filtration, and the filtrate was concentrated under reduced pressure. The resulting residue was purified by silica gel column chromatography (ethyl acetate/n-heptane, 5% to 30%) to give the title compound (40% solution in n-heptane, 250 mg).

$^1$H-NMR (400 MHz, CDCl$_3$) δ (ppm): 1.43 (t, J=7.0 Hz, 3H), 2.39 (s, 3H), 4.41 (q, J=7.0 Hz, 2H), 6.57-6.88 (m, 1H), 7.80-8.04 (m, 1H).

Preparation Example 45

Synthesis of 2-(difluoromethoxy)-4-iodo-3,5-dimethylpyridine

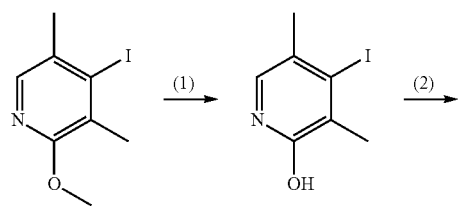

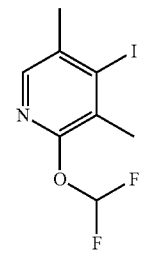

(1) Synthesis of 4-iodo-3,5-dimethylpyridin-2-ol 4-iodo-2-methoxy-3,5-methylpyridine obtained in Preparation Example 29(3) (3 g) and sodium iodide (4.27 g) were added to acetonitrile (132 mL), and the mixture was stirred at room temperature for one hour. Chlorotrimethylsilane (3.61 mL) was added to the mixed solution, and the mixture was stirred at room temperature for 30 minutes and then at 70° C. for five hours. The reaction mixture was cooled to room temperature, and water and chloroform were then added. The precipitated solid was collected by filtration to give the title compound (2.33 g).

$^1$H-NMR (400 MHz, DMSO-d$_6$) δ (ppm): 2.10 (s, 3H), 2.20 (s, 3H), 7.15 (s, 1H), 11.59 (brs, 1H).

ESI-MS m/z 250 [M+H]$^+$ (2) Synthesis of 2-(difluoromethoxy)-4-iodo-3,5-dimethylpyridine 4-iodo-3,5-dimethylpyridin-2-ol (350 mg), 2-(fluorosulfonyl)difluoroacetic acid (0.17 mL), and sodium sulfate (39.9 mg) were added to acetonitrile (5.7 mL). The mixture was stirred at room temperature for 3.5 hours. A saturated aqueous sodium bicarbonate solution was added to the reaction mixture, followed by extraction with ethyl acetate. The organic layer was concentrated under reduced pressure to give the title compound (378.6 mg).

$^1$H-NMR (400 MHz, CDCl$_3$) δ (ppm): 2.39 (s, 3H), 2.43 (s, 3H), 7.42 (t, J=72.0 Hz, 1H), 7.79 (s, 1H).

ESI-MS m/z 300 [M+H]$^+$

Preparation Example 46

Synthesis of 2-ethoxy-4-iodo-3,5-dimethylpyridine

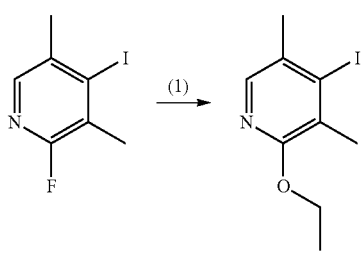

A 20% solution of sodium ethoxide in ethanol (123 mL) was added to a solution of 2-fluoro-4-iodo-3,5-dimethylpyridine obtained in Preparation Example 29(2) (400 mg) in THF (5 mL), and the mixed solution was stirred at room temperature overnight. The reaction mixture was cooled at 0° C., and MTBE (20 mL) and water (20 mL) were then added. The organic layer was separated. The organic layer was washed with brine. The combined aqueous layers were extracted with MTBE. The combined organic layers were dried over anhydrous magnesium sulfate and filtered. The filtrate was concentrated under reduced pressure to give the title compound (423.8 mg).

$^1$H-NMR (400 MHz, CDCl$_3$) (ppm): 1.38 (t, J=7.0 Hz, 3H), 2.32 (s, 3H), 2.37 (s, 3H), 4.33 (q, 0.1=7.0 Hz, 2H), 7.74 (s, 1H).

ESI-MS m/z 278 [M+H]$^+$

Preparation Example 47

Synthesis of 4-iodo-2-isopropyloxy-3,5-dimethylpyridine

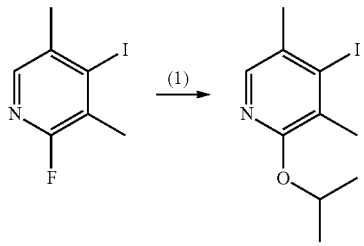

Sodium hydride (60% oil dispersion, 191 mg) was added to a solution of IPA (0.77 mL) in THF (5 mL). After foaming was stopped, a solution of 2-fluoro-4-iodo-3,5-dimethylpyridine obtained in Preparation Example 29 (500 mg) in THF (5 mL) was added to the solution, and the mixture was stirred at mom temperature for two hours. The mixture was stirred at 50° C. for two hours, and the reaction mixture was then cooled to room temperature. The reaction mixture was cooled at 0° C., and MTBE (20 mL) and water (20 mL) were then added. The organic layer was separated. The organic layer was washed with brine. The combined aqueous layers were extracted with MTBE. The combined organic layers were dried over anhydrous magnesium sulfate and filtered. The filtrate was concentrated under reduced pressure to give the title compound (490 mg).

$^1$H-NMR (400 MHz, CDCl$_3$) δ (ppm): 1.33 (d, J=6.3 Hz, 6H), 2.31-2.32 (m, 3H), 2.34-2.35 (m, 3H), 5.21-5.27 (m, 1H), 7.73-7.75 (m, 1H).
ESI-MS m/z 292 [M+H]$^+$ Preparation Example 48

Synthesis of 3-bromo-6-isopropyloxy-2,4-dimethylpyridine

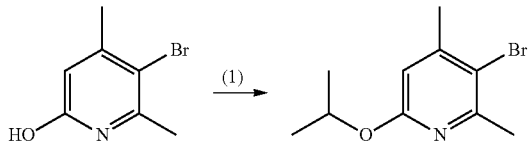

KTB (222 mg) was added to a suspension of 5-bromo-4,6-dimethylpyridin-2-ol obtained in Preparation Example 23(1) (400 mg) in DME (2 mL), and the mixture was stirred at room temperature for 30 minutes. Potassium carbonate (192 mg) and 2-iodopropane (572 mg) were added to the reaction mixture. The mixture was heated under reflux overnight. The reaction mixture was cooled to mom temperature, and the insoluble matter was removed by filtration and washed with DME. The filtrate was concentrated under reduced pressure. Chloroform was added to the residue. The solution was washed with a 0.1 N aqueous hydrochloric acid solution. The organic layer was dried over anhydrous magnesium sulfate and filtered. The filtrate was concentrated under reduced pressure. The resulting residue was purified by silica gel column chromatography (ethyl acetate/n-heptane, 10% to 50%) to give the title compound (133.9 mg).

$^1$H-NMR (400 MHz, CDCl$_3$) δ (ppm): 1.31 (d, J=6.25 Hz, 6H), 2.32 (s, 3H), 2.25 (s, 3H), 5.17-5.27 (m, 1H), 6.37-6.46 (m, 1H).
ESI-MS m/z 244 [M+H]$^+$ Preparation Example 49

Synthesis of 3-ethyl-4-iodo-2-methoxy-5-methylpyridine

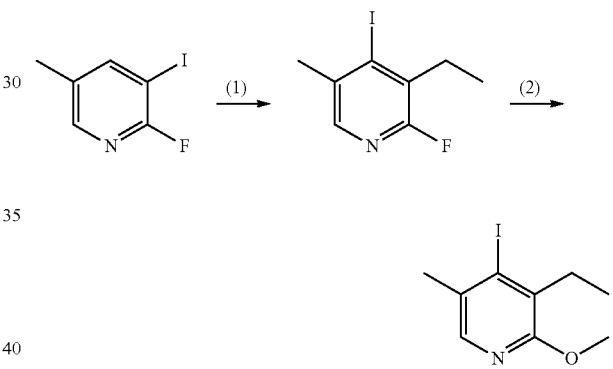

(1) Synthesis of 3-ethyl-2-fluoro-4-iodo-5-methylpyridine

The title compound was synthesized in accordance with Preparation Examples 29(2) and 29(3) using 2-fluoro-3-iodo-5-methylpyridine and ethyl iodide as raw materials. However, the temperature was gradually raised to −17° C. after adding ethyl iodide.

$^1$H-NMR. (400 MHz, CDCl$_3$) δ (ppm): 1.11-1.22 (m, 3H), 2.35-2.45 (m, 3H), 2.80-2.91 (m, 2H), 7.81 (s, 1H)

(2) Synthesis of 3-ethyl-4-iodo-2-methoxy-5-methylpyridine

The title compound was synthesized in accordance with Preparation Example 29(3) using 3-ethyl-2-fluoro-4-iodo-5-methylpyridine.

$^1$H-NMR (400 MHz, CDCl$_3$) δ (ppm): 1.04-1.13 (m, 3H), 2.29-2.37 (m, 3H), 2.83 (q, J=7.42 Hz, 2H), 3.89-3.93 (m, 3H), 7.76 (s, 1H)

Preparation Example 50

Synthesis of 4-(4-bromo-3,5-dimethylphenyl)-3,6-dihydro-2,1-pyran

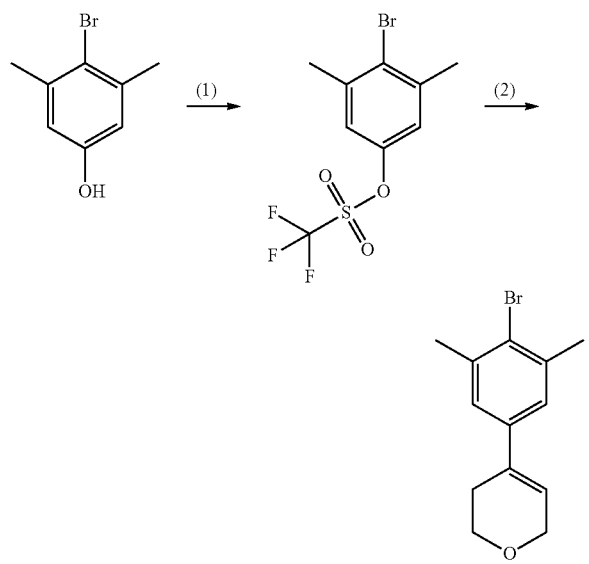

(1) Synthesis of 4-bromo-3,5-dimethylphenyl trifluoromethanesulfonate

Trifluoromethanesulfonic anhydride (2.0 mL) was added dropwise to a solution of 4-bromo-3,5-dimethylphenol (CAS No. 7463-51-6) (2.0 g) and TEA (1.94 mL) in DCM (20 mL) under ice-cooling over three minutes. The reaction mixture was stirred at room temperature for 30 minutes. Ice and ethyl acetate were added to the reaction mixture, and the organic layer was separated. The organic layer was sequentially washed with 1 N hydrochloric acid, water, a saturated aqueous sodium bicarbonate solution and brine, dried over anhydrous magnesium sulfate, filtered and concentrated under reduced pressure. The resulting residue was purified by silica gel column chromatography (ethyl acetate/n-heptane, 5%) to give the title compound (3.20 g).

$^1$H-NMR (400 MHz, CDCl$_3$) δ (ppm): 2.45 (s, 6H), 7.01 (s, 2H).

(2) Synthesis of 4-(4-bromo-3,5-dimethylphenyl)-3,6-dihydro-2H-pyran

Potassium carbonate (1.99 g) and Pd(dppf)Cl$_2$-DCM complex (196 mg) were added to a solution of 4-bromo-3,5-dimethylphenyl trifluoromethanesulfonate (1.6 g) and 3,6-dihydro-2H-pyran-4-boronic acid pinacol ester (CAS No. 287944-16-5) (1.11 g) in DMF (16 mL). The reaction mixture was stirred at 85° C. for four hours. The reaction mixture was returned to room temperature, and the reaction mixture was then concentrated under reduced pressure. MTBE, water and brine were added to the residue, and the organic layer was separated. The organic layer was washed with brine, dried over anhydrous magnesium sulfate, filtered and concentrated under reduced pressure. The resulting residue was purified by silica gel column chromatography (ethyl acetate/n-heptane, 2%) to give the title compound (747 mg).

$^1$H-NMR (400 MHz, CDCl$_3$) δ (ppm): 2.42 (s, 6H), 2.45-2.51 (m, 2H), 3.92 (t, J=5.6 Hz, 2H), 4.30 (dd, J=6.0, 2.8 Hz, 2H), 6.08-6.12 (m, 1H), 7.09 (s, 2H).
ESI-MS m/z 267, 269 [M+H]$^+$

Preparation Example 51

Synthesis of 3-bromo-6-ethoxy-2,4-dimethylpyridine

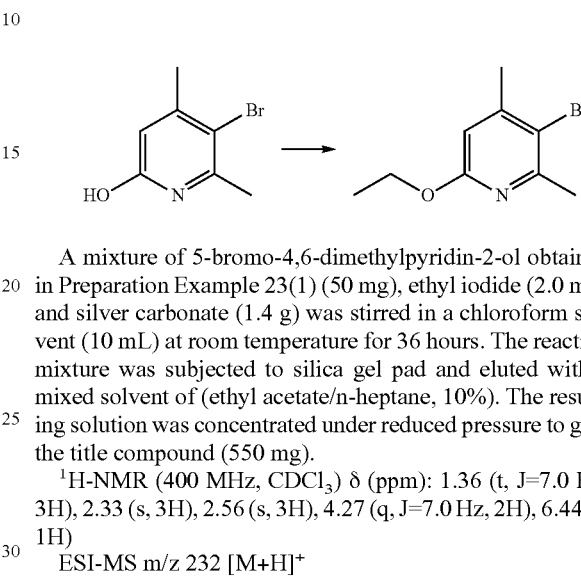

A mixture of 5-bromo-4,6-dimethylpyridin-2-ol obtained in Preparation Example 23(1) (50 mg), ethyl iodide (2.0 mL) and silver carbonate (1.4 g) was stirred in a chloroform solvent (10 mL) at room temperature for 36 hours. The reaction mixture was subjected to silica gel pad and eluted with a mixed solvent of (ethyl acetate/n-heptane, 10%). The resulting solution was concentrated under reduced pressure to give the title compound (550 mg).

$^1$H-NMR (400 MHz, CDCl$_3$) δ (ppm): 1.36 (t, J=7.0 Hz, 3H), 2.33 (s, 3H), 2.56 (s, 3H), 4.27 (q, J=7.0 Hz, 2H), 6.44 (s, 1H)
ESI-MS m/z 232 [M+H]$^+$

Preparation Example 52

Synthesis of (−)benzyl 2-(tetrahydrofuran-3-yl)hydrazinecarboxylate and (+)-benzyl 2-(tetrahydrofuran-3-yl)hydrazinecarboxylate

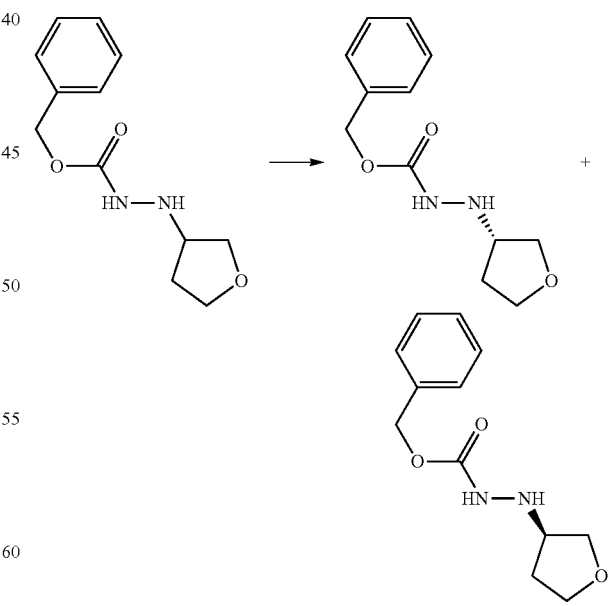

A saturated aqueous sodium bicarbonate solution (30 mL) was added to a solution of (±)-benzyl 2-(tetrahydrofuran-3-yl)hydrazinecarboxylate obtained in Preparation Example 12-(2) (11.5 g) in MTBE (110 mL). The mixture was stirred for 10 minutes at room temperature, and the organic layer was then separated. The resulting organic layer was sequentially washed with saturated sodium bicarbonate and brine and dried over anhydrous magnesium sulfate, and the desiccant was removed by filtration. The filtrate was concentrated under reduced pressure. The resulting residue was purified by silica gel column chromatography (ethyl acetate/hexane, 25 to 50%), and the target fraction was concentrated. Diethyl ether (30 mL) and hexane (15 mL) were added to the residue. The precipitated solid was collected by filtration and dried under reduced pressure to give pure (±)-benzyl 2-(tetrahydrofuran-3-yl)hydrazinecarboxylate (6.17 g).

This product was dissolved in ethanol and filtered through a millipore filter. The resulting filtrate was optically resolved under two conditions. Condition 1: OD-H (20 mm Φ×250 mm L), 20% IPA-hexane, 25 mL/min. Condition 2: AD-H (20 mmΦ×250 mm L), 20% IPA-hexane, 24 mL/min. The target fraction was concentrated to give the title compound with a short retention time and a (−) optical rotation (2.60 g, >99% ee [OD-H, 20% IPA/hexane, retention time=11.2 min]), and the title compound with a long retention time and a (+) optical rotation (2.59 g, 97.2% ee [OD-H, 20% IPA/hexane, retention time=12.4 min]).

Preparation Example 53

Synthesis of (S)-(tetrahydrofuran-3-yl)hydrazine hydrochloride

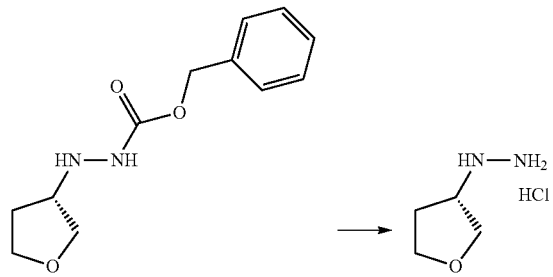 [SMILES: O=C(NN[C@H]1CCOC1)OCc1ccccc1 ; NN[C@H]1CCOC1 ; Cl]

(−)-Benzyl 2-(tetrahydrofuran-3-yl)hydrazinecarboxylate (50 g) was dissolved in methanol (500 mL), and di-t-butyl dicarbonate (92.4 g) and palladium carbon (50% wet) (5 g) were added. The mixture was stirred at 25° C. and 15 psi for 48 hours in a hydrogen atmosphere. The reaction mixture was filtered, and the filtrate was concentrated under reduced pressure. The resulting residue was dissolved hi diisopropyl ether (300 mL). After cooling at 0° C., hydrochloric acid/diisopropyl ether (500 mL) was added to the solution The mixture was stirred at 10° C. for 14 hours. The precipitated solid was collected by filtration. The same operation from (−)benzyl 2-(tetrahydrofuran-3-yl)hydrazinecarboxylate (70 g) was performed nine times, and the same operation from (−)-benzyl 2-(tetrahydrofuran-3-yl)hydrazinecarboxylate (50 g) was performed once. The resulting solid was triturated with DCM/ethanol (10/1) (1 L) for two hours. The precipitated solid was collected by filtration. The resulting solid was dried under reduced pressure to give the title compound (235 g).

$^1$H-NMR (400 MHz, DMSO-$d_6$) δ (ppm): 1.87-2.09 (m, 2H), 3.55-3.71 (m, 2H), 3.71-3.84 (m, 3H).

Both of the optical rotation of the Z-derivative of the title compound and the optical rotation of the Z-derivative of (S)-(tetrahydrofuran-3-yl)hydrazine hydrochloride obtained in Preparation Example 14 are negative. The retention times of both compounds were identical according to chiral HPLC analysis.

The absolute configuration of the resulting title compound was confirmed to be an (S)-form according to X-ray crystallography. The result is shown in FIG. 1 as its ORTEP representation (flack parameter=−0.05).

Preparation Example 54

Synthesis of (R)-(tetrahydrofuran-3-yl)hydrazine hydrochloride

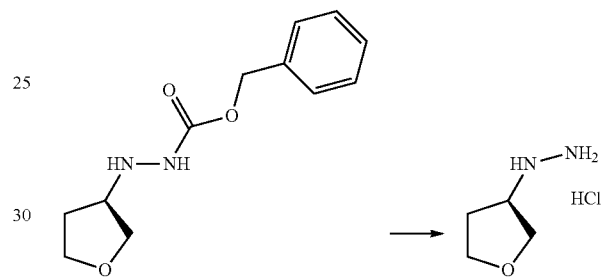

The title compound was obtained by the same method as in Preparation Example 53 from (+)-benzyl 2-(tetrahydrofuran-3-yl)hydrazinecarboxylate.

$^1$H-NMR (400 MHz, DMSO-$d_6$) δ (ppm): 1.85-2.07 (m, 2H), 3.55-3.71 (m, 2H), 3.71-3.80 (m, $^3$H).

Example 1

Synthesis of 7-(2,6-dimethylphenyl)-1-(tetrahydro-2H-pyran-4-yl)-1H-pyrazolo[4,3-c]quinolin-4(5H)-one

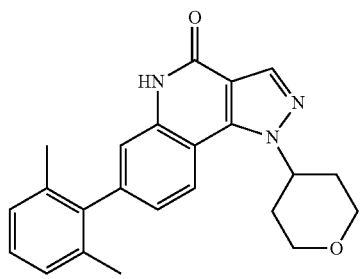 [SMILES: Cc1cccc(C)c1-c1ccc2c(c1)[nH]c(=O)c1cnn(C3CCOCC3)c12]

7-chloro-5-(2,4-dimethoxybenzyl)-1-(tetrahydro-2H-pyran-4-yl)-1H-pyrazolo[4,3-c]quinolin-4(5H)-one obtained in Preparation Example 2 (100 mg) was dissolved in DMF (3.3 mL). 2,6-dimethylphenylboronic acid (33 mg), Pd(PPh$_3$)$_4$ (13 mg), potassium carbonate (91 mg) and water (0.7 mL) were added to the solution, and the mixture was reacted using a microwave reactor at 150° C. for two hours. The reaction mixture was returned to room temperature and then concentrated under reduced pressure. The resulting residue was purified by silica gel column chromatography (ethyl acetate/n-heptane, 30% to 50% to 80%) to give 5-(2,4-dimethoxybenzyl)-7-(2,6-dimethylphenyl)-1-(tetrahydro-2H-pyran-4-yl)-1H-pyrazolo[4,3-c]quinolin-4(5H)-one (80 mg). The 5-(2,4-dimethoxybenzyl)-7-(2,6-dimethylphenyl)-1-(tetrahydro-2H-pyran-4-yl)-1H-pyrazolo[4,3-c]quinolin-4(5H)-one (75 mg) was dissolved in TFA. (1 mL), and the mixture was stirred at 65° C. for two hours. The reaction mixture was cooled to room temperature and then concentrated under reduced pressure. The resulting residue was neutralized by adding a saturated aqueous sodium bicarbonate solution. The aqueous solution was extracted with DCM. The organic layer was dried over anhydrous magnesium sulfate. The desiccant was removed by filtration. The filtrate was concentrated under reduced pressure. The resulting residue was purified by silica gel column chromatography (ethyl acetate/n-heptane, 50% to 70% to 80%) to give the title compound (10 mg).

$^1$H-NMR. (400 MHz, CDCl$_3$) δ (ppm): 2.06 (s, 6H), 2.18-2.22 (m, 2H), 2.42-2.60 (m, 2H), 3.69-3.78 (m, 2H), 4.19-4.26 (m, 2H), 5.00-5.10 (m, 1H), 7.09-7.26 (m, 5H), 8.03 (d, J=8.4 Hz, 1H), 8.31 (s, 1H), 8.83 (s, 1H).

ESI-MS m/z 374 [M+H]$^+$

Example 2

Synthesis of 7-(2,4,6-trimethylpyridin-3-yl)-1-(tetrahydro-2H-pyran-4-yl)-1H-pyrazolo[4,3-c]quinolin-4(5H)-one

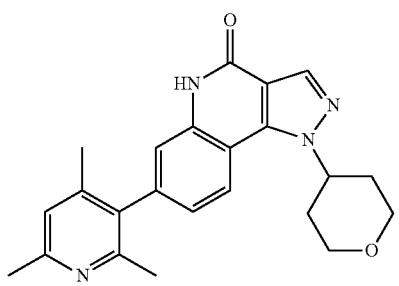 [SMILES: Cc1cc(C)c(-c2ccc3c(c2)[nH]c(=O)c2cnn(C4CCOCC4)c23)c(C)n1]

The title compound was obtained by the same method as in Example 1 from 7-chloro-5-(2,4-dimethoxybenzyl)-1-(tetrahydro-2H-pyran-4-yl)-1H-pyrazolo[4,3-c]quinolin-4(5H)-one obtained in Preparation Example 2 and (2,4,6-trimethylpyridin-3-yl)boronic acid obtained in Preparation Example 19.

$^1$H-NMR (400 MHz, CDCl$_3$) δ (ppm): 2.05 (s, 3H), 2.17-2.21 (m, 2H), 2.29 (s, 3H), 2.48-2.60 (m, 2H), 2.57 (s, 3H), 3.67-3.76 (m, 2H), 4.20-4.28 (m, 2H), 5.01-5.11 (m, 1H), 6.99 (s, 1H), 7.13 (dd, J=8.2 Hz, 1.6 Hz, 1H), 7.27 (d, J=1.6 Hz, 1H), 8.05 (d, J=8.2 Hz, 1H), 8.31 (s, 1H), 10.60 (s, 1H).

ESI-MS m/z 389 [M+11]$^+$

Example 3

Synthesis of 7-(6-methoxy-2,4-dimethylpyridin-3-yl)-1-(tetrahydro-2H-pyran-4-yl)-1H-pyrazolo[4,3-c]quinolin-4(5H)-one

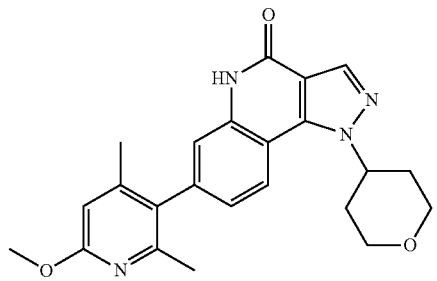 [SMILES: COc1cc(C)c(-c2ccc3c(c2)[nH]c(=O)c2cnn(C4CCOCC4)c23)c(C)n1]

7-bromo-5-(2,4-dimethoxybenzyl)-1-(tetrahydro-2H-pyran-4-yl)-1H-pyrazolo[4,3-c]quinolin-4(5H)-one obtained in Preparation Example 1(4) (41 mg) was dissolved in DMF (2 mL). (6-methoxy-2,4-dimethylpyridin-3-yl)boronic acid obtained in Preparation Example 24 (15 mg), Pd(PPh$_3$)$_4$ (4.8 mg), cesium carbonate (54 mg) and water (0.5 mL) were added to the solution, and the mixture was reacted using a microwave reactor at 150° C. for two hours. The reaction mixture was returned to room temperature and then concentrated under reduced pressure. The resulting residue was dissolved in TFA (1 mL), and the mixture was stirred at 65° C. for two hours. The reaction mixture was cooled to room temperature and then concentrated under reduced pressure. The resulting residue was neutralized by adding a 5 N aqueous sodium hydroxide solution. The aqueous solution was extracted with DCM. The organic layer was dried over anhydrous magnesium sulfate. The desiccant was removed by filtration. The filtrate was concentrated under reduced pressure. The resulting residue was purified by silica gel column chromatography (ethyl acetate/n-heptane, 50% to 100%) to give the title compound (3.7 mg).

$^1$H-NMR (400 MHz, CDCl$_3$) δ (ppm): 2.03 (s, 3H), 2.17-2.21 (m, 2H), 2.22 (s, 3H), 2.48-2.60 (m, 2H), 3.67-3.76 (m, 2H), 3.97 (s, 3H), 4.20-4.28 (m, 2H), 5.01-5.11 (m, 1H), 6.55 (s, 1H), 7.13 (dd, J=8.2 Hz, 1.6 Hz, 1H), 7.19 (d, J=1.6 Hz, 1H), 8.03 (d, J=8.2 Hz, 1H), 8.32 (s, 1H), 10.60 (s, 1H).

ESI-MS m/z 405 [M+H]$^+$

Example 4

Synthesis of 7-(2-methoxy-4,6-dimethylpyridin-3-yl)-1-(tetrahydro-2H-pyran-4-yl)-1H-pyrazolo[4,3-c]quinolin-4(5H)-one

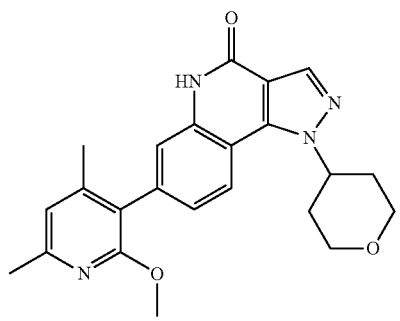 [SMILES: COc1nc(C)cc(C)c1-c1ccc2c(c1)[nH]c(=O)c1cnn(C3CCOCC3)c12]

5-(2,4-dimethoxybenzyl)-1-(tetrahydro-2H-pyran-4-yl)-7-(4,4,5,5-tetramethyl-1,3,2-dioxaborolan-2-yl)-1H-pyrazolo[4,3-c]quinolin-4(5H)-one (100 mg) obtained in Preparation Example 1(5) was dissolved in 1,4-dioxane (4 mL). 3-chloro-2-methoxy-4,6-dimethylpyridine obtained in Preparation Example 25 (472 mg), [(t-Bu)₂P(OH)]₂PdCl₂ (4.6 mg), cesium carbonate (119 mg) and water (1 mL) were added to the solution, and the mixture was reacted using a microwave reactor at 130° C. for four hours. The reaction mixture was extracted with DCM. The organic layer was washed with brine and dried over sodium sulfate. The desiccant was removed by filtration, and the filtrate was concentrated under reduced pressure. The resulting residue was purified by silica gel column chromatography (ethyl acetate/n-heptane, 50% to 100%) to give a 1:1 mixture of 5-(2,4-dimethoxybenzyl)-7-(2-methoxy-4,6-dimethylpyridin-3-yl)-1-(tetrahydro-2H-pyran-4-yl)-1H-pyrazolo[4,3-c]quinolin-4(5H)-one and 5-(2,4-dimethoxybenzyl)-1-(tetrahydro-2H-pyran-4-yl)-1H-pyrazolo[4,3-c]quinolin-4(5H)-one (76 mg). The mixture (76 mg) was dissolved in TFA (1.5 mL), and the mixture was stirred at 65° C. for three hours. The reaction mixture was concentrated under reduced pressure. DCM and a saturated aqueous sodium bicarbonate solution were added to the resulting residue, followed by extraction with DCM. The organic layer was washed with brine and dried over sodium sulfate. The desiccant was removed by filtration, and the filtrate was concentrated under reduced pressure. The resulting residue was purified by silica gel column chromatography (ethyl acetate/n-heptane, 50% to 100%) to give the title compound (22 mg).

¹H-NMR (400 MHz, CDCl₃) δ (ppm): 2.10 (s, 3H), 2.15-2.23 (m, 2H), 2.47-2.59 (m, 2H), 2.48 (s, 3H), 3.65-3.73 (m, 2H), 3.86 (s, 3H), 4.20-4.26 (m, 2H), 5.01-5.10 (m, 1H), 6.74 (s, 1H), 720 (dd, J=8.4 Hz, 1.6 Hz, 1H), 7.27 (d, J=1.6 Hz, 1H), 8.01 (d, J=8.4 Hz, 1H), 8.30 (s, 1H), 10.01 (s, 1H).

ESI-MS m/z 405 [M+H]⁺

Example 5

Synthesis of 7-(2-methoxy-4,6-dimethylpyridin-3-yl)-1-(tetrahydro-2H-pyran-4-yl)-1H-pyrazolo[4,3-c]quinolin-4(5H)-one

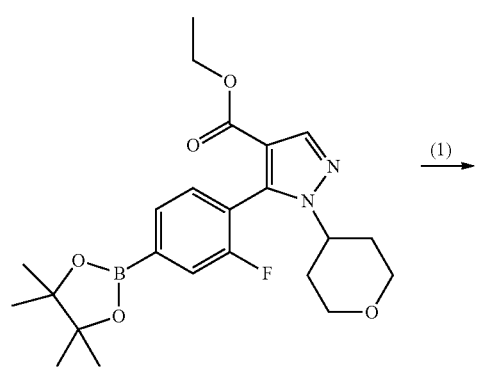

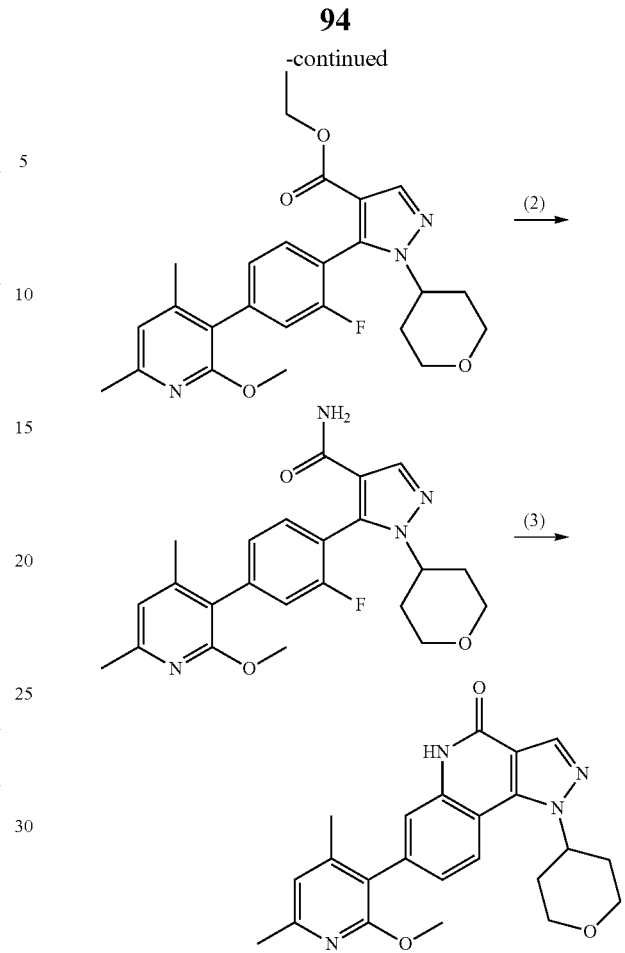

(1) Synthesis of ethyl 5-[2-fluoro-4-(2-methoxy-4,6-dimethylpyridin-3-yl)phenyl]-1-(tetrahydro-2H-pyran-4-yl)-1H-pyrazole-4-carboxylate Water (5 mL), 3-bromo-2-methoxy-4,6-dimethylpyridine obtained in Preparation Example 26 (784 mg), Pd(PPh₃)₄ (380 mg) and cesium carbonate (2.36 g) were added to a solution of ethyl 5-[2-fluoro-4-(4,4,5,5-tetramethyl-1,3,2-dioxaborolan-2-yl)phenyl]-1-(tetrahydro-2H-pyran-4-yl)-1H-pyrazole-4-carboxylate obtained in Preparation Example 3 (2.04 g) in 1,4-dioxane (20 mL), and the reaction mixture was reacted at 110° C. for two hours in a nitrogen atmosphere. The reaction mixture was returned to room temperature and then filtered through Celite™. The filtrate was concentrated under reduced pressure. Ethyl acetate (100 mL) and water (100 mL) were added to the residue. The aqueous layer was extracted with ethyl acetate (50 mL×2). The combined organic layers were dried over anhydrous magnesium sulfate and filtered, and the filtrate was concentrated under reduced pressure. The residue was purified by NH silica gel column chromatography (ethyl acetate/n-heptane, 10% to 23%). The title compound obtained by the same method (578 mg) was combined, and the combined product was purified again by silica gel column chromatography (ethyl acetate/n-heptane, 50% to 70%) to give the title compound (2.07 g).

¹H-NMR (400 MHz, CDCl₃) δ (ppm): 1.11-1.18 (m, 3H), 1.72-1.80 (m, 1H), 1.85-1.92 (m, 1H), 2.14 (s, 3H), 2.30-2.48 (m, 5H), 3.35-3.46 (m, 2H), 3.88 (s, 3H), 4.03-4.18 (m, 5H), 6.71-6.73 (m, 1H), 7.08-7.15 (m, 2H), 7.30-7.35 (m, 1H), 8.09-8.10 (m, 1H).

ESI-MS m/z 454 [M+1-1]⁺

(2) Synthesis of 5-[2-fluoro-4-(2-methoxy-4,6-dimethylpyridin-3-yl)phenyl]-1-(tetrahydro-2H-pyran-4-yl)-1H-pyrazole-4-carboxamide Ethyl 5-[2-fluoro-4-(2-methoxy-4,6-dimethylpyridin-3-yl)phenyl]-1-(tetrahydro-2H-pyran-4-yl]-1H-pyrazole-4-carboxylate (2.06 g) was added to ethanol (30 mL). After stilling the suspension at 60° C. for three minutes, a 5 N aqueous sodium hydroxide solution (3.6 mL) was added, and the mixture was stirred at 60° C. to 70° C. for one hour. The reaction mixture was cooled to room temperature and then concentrated under reduced pressure. Chloroform (20 mL) and 5 N hydrochloric acid (6 mL) were added to the residue. The precipitated solid was collected by filtration. Toluene was added to the resulting solid, and the mixture was concentrated under reduced pressure. The resulting residue was dissolved in DMF (15 mL). CDI (935 mg) was added to the solution, and the mixture was stirred at room temperature for one hour in a nitrogen atmosphere. 28% aqueous ammonia (1.4 mL) was added to the reaction mixture, and the mixture was stirred at room temperature for five hours. The reaction mixture was concentrated under reduced pressure. The residue was partitioned by adding chloroform (100 mL) and water (50 mL). The aqueous layer was extracted with chloroform (50 mL). The combined organic layers were washed with a saturated aqueous sodium bicarbonate solution (50 mL). The washings were extracted with chloroform (5 mL). The combined organic layers were dried over anhydrous magnesium sulfate and filtered. The filtrate was concentrated under reduced pressure. The residue was triturated by adding MTBE (5 mL). The precipitated solid was collected by filtration to give the title compound (1.5 g).

$^1$H-NMR (400 MHz, CDCl$_3$) δ (ppm): 1.68-1.78 (m, 1H), 1.86-1.95 (m, 1H), 2.13 (s, 3H), 2.29-2.45 (m, 2H), 2.47 (s, 3H), 3.32-3.47 (m, 2H), 3.69 (s, 3H), 4.00-4.15 (m, 3H), 5.29 (brs, 2H), 6.72 (s, 1H), 7.14-7.26 (m, 2H), 7.37-7.43 (m, 1H), 8.07 (s, 1H).

ESI-MS m/z 447 [M+Na]$^+$

(3) Synthesis of 7-(2-methoxy-4,6-dimethylpyridin-3-yl)-1-(tetrahydro-2H-pyran-4-yl)-1H-pyrazolo[4,3-c]quinolin-4(5H)-one KTB (655 mg) was added to a solution of 5-[2-fluoro-4-(2-methoxy-4,6-dimethylpyridin-3-yl)phenyl]-(tetrahydro-2H-pyran-4-yl)-1H-pyrazole-4-carboxamide (1.52 g) in NMP (15 mL), and the mixture was stirred at 90° C. for 30 minutes. KTB (40 mg) was added to the reaction mixture, and the mixture was stirred at 90° C. for 30 minutes. Further, KTB (40 mg) was added to the reaction mixture, and the mixture was stirred at 90° C. for 30 minutes. The reaction mixture was cooled to room temperature. Water (3 mL) was added to the reaction mixture. The solid was precipitated. After stirring for one hour directly, the precipitated solid was collected by filtration. The residue was washed with water (1 mL). The resulting solid was suspended in 1-propanol/water (9/1) (2 mL) and dissolved by heating under reflux. The solution was cooled to room temperature over one hour. The precipitated solid was collected by filtration. The resulting solid was dried under reduced pressure at 50° C. to give the title compound (872 mg). The instrumental data were identical to those of the title compound synthesized in Example 4.

Example 6

Synthesis of 7-(2-methoxy-4-methylpyridin-3-yl)-1-(tetrahydro-2H-pyran-4-yl)-1H-pyrazolo[4,3-c]quinolin-4(5H)-one

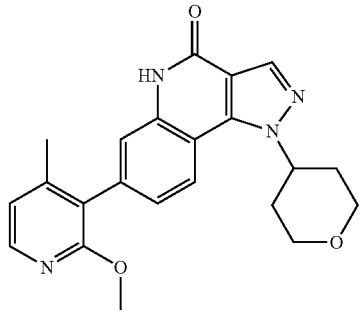 [SMILES: COc1nccc(C)c1-c1ccc2c(c1)[nH]c(=O)c1cnn(C3CCOCC3)c12]

5-(2,4-dimethoxybenzyl)-1-(tetrahydro-2H-pyran-4-yl)-7-(4,4,5,5-tetramethyl-1,3,2-dioxaborolan-2-yl)-1H-pyrazolo[4,3-c]quinolin-4(5H)-one (100 mg) obtained in Preparation Example 1(5) was dissolved in 1,4-dioxane (4 mL). 3-bromo-2-methoxy-4-methylpyridine obtained in Preparation Example 37 (2) (55.6 mg), Pd(PPh$_3$)$_4$ (10.6 mg), cesium carbonate (179 mg) and water (1 mL) were added to the solution, and the mixture was reacted using a microwave reactor at 130° C. for three hours. The reaction mixture was returned to room temperature and then partitioned by adding ethyl acetate. The organic layer was washed with brine and then dried over magnesium sulfate. The desiccant was removed by filtration, and the filtrate was concentrated under reduced pressure. The resulting residue was purified by silica gel column chromatography (ethyl acetate/n-heptane, 30% to 50% to 80%) to give 5-(2,4-dimethoxybenzyl)-7-(2-methoxy-4-methylpyridin-3-yl)-1-(tetrahydro-2H-pyran-4-yl)-1H-pyrazolo[4,3-c]quinolin-4(5H)-one (78 mg). The 5-(2,4-dimethoxybenzyl)-7-(2-methoxy-4-methylpyridin-3-yl)-1-(tetrahydro-2H-pyran-4-yl)-1H-pyrazolo[4,3-c]quinolin-4 (5H)-one (78 mg) was dissolved in TFA (1 mL), and the mixture was stirred at 65° C. for two hours. The reaction mixture was cooled to room temperature and then concentrated under reduced pressure. The resulting residue was neutralized by adding a saturated aqueous sodium bicarbonate solution. The aqueous solution was extracted with DCM. The organic layer was dried over anhydrous magnesium sulfate. The desiccant was removed by filtration. The filtrate was concentrated under reduced pressure. The resulting residue was purified by silica gel column chromatography (ethyl acetate/n-heptane, 50% to 70% to 80% to 100%) to give the title compound (30 mg).

$^1$H-NMR (400 MHz, CDCl$_3$) δ (ppm): 2.15 (s, 3H), 2.15-2.24 (m, 2H), 2.45-2.59 (m, 2H), 3.70 (t, J=12.0 Hz, 2H), 3.87 (s, 3H), 420-4.27 (m, 2H), 5.02-5.11 (m, 1H), 6.89 (d, J=5.1 Hz, 1H), 7.21 (dd, J=8.2 Hz, 1.6 Hz, 1H), 7.34 (d, J=1.6 Hz, 1H), 8.03 (d, J=8.6 Hz, 1H), 8.11 (d, J=5.1 Hz, 1H), 8.31 (s, 1H), 10.57 (brs, 1H).

ESI-MS m/z 391 [M+H]$^+$

The compounds of Examples 7 to 22 were synthesized as in Example 6.

TABLE 1

| Example | R² | NMR, Mass |
|---|---|---|
| 7 | 3,5-dimethyl-4-(methoxymethyl)phenyl (methoxymethyl at para) | ¹H-NMR (400 MHz, CDCl₃) δ (ppm): 2.06 (s, 6H), 2.18-2.24 (m, 2H), 2.49-2.60 (m, 2H), 3.47 (s, 3H), 3.70-3.82 (m, 2H), 4.22-4.30 (m, 2H), 4.46 (s, 2H), 4.97-5.13 (m, 1H), 7.13 (dd, J = 8.4 Hz, 1.6 Hz, 1H), 7.14 (s, 2H), 7.19 (d, J = 1.6 Hz, 1H), 8.03 (d, J = 8.4 Hz, 1H), 8.31 (s, 1H), 9.01 (s, 1H). ESI-MS m/z 418 [M + H]⁺ |
| 8 | 6-fluoro-2,4-dimethylpyridin-3-yl | ¹H-NMR (400 MHz, CDCl₃) δ (ppm): 2.12 (s, 3H), 2.15-2.24 (m, 2H), 2.26 (s, 3H), 2.47-2.61 (m, 2H), 3.64-3.77 (m, 2H), 4.21-4.30 (m, 2H), 5.02-5.13 (m, 1H), 6.76 (s, 1H), 7.12 (dd, J = 8.0 Hz, 1.2 Hz, 1H), 7.35 (d, J = 1.2 Hz, 1H), 8.07 (d, J = 8.0 Hz, 1H), 8.32 (s, 1H), 11.34 (brs, 1H). ESI-MS m/z 393 [M + H]⁺ |
| 9 | 4-chloro-2,6-dimethylpyridin-3-yl | ¹H-NMR (400 MHz, CDCl₃) δ (ppm): 2.16-2.14 (m, 2H), 2.36 (s, 3H), 2.47-2.60 (m, 2H), 2.60 (s, 3H), 3.65-3.77 (m, 2H), 4.21-4.28 (m, 2H), 5.01-5.12 (m, 1H), 7.18 (dd, J = 8.2 Hz, 1.6 Hz, 1H), 7.21 (s, 1H), 7.36 (d, J = 1.6 Hz, 1H), 8.07 (d, J = 8.6 Hz, 1H), 8.32 (s, 1H), 10.86 (brs, 1H). ESI-MS m/z 409 [M + H]⁺ |
| 10 | 5-chloro-2-methoxy-4-methylpyridin-3-yl | ¹H-NMR (400 MHz, CDCl₃) δ (ppm): 2.15-2.24 (m, 2H), 2.18 (s, 3H), 2.46-2.59 (m, 2H), 3.74-3.76 (m, 2H), 3.85 (s, 3H), 4.20-4.27 (m, 2H), 5.01-5.11 (m, 1H), 7.17 (dd, J = 8.2 Hz, 1.6 Hz, 1H), 7.26 (d, J = 1.6 Hz, 1H), 8.04 (d, J = 8.6 Hz, 1H), 8.18 (s, 1H), 8.31 (s, 1H), 10.22 (brs, 1H). ESI-MS m/z 425 [M + H]⁺ |
| 11 | 5-chloro-2-methoxy-4,6-dimethylpyridin-3-yl | ¹H-NMR (400 MHz, CDCl₃) δ (ppm): 2.15-2.23 (m, 2H), 2.17 (s, 3H), 2.48-2.59 (m, 2H), 2.61 (s, 3H), 3.63-3.75 (m, 2H), 3.84 (s, 3H), 4.20-4.27 (m, 2H), 5.01-5.11 (m, 1H), 7.14-7.20 (m, 1H), 7.27 (s, 1H), 8.02 (d, J = 8.2 Hz, 1H), 8.30 (s, 1H), 9.44 (brs, 1H). ESI-MS m/z 439 [M + H]⁺ |
| 12 | 5-fluoro-2-methoxy-4-methylpyridin-3-yl | ¹H-NMR (400 MHz, CDCl₃) δ (ppm): 2.11 (s, 3H), 2.15-2.24 (m, 2H), 2.46-2.59 (m, 2H), 3.64-3.76 (m, 2H), 3.85 (s, 3H), 4.20-4.29 (m, 2H), 5.00-5.12 (m, 1H), 7.19 (d, J = 9.0 Hz, 1H), 7.31 (s, 1H), 8.02 (s, 1H), 8.05 (d, J = 9.0 Hz, 1H), 8.31 (s, 1H), 10.35 (s, 1H). ESI-MS m/z 409 [M + H]⁺ |
| 13 | 6-cyano-2,4-dimethylpyridin-3-yl | ¹H-NMR (400 MHz, CDCl₃) δ (ppm): 2.15 (s, 3H), 2.15-2.25 (m, 2H), 2.36 (s, 3H), 2.48-2.62 (m, 2H), 3.65-3.77 (m, 2H), 4.20-4.27 (m, 2H), 5.01-5.11 (m, 1H), 7.11 (dd, J = 8.4 Hz, 1.5 Hz, 1H), 7.24 (d, J = 1.5 Hz, 1H), 7.54 (s, 1H), 8.11 (d, J = 8.4 Hz, 1H), 8.32 (s, 1H), 10.45 (s, 1H). ESI-MS m/z 400 [M + H]⁺ |
| 14 | 2,6-dimethoxy-4-methylpyrimidin-5-yl | ¹H-NMR (400 MHz, CDCl₃) δ (ppm): 2.15-2.24 (m, 2H), 2.28 (s, 3H), 2.47-2.59 (m, 2H), 3.64-3.76 (m, 2H), 3.93 (s, 3H), 4.06 (s, 3H), 4.20-4.28 (m, 2H), 5.02-5.11 (m, 1H), 7.20 (dd, J = 8.2 Hz, 1.6 Hz, 1H), 7.32 (d, J = 1.6 Hz, 1H), 8.02 (d, J = 8.6 Hz, 1H), 8.31 (s, 1H), 10.36 (s, 1H). ESI-MS m/z 422 [M + H]⁺ |

TABLE 1-continued

| Example | R² | NMR, Mass |
|---|---|---|
| 15 | 2-methoxy-3,5-dimethylpyridin-4-yl | ¹H-NMR (400 MHz, CDCl₃) δ (ppm): 1.94 (s, 3H), 1.96 (s, 3H), 2.15-2.26 (m, 2H), 2.47-2.61 (m, 2H), 3.66-3.76 (m, 2H), 4.01 (s, 3H), 4.20-4.29 (m, 2H), 5.01-5.11 (m, 1H), 7.09 (dd, J = 8.3 Hz, 1.4 Hz, 1H), 7.19 (d, J = 1.4 Hz, 1H), 7.95 (s, 1H), 8.05 (d, J = 8.3 Hz, 1H), 8.32 (s, 1H), 10.26 (brs, 1H). ESI-MS m/z 405 [M + H]⁺ |
| 16 | 6-(difluoromethyl)-2,4-dimethylpyridin-3-yl | ¹H-NMR (400 MHz, CDCl₃) δ (ppm): 2.16 (s, 3H), 2.17-2.26 (m, 2H), 2.35 (s, 3H), 2.47-2.61 (m, 2H), 3.66-3.76 (m, 2H), 4.20-4.29 (m, 2H), 5.01-5.11 (m, 1H), 6.50-6.80 (m, 1H), 7.13 (dd, J = 8.4 Hz, 1.6 Hz, 1H), 7.24 (d, J = 1.6 Hz, 1H), 7.46 (s, 1H), 8.09 (d, J = 8.4 Hz, 1H), 8.32 (s, 1H), 10.28 (brs, 1H). ESI-MS m/z 425 [M + H]⁺ |
| 17 | 6-(fluoromethyl)-2-methoxy-4-methylpyridin-3-yl | ¹H-NMR (400 MHz, CDCl₃) δ (ppm): 2.13-2.24 (m, 5H), 2.46-2.60 (m, 2H), 3.64-3.75 (m, 2H), 3.85 (s, 3H), 4.18-4.28 (m, 2H), 4.99-5.11 (m, 1H), 5.32-5.50 (m, 2H), 7.03 (s, 1H), 7.16 (d, J = 1.5 Hz, 1H), 7.19 (dd, J = 8.3 Hz, 1.5 Hz, 1H), 8.03 (d, J = 8.3 Hz, 1H), 8.30 (s, 1H), 8.91 (s, 1H). ESI-MS m/z 423 [M + H]⁺ |
| 18 | 6-(difluoromethoxy)-2,4-dimethylpyridin-3-yl | ¹H-NMR (400 MHz, CDCl₃) δ (ppm): 2.08 (s, 3H), 2.15-2.26 (m, 5H), 2.47-2.60 (m, 2H), 3.66-3.76 (m, 2H), 4.20-4.29 (m, 2H), 5.00-5.10 (m, 1H), 6.71 (s, 1H), 7.11 (dd, J = 8.4 Hz, 1.5 Hz, 1H), 7.16 (d, J = 1.5 Hz, 1H), 7.37-7.76 (m, 1H), 8.06 (d, J = 8.4 Hz, 1H), 8.31 (s, 1H), 9.71 (brs, 1H). ESI-MS m/z 441 [M + H]⁺ |
| 19 | 6-(fluoromethyl)-2,4-dimethylpyridin-3-yl | ¹H-NMR (400 MHz, CDCl₃) δ (ppm): 2.13 (s, 3H), 2.17-2.26 (m, 2H), 2.31 (s, 3H), 2.47-2.62 (m, 2H), 3.65-3.77 (m, 2H), 4.20-4.30 (m, 2H), 5.01-5.13 (m, 1H), 5.43-5.58 (m, 2H), 7.14 (dd, J = 8.4 Hz, 1.6 Hz, 1H), 7.24 (d, J = 1.6 Hz, 1H), 7.28 (s, 1H), 8.07 (d, J = 8.4 Hz, 1H), 8.32 (s, 1H), 10.24 (brs, 1H). ESI-MS m/z 407 [M + H]⁺ |
| 20 | 2-(fluoromethyl)-4,6-dimethylpyridin-3-yl | ¹H-NMR (400 MHz, CDCl₃) δ (ppm): 2.12 (s, 3H), 2.16-2.24 (m, 2H), 2.46-2.60 (m, 2H), 2.64 (s, 3H), 3.66-3.76 (m, 2H), 4.20-4.29 (m, 2H), 5.01-5.11 (m, 1H), 5.11-5.26 (m, 2H), 7.16-7.18 (m, 1H), 7.18-7.22 (m, 1H), 7.30 (d, J = 1.8 Hz, 1H), 8.05 (d, J = 8.4 Hz, 1H), 8.31 (s, 1H), 10.39 (brs, 1H). ESI-MS m/z 407 [M + H]⁺ |

TABLE 1-continued

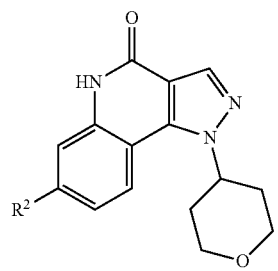

| Example | R² | NMR, Mass |
|---|---|---|
| 21 | ![structure] | ¹H-NMR (400 MHz, CDCl₃) δ (ppm): 2.12 (s, 3H), 2.16-2.24 (m, 2H), 2.47-2.60 (m, 2H), 2.65 (s, 3H), 3.66-3.75 (m, 2H), 4.21-4.28 (m, 2H), 5.01-5.10 (m, 1H), 6.29-6.57 (m, 1H), 7.18 (dd, J = 8.4 Hz, 1.6 Hz, 1H), 7.22 (d, J = 1.6 Hz, 1H), 7.25-7.26 (m, 1H), 8.05 (d, J = 8.4 Hz, 1H), 8.31 (s, 1H), 9.58 (s, 1H).<br>ESI-MS m/z 425 [M + H]⁺ |
| 22 | ![structure] | ¹H-NMR (400 MHz, CDCl₃) δ (ppm): 2.15-2.24 (m, 2H), 2.26 (s, 3H), 2.47-2.60 (m, 2H), 3.66-3.76 (m, 2H), 4.00 (s, 3H), 4.19-4.30 (m, 2H), 4.98-5.14 (m, 3H), 6.81 (s, 1H), 7.14 (dd, J = 8.4 Hz, 1.6 Hz, 1H), 7.21 (d, J = 1.6 Hz, 1H), 8.04 (d, J = 8.4 Hz, 1H), 8.31 (s, 1H), 9.91 (brs, 1H).<br>ESI-MS m/z 423 [M + H]⁺ |

Example 23

Synthesis of 7-(2-ethoxy-4-methylpyridin-3-yl)-1-(tetrahydro-2H-pyran-4-yl)-1H-pyrazolo[4,3-c]quinolin-4(5H)-one

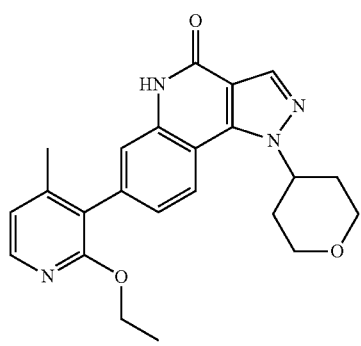 [SMILES: CCOc1nccc(C)c1-c1ccc2c(c1)[nH]c(=O)c1cnn(C3CCOCC3)c12]

[5-(2,4-dimethoxybenzyl)-4-oxo-1-(tetrahydro-2H-pyran-4-yl)-4,5-dihydro-1H-pyrazolo[4,3-c]quinolin-7-yl]boronic acid obtained in Preparation Example 1 (70 mg) was dissolved in 1,4-dioxane (4 mL). 3-bromo-2-ethoxy-4-methylpyridine obtained in Preparation Example 44 (49 mg), Pd(PPh₃)₄ (8.7 mg), cesium carbonate (148 mg) and water (1 mL) were added to the solution, and the mixture was reacted using a microwave reactor at 130° C. for two hours. The reaction mixture was returned to room temperature and then partitioned by adding ethyl acetate. The organic layer was washed with brine and then dried over magnesium sulfate. The desiccant was removed by filtration, and the filtrate was concentrated under reduced pressure. The resulting residue was purified by silica gel column chromatography (ethyl acetate/n-heptane, 30% to 50% to 80%) to give 5-(2,4-dimethoxybenzyl)-7-(2-ethoxy-4-methylpyridin-3-yl)-1-(tetrahydro-2H-pyran-4-yl)-1H-pyrazolo[4,3-c]quinolin-4(5H)-one (55 mg). The 5-(2,4-dimethoxybenzyl)-7-(2-ethoxy-4-methylpyridin-3-yl)-1-(tetrahydro-2H-pyran-4-yl)-1H-pyrazolo[4,3-c]quinolin-4(5H)-one (55 mg) was dissolved in TFA (1 mL), and the mixture was stirred at 65° C. for two hours. The reaction mixture was cooled to room temperature and then concentrated under reduced pressure. The resulting residue was neutralized by adding a saturated aqueous sodium bicarbonate solution. The aqueous solution was extracted with DCM. The organic layer was dried over anhydrous magnesium sulfate. The desiccant was removed by filtration. The filtrate was concentrated under reduced pressure. The resulting residue was purified by silica gel column chromatography (ethyl acetate/n-heptane, 50% to 70% to 80% to 100%) to give the title compound (17 mg).

¹H-NMR (400 MHz, CDCl₃) δ (ppm): 1.25 (t, J=7.5 Hz, 3H), 2.15 (s, 3H), 2.15-2.25 (m, 2H), 2.46-2.60 (m, 2H), 3.65-3.77 (m, 2H), 4.20-4.29 (m, 2H), 4.35 (q, J=7.5 Hz, 2H), 5.03-5.12 (m, 1H), 6.86 (d, J=5.5 Hz, 1H), 721 (dd, J=1.6 Hz, 8.2 Hz, 1H), 7.35 (s, 1H), 8.01 (d, J=8.2 Hz, 1H), 8.08 (d, J=5.5 Hz, 1H), 8.30 (s, 1H), 10.51 (brs, 1H).

ESI-MS m/z 405 [M+H]⁺

The compound of Example 24 was synthesized as in Example 23.

TABLE 2

| Example | R² | NMR, Mass |
|---|---|---|
| 24 | (4-methyl-2-methoxy-pyridin-3-yl)methyl, F-substituted | ¹H-NMR (400 MHz, CDCl₃) δ (ppm): 2.10 (s, 3H), 2.15-2.25 (m, 2H), 2.47-2.60 (m, 2H), 3.66-3.76 (m, 2H), 4.01 (s, 3H), 4.19-4.29 (m, 2H), 5.00-5.19 (m, 3H), 6.74 (s, 1H), 7.16-7.23 (m, 2H), 8.04 (d, J = 8.2 Hz, 1H), 8.31 (s, 1H), 9.45 (brs, 1H). ESI-MS m/z 423 [M + H]⁺ |

Example 25

Synthesis of (+)-7-(2-methoxy-3,5-dimethylpyridin-4-yl)-1-(tetrahydrofuran-3-yl)-1H-pyrazolo[4,3-c]quinolin-4(5H)-one and (−)-7-(2-methoxy-3,5-dimethylpyridin-4-yl)-1-(tetrahydrofuran-3-yl)-1H-pyrazolo[4,3-c]quinolin-4(5H)-one

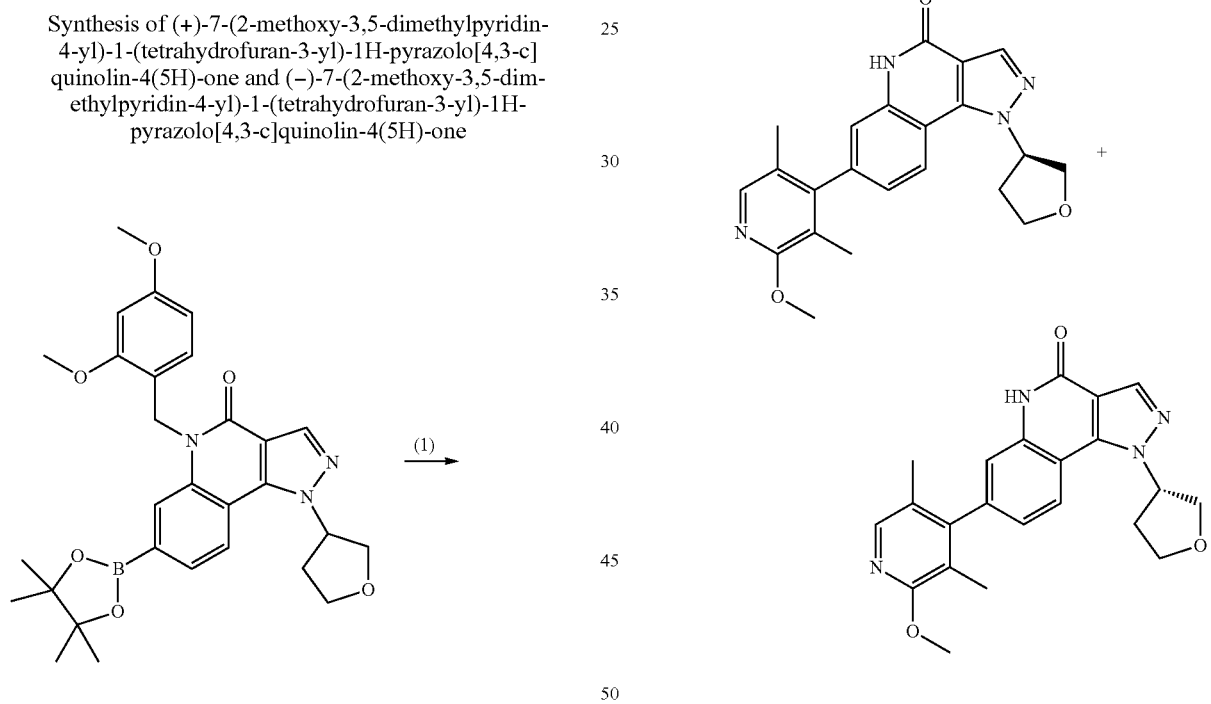

(1) Synthesis of (±)-7-(2-methoxy-3,5-dimethylpyridin-4-yl)-1-(tetrahydrofuran-3-yl)-1H-pyrazolo[4,3-c]quinolin-4(5H)-one A mixture of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one obtained in Preparation Example 5 (219 mg), 4-bromo-2-methoxy-3,5-dimethylpyridine obtained in Preparation Example 28 (134 mg), Pd(PPh₃)₄ (23.8 mg) and cesium carbonate (403 mg) was reacted in a mixed solvent of 1,4-dioxane (8 mL) and water (2 mL) using a microwave reactor at 130° C. for 70 minutes. The reaction mixture was cooled to mom temperature and then directly purified by silica gel column chromatography (ethyl acetate/n-heptane, 10% to 90%). The resulting coupling product was dissolved in TFA (4 mL), and the mixture was stirred at 70° C. for two hours. The reaction mixture was cooled to room temperature and then concentrated under reduced pressure. A saturated aqueous sodium bicarbonate solution was added to the residue, followed by extraction with ethyl acetate. The organic layer was concentrated under reduced pressure, and the residue was purified by silica gel column chromatography (DCM, 100%, then ethyl acetate/n-heptane, 50% to 100%) to give the title compound (78 mg).

ESI-MS m/z 391 [M+H]+

(2) Synthesis of (+)-7-(2-methoxy-3,5-dimethylpyridin-4-yl)-1-(tetrahydrofuran-3-yl)-1H-pyrazolo[4,3-c]quinolin-4(5H)-one and (−)-7-(2-methoxy-3,5-dimethylpyridin-4-yl)-1-(tetrahydrofuran-3-yl)-1H-pyrazolo[4,3-c]quinolin-4(5H)-one (±)-7-(2-Methoxy-3,5-dimethylpyridin-4-yl)-1-(tetrahydrofuran-3-yl)-1H-pyrazolo[4,3-c]quinolin-4(5H)-one was analyzed by a chiral column [AD-H (0.46 cm Φ×15 cm), mobile phrase; 100% ethanol] to identify (+)-form at 7.8 min and (−)-form at 9.7 min and confirm that optical resolution is possible. (±)-7-(2-Methoxy-3,5-dimethylpyridin-4-yl)-1-(tetrahydrofuran-3-yl)-1H-pyrazolo[4,3-c]quinolin-4(5H)-one (78 mg) was dissolved in a mixed solvent of ethanol (121a) and methanol (12 mL), and the solution was filtered through a cotton plug. The filtrate was optically resolved by chiral column chromatography [chiral column: AD-H column, elution solvent: 100% ethanol, flow rate: 10 mL/min, elution time: 80 minutes/elution, injection: 2 mL/injection, short retention time: (+)-form, long retention time: (−)-form] to give 26.4 mg of a (+)-form and 25.2 mg of a (−)-form of the title compound.

$^1$H-NMR (400 MHz, CDCl$_3$) δ (ppm): 1.92-1.94 (m, 3H), 1.94-1.96 (m, 3H), 2.55-2.66 (m, 1H), 2.76-2.86 (m, 1H), 4.00 (s, 3H), 4.09-4.16 (m, 1H), 4.24-4.37 (m, 2H), 4.39-4.45 (m, 1H), 5.61-5.68 (m, 1H), 7.04 (dd, J=1.5 Hz, 1H), 7.08 (dd, J-1.5 Hz, 8.3 Hz, 1H), 7.94 (s, 1H), 8.13 (d, Hz, 1H), 8.31 (s, 1H), 8.86 (s, 1H).

ESI-MS m/z 391 [M+H]+

Example 26

Synthesis of (S)-7-(2-methoxy-3,5-dimethylpyridin-4-yl)-1-(tetrahydrofuran-3-yl)-1H-pyrazolo[4,3-c]quinolin-4(5H)-one

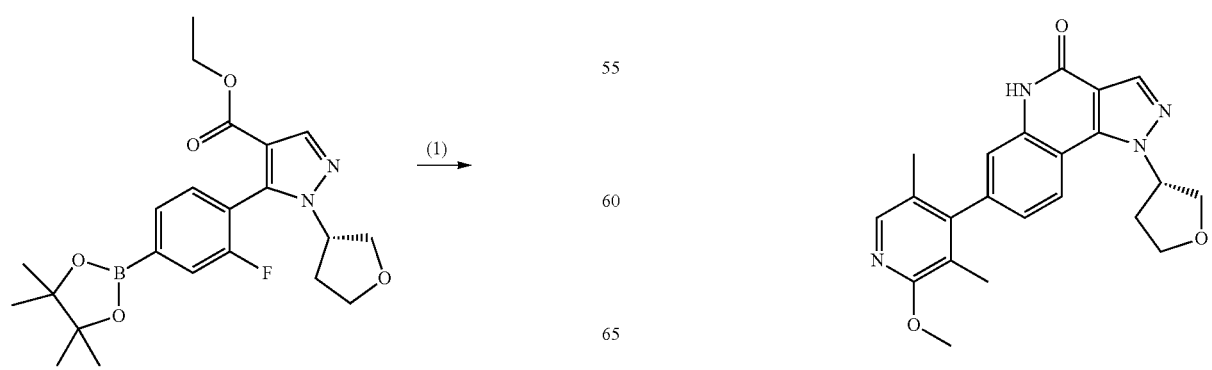

(1) Synthesis of ethyl 5-[2-fluoro-4-(2-methoxy-3,5-dimethylpyridin-4-yl)phenyl]-1-[(S)-tetrahydrofuran-3-yl]-1H-pyrazole-4-carboxylate Water (170 mL), 4-iodo-2-methoxy-3,5-dimethylpyridine obtained in Preparation Example 29(3) (35.6 g), Pd(PPh$_3$)$_4$ (6.52 g) and cesium carbonate (110 g) were added to a solution of ethyl 5-[2-fluoro-4-(4,4,5,5-tetramethyl-1,3,2-dioxaborolan-2-yl)phenyl]-1-[(S)-tetrahydrofuran-3-yl]-1H-pyrazole-4-carboxylate obtained in Preparation Example 6 (51.9 g) in 1,4-dioxane (500 mL), and the reaction mixture was reacted at 110° C. for six hours. The reaction mixture was returned to room temperature, and the organic layer was then separated. The organic layer was concentrated under reduced pressure. The aqueous layer, ethyl acetate (700 m) and water (100 mL) were added to the resulting residue, and the organic layer was separated. The aqueous layer was re-extracted with ethyl acetate (50 mL). The combined organic layers were sequentially washed with water and brine, dried over anhydrous magnesium sulfate, filtered and concentrated under reduced pressure. The residue was purified by NH silica gel column chromatography (ethyl acetate/n-heptane, 5% to 14%). The product was then purified again by NH silica gel column chromatography (ethyl acetate/n-heptane, 2% to 10%) to give the title compound (435 g).

$^1$H-NMR (400 MHz, CDCl$_3$) δ (ppm): 1.16 (t, J=7.2 Hz, 1.5H), 1.17 (t, J=7.2 Hz, 1.5H), 1.97 (s, 1.5H), 1.98 (s, 1.5H), 1.99 (s, 1.5H), 2.00 (s, 1.5H), 225-2.55 (m, 2H), 3.92-4.27 (m, 6H), 3.99 (s, 1.5H), 4.00 (s, 1.5H), 4.65-4.75 (m, 1H), 7.01 (d, J=9.2 Hz, 1H), 7.05 (d, J=7.2 Hz, 1H), 7.39 (t, J=7.2 Hz, 0.5H), 7.45 (t, J=72 Hz, 0.5H), 7.93 (s, 1H), 8.12 (s, 1H).

ESI-MS m/z 440 [M+H]$^+$

(2) Synthesis of 5-[2-fluoro-4-(2-methoxy-3,5-dimethylpyridin-4-yl)phenyl]-1-[(S)-tetrahydrofuran-3-yl]-1H-pyrazole-4-carboxylic acid A 5 N aqueous sodium hydroxide solution (79 mL) was added to a solution of ethyl 5-[2-fluoro-4-(2-methoxy-3,5-dimethylpyridin-4-yl)phenyl]-1-[(S)-tetrahydrofuran-3-yl]-1H-pyrazole-4-carboxylate (43.2 g) in ethanol (574 mL) at mom temperature, and the reaction mixture was stirred at 60° C. for two hours and 10 minutes. The reaction mixture was cooled to room temperature and then concentrated to half volume under reduced pressure. Water (300 mL) was added to the residue, and ethanol was distilled off under reduced pressure. MTBE (130 mL) was added to the resulting residue, and the aqueous layer was separated. The organic layer was extracted with water (30 mL). The combined aqueous layers were made acidic with 5 N hydrochloric acid (78 mL) under ice-cooling and extracted with ethyl acetate twice. The combined organic layers were dried over anhydrous magnesium sulfate, filtered and concentrated under reduced pressure to give the title compound (39.0 g).

$^1$H-NMR (400 MHz, CDCl$_3$) δ (ppm): 1.91 (s, 1.5H), 1.94 (s, 1.5H), 1.98 (s, 1.5H), 2.01 (s, 1.5H), 2.25-2.56 (m, 2H), 3.92-4.17 (m, 3H), 3.96 (s, 1.5H), 4.00 (s, 1.5H), 4.23 (dd, J=16.0, 8.0 Hz, 1H), 4.65-4.77 (m, 1H), 6.99 (brd, J=10.0 Hz, 1H), 7.03 (dr d, J=7.6 Hz, 1H), 7.38 (t, J=7.6 Hz, 0.5H), 7.44 (t, J=7.6 Hz, 0.5H), 7.90 (s, 0.5H), 7.94 (s, 0.5H), 8.14 (s, 1H).

ESI-MS m/z 434 [M+Na]$^+$

(3) Synthesis of 5-[2-fluoro-4-(2-methoxy-3,5-dimethylpyridin-4-yl)phenyl]-1-[(S)tetrahydrofuran-3-yl]-1H-pyrazole-4-carboxamide CDI (21.4 g) was added at one time to a solution of 5-[2-fluoro-4-(2-methoxy-3,5-dimethylpyridin-4-yl)phenyl]-1-[(S)-tetrahydrofuran-3-yl]-1H-pyrazole-4-carboxylic acid (38.7 g) in DMF (290 mL) at room temperature, and the mixture was stirred at room temperature for 95 minutes. 28% aqueous ammonia (95 mL) was added to the reaction mixture, and the mixture was stirred at room temperature for 35 minutes. 28% aqueous ammonia (95 mL) was added again to the reaction mixture, and the mixture was stirred at room temperature for 90 minutes. The reaction mixture was concentrated under reduced pressure. Chloroform (250 mL) and water (80 mL) were added to the resulting residue, and the organic layer was separated. The aqueous layer was re-extracted with chloroform (50 mL). The combined organic layers were sequentially washed with a saturated aqueous ammonium chloride solution (60 mL×3) and brine, dried over anhydrous magnesium sulfate and filtered. The filtrate was passed through a silica pad (NH-silica gel). The filtrate was concentrated under reduced pressure to give the title compound (37.2 g).

$^1$H-NMR (400 MHz, CDCl$_3$) δ (ppm): 1.98 (brs, 6H), 2.24-2.60 (m, 2H), 3.90-4.20 (m, 3H), 3.99 (s, 3H), 4.23 (dd, J=16.0, 8.0 Hz, 1H), 4.62-4.71 (m, 1H), 5.32 (brs, 2H), 7.05 (brd, J=10.0 Hz, 1H), 7.10 (dd, J=7.6, 1.2 Hz, 1H), 7.42-7.56 (m, 1H), 7.94 (brs, 1H), 8.03 (s, 1H).

ESI-MS m/z 411 [M+H]$^+$

(4) Synthesis of (S)-7-(2-methoxy-3,5-dimethylpyridin-4-yl)-1-(tetrahydrofuran-3-yl)-1H-pyrazolo[4,3-c]quinolin-4(5H)-one Sodium hydroxide powder (9.43 g) was added at one time to a solution of 5-[2-fluoro-4-(2-methoxy-3,5-dimethylpyridin-4-yl)phenyl]-1-[(S)-tetrahydrofuran-3-yl]-1H-pyrazole-4-carboxamide (37.2 g) in DMSO (186 mL) at room temperature. The reaction mixture was stirred at the same temperature for 50 minutes and then at 70° C. for 45 minutes. Under water-cooling, water (600 mL) was added dropwise to the reaction mixture, and then acetic acid (13.5 mL) was added dropwise. The precipitated powder was collected by filtration. The collected subject was washed with water and MTBE and then dried under reduced pressure to give the title compound (34.0 g).

The $^1$H-NMR and ESI-MS of the title compound were identical to those of Example 25. The title compound showed a (−) optical rotation and had >99% ee of an optical purity [AD-H, 100% ethanol, retention time: 9.7 min].

Example 27

Synthesis of (S)-7-(2-methoxy-3,5-dimethylpyridin-4-yl)-1-(tetrahydrofuran-3-yl)-1H-pyrazolo[4,3-c]quinolin-4(5H)-one

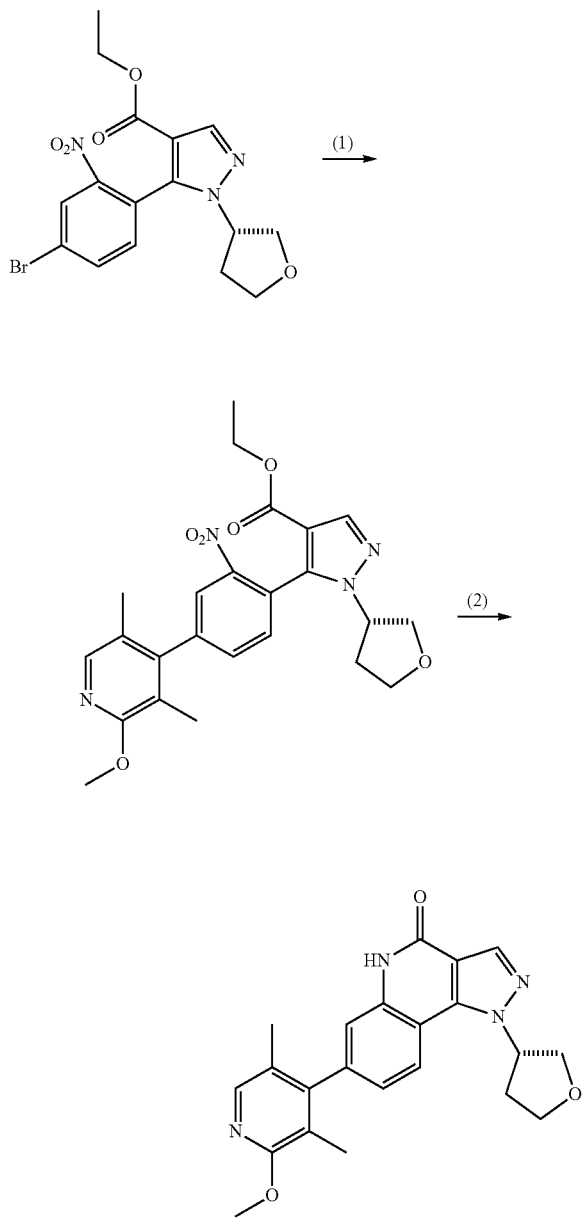

(1) Synthesis of ethyl 5-[4-(2-methoxy-3,5-dimethylpyridin-4-yl)-2-nitrophenyl]-1-[(S)-tetrahydrofuran-3-yl]-1H-pyrazole-4-carboxylate Ethyl 5-(4-bromo-2-nitrophenyl)-1-[(S)-tetrahydrofuran-3-yl]-1H-pyrazole-4-carboxylate obtained in Preparation Example 7(1) (1.5 g) was dissolved in toluene (50 mL). (2-methoxy-3,5-dimethylpyridin-4-yl)boronic acid (728 mg) obtained in Preparation Example 29, bis(triphenylphosphine)dichloropalladium(II) (128 mg), sodium carbonate (1.16 g) and water (10 mL) were added to the solution, and the mixture was reacted at 100° C. for four hours. After cooling the reaction mixture to room temperature, ethyl acetate (50 mL) and water (50 mL) were added, and the reaction mixture was filtered through Celite™. The filtrate was partitioned by adding ethyl acetate (100 mL). The organic layer was washed with brine and dried over anhydrous magnesium sulfate. The desiccant was removed by filtration, and the filtrate was concentrated under reduced pressure. Ethanol (2 mL) was added to the resulting residue which was dissolved with heating under reflux. The solution was cooled with ice water. After one hour, the precipitated solid was collected by filtration to give the title compound (750 mg). The filtrate was concentrated under reduced pressure. Ethanol (1 mL) was added to the resulting residue which was dissolved with heating under reflux. The solution was cooled with ice water. After one hour, the precipitated solid was collected by filtration to give the title compound (450 mg).

$^1$H-NMR (400 MHz, CDCl$_3$) δ (ppm): 1.07-1.14 (m, 3H), 1.98 (d, J=3.9 Hz, 3H), 2.01 (d, J=3.9 Hz, 3H), 2.21-2.40 (m, 1H), 2.47-2.58 (m, 1H), 3.92-4.00 (m, 1H), 4.00 (s, 3H), 4.02-4.18 (m, 4H), 4.23 (q, J=7.7 Hz, 1H), 4.56-4.66 (m, 1H), 7.43 (d, J=8.2 Hz, 0.67H), 7.48 (d, J=82 Hz, 0.33H), 7.51-7.56 (m, 1H), 7.96-8.02 (m, 2H), 8.08 (s, 1H).

ESI-MS m/z 467 [M+H]$^+$ (2) Synthesis of (S)-7-(2-methoxy-3,5-dimethylpyridin-4-yl)-1-(tetrahydrofuran-3-yl)-1H-pyrazolo[4,3-c]quinolin-4(5H)-one Ethyl 5-[4-(2-methoxy-3,5-dimethylpyridin-4-yl)-2-nitrophenyl]-1-[(S)-tetrahydrofuran-3-yl]-1H-pyrazole-4-carboxylate (1.1 g) was suspended in ethanol (13 mL) Iron powder (280 mg) and a saturated aqueous ammonium chloride solution (3 mL) were added to the solution, and the mixture was stirred at 100° C. for 3.5 hours. The reaction mixture was cooled to room temperature and then filtered through Celite™. The filtrate was partitioned by adding ethyl acetate (100 mL) and water (50 mL). The organic layer was washed with brine and dried over anhydrous magnesium sulfate. The desiccant was removed by filtration, and the filtrate was concentrated under reduced pressure. The resulting residue was dissolved in acetic acid (2 mL), followed by stirring at 50° C. After four hours, the reaction mixture was cooled to mom temperature, and water (20 mL) was added. The precipitated solid was collected by filtration. 1-propanol (10 ml) and water (1.5 mL) were added to the resulting solid which was dissolved with heating under reflux. The solution was cooled with ice water. After one hour, the precipitated solid was collected by filtration and washed with MTBE (5 mL) to give the title compound (780 mg).

The compounds of Examples 28 to 32 were synthesized as in Example 25.

TABLE 3

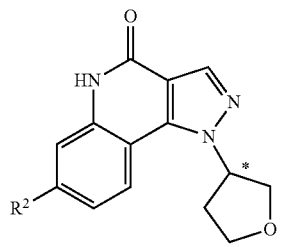

| Example<br>Chiral column<br>Mobile phase<br>Optical rotation (+/−)<br>Retention time (min) | R² | NMR, Mass |
|---|---|---|
| Example 28<br>OD-H<br>100% ethanol<br>(+): 7.0<br>(−): 6.0 | 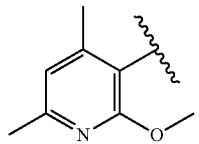 | ¹H-NMR (400 MHz, CDCl₃) δ (ppm): 2.10 (s, 3H), 2.48 (s, 3H), 2.54-2.65 (m, 1H), 2.75-2.84 (m, 1H), 3.86 (s, 3H), 4.08-4.16 (m, 1H), 4.22-4.28 (m, 1H), 4.28-4.36 (m, 1H), 4.38-4.44 (m, 1H), 5.59-5.69 (m, 1H), 6.73 (s, 1H), 7.18 (dd, J = 8.4 Hz, 1.6 Hz, 1H), 7.23 (d, J = 1.6 Hz, 1H), 8.08 (d, J = 8.4 Hz, 1H), 8.29 (s, 1H), 9.60 (brs, 1H).<br>ESI-MS m/z 391 [M + H]⁺ |
| Example 29<br>OD-H<br>100% ethanol<br>(+): 8.5<br>(−): 6.2 | 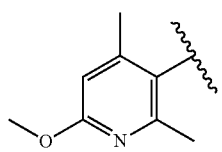 | ¹H-NMR (400 MHz, CDCl₃) δ (ppm): 2.03 (s, 3H), 2.22 (s, 3H), 2.55-2.67 (m, 1H), 2.76-2.86 (m, 1H), 3.97 (s, 3H), 4.09-4.17 (m, 1H), 4.23-4.29 (m, 1H), 4.30-4.37 (m, 1H), 4.39-4.46 (m, 1H), 5.62-5.69 (m, 1H), 6.54 (s, 1H), 7.12 (dd, J = 8.4 Hz, 1.6 Hz, 1H), 7.21 (d, J = 1.6 Hz, 1H), 8.10 (d, J = 8.4 Hz, 1H), 8.31 (s, 1H), 10.00 (brs, 1H).<br>ESI-MS m/z 391 [M + H]⁺ |
| Example 30<br>IA<br>100% ethanol<br>(+): 9.0<br>(−): 9.7 | 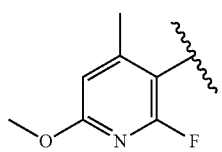 [SMILES: *c1c(C)cc(OC)nc1F] | ¹H-NMR (400 MHz, CDCl₃) δ (ppm): 2.10 (s, 3H), 2.56-2.67 (m, 1H), 2.76-2.86 (m, 1H), 4.01 (s, 3H), 4.08-4.17 (m, 1H), 4.23-4.37 (m, 2H), 4.39-4.46 (m, 1H), 5.01-5.20 (m, 2H), 5.61-5.69 (m, 1H), 6.74 (s, 1H), 7.15-7.22 (m, 1H), 7.27-7.30 (m, 1H), 8.11 (d, J = 8.2 Hz, 1H), 8.31 (s, 1H), 10.11-10.25 (m, 1H).<br>ESI-MS m/z 409 [M + H]⁺ |
| Example 31<br>AD-H<br>100% ethanol<br>(+): 6.0<br>(−): 7.1 | 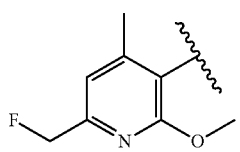 | ¹H-NMR (400 MHz, CDCl₃) δ (ppm): 2.17 (s, 3H), 2.54-2.65 (m, 1H), 2.76-2.85 (m, 1H), 3.85 (s, 3H), 4.08-4.16 (m, 1H), 4.23-4.29 (m, 1H), 4.29-4.36 (m, 1H), 4.38-4.44 (m, 1H), 5.33-5.49 (m, 2H), 5.61-5.68 (m, 1H), 7.03 (s, 1H), 7.18 (d, J = 8.5 Hz, 1H), 7.21 (s, 1H), 8.10 (d, J = 8.5 Hz, 1H), 8.30 (s, 1H), 9.41 (brs, 1H).<br>ESI-MS m/z 409 [M + H]⁺ |
| Example 32<br>AD-H<br>100% ethanol<br>(+): 5.8<br>(−): 7.5 | 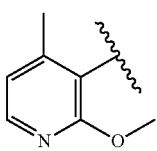 [SMILES: *c1c(C)ccnc1OC] | ¹H-NMR (400 MHz, CDCl₃) δ (ppm): 2.15 (s, 3H), 2.54-2.66 (m, 1H), 2.76-2.85 (m, 1H), 3.85 (s, 3H), 4.12 (td, J = 8.4 Hz, 4.7 Hz, 1H), 4.27 (q, J = 7.8 Hz, 1H), 4.33 (dd, J = 7.8 Hz, 1.6 Hz, 1H), 4.42 (dd, J = 8.4 Hz, 3.4 Hz, 1H), 5.61-5.69 (m, 1H), 6.89 (d, J = 5.5 Hz, 1H), 7.19 (dd, J = 8.4 Hz, 1.4 Hz, 1H), 7.33 (d, J = 1.4 Hz, 1H), 8.08-8.14 (m, 2H), 8.30 (s, 1H), 10.49 (brs, 1H).<br>ESI-MS m/z 377 [M + H]⁺ |

Example 33

Synthesis of (+)-7-(2,6-dimethylphenyl)-1-(tetrahydrofuran-3-yl)-1H-pyrazolo[4,3-c]quinolin-4(5H)-one and (−)-7-(2-methoxy-4-methylpyridin-3-yl)-1-(tetrahydrofuran-3-yl)-1H-pyrazolo[4,3-c]quinolin-4(5H)-one

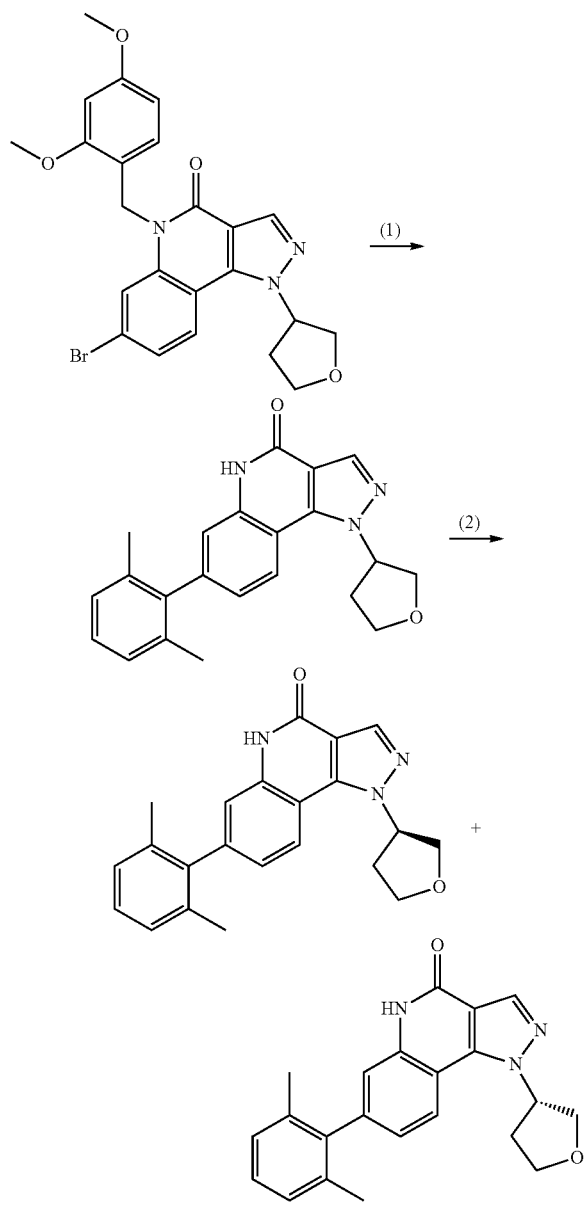

The title compound was obtained by performing the reactions (1) to (2) by the same method as in Example 25 using (±)-7-bromo-5-(2,4-dimethoxybenzyl)-1-(tetrahydrofuran-3-yl)-1H-pyrazolo[4,3-c]quinolin-4(5H)-one obtained in Preparation Example 5(4) and 2,6-dimethylphenylboronic acid as raw materials. The optical resolution of (2) under the conditions of chiral column: IB, mobile phase: 100% ethanol, and flow rate: 1.00 mL/min identified (−)-form at 4.0 min and (+)-form at 4.4 min. Thus, the optical resolution was performed using IB column for optical resolution under the conditions of mobile phase: 100% ethanol, flow rate: 10.0 mL/min, elution time: 60 min/run and injection: 1.5 mL/run and (−)-form of a shorter retention time and (+)-form of a longer retention time were obtained.

$^1$H-NMR (400 MHz, CDCl$_3$) δ (ppm): 2.06 (s, 6H), 2.60-2.64 (m, 1H), 2.79-2.83 (m, 1H), 4.12-413 (m, 1H), 4.24-4.37 (m, 2H), 4.40-4.45 (m, 1H), 5.62-5.70 (m, 1H), 7.10-7.19 (m, 4H), 7.21-7.24 (m, 1H), 8.10-8.12 (m, 1H), 8.30 (s, 1H), 9.57 (brs, 1H).

ESI-MS m/z 360 [M+H]$^+$

Example 34

Synthesis of (+)-7-(2-methoxy-4,6-dimethylpyridin-3-yl)-1-(tetrahydro-2H-pyran-3-yl)-1H-pyrazolo[4,3-c]quinolin-4(5H)-one and (−)-7-(2-methoxy-4,6-dimethylpyridin-3-yl)-1-(tetrahydro-2H-pyran-3-yl)-1H-pyrazolo[4,3-c]quinolin-4(5H)-one

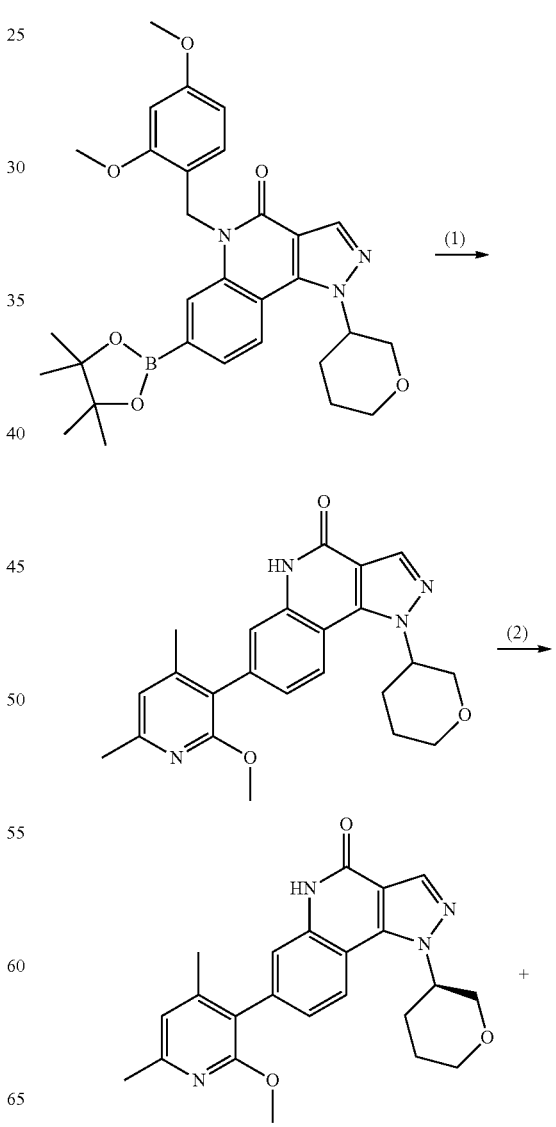

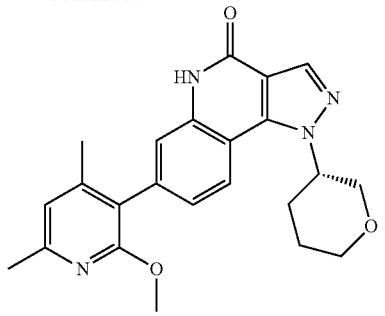

The title compound was obtained by performing the reactions (1) to (2) by the same method as in Example 25 using (±)-5-(2,4-dimethoxybenzyl)-1-(tetrahydro-2H-pyran-3-yl)-7-(4,4,5,5-tetramethyl-1,3,2-dioxaborolan-2-yl)-1H-pyrazolo[4,3-c]quinolin-4(5H)-one obtained in Preparation Example 4 and 3-bromo-2-methoxy-4,6-dimethylpyridine obtained in Preparation Example 26 as raw materials. The optical resolution of (2) under the conditions of chiral column: OD-H, mobile phase: 100% ethanol, and flow rate: 1.00 mL/min identified (+)-form at 4.8 min and (−)-form at 5.2 min. Thus, the optical resolution was performed using OD-H column for optical resolution and using an elution solvent of 100% ethanol and (+)-form of a shorter retention time and (−)-form of a longer retention time were obtained.

$^1$H-NMR (400 MHz, CDCl$_3$) δ (ppm): 1.92-2.00 (m, 2H), 2.10 (s, 3H), 2.38-2.54 (m, 5H), 3.53-3.61 (m, 1H), 3.86 (s, 3H), 3.88-3.95 (m, 1H), 4.04-4.10 (m, 1H), 4.28-4.35 (m, 1H), 4.95-5.05 (m, 1H), 6.72-6.75 (m, 1H), 7.18-7.21 (m, 1H), 7.22 (d, J=1.4 Hz, 1H), 8.09 (d, J=8.4 Hz, 1H), 8.28 (s, 1H), 9.63 (s, 1H).

ESI-MS m/z 405 [M+H]$^+$

The compounds of Examples 35 to 39 were synthesized as in Example 34.

TABLE 4

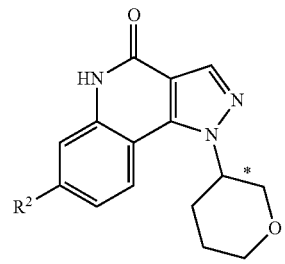

| Example<br>Chiral column<br>Mobile phase<br>Optical rotation (+/−)<br>Retention time (min) | R$^2$ | NMR, Mass |
|---|---|---|
| Example 35<br>AD-H<br>100% ethanol<br>(+): 5.8<br>(−): 6.4 | ![structure with F-CH2 pyridine OMe] | $^1$H-NMR (400 MHz, CDCl$_3$) δ (ppm): 1.93-2.02 (m, 2H), 2.17 (s, 3H), 2.37-2.55 (m, 2H), 3.53-3.62 (m, 1H), 3.85 (s, 3H), 3.88-3.96 (m, 1H), 4.04-4.11 (m, 1H), 4.27-4.35 (m, 1H), 4.95-5.05 (m, 1H), 5.33-5.48 (m, 2H), 7.03 (s, 1H), 7.17-7.22 (m, 2H), 8.11 (d, J = 8.6 Hz, 1H), 8.28 (s, 1H), 9.35 (s, 1H).<br>ESI-MS m/z 423 [M + H]$^+$ |
| Example 36<br>OD-H<br>100% ethanol<br>(+): 4.6<br>(−): 5.1 | ![structure] | $^1$H-NMR (400 MHz, CDCl$_3$) δ (ppm): 1.91-2.04 (m, 8H), 2.39-2.56 (m, 2H), 3.54-3.62 (m, 1H), 3.89-3.97 (m, 1H), 4.00 (s, 3H), 4.04-4.14 (m, 1H), 4.28-4.36 (m, 1H), 4.96-5.06 (m, 1H), 7.07-7.12 (m, 1H), 7.14 (d, J = 1.4 Hz, 1H), 7.94 (s, 1H), 8.14 (d, J = 8.2 Hz, 1H), 8.30 (s, 1H), 9.83 (brs, 1H).<br>ESI-MS m/z 405 [M + H]$^+$ |
| Example 37<br>AD-H<br>100% ethanol<br>(+): 8.0<br>(−): 10.7 | ![structure] | $^1$H-NMR (400 MHz, CDCl$_3$) δ (ppm): 1.94-2.00 (m, 2H), 2.02 (d, J = 0.6 Hz, 3H), 2.22 (s, 3H), 2.40-2.53 (m, 2H), 3.52-3.62 (m, 1H), 3.89-3.95 (m, 1H), 3.96 (s, 3H), 4.05-4.11 (m, 1H), 4.28-4.35 (m, 1H), 4.96-5.05 (m, 1H), 6.54 (s, 1H), 7.09 (d, J = 1.6 Hz, 1H), 7.13 (dd, J = 8.4 Hz, 1.6 Hz, 1H), 8.11 (d, J = 8.4 Hz, 1H), 8.29 (s, 1H), 9.01 (brs, 1H).<br>ESI-MS m/z 405 [M + H]$^+$ |

TABLE 4-continued

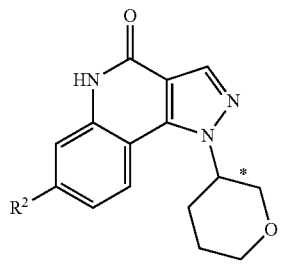

Example
Chiral column
Mobile phase
Optical rotation (+/−)
Retention time (min) | R² | NMR, Mass

| Example | R² | NMR, Mass |
|---|---|---|
| Example 38<br>OD-H<br>100% ethanol<br>(+): 5.2<br>(−): 5.8 | 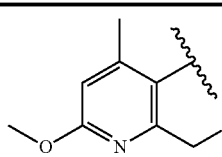 | ¹H-NMR (400 MHz, CDCl₃) δ (ppm):<br>1.92-2.03 (m, 2H), 2.09 (s, 3H), 2.39-<br>2.54 (m, 2H), 3.53-3.62 (m, 1H), 3.89-<br>3.97 (m, 1H), 4.01 (s, 3H), 4.05-4.13 (m,<br>1H), 4.26-4.37 (m, 1H), 4.95-5.20 (m,<br>3H), 6.74 (s, 1H), 7.17-7.23 (m, 2H),<br>8.12 (d, J = 8.4 Hz, 1H), 8.29 (s, 1H),<br>9.56-9.67 (m, 1H).<br>ESI-MS m/z 423 [M + H]⁺ |
| Example 39<br>AD-H<br>100% ethanol<br>(+): 6.0<br>(−): 6.6 | 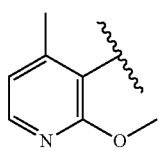 [SMILES: *c1c(C)ccnc1OC] | ¹H-NMR (400 MHz, CDCl₃) δ (ppm):<br>1.93-2.01 (m, 2H), 2.14 (s, 3H), 2.38-<br>2.53 (m, 2H), 3.53-3.61 (m, 1H), 3.87 (s,<br>3H), 3.88-3.95 (m, 1H), 4.04-4.11 (m,<br>1H), 4.27-4.35 (m, 1H), 4.95-5.04 (m,<br>1H), 6.88 (d, J = 5.3 Hz, 1H), 7.17 (d,<br>J = 1.5 Hz, 1H), 7.21 (dd, J = 8.2 Hz, 1.5<br>Hz, 1H), 8.08-8.14 (m, 2H), 8.28 (s, 1H),<br>9.06 (brs, 1H).<br>ESI-MS m/z 391 [M + H]⁺ |

Example 40

Synthesis of 7-[2,6-dimethyl-4-(tetrahydro-2H-pyran-4-yl)phenyl]-1-(tetrahydro-2H-pyran-4-yl)-1H-pyrazolo[4,3-c]quinolin-4(5H)-one

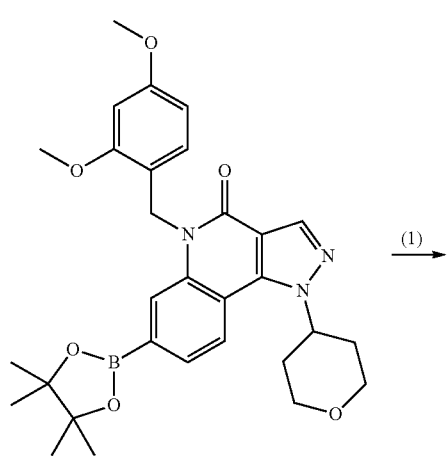

(1) →

-continued

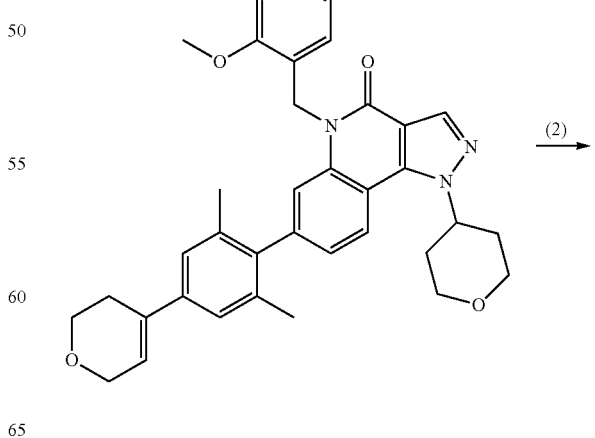

(2) →

-continued

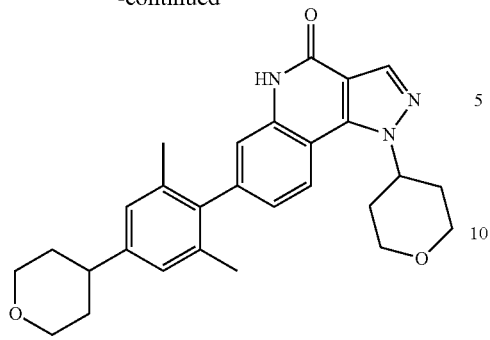

(1) Synthesis of 7-[4-(3,6-dihydro-2H-pyran-4-yl)-2,6-dimethylphenyl]-5-(2,4-dimethoxybenzyl)-1-(tetrahydro-2H-pyran-4-yl)-1H-pyrazolo[4,3-c]quinolin-4(5H)-one Water (0.2 mL), 4-(4-bromo-3,5-dimethylphenyl)-3,6-dihydro-2H-pyran (44.1 mg) obtained in Preparation Example 50, Pd(PPh₃)₄ (12.7 mg) and cesium carbonate (108 mg) were added to a solution of 5-(2,4-dimethoxybenzyl)-1-(tetrahydro-2H-man-4-yl)-7-(4,4,5,5-tetramethyl-1,3,2-dioxaborolan-2-yl)-1H-pyrazolo[4,3-c]quinolin-4(5H)-one obtained in Preparation Example 1(5) (60 mg) in 1,4-dioxane (1.5 mL). The reaction mixture was stirred at 100° C. overnight. After returning the reaction mixture to room temperature, ethyl acetate and water were added to the reaction mixture, and the organic layer was separated. The organic layer was washed with brine, dried over anhydrous magnesium sulfate, filtered and concentrated under reduced pressure. The resulting residue was purified by NH silica gel column chromatography (ethyl acetate/n-heptane, 20 to 50%) to give the title compound (44 mg).

ESI-MS m/z 606 [M+H]⁺

(2) Synthesis of 7-[2,6-dimethyl-4-(tetrahydro-2H-pyran-4-yl)phenyl]-1-(tetrahydro-2H-pyran-4-yl)-1H-pyrazolo[4,3-c]quinolin-4(5H)-one 10% palladium carbon (50% wet, 15 mg) was added to a solution of 7-[4-(3,6-dihydro-2H-pyran-4-yl)-2,6-dimethylphenyl]-5-(2,4-dimethoxybenzyl)-1-(tetrahydro-2H-pyran-4-yl)-1H-pyrazolo[4,3-c]quinolin-4(5H)-one (44 mg) in ethanol (2 mL)-THF (2 mL). The reaction mixture was stirred at mom temperature for four hours and 35 minutes in a hydrogen atmosphere. The catalyst was removed from the reaction mixture by filtration, and the filtrate was then concentrated under reduced pressure. TFA (1.5 mL) was added to the resulting residue. The reaction mixture was stirred at 60° C. for 14 hours. The reaction mixture was returned to room temperature, and the reaction mixture was then concentrated under reduced pressure. Chloroform and a saturated aqueous sodium bicarbonate solution were added to the residue, and the organic layer was separated. The aqueous layer was re-extracted with chloroform. The combined organic layers were dried over anhydrous magnesium sulfate, filtered and concentrated under reduced pressure. The resulting residue was purified by silica gel column chromatography (chloroform 100%, then ethyl acetate 100%). The target fraction was collected and concentrated. Ethyl acetate and MTBE were added to the resulting residue. The precipitated solid was collected by filtration and dried under reduced pressure to give the title compound (14.8 mg).

¹H-NMR (400 MHz, CDCl₃) δ (ppm): 1.79-1.95 (m, 4H), 2.07 (s, 6H), 2.20 (d, J=12.8 Hz, 2H), 2.53 (ddd, J=15.6, 11.6, 4.0 Hz, 2H), 2.72-2.81 (m, 1H), 3.56 (td, J=10.8, 2.8 Hz, 2H), 3.71 (t, J=10.4 Hz, 2H), 4, 12 (dd, J=10.4, 2.8 Hz, 2H), 4.24 (d, J=10.8 Hz, 2H), 5.03-5.11 (m, 1H), 7.03 (s, 2H), 7.13 (dd, J=8.0, 12 Hz, 1H), 7.25 (d, J=1.2 Hz, 1H), 8.01 (d, J=8.0 Hz, 1H), 8.31 (s, 1H), 10.26 (brs, 1H).

ESI-MS m/z 458 [M+H]⁺

Example 41

Synthesis of (±)-7-(2-methoxy-3,5-dimethylpyridin-4-yl)-1-(oxepan-4-yl)-1H-pyrazolo[4,3-c]quinolin-4(5H)-one and (−)-7-(2-methoxy-3,5-dimethylpyridin-4-yl)-1-(oxepan-4-yl)-1H-pyrazolo[4,3-c]quinolin-4(5H)-one

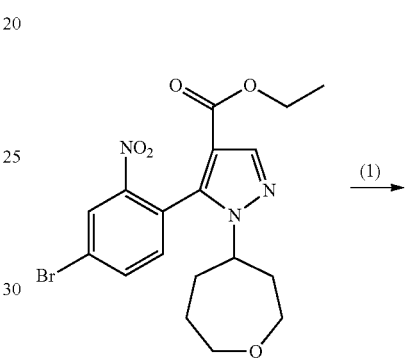

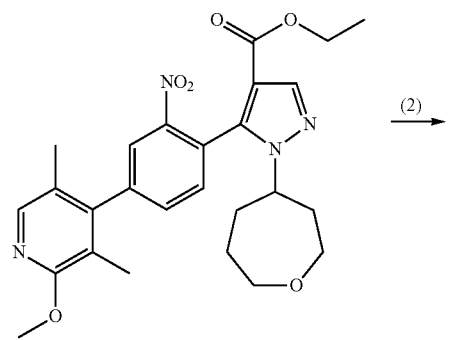

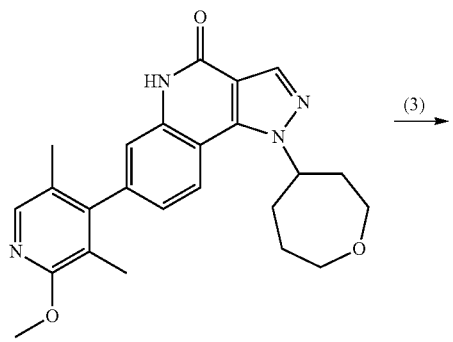

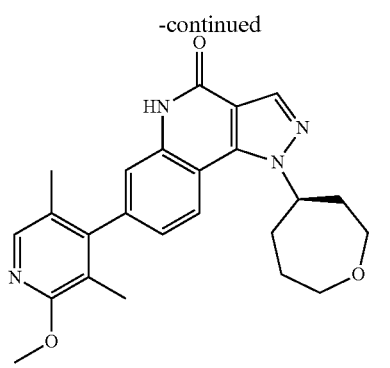

(1) Synthesis of (±)-ethyl 5-[4-(2-methoxy-3,5-dimethylpyridin-4-yl)-2-nitrophenyl]-1-(oxepan-4-yl)-1H-pyrazole-4-carboxylate The title compound (80 mg) was obtained by the same method as in Example 27-(1) from (±)-ethyl 5-(4-bromo-2-nitrophenyl)-1-(oxepan-4-yl)-1H-pyrazole-4-carboxylate obtained in Preparation Example 8 (85 mg) and (2-methoxy-3,5-dimethylpyridin-4-yl)boronic acid obtained in Preparation Example 29 (42.1 mg).
ESI-MS m/z 495 [M+H]$^+$ (2) Synthesis of (±)-7-(2-methoxy-3,5-dimethylpyridin-4-yl)-1-(oxepan-4-yl)-1H-pyrazolo[4,3-c]quinolin-4(5H)-one The title compound (53 mg) was obtained by the same method as in Example 45-(2) from (±)-ethyl 5-[4-(2-methoxy-3,5-dimethylpyridin-4-yl)-2-nitrophenyl]-1-(oxepan-4-yl)-1H-pyrazole-4-carboxylate (80 mg).
$^1$H-NMR. (400 MHz, CDCl$_3$) δ (ppm): 1.90-2.05 (m, 2H), 1.94, 1.95, 1.96 (s, 3H), 1.97 (s, 3H), 2.33-2.70 (m, 4H), 3.70-3.80 (m, 1H), 3.92-4.08 (m, 3H), 4.01 (s, 3H), 5.20-5.29 (m, 1H), 7.08 (dd, J=8.4, 1.6 Hz, 1H), 7.19 (d, J=1.6 Hz, 1H), 7.95 (s, 1H), 8.11 (d, J=8.4 Hz, 1H), 8.30 (s, 1H), 10.30 (brs, 1H).
ESI-MS m/z 419 [M+H]$^+$ (3) Synthesis of (+)-7-(2-methoxy-3,5-dimethylpyridin-4-yl)-1-(oxepan-4-yl)-1H-pyrazolo[4,3-c]quinolin-4(5H)-one and (−)-7-(2-methoxy-3,5-dimethylpyridin-4-yl)-1-(oxepan-4-yl)-1H-pyrazolo[4,3-c]quinolin-4(5H)-one 7-(2-methoxy-3,5-dimethylpyridin-4-yl)-1-(oxepan-4-yl)-1H-pyrazolo[4,3-c]quinolin-4(5H)-one (53 mg) was dissolved in ethanol (5 mL), and the solution was filtered through a millipore filter. The filtrate was optically resolved by CIR-ALCEL® OD-H manufactured by DAICEL Corporation (20 mm diameter×250 mm long) under the condition of ethanol 100% and 10 mL/min. The title compound with a retention time of 11 minutes and a (+) optical rotation (15.9 mg, >98% ee [CIRALCEL® OD-H (0.46 cm (1)×25 cm), 20% ethanol/hexane, retention time=7.3 min]) and the title compound with a retention time of 12 minutes and a (−) optical rotation (16.7 mg, >98% ee [CIRALCEL® OD-H (0.46 cm Φ×25 cm), 20% ethanol/hexane, retention time=7.9 min]) were obtained.

The compound of Example 42 was synthesized as in Example 41.

TABLE 5

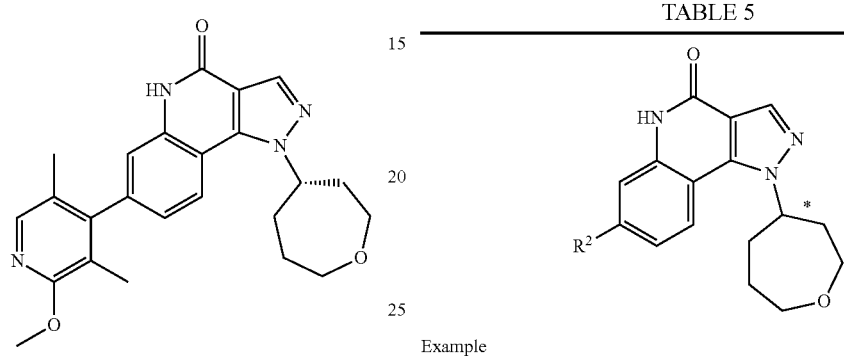

| Example<br>Chiral column<br>Mobile phase<br>Optical rotation (+/−)<br>Retention time (min) | R$^2$ | NMR, Mass |
|---|---|---|
| Example 42<br>IA<br>100% IPA<br>(+): 8.3<br>(−): 9.4 | | $^1$H-NMR (400 MHz, CDCl$_3$) δ (ppm): 1.90-2.05 (m, 2H), 2.05 (s, 3H), 2.06 (s, 3H), 2.31-2.68 (m, 4H), 3.70-3.78 (m, 1H), 3.85 (s, 3H), 3.92-4.07 (m, 3H), 5.19-5.28 (m, 1H), 6.71 (s, 2H), 7.12 (d, J = 8.4 Hz, 1H), 7.15 (s, 1H), 8.07 (d, J = 8.4 Hz, 1H), 8.30 (s, 1H), 9.62 (brs, 1H).<br>ESI-MS m/z 418 [M + H]$^+$ |

Example 43

Synthesis of 1-(1,4-dioxepan-6-yl)-7-(2-methoxy-3,5-dimethylpyridin-4-yl)-1H-pyrazolo[4,3-c]quinolin-4(5H)-one

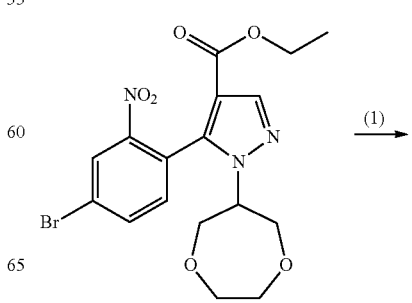

(1)

-continued

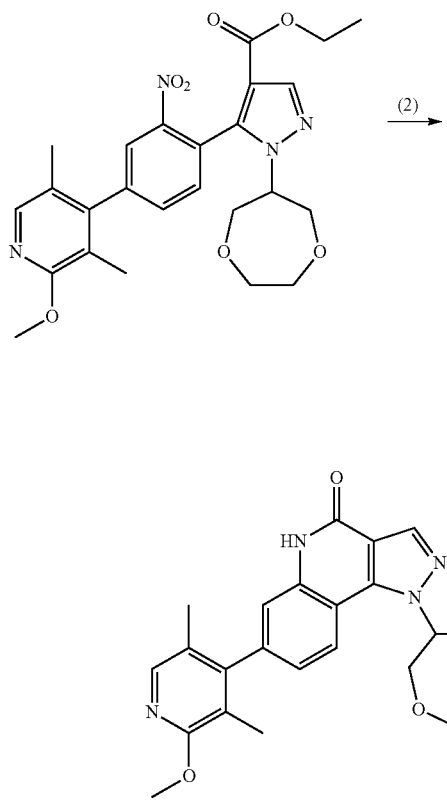

(1) Synthesis of ethyl 1-(1,4-dioxepan-6-yl)-5-[4-(2-methoxy-3,5-dimethylpyridin-4-yl)-2-nitrophenyl]-1H-pyrazole-4-carboxylate Water (0.2 mL), (2-methoxy-3,5-dimethylpyridin-4-yl)boronic acid (39.5 mg) obtained in Preparation Example 29, Pd(PPh$_3$)$_4$ (10.5 mg) and cesium carbonate (178 mg) were added to a solution of ethyl 5-(4-bromo-2-nitrophenyl)-1-(1,4-dioxepan-6-yl)-1H-pyrazole-4-carboxylate (80 mg) obtained in Preparation Example 9-(2) in 1,4-dioxane (1.3 mL), and the reaction mixture was stirred at 100° C. for 6.75 hours. (2-methoxy-3,5-dimethylpyridin-4-yl)boronic acid (15 mg) was added to the reaction mixture and the reaction mixture was stirred at 100° C. for 2.5 hours. After the reaction mixture was returned to mom temperature, ethyl acetate and water were added to the reaction mixture, and the organic layer was separated. The resulting organic layer was washed with brine, dried over anhydrous magnesium sulfate, filtered, and concentrated under reduced pressure. The residue was purified by silica gel column chromatography (silica gel, ethyl acetate/n-heptane, 20 to 33%) to give the title compound (64 mg).

$^1$H-NMR (400 MHz, CDCl$_3$) δ (ppm): 1.09 (t, J=7.2 Hz, 1.5H), 1.11 (t, J=7.2 Hz, 1.5H), 1.98 (s, 1.5H), 1.99 (s, 1.5H), 2.01 (s, 1.5H), 2.02 (s, 1.5H), 3.73-3.87 (m, 2H), 3.90-4.02 (m, 2H), 4.00 (s, 3H), 4.03-4.17 (m, 4H), 4.30-4.40 (m, 2H), 4.41-4.49 (m, 1H), 7.39 (d, J=7.6 Hz, 1H), 7.52 (dd, J=7.6, 1.6 Hz, 1H), 7.95-8.01 (m, 2H), 8.11 (s, 1H).

ESI-MS m/z 519 [M+Na]$^+$ (2) Synthesis of 1-(1,4-dioxepan-6-yl)-7-(2-methoxy-3,5-dimethylpyridin-4-yl)-1H-pyrazolo[4,3-c]quinolin-4(5H)-one Iron powder (28.8 mg) was added to a solution of ethyl 1-(1,4-dioxepan-6-yl)-5-[4-(2-methoxy-3,5-dimethylpyridin-4-yl)-2-nitrophenyl]-1H-pyrazole-4-carboxylate (64 mg) in acetic acid (2 mL)-water (0.1 mL), and the reaction mixture was stirred at 80° C. for 2.5 hours in a nitrogen atmosphere. The reaction mixture was returned to room temperature, and ethyl acetate (10 mL) was added to the reaction mixture. The insoluble matter was removed by filtration through Celite™. The filtrate was concentrated under reduced pressure. A solution of the residue in ethyl acetate was sequentially washed with a saturated aqueous sodium bicarbonate solution and brine, dried over anhydrous magnesium sulfate, filtered. The filtrate was passed through a NH silica gel pad. The resulting solution was concentrated under reduced pressure. Ethyl acetate (0.3 mL) and MTBE (0.3 mL) were added to the residue. The precipitated solid was collected by filtration to give the title compound (29.1 mg).

$^1$H-NMR (400 MHz, CDCl$_3$) δ (ppm): 1.93 (s, 3H), 1.96 (s, 3H), 3.90-4.07 (m, 4H), 4.00 (s, 3H), 4.38 (dd, J=12.0, 6.0 Hz, 2H), 4.40 (dd, J=12.0, 6.8 Hz, 2H), 5.50 (tt, J=6.8, 6.0 Hz, 1H), 7.08 (d, J=8.0 Hz, 1H), 7.17 (s, 1H), 7.94 (s, 1H), 8.13 (d, J=8.0 Hz, 1H), 836 (s, 1H), 10.23 (brs, 1H).

ESI-MS m/z 421 [M+H]$^+$

The compound of Example 44 was synthesized as in Example 43.

TABLE 6

| # | R$^2$ | Mass, NMR |
|---|---|---|
| 44 | (2,6-dimethyl-4-methoxyphenyl) | $^1$H-NMR (400 MHz, CDCl$_3$) δ (ppm): 2.05 (s, 6H), 3.85 (s, 3H), 3.91-4.07 (m, 4H), 4.38 (dd, J = 12.8, 6.0 Hz, 2H), 4.44 (dd, J = 12.8, 6.8 Hz, 2H), 5.51 (tt, J = 6.8, 6.0 Hz, 1H), 6.71 (s, 2H), 7.12 (dd, J = 8.4, 1.6 Hz, 1H), 7.24 (brs, 1H), 8.08 (d, J = 8.4 Hz, 1H), 8.36 (s, 1H), 10.43 (brs, 1H). ESI-MS m/z 420 [M + H]$^+$ |

Example 45

Synthesis of 1-(1,4-dioxepan-6-yl)-7-(2-methoxy-4,6-dimethylpyridin-3-yl)-1H-pyrazolo[4,3-c]quinolin-4(5H)-one

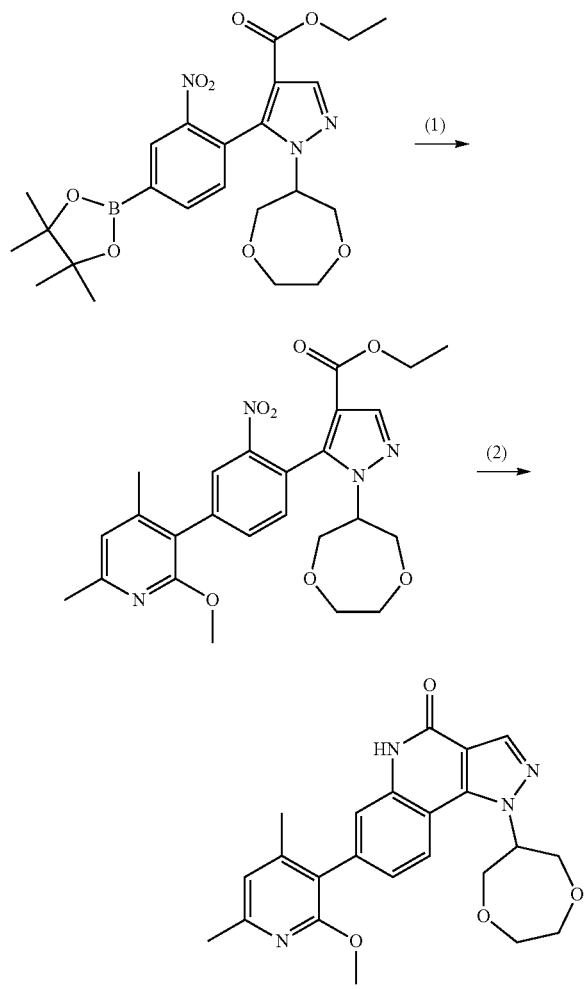

(1) Synthesis of ethyl 1-(1,4-dioxepan-6-yl)-5-{4-(2-methoxy-4,6-dimethylpyridin-3-yl)-2-nitrophenyl}-1H-pyrazole-4-carboxylate Water (0.3 mL), 3-bromo-2-methoxy-4,6-dimethylpyridine (32.5 mg) obtained in Preparation Example 26, Pd(PPh$_3$)$_4$ (7.2 mg) and cesium carbonate (122 mg) were added to a solution of ethyl 1-(1,4-dioxepan-6-yl)-5-[2-nitro-4-(4,4,5,5-tetramethyl-1,3,2-dioxaborolan-2-yl)phenyl]-1H-pyrazole-4-carboxylate (61 mg) in 1,4-dioxane (1.2 mL), and the reaction mixture was stirred at 100° C. for 4 hours. Pd(PPh$_3$)$_4$ (7.2 mg) was added to the reaction mixture, and the reaction mixture was stirred at 100° C. for 1 hour and 10 minutes. The reaction mixture was returned to room temperature and partitioned by adding ethyl acetate and water, and the organic layer was separated. The resulting organic layer was sequentially washed with water and brine, dried over anhydrous magnesium sulfate, filtered and concentrated under reduced pressure. The residue was purified by silica gel column chromatography (ethyl acetate/n-heptane, 15 to 20%) to give the title compound (15 mg).

$^1$H-NMR (400 MHz, CDCl$_3$) δ (ppm): 1.06 (t, J=7.2 Hz, 3H), 2.16 (s, 3H), 2.48 (s, 3H), 3.74-3.88 (m, 2H), 3.88 (s, 3H), 3.91-4.16 (m, 6H), 4.28-4.37 (m, 2H), 4.47-4.55 (m, 1H), 6.74 (s, 1H), 7.29 (d, J=7.6 Hz, 1H), 7.60 (dd, J=7.6, 1.6 Hz, 1H), 8.07 (d, J=1.6 Hz, 1H), 8.10 (s, 1H).

ESI-MS m/z 519 [M+Na]$^+$

(2) Synthesis of 1-(1,4-dioxepan-6-yl)-7-(2-methoxy-4,6-dimethylpyridin-3-yl)-1H-pyrazolo[4,3-c]quinolin-4(5H)-one Iron powder (17 mg) was added to a solution of ethyl 1-(1,4-dioxepan-6-yl)-5-{4-(2-methoxy-4,6-dimethylpyridin-3-yl)-2-nitrophenyl}-1H-pyrazole-4-carboxylate (15 mg) in acetic acid (1 mL)-water (0.05 mL), and the mixture was stirred at 80° C. for 4.25 hours in a nitrogen atmosphere. The reaction mixture was returned to room temperature, and ethyl acetate (5 mL) was added to the reaction mixture. The insoluble matter was removed by filtration through Celite™. The filtrate was concentrated under reduced pressure. A solution of the residue in ethyl acetate was sequentially washed with a saturated aqueous sodium bicarbonate solution and brine, dried over anhydrous magnesium sulfate, filtered and concentrated. The residue was purified by preparative thin-layer chromatography (silica gel, ethyl acetate/n-heptane, 66%) to give the title compound (1.5 mg).

$^1$H-NMR (400 MHz, CDCl$_3$) δ (ppm): 2.09 (s, 3H), 2.48 (s, 3H), 3.85 (s, 3H), 3.91-3.99 (m, 2H), 4.00-4.08 (m, 2H), 4.36 (dd, J=12.8, 6.4 Hz, 2H), 4.42 (dd, J=12.8, 6.4 Hz, 2H), 5.49 (tt, J=6.8, 6.4 Hz, 1H), 6.72 (s, 1H), 7.15-7.21 (m, 2H), 8.08 (d, J=8.0 Hz, 1H), 8.34 (s, 1H), 9.17 (br s, 1H).

ESI-MS m/z 421 [M+H]$^+$

The compounds of Examples 46 and 47 were synthesized as in Example 45.

TABLE 7

| # | R$^2$ | NMR, Mass |
|---|---|---|
| 46 | (2-methoxy-4,6-dimethylpyridin-3-yl) | $^1$H-NMR (400 MHz, CDCl$_3$) δ (ppm): 2.02 (s, 3H), 2.21 (s, 3H), 3.91-3.99 (m, 2H), 3.96 (s, 3H), 4.00-4.07 (m, 2H), 4.38 (ddd, J = 13.2, 6.4, 2.4 Hz, 2H), 4.44 (dd, J = 13.2, 6.4 Hz, 2H), 5.50 (tt, J = 6.8, 6.4 Hz, 1H), 6.54 (s, 1H), 7.12 (dd, J = 8.0, 1.6 Hz, 1H), 7.17 (d, J = 1.6 Hz, 1H), 8.10 (d, J = 8.0 Hz, 1H), 8.34 (s, 1H), 9.78 (brs, 1H). ESI-MS m/z 421 [M + H]$^+$ |

TABLE 7-continued

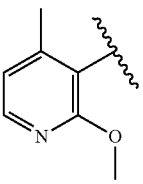 [SMILES: *c1c(C)ccnc1OC]

| # | R² | NMR, Mass |
|---|----|-----------|
| 47 | <image structure: 4-methyl-2-methoxypyridin-3-yl> | ¹H-NMR (400 MHz, CDCl₃) δ (ppm): 2.14 (s, 3H), 3.87 (s, 3H), 3.91-3.99 (m, 2H), 4.00-4.07 (m, 2H), 4.37 (dd, J = 12.8, 6.4 Hz, 2H), 4.43 (dd, J = 12.8, 6.4 Hz, 2H), 5.50 (tt, J = 6.4, 6.0 Hz, 1H), 6.88 (d, J = 5.6 Hz, 1H), 7.18-7.22 (m, 2H), 8.08-8.13 (m, 2H), 8.35 (s, 1H), 9.29 (brs, 1H). ESI-MS m/z 407 [M + H]⁺ |

Example 48

Synthesis of (S)-7-(2-isopropyloxy-3,5-dimethylpyridin-4-yl)-1-(tetrahydrofuran-3-yl)-1H-pyrazolo[4,3-c]quinolin-4(5H)-one

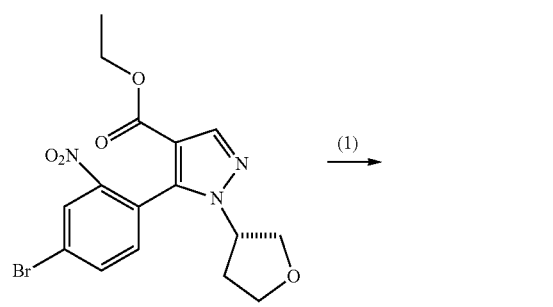

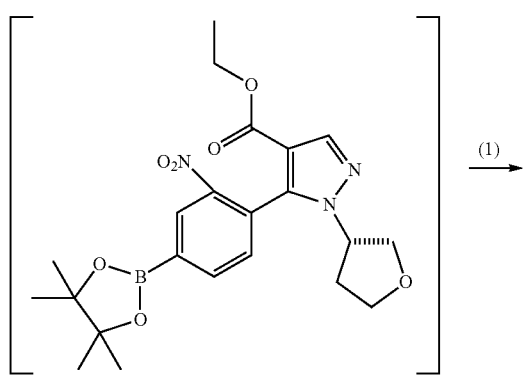

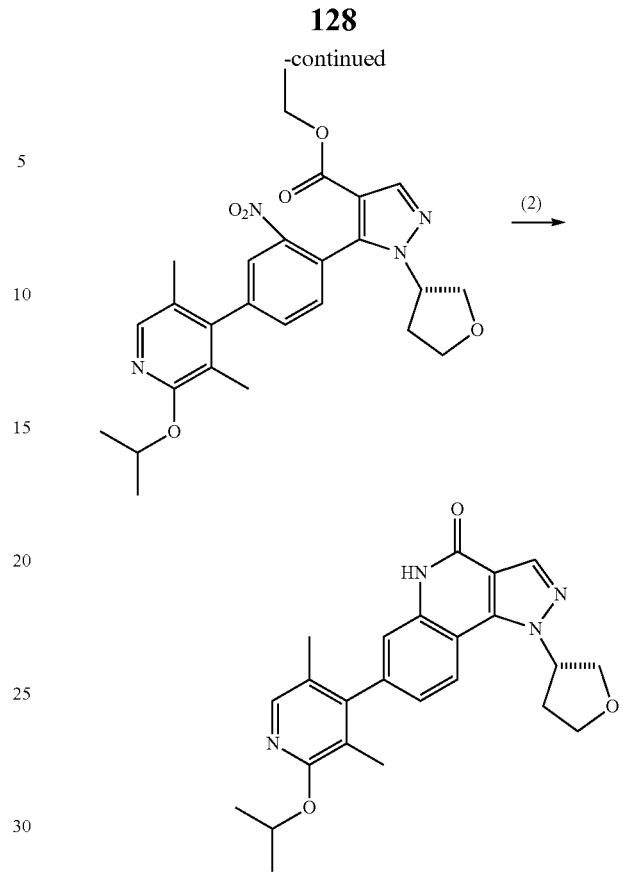

(1) Synthesis of ethyl 5-[4-(2-isopropyloxy-3,5-dimethylpyridin-4-yl)-2-nitrophenyl]-1-[(S)-tetrahydrofuran-3-yl]-1H-pyrazole-4-carboxylate Ethyl 5-(4-bromo-2-nitrophenyl)-1-[(S)-tetrahydrofuran-3-yl]-1H-pyrazole-4-carboxylate obtained in Preparation Example 7-(1) (200 mg) was converted to ethyl 5-[2-nitro-4-(4,4,5,5-tetramethyl-1,3,2-dioxaborolan-2-yl)phenyl]-1-[(S)-tetrahydrofuran-3-yl]-1H-pyrazole-4-carboxylate by the same method as in Preparation Example 7-(2). A solution of 4-iodo-2-isopropyloxy-3,5-dimethylpyridine obtained in Preparation Example 47 (142 mg) in DMF (0.5 mL), and water (0.5 mL) were added to the reaction mixture, and the mixture was stirred at 110° C. for two hours. The reaction mixture was cooled to room temperature and then partitioned by adding ethyl acetate and water. The aqueous layer was extracted with ethyl acetate. The combined organic layers were dried over anhydrous magnesium sulfate and filtered. The filtrate was concentrated under reduced pressure. The residue was purified by silica gel column chromatography (ethyl acetate/n-heptane, 50% to 100%) to give the title compound (138.1 mg).

ESI-MS m/z 517 [M+Na]⁺

(2) Synthesis of (S)-7-(2-isopropyloxy-3,5-dimethylpyridin-4-yl)-1-(tetrahydrofuran-3-yl)-1H-pyrazolo[4,3-c]quinolin-4(5H)-one The title compound (67.1 mg) was obtained by the same method as in Example 45-(2) from ethyl 5-[4-(2-isopropyloxy-3,5-dimethylpyridin-4-yl)-2-nitrophenyl]-1-[(S)-tetrahydrofuran-3-yl]-1H-pyrazole-4-carboxylate (138.1 mg).

¹H-NMR. (400 MHz, CDCl₃) δ (ppm): 1.37-1.41 (m, 6H), 1.91 (s, 3H), 1.95 (s, 3H), 2.59-2.64 (m, 1H), 2.79-2.83 (m, 1H), 4.12-4.29 (m, 1H), 4.23-4.27 (m, 2H), 4.39-4.46 (m, 1H), 5.29-5.40 (m, 1H), 5.62-5.69 (m, 1H), 7.07-7.09 (m, 1H), 7.19-7.20 (m, 1H), 7.90-7.92 (m, 1H), 8.13 (d, 0.1=8.40 Hz, 1H), 8.31 (s, 1H), 10.18 (s, 1H).

ESI-MS m/z 419 [M+H]⁺

The compounds of Examples 49 and 50 were synthesized as in Example 48.

TABLE 8

| # | R² | NMR, Mass |
|---|---|---|
| 49 | *pyridine structure with CHF₂O and dimethyl* | ¹H-NMR (400 MHz, CDCl₃) δ (ppm): 2.01 (s, 6H), 2.59-2.64 (m, 1H), 2.70-2.90 (m, 1H), 4.10-4.20 (m, 1H), 4.25-4.35 (m, 2H), 4.40-4.45 (m, 1H), 5.60-5.63 (m, 1H), 6.99-7.10 (m, 2H), 7.52 (t, J = 72.0 Hz, 1H), 7.96 (s, 1H), 8.14-8.17 (m, 1H), 8.31 (s, 1H), 9.01 (brs, 1H). ESI-MS m/z 449 [M + Na]⁺ |
| 50 | *pyridine structure with OEt and dimethyl* | ¹H-NMR (400 MHz, CDCl₃) δ (ppm): 1, 43 (t, J = 7.13 Hz, 3H), 1.94 (s, 3H), 1.95 (s, 3H), 2.55-2.68 (m, 1H), 2.76-2.87 (m, 1H), 4.12-4.20 (m, 1H), 4.23-4.37 (m, 2H), 4.38-4.46 (m, 3H), 5.57-5.72 (m, 1H), 7.07-7.09 (m, 1H), 7.17-7.18 (m, 1H), 7.92 (s, 1H), 8.12-8.14 (m, 1H), 8.31 (s, 1H), 10.07 (brs, 1H). ESI-MS m/z 405 [M + H]⁺ |

Example 51

Synthesis of (S)-7-(6-isopropyloxy-2,4-dimethylpyridin-3-yl)-1-(tetrahydrofuran-3-yl)-1H-pyrazolo[4,3-c]quinolin-4(5H)-one

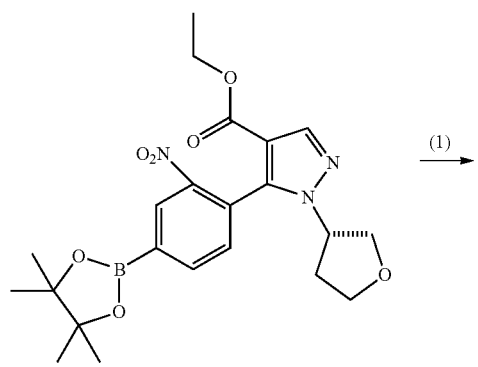

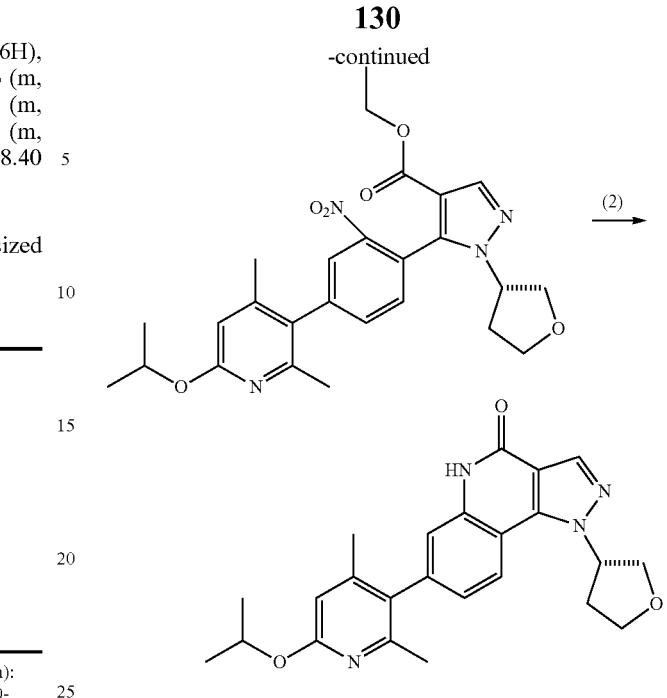

(1) Synthesis of ethyl 5-[4-(6-isopropyloxy-2,4-dimethylpyridin-3-yl)-2-nitrophenyl]-1-[(S)-tetrahydrofuran-3-yl]-1H-pyrazole-4-carboxylate Ethyl 5-[2-nitro-4-(4,4,5,5-tetramethyl-1,3,2-dioxaborolan-2-yl)phenyl]-1-[(S)-tetrahydrofuran-3-yl]-1H-pyrazole-4-carboxylate obtained in Preparation Example 7-(2) (70 mg) was dissolved in a mixed solution of 1,4-dioxane (1 mL) and water (0.2 mL), and 3-bromo-6-isopropyloxy-2,4-dimethylpyridine (41.1 mg), Pd(PPh₃)₄ (17.7 mg) and cesium carbonate (150 mg) were added. The reaction mixture was stirred at 110° C. overnight. After returning the reaction mixture to room temperature, the reaction mixture was purified by silica gel column chromatography (ethyl acetate/n-heptane, 10 to 50% to 100%) to give the title compound (66.5 mg).

ESI-MS m/z 495 [M+H]⁺

(2) Synthesis of (S)-7-(6-isopropyloxy-2,4-dimethylpyridin-3-yl)-1-(tetrahydrofuran-3-yl)-1H-pyrazolo[4,3-c]quinolin-4(5H)-one A solution of ethyl 5-[4-(6-isopropyloxy-2,4-dimethylpyridin-3-yl)-2-nitrophenyl]-1-[(S)-tetrahydrofuran-3-yl]-1H-pyrazole-4-carboxylate (65.1 mg) in acetic acid (1.5 mL)-water (0.15 mL) was stirred at 80° C. for 15 minutes. Iron powder (45.1 mg) was added to the solution, and the mixture was stirred at the same temperature for two hours in a nitrogen atmosphere. The reaction mixture was returned to room temperature, and ethyl acetate (5 mL) was added to the reaction mixture. The insoluble matter was removed by filtration through Celite™. The filtrate was concentrated under reduced pressure. A solution of the residue in ethyl acetate was washed with a saturated aqueous sodium bicarbonate solution, dried over anhydrous magnesium sulfate and filtered. The filtrate was concentrated under reduced pressure. The residue was suspended and triturated by adding MTBE. The precipitated solid was collected by filtration to give the title compound (35.1 mg).

¹H-NMR (400 MHz, CDCl₃) δ (ppm): 1.38 (d, J=625 Hz, 6H), 2.01 (s, 3H), 2.20 (s, 3H), 2.55-2.67 (m, 1H), 2.76-2.87 (m, 1H), 4.12-4.14 (m, 1H), 4.23-4.37 (m, 2H), 4.39-4.45 (m, 1H), 5.30-5.35 (m, 1H), 5.61-5.69 (m, 1H), 6.48 (s, 1H), 7.11-7.13 (m, 1H), 7.16-7.17 (m, 1H), 8.09-8.11 (m, 1H), 8.31 (s, 1H), 9.58 (brs, 1H).
ESI-MS m/z 419 [M+H]⁺

Example 52

Synthesis of 8-fluoro-7-(2-methoxy-4,6-dimethylpyridin-3-yl)-1-(tetrahydro-2H-pyran-4-yl)-1H-pyrazolo[4,3-c]quinolin-4(5H)-one

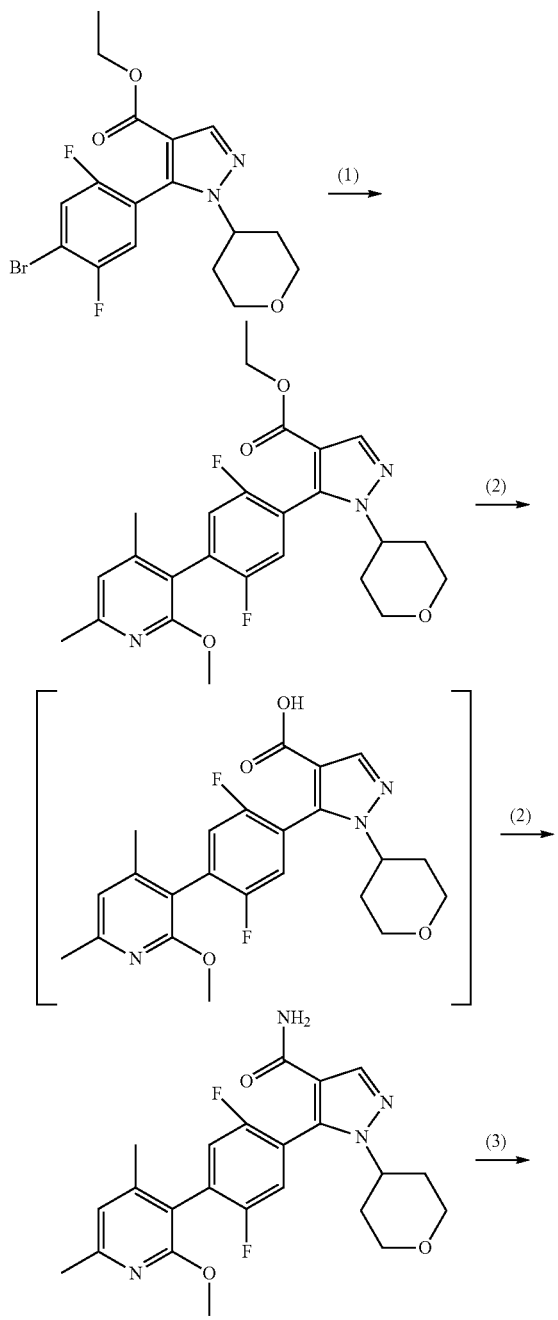

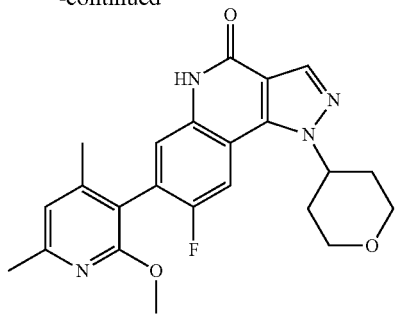

(1) Synthesis of ethyl 5-[2,5-difluoro-4-(2-methoxy-4,6-dimethylpyridin-3-yl)phenyl]-1-(tetrahydro-2H-pyran-4-yl)-1H-pyrazole-4-carboxylate Pd(PPh₃)₄ (50 mg), cesium carbonate (282 mg) and water (0.5 mL) were added to a mixed solution of ethyl 5-(4-bromo-2,5-difluorophenyl)-1-(tetrahydro-2H-pyran-4-yl)-1H-pyrazole-4-carboxylate obtained in Preparation Example 10 (180 mg), (2-methoxy-4,6-dimethylpyridin-3-yl)boronic acid obtained in Preparation Example 27 (90 mg) and 1,4-dioxane (2 mL), and the mixture was stirred at 110° C. for six hours. After cooling the reaction mixture to room temperature, ethyl acetate and brine were added, and the mixture was filtered through a cotton plug. The organic layer was separated and dried over anhydrous magnesium sulfate. The desiccant was removed by filtration, and the filtrate was concentrated under reduced pressure. The residue was subjected to silica gel column chromatography (ethyl acetate/n-heptane, 25% to 46% to 53%) to give the title compound (157 mg).
ESI-MS m/z 494 [M+Na]⁺

(2) Synthesis of 5-[2,5-difluoro-4-(2-methoxy-4,6-dimethylpyridin-3-yl)phenyl]-1-(tetrahydro-2H-pyran-4-yl)-1H-pyrazole-4-carboxamide A 5 N aqueous sodium hydroxide solution (0.3 mL) was added to a solution of ethyl 5-[2,5-difluoro-4-(2-methoxy-4,6-dimethylpyridin-3-yl)phenyl]-1-(tetrahydro-2H-pyran-4-yl)-1H-pyrazole-4-carboxylate (157 mg) in ethanol (3 mL), and the mixture was stirred at 55° C. for two hours. The reaction mixture was cooled to room temperature and then concentrated under reduced pressure. The residue was partitioned by adding chloroform, 5 N hydrochloric acid and a saturated aqueous ammonium chloride solution. The organic layer was dried over anhydrous magnesium sulfate. The desiccant was removed by filtration, and the filtrate was concentrated under reduced pressure to give 5-[2,5-difluoro-4-(2-methoxy-4,6-dimethyl-pyridin-3-yl)phenyl]-1-(tetrahydro-2H-pyran-4-yl)-1H-pyrazole-4-carboxylic acid (155 mg) as a crude purified product. The carboxylic acid (155 mg) was dissolved in DMF (1 mL) and THF (3 mL). CDI (108 mg) was then added, and the mixture was stirred at room temperature for about 1.5 hours. A 28% aqueous ammonia solution (0.35 mL) was added to the reaction mixture, and the mixture was stirred at room temperature overnight. The reaction mixture was concentrated under reduced pressure, and the residue was partitioned by adding ethyl acetate and brine. The organic layer was washed with a saturated aqueous sodium bicarbonate solution and dried over anhydrous magnesium sulfate. The desiccant was removed by filtration, and the filtrate was concentrated under reduced pressure. The residue was solidified by adding n-heptane/MTBE (119) to give the title compound (82 mg). The title compound was used for the next reaction without further purification.

ESI-MS m/z 465 [M+Na]$^+$

(3) Synthesis of 8-fluoro-7-(2-methoxy-4,6-dimethylpyridin-3-yl)-1-(tetrahydro-2H-pyran-4-yl)-1H-pyrazolo[4,3-c]quinolin-4(5H)-one KTB (41 mg) was added to a solution of 5-(2,5-difluoro-4-(2-methoxy-4,6-dimethylpyridin-3-yl)phenyl)-1-(tetrahydro-2H-pyran-4-yl)-1H-pyrazole-4-carboxamide (81 mg) in NMP (0.4 mL), and the mixture was heated to 90° C. After one hour, KTB (20 mg) was further added, followed by stirring for 30 minutes. The reaction mixture was cooled to room temperature, followed by adding a saturated aqueous ammonium chloride solution (2 mL) and water (1 mL). The generated solid was filtered off, washed with water (2 mL) and dried under reduced pressure at 60° C. to give the title compound (57 mg).

$^1$H-NMR (400 MHz, CDCl$_3$) δ (ppm): 2.11 (s, 3H), 2.14-2.24 (m, 2H), 2.50 (s, 3H), 2.42-2.63 (m, 2H), 3.65-3.79 (m, 2H), 3.87 (s, 3H), 4.20-4.28 (m, 2H), 4.93-5.03 (m, 1H), 6.76 (s, 1H), 7.35 (d, J=6.44 Hz, 1H), 7.71 (d, J=10.35 Hz, 1H), 8.30 (s, 1H), 10.93 (brs, 1H).

ESI-MS m/z 423 [M+H]$^+$

Example 53

Synthesis of (S)-8-fluoro-7-(2-methoxy-3,5-dimethylpyridin-4-yl)-1-(tetrahydrofuran-3-yl)-1H-pyrazolo[4,3-c]quinolin-4(5H)-one

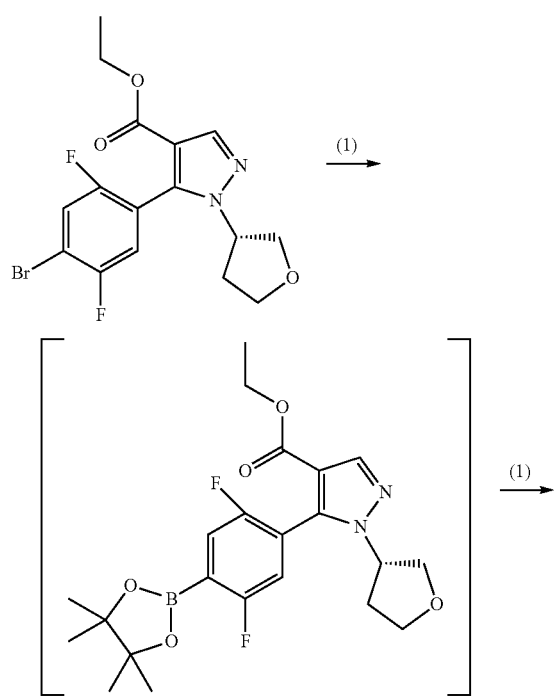

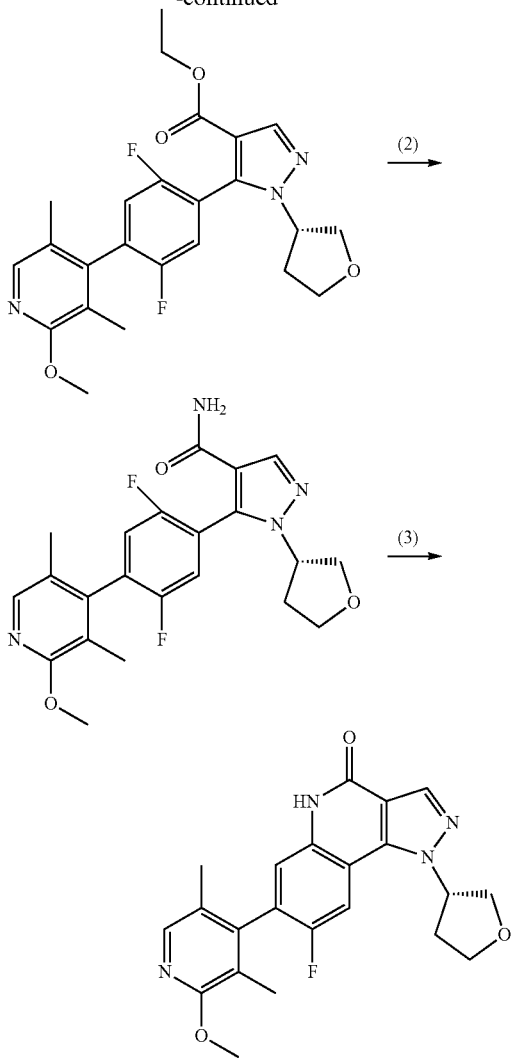

(1) Synthesis of ethyl 5-(2,5-difluoro-4-(2-methoxy-3,5-dimethylpyridin-4-yl)phenyl)-1-[(S)-tetrahydrofuran-3-yl]-1H-pyrazole-4-carboxylate Ethyl 5-(4-bromo-2,5-difluorophenyl)-1-((S)-tetrahydrofuran-3-yl)-1H-pyrazole-4-carboxylate obtained in Preparation Example 11-1 (4.31 g), bis(pinacolato)diboron (3.27 g), potassium acetate (3.16 g) and Pd(dppf)Cl$_2$-DCM complex (439 mg) were added to DMF (41.6 mL), and the mixture was stirred at 95° C. in a nitrogen atmosphere. After two hours, the reaction mixture was stirred at 105° C. for four hours. The reaction mixture was cooled to room temperature and filtered through Celite™. The filtrate was concentrated under reduced pressure, brine and ethyl acetate were added to the residue, and the mixture was then stirred at room temperature for five minutes. The mixture was filtered again through Celite™, and the filtrate was extracted with ethyl acetate. The organic layer was dried over anhydrous magnesium sulfate and filtered through Celite™. The filtrate was concentrated. The residue was purified by silica gel chromatography (n-heptane/ethyl acetate, 20% to 30% to 80%) to give ethyl 5-(2,5-difluoro-4-(4,4,5,5-tetramethyl-1,3,2-dioxaborolan-2-yl)phenyl)-1-((S)-tetrahydrofuran-3-yl)-1H-pyrazole-4- carboxylate (2.95 g). The resulting ethyl 5-(2,5-difluoro-4-(4,4,5,5-tetramethyl-1,3,2-dioxaborolan-2-yl)phenyl)-1-((S)-tetrahydrofuran-3-yl)-1H-pyrazole-4-carboxylate (900 mg), 4-iodo-2-methoxy-3,5-dimethylpyridine obtained in Preparation Example 29(3) (634 mg), Pd(PPh$_3$)$_4$ (116 mg) and cesium carbonate (1.96 g) were added to a mixed solvent of 1,4-dioxane (9.3 mL) and water (3.1 mL), and the mixture was heated under reflux for 2.5 hours. The reaction mixture was cooled to room temperature and partitioned by adding ethyl acetate and brine. The organic layer was dried over anhydrous magnesium sulfate and filtered. The filtrate was concentrated, and the residue was purified by NH silica gel column chromatography (ethyl acetate/n-heptane, first time: 15% to 36% to 47%, second time: 10% to 30% to 35%) to give the title compound (280 mg).

$^1$H-NMR (400 MHz, CDCl$_3$) δ (ppm): 1.17-1.23 (m, 3H), 1.99-2.06 (m, 6H), 2.26-2.55 (m, 2H), 3.92-4.29 (m, 9H), 4.65-4.75 (m, 1H), 6.95-7.03 (m, 1H), 7.14-725 (m, 1H), 7.96 (s, 1H), 8.12 (s, 1H).

ESI-MS m/z 480 [M+Na]$^+$ (2) Synthesis of 5-(2,5-difluoro-4-(2-methoxy-3,5-dimethylpyridin-4-yl)phenyl)-1-[(S)-tetrahydrofuran-3-yl]-1H-pyrazole-4-carboxamide 5 N sodium hydroxide (0.5 mL) was added to a solution of ethyl 5-[2,5-difluoro-4-(2-methoxy-3,5-dimethylpyridin-4-yl)phenyl]-1-[(S)-tetrahydrofuran-3-yl]-1H-pyrazole-4-carboxylate (280 mg) in ethanol (3.6 mL), and the mixture was stirred at 65° C. for three hours. After cooling the reaction mixture to room temperature, chloroform and brine were added, and the mixture was adjusted to pH 6 with 5 N hydrochloric acid and saturated ammonium chloride solution. The organic layer was dried over anhydrous magnesium sulfate, and the desiccant was removed by filtration. The filtrate was concentrated under reduced pressure to give 5-(2,5-difluoro-4-(2-methoxy-3,5-dimethylpyridin-4-yl)phenyl)-1-((S)-tetrahydrofuran-3-yl)-1H-pyrazole-4-carboxylic acid (238 mg) as a crude purified product. CDI (121 mg) was added to a solution of the carboxylic acid (238 mg) in DMF (3 mL), and the mixture was stirred at room temperature for one hour. A 28% aqueous ammonia solution (0.6 mL) was added to the reaction mixture, followed by stirring overnight. The reaction mixture was concentrated under reduced pressure, and the residue was partitioned by adding chloroform and a saturated aqueous sodium bicarbonate solution. The organic layer was washed with brine and then dried over anhydrous magnesium sulfate, and the desiccant was removed by filtration. The filtrate was passed through a silica gel pad (NH silica gel; eluting with ethyl acetate), and the resulting filtrate was concentrated under reduced pressure to give the title compound (186 mg).

$^1$H-NMR (400 MHz, CDCl$_3$) δ (ppm): 1.95-2.10 (m, 6H), 2.25-2.57 (m, 2H), 3.91-429 (m, 7H), 4.69 (brs, 1H), 5.24-5.57 (m, 2H), 7.01 (dd, J=8.79, 5.66 Hz, 1H), 7.17-7.26 (m, 1H), 7.94-7.99 (m, 2H).

ESI-MS m/z 451 [M+Na]$^+$ (3) Synthesis of (S)-8-fluoro-7-(2-methoxy-3,5-dimethylpyridin-4-yl)-1-(tetrahydrofuran-3-yl)-1H-pyrazolo[4,3-c]quinolin-4(5H)-one Sodium hydroxide (powder, 82 mg) was added to a solution of 5-(2,5-difluoro-4-(2-methoxy-3,5-dimethylpyridin-4-yl)phenyl)-1-[(S)-tetrahydrofuran-3-yl]-1H-pyrazole-4-carboxamide (186 mg) in DMSO (1.5 mL), and the mixture was stirred at 75° C. for 1.5 hours. The reaction mixture was cooled to room temperature, and water (5.5 mL) was then added with stirring. Acetic acid (0.12 mL) was further added, followed by stirring for 30 minutes. The generated solid was filtered, washed with water (5 mL) and then dried under reduced pressure at 60° C. for one hour to give the title compound (155 mg).

$^1$H-NMR. (400 MHz, CDCl$_3$) δ (ppm): 1.98 (s, 3H), 2.00 (s, 3H), 2.55-2.72 (m, 1H), 2.73-2.86 (m, 1H), 4.01 (s, 3H), 4.13 (td, J=8.40, 4.69 Hz, 1H), 4.20-4.39 (m, 2H), 4.43 (dt, J=9.57, 3.03 Hz, 1H), 5.52-5.62 (m, 1H), 7.23 (d, J=5.25 Hz, 1H), 7.84 (d, J=9.96 Hz, 1H), 7.98 (s, 1H), 8.32 (s, 1H), 10.82 (brs, 1H).

ESI-MS m/z 409 [M+1]$^+$

Example 54

Synthesis of (S)-8-fluoro-7-(2-methoxy-4,6-dimethylpyridin-3-yl)-1-(tetrahydrofuran-3-yl)-1H-pyrazolo[4,3-c]quinolin-4(5H)-one

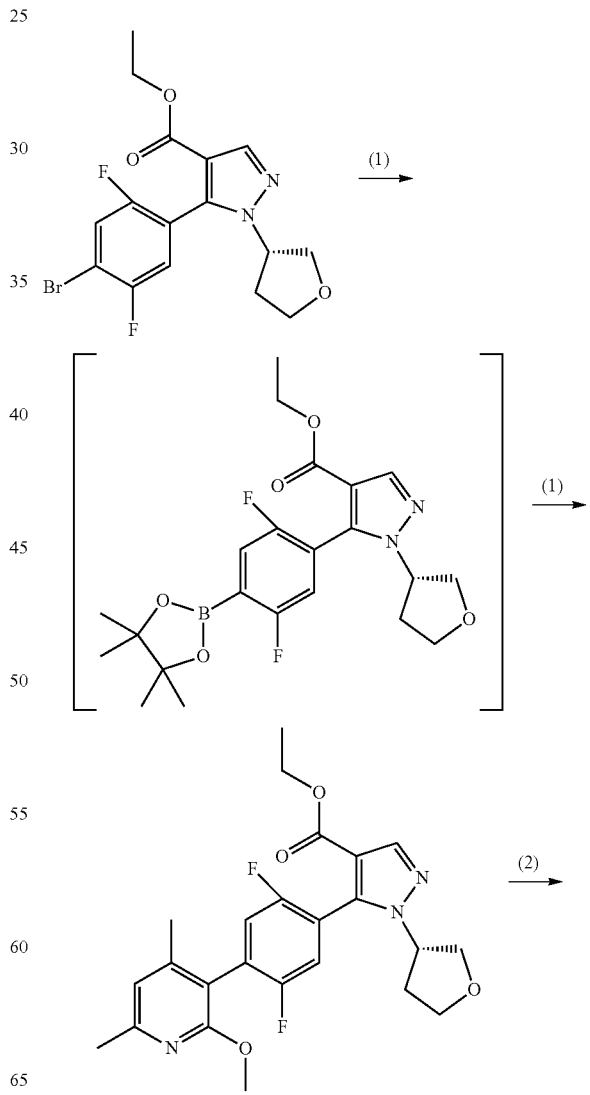

(2) Synthesis of 5-(2,5-difluoro-4-(2-methoxy-4,6-dimethylpyridin-3-yl)phenyl)-1-[(S)-tetrahydrofuran-3-yl]-1H-pyrazole-4-carboxamide A 5 N aqueous sodium hydroxide solution (0.8 mL) was added to a solution of ethyl 5-(2,5-difluoro-4-(2-methoxy-4,6-dimethylpyridin-3-yl)phenyl)-1-[(S)-tetrahydrofuran-3-yl]-1H-pyrazole-4-carboxylate (397 mg) in ethanol (5 mL), and the reaction mixture was stirred at 70° C. for 1 hour. After cooling the reaction mixture to room temperature, chloroform and brine were added, and the mixture was adjusted to pH 6 with 5 N hydrochloric acid and a saturated aqueous ammonium chloride solution. The organic layer was dried over anhydrous magnesium sulfate, and the desiccant was removed by filtration. The filtrates was concentrated under reduced pressure to give 5-(2,5-difluoro-4-(2-methoxy-4,6-dimethylpyridin-3-yl)phenyl)-1-[(S)-tetrahydrofuran-3-yl]-1H-pyrazole-4-carboxylic acid (457 mg) as a crude. CDI (211 mg) was added to a solution of the carboxylic acid (457 mg) in DMF (6 mL), and the reaction mixture was stirred at room temperature. After 75 minutes, a 28% aqueous ammonia solution (0.88 mL) was added to the reaction mixture and the reaction mixture was stirred at room temperature overnight. The reaction mixture was concentrated under reduced pressure, and the residue was partitioned by adding ethyl acetate and a saturated aqueous ammonium chloride solution. The organic layer was washed with a saturated aqueous sodium bicarbonate solution, dried over anhydrous magnesium sulfate, and the desiccant was removed by filtration. After the filtrate was concentrated under reduced pressure, the precipitated solid was removed by filtration and washed with dichloromethane and ethyl acetate. The filtrate was concentrated under reduced pressure and the residue was purified by silica gel chromatography (ethyl acetate/n-heptane, 60% to 80% to 85%) to give title compound (199 mg). This title compound was used for the next reaction without further purification.

ESI-MS m/z 451 [M+Na]$^+$

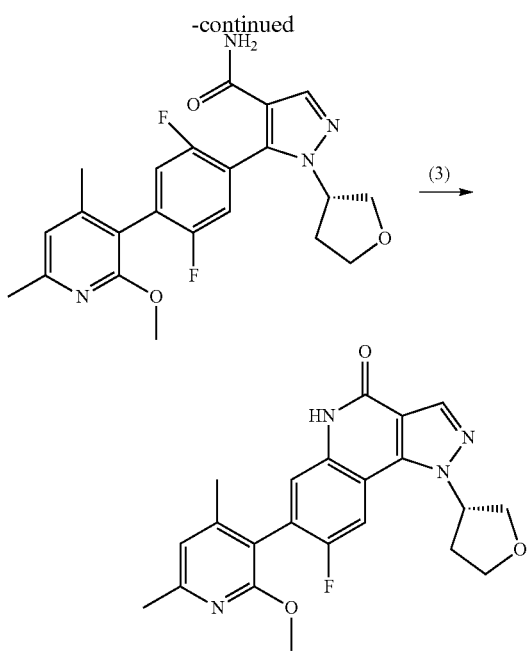

(1) synthesis of ethyl 5-(2,5-difluoro-4-(2-methoxy-4,6-dimethylpyridin-3-yl)phenyl)-1-[(S)-tetrahydrofuran-3-yl]-1H-pyrazole-4-carboxylate Ethyl 5-(4-bromo-2,5-difluorophenyl)-1-[(S)-tetrahydrofuran-3-yl]-1H-pyrazole-4-carboxylate (4.31 g), bis(pinacolato)diboron (3.27 g), potassium acetate (3.16 g), Pd(dppf)Cl$_2$-DCM complex (439 mg) were added to DMF (41.6 mL), and the reaction mixture was stirred at 95° C. in a nitrogen atmosphere. After stirring the reaction mixture for about 2 hours, the reaction mixture was stirred at 105° C. for about 4 hours. The reaction mixture was cooled to room temperature and then filtered through Celite™. The filtrate was concentrated under reduced pressure, and after brine and ethyl acetate were added to the residue the solution was stirred at room temperature for 5 minutes. The reaction mixture was again filtered through Celite™, and the filtrate was extracted with ethyl acetate. The organic layer was dried over anhydrous magnesium sulfate and filtrated through Celite™. The filtrate was concentrated, and the residue was purified by silica gel chromatography (heptane/ethyl acetate, 20% to 30% to 80%) to give ethyl 5-(2,5-difluoro-4-(4,4,5,5-tetramethyl-1,3,2-dioxaborolan-2-yl)phenyl)-1-[(S)-tetrahydrofuran-3-yl]-1H-pyrazole-4-carboxylate (2.95 g). Eethyl 5-(2,5-difluoro-4-(4,4,5,5-tetramethyl-1,3,2-dioxaborolan-2-yl)phenyl)-1-[(S)-tetrahydrofuran-3-yl]-1H-pyrazole-4-carboxylate (812 mg), 3-bromo-2-methoxy-4,6-dimethylpyridine (490 mg), Pd(PPh$_3$)$_4$ (130 mg) and cesium carbonate (1.77 g) were added to a mixed solvent of 1,4-dioxane (9.00 mL) and water (3.00 mL), and the reaction mixture was heated under reflux for 4 hours. The reaction mixture was cooled to room temperature and partitioned by adding ethyl acetate and brine. The organic layer was dried over anhydrous magnesium sulfate and filtered. The filtrate was concentrated, and the residue was purified by NH silica gel column chromatography (ethyl acetate/n-heptane, 11% to 30% to 50%) to give the title compound (397 mg). The title compound was used for the next reaction without further purification.

ESI-MS m/z 480 [M+Na]

(3) Synthesis of (S)-8-fluoro-7-(2-methoxy-4,6-dimethylpyridin-3-yl)-1-(tetrahydrofuran-3-yl)-1H-pyrazolo[4,3-c]quinolin-4(5H)-one Sodium hydroxide (powder, 74 mg) was added to a solution of 5-(2,5-difluoro-4-(2-methoxy-4,6-dimethylpyridin-3-yl)phenyl)-1-[(S)-tetrahydrofuran-3-yl]-1H-pyrazole-4-carboxamide (199 mg) in DMSO (2 mL), and the reaction mixture was stirred at 75° C. for 1.5 hours. After the reaction mixture was cooled to room temperature, water, acetic acid (0.106 mL) and ethyl acetate were added to the reaction mixture with stirring. After the precipitated solid was filtered, organic layer was washed with water, a saturated aqueous sodium bicarbonate solution and brine, dried over anhydrous magnesium sulfate, and the desiccant was removed by filtration. After the filtrate was concentrated under reduced pressure, the residue was purified by silica gel column chromatography (ethyl acetate/n-heptane, 55% to 90% to 96%), and the resulting crude was solidified by adding n-heptane/MTBE to give the title compound (33 mg).

$^1$H-NMR (400 MHz, CDCl$_3$) δ (ppm): 2.11 (s, 3H), 2.49 (s, 3H), 2.56-2.67 (m, 1H), 2.71-2.84 (m, 1H), 3.86 (s, 3H), 4.07-4.40 (m, 4H), 5.49-5.62 (m, 1H), 6.68-6.78 (m, 1H), 7.24-731 (m, 1H), 7.74-7.84 (m, 1H), 8.25-8.32 (m, 1H), 10.16 (br. s., 1H).

ESI-MS m/z 409 [M+1]$^+$

Example 55

Synthesis of (S)-8-fluoro-7-(6-methoxy-2,4-dimethylpyridin-3-yl)-1-(tetrahydrofuran-3-yl)-1H-pyrazolo[4,3-c]quinolin-4(5H)-one

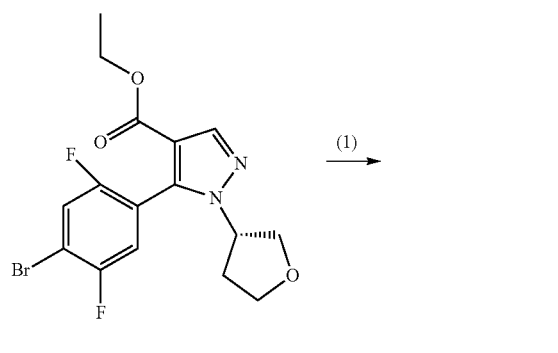

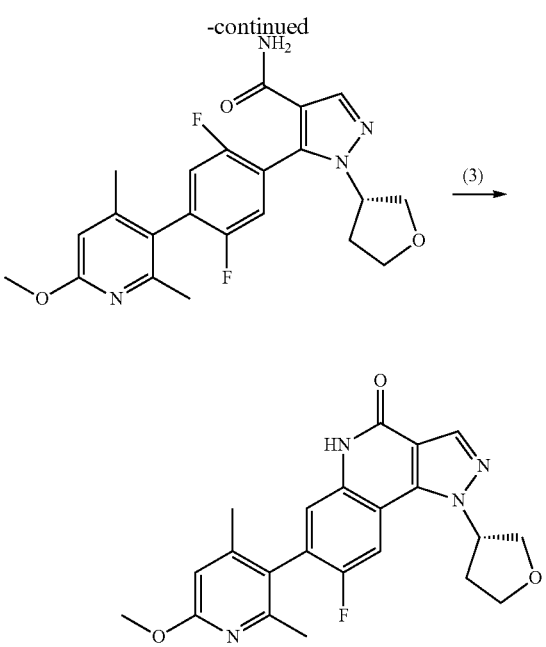

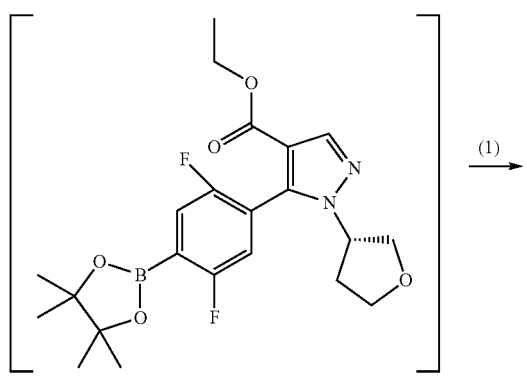

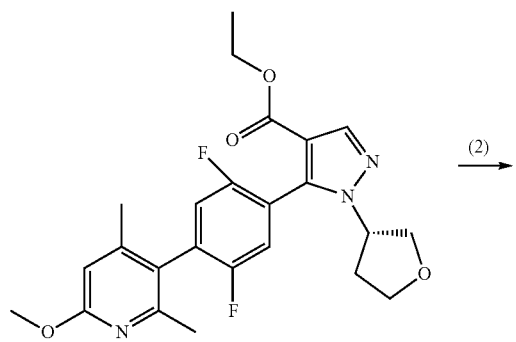

(1) Synthesis of ethyl 5-(2,5-difluoro-4-(6-methoxy-2,4-dimethylpyridin-3-yl)phenyl)-1-[(S)-tetrahydrofuran-3-yl]-1H-pyrazole-4-carboxylate A mixture of ethyl 5-[2,5-difluoro-4-(4,4,5,5-tetramethyl-1,3,2-dioxaborolan-2-yl)phenyl]-1-[(S)-tetrahydrofuran-3-yl]-1H-pyrazole-4-carboxylate synthesized in accordance with Example 53 (430 mg), 3-bromo-6-methoxy-2,4-dimethylpyridine obtained in Preparation Example 23 (223 mg), potassium hydrogen fluoride (254 mg), Pd(PPh$_3$)$_4$ (90 mg) and tripotassium phosphate n-hydrate (400 mg) in DME (8 mL) and water (2 mL) was heated under reflux at 110° C. for seven hours. The reaction mixture was cooled to room temperature and partitioned by adding ethyl acetate and brine. The organic layer was dried over anhydrous magnesium sulfate and filtered. The filtrate was concentrated, and the residue was purified by NH silica gel column chromatography (ethyl acetate/n-heptane: 16% to 37% to 46%) and silica gel column chromatography (ethyl acetate/n-heptane: 28% to 49% to 54%) to give the title compound (144 mg). This compound was used for the next reaction without further purification.

ESI-MS m/z 458 [M+H]$^+$

The reactions of (2) to (3) were performed in accordance with Example 53. However, in the reaction (3), the title compound obtained as a crude purified product was subjected to silica gel column chromatography (ethyl acetate/n-heptane, 60% to 95%) and then purified by solidification from MTBE to give the title compound.

$^1$H-NMR (400 MHz, CDCl$_3$) δ (ppm): 2.02-2.10 (m, 3H), 2.23-2.27 (m, 3H), 2.56-2.69 (m, 1H), 2.72-2.87 (m, 1H), 3.97 (s, 3H), 4.13 (td, J=8.44, 4.59 Hz, 1H), 4.20-4.37 (m, 2H), 4.43 (dd, J=9.86, 3.22 Hz, 1H), 5.51-5.63 (m, 1H), 6.57 (d, J=0.59 Hz, 1H), 720-7.25 (m, 1H), 7.82 (d, J=10.15 Hz, 1H), 8.31 (s, 1H), 10.38 (brs, 1H).

ESI-MS m/z 409 [M+H]$^+$

Example 56

Synthesis of (S)-7-(3-ethyl-2-methoxy-5-methylpyridin-4-yl)-1-(tetrahydrofuran-3-yl)-1H-pyrazolo[4,3-c]quinolin-4(5H)-one

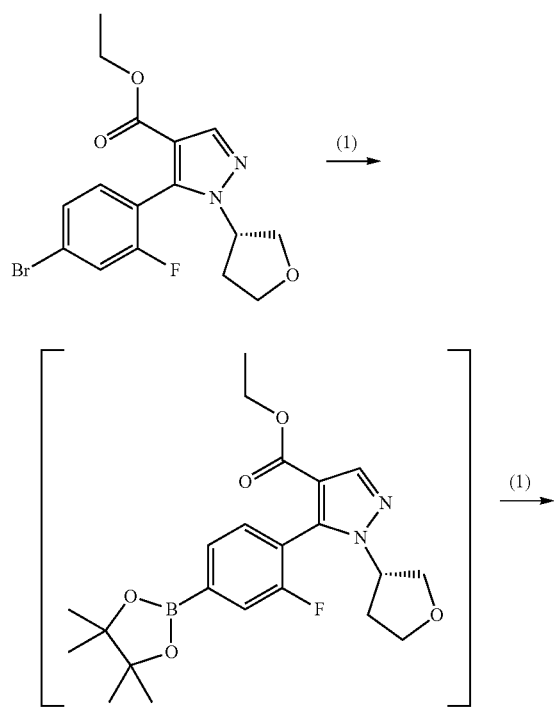

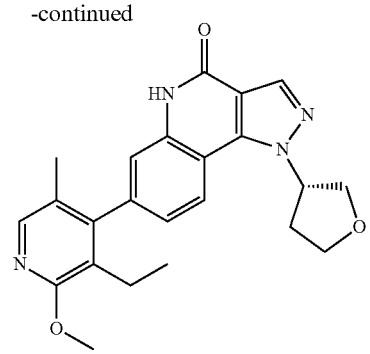

The title compound was obtained by performing the reactions (1) to (3) in accordance with Example 53 using ethyl 5-(4-bromo-2-fluorophenyl)-1-[(S)-tetrahydrofuran-3-yl]-1H-pyrazole-4-carboxylate obtained in Preparation Example 6(1) and 3-ethyl-4-iodo-2-methoxy-5-methylpyridine obtained in Preparation Example 49.

$^1$H-NMR (400 MHz, CDCl$_3$) δ (ppm): 0.94-1.06 (m, 3H), 1.88-1.96 (m, 3H), 2.35 (q, J=7.48 Hz, 2H), 2.55-2.69 (m, 1H), 2.75-2.88 (m, 1H), 3.96-4.05 (m, 3H), 4.08-4.19 (m, 1H), 4.22-4.38 (m, 2H), 4.38-4.48 (m, 1H), 5.60-5.72 (m, 1H), 7.09 (dd, J=8.30, 1.66 Hz, 1H), 7.20-725 (m, 1H), 7.93-7.95 (m, 1H), 8.12 (d, J=8.20 Hz, 1H), 8.30 (s, 1H), 10.38 (brs, 1H).

ESI-MS m/z 405 [M+H]$^+$

Example 57

Synthesis of (R)-8-fluoro-7-(2-methoxy-3,5-dimethylpyridin-4-yl)-1-(tetrahydrofuran-3-yl)-1H-pyrazolo[4,3-c]quinolin-4(5H)-one

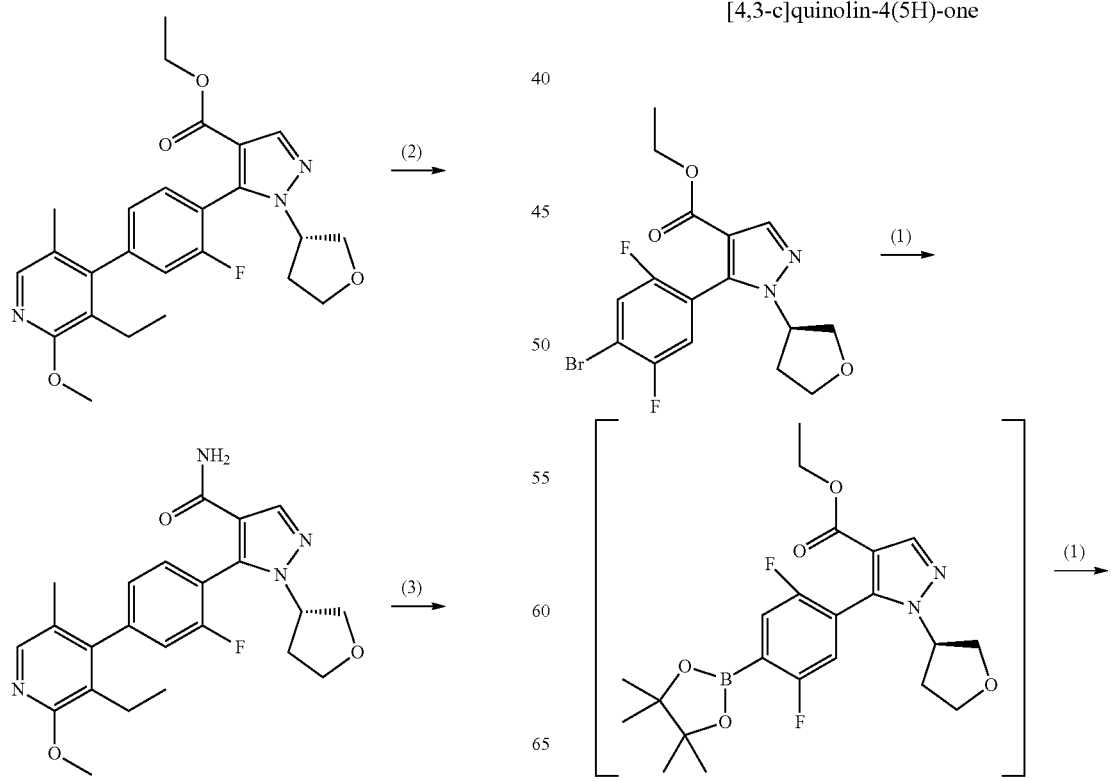

143
-continued

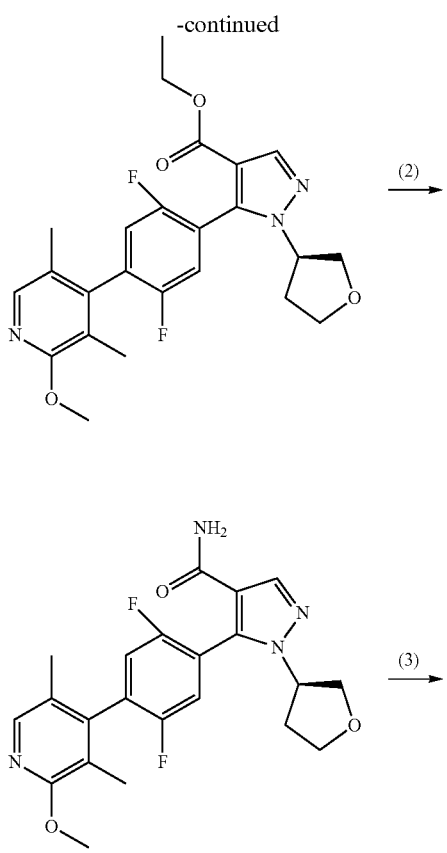

The title compound was obtained by performing the reactions (1) to (3) in accordance with Example 53 using ethyl 5-(4-bromo-2,5-difluorophenyl)-1-((R)-tetrahydrofuran-3-yl)-1H-pyrazole-4-carboxylate obtained in Preparation Example 11-2 and 4-iodo-2-methoxy-3,5-dimethylpyridine obtained in Preparation Example 29(3). However, in the reaction (3), the title compound obtained as a crude purified product was purified by washing with 1-propanol.

$^1$H-NMR (400 MHz, CDCl$_3$) δ (ppm): 1.98 (s, 3H), 2.00 (s, 3H), 2.56-2.71 (m, 1H), 2.73-2.89 (m, 1H), 4.01 (s, 3H), 4.13 (td, J=8.40, 4.69 Hz, 1H), 4.18-4.38 (m, 2H), 4.40-4.48 (m, 1H), 5.51-5.64 (m, 1H), 7.21-7.30 (m, 1H), 7.84 (d, J=10.15 Hz, 1H), 7.98 (d, J=0.78 Hz, 1H), 8.32 (s, 1H), 11.05 (brs, 1H).

ESI-MS m/z 409 [M+H]$^+$

The compounds of Examples 58 and 59 were synthesized as in Example 57.

144

TABLE 9

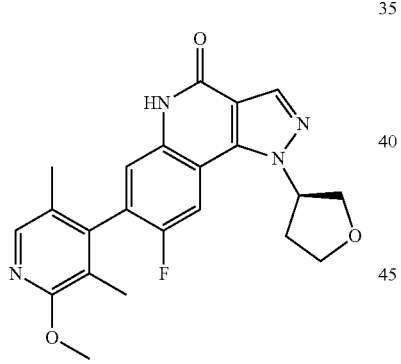

| # | R$^2$ | NMR, Mass |
|---|---|---|
| 58 | ![pyridine1] | $^1$H-NMR (400 MHz, CDCl$_3$) δ (ppm): 2.11 (s, 3H), 2.50 (s, 3H), 2.56-2.69 (m, 1H), 2.71-2.87 (m, 1H), 3.87 (s, 3H), 4.12 (td, J = 8.40, 4.69 Hz, 1H), 4.21-4.36 (m, 1H), 4.38-4.47 (m, 1H), 5.50-5.61 (m, 1H), 6.73-6.78 (m, 1H), 7.36 (d, J = 6.44 Hz, 1H), 7.79 (d, J = 10.15 Hz, 1H), 8.30 (s, 1H), 11.05 (d, J = 8.01 Hz, 1H). ESI-MS m/z 409 [M + H]$^+$ |
| 59 | ![pyridine2] | $^1$H-NMR (400 MHz, CDCl$_3$) δ (ppm): 2.06 (s, 3H), 2.25 (s, 3H), 2.57-2.70 (m, 1H), 2.74-2.85 (m, 1H), 3.98 (s, 3H), 4.13 (td, J = 8.35, 4.59 Hz, 1H), 4.22-4.37 (m, 2H), 4.43 (dd, J = 9.57, 3.32 Hz, 1H), 5.54-5.62 (m, 1H), 6.57 (s, 1H), 7.30 (d, J = 6.64 Hz, 1H), 7.82 (d, J = 9.96 Hz, 1H), 8.32 (s, 1H), 10.96 (brs, 1H). ESI-MS m/z 409 [M + H]$^+$ |

Example 60

Synthesis of 7-(2-methoxy-4,6-dimethylpyridin-3-yl)-1-[3RS,4SR)-4-methoxytetrahydrofuran-3-yl]-1H-pyrazolo[4,3-c]quinolin-4(5H)-one

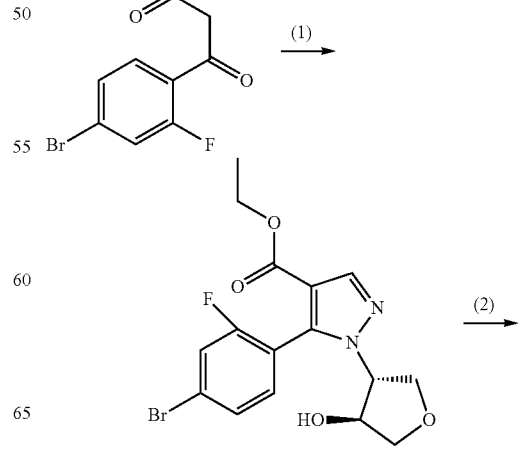

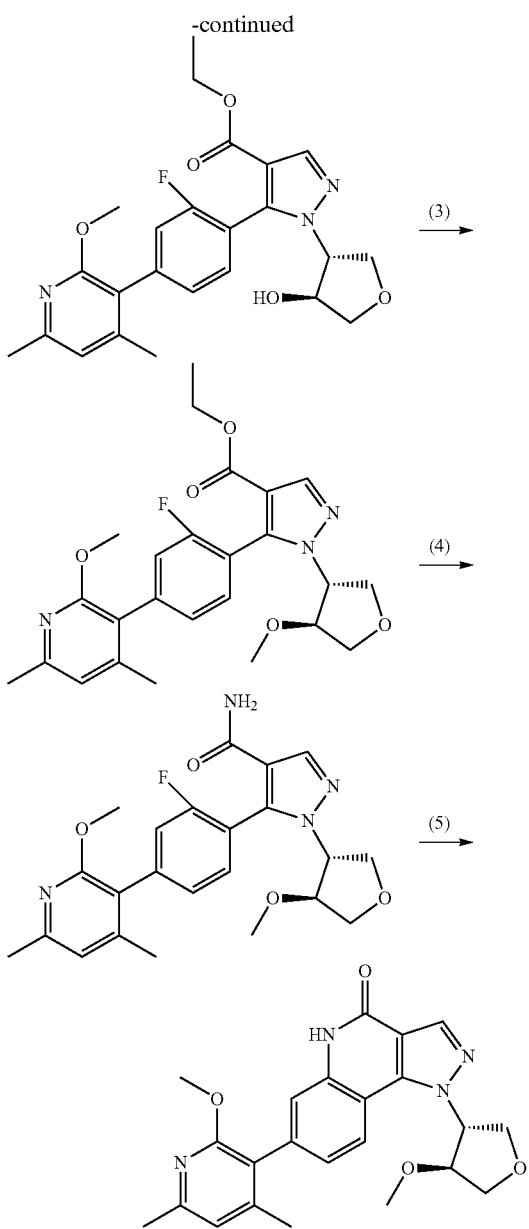

(1) Synthesis of ethyl 5-(4-bromo-2-fluorophenyl)-1-[(3RS,4SR)-4-hydroxytetrahydrofuran-3-yl]-1H-pyrazole-4-carboxylate The title compound was synthesized in accordance with Preparation Example 7 using (3SR,4RS)-4-hydrazinyltetrahydrofuran-3-ol hydrochloride obtained in Preparation Example 18 in place of (S)-(tetrahydrofuran-3-yl)hydrazine hydrochloride.

ESI-MS m/z 421 [M+Na]$^+$ (2) Synthesis of ethyl 5-(2-fluoro-4-(2-methoxy-4,6-dimethylpyridin-3-yl)phenyl)-1-[(3RS,4SR)-4-hydroxytetrahydrofuran-3-yl]-1H-pyrazole-4-carboxylate Ethyl 5-(4-bromo-2-fluorophenyl)-1-[(3RS,4SR)-4-hydroxytetrahydrofuran-3-yl]-1H-pyrazole-4-carboxylate (3.8 g), bis(pinacolato)diboron (2.90 g), potassium acetate (2.80 g) and Pd(dppf)Cl$_2$-DCM complex (480 mg) were added to DMF (38.3 mL), and the mixture was stirred at 90° C. in a nitrogen atmosphere. After stirring the reaction mixture for about two hours, a solution of 3-bromo-2-methoxy-4,6-dimethylpyridine obtained in Preparation Example 26 (3.09 g) in DMF (15 mL), and water (22 mL) were added, and the mixture was warmed to 120° C. and further stirred for about five hours. The reaction mixture was cooled to room temperature and concentrated under reduced pressure, and the residue was passed through a silica gel pad (NH silica gel, eluting with ethyl acetate). The filtrate was concentrated to about 200 mL and then partitioned by adding brine. The organic layer was dried over anhydrous magnesium sulfate and filtered. The filtrate was concentrated, and the residue was purified by NH silica gel column chromatography (ethyl acetate/n-heptane, 70% to 90%) to give the title compound (2.26 g).

ESI-MS m/z 456 [M+H]$^+$ (3) Synthesis of ethyl 5-(2-fluoro-4-(2-methoxy-4,6-dimethylpyridin-3-yl)phenyl)-1-[(3RS,4SR)-4-methoxytetrahydrofuran-3-yl]-1H-pyrazole-4-carboxylate Sodium hydride (60% oil dispersion, 86 mg) was added to a solution of ethyl 5-(2-fluoro-4-(2-methoxy-4,6-dimethylpyridin-3-yl)phenyl)-1-[(3RS,4SR)-4-hydroxytetrahydrofuran-3-yl]-1H-pyrazole-4-carboxylate (612 mg) in THF (5 mL) under ice-cooling, followed by stirring for three minutes. Methyl iodide (0.142 mL) was added to the reaction mixture, and the mixture was stirred at the same temperature for five minutes, and then warmed to room temperature and stirred for further two hours. A saturated aqueous ammonium chloride solution was added to the reaction mixture, followed by extraction with ethyl acetate. The organic layer was washed with brine, dried over anhydrous magnesium sulfate and filtered. The filtrate was concentrated, and the residue was purified by silica gel column chromatography (ethyl acetate/n-heptane, 27% to 48%) to give the title compound (379 mg).

ESI-MS m/z 492 [M+Na]$^+$ (4) Synthesis of 5-(2-fluoro-4-(2-methoxy-4,6-dimethylpyridin-3-yl)phenyl)-1-[(3RS,4SR)-4-methoxytetrahydrofuran-3-yl]-1H-pyrazole-4-carboxamide The title compound was synthesized in accordance with Example 53(2).

ESI-MS m/z 463 [M+Na]

(5) Synthesis of 7-(2-methoxy-4,6-dimethylpyridin-3-yl)-1-[(3RS,4SR)-4-methoxytetrahydrofuran-3-yl]-1H-pyrazolo[4,3-c]quinolin-4(5H)-one The title compound was obtained in accordance with Example 53. However, the title compound obtained as a crude purified product was purified by washing with MTBE.
$^1$H-NMR (400 MHz, CDCl$_3$) δ (ppm): 2.10 (s, 3H), 2.49 (s, 3H), 3.42 (s, 3H), 3.86 (s, 3H), 4.10 (dd, J=10.15, 2.15 Hz, 1H), 4.24-4.37 (m, 2H), 4.47 (dd, J=9.47, 6.35 Hz, 1H), 4.64-4.70 (m, 1H), 5.47-5.51 (m, 1H), 6.73-6.74 (m, 1H), 7.17-7.23 (m, 1H), 7.27-7.30 (m, 1H), 8.16 (d, J=8.40 Hz, 1H), 8.27-8.32 (m, 1H), 10.11 (s, 1H).

ESI-MS m/z 421 [M+H]$^+$

Example 61

Synthesis of 7-(2-methoxy-3,5-dimethylpyridin-4-yl)-1-[(3RS,4SR)-4-methoxytetrahydrofuran-3-yl]-1H-pyrazolo[4,3-c]quinolin-4(5H)-one

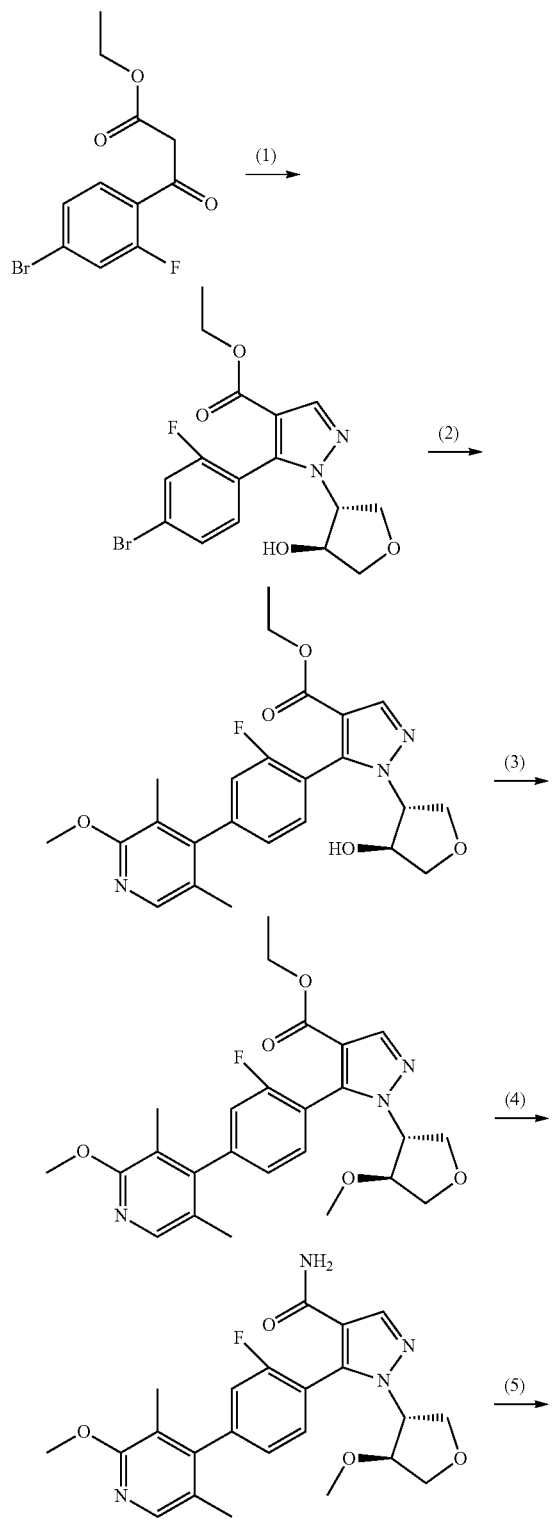

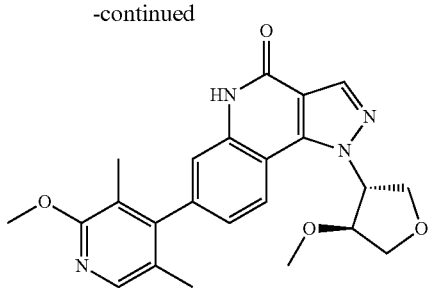

The title compound was obtained by performing the reactions (1) to (5) in accordance with Example 60 using 4-iodo-2-methoxy-3,5-dimethylpyridine obtained in Preparation Example 29(3).

$^1$H-NMR (400 MHz, CDCl$_3$) δ (ppm): 1.89-2.00 (m, 6H), 3.42 (d, J=3.59 Hz, 3H), 4.00 (s, 3H), 4.07-4.16 (m, 1H), 4.25-4.39 (m, 2H), 4.48 (dd, J=9.47, 6.35 Hz, 1H), 4.68 (dd, 1.95 Hz, 1H), 5.50 (ddd, J=6.20, 4.25, 1.86 Hz, 1H), 7.06-7.14 (m, 1H), 7.16-7.21 (m, 1H), 7.95 (s, 1H), 8.22 (d, J=8.40 Hz, 1H), 8.29-8.34 (m, 1H), 10.11 (s, 1H).

ESI-MS m/z 421 [M+H]$^+$

Example 62

Synthesis of (S)-7-(6-ethoxy-2,4-dimethylpyridin-3-yl)-1-(tetrahydrofuran-3-yl)-1H-pyrazolo[4,3-c]quinolin-4(5H)-one

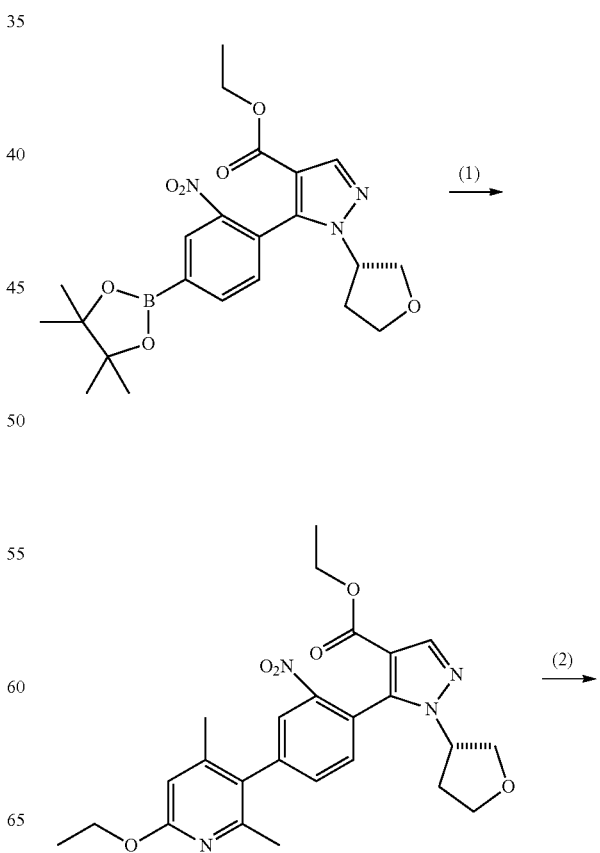

-continued

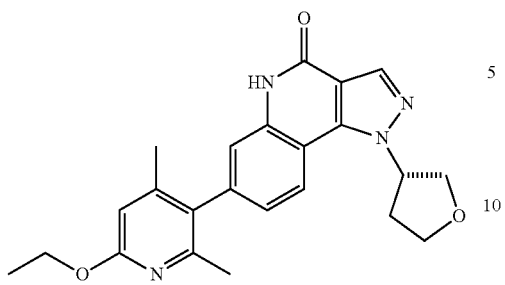

(1) Synthesis of ethyl 5-[4-(6-ethoxy-2,4-dimethylpyridin-3-yl)-2-nitrophenyl]-1-[(S)-tetrahydrofuran-3-yl]-1H-pyrazole-4-carboxylate Ethyl 5-[2-nitro-4-(4,4,5,5-tetramethyl-1,3,2-dioxaborolan-2-yl)phenyl][(S)-tetrahydrofuran-3-yl]-1H-pyrazole-4-carboxylate obtained in Preparation Example 7-(2) (200 mg) was dissolved in a mixed solution of 1,4-dioxane (4 mL) and water (1 mL). 3-bromo-6-ethoxy-2,4-dimethylpyridine obtained in Preparation Example 51 (121 mg), Pd(PPh$_3$)$_4$ (25 mg) and cesium carbonate (428 mg) were added, and the mixture was reacted using a microwave reactor at 130° C. for three hours. The reaction mixture was returned to room temperature, followed by extraction with ethyl acetate. The organic layer was washed with brine and dried over anhydrous sodium sulfate. The desiccant was removed by filtration, and the filtrate was concentrated under reduced pressure. The residue was purified by silica gel column chromatography (ethyl acetate/n-heptane, 30% to 100%) to give the title compound (97 mg).

ESI-MS m/z 481 [M+H]$^+$ (2) Synthesis of (S)-7-(6-ethoxy-2,4-dimethylpyridin-3-yl)-1-(tetrahydrofuran-3-yl)-1H-pyrazolo[4,3-c]quinolin-4(5H)-one Ethyl 5-[4-(6-ethoxy-2,4-dimethylpyridin-3-yl)-2-nitrophenyl]-1-[(S)-tetrahydrofuran-3-yl]-1H-pyrazole-4-carboxylate (97 mg) was dissolved in acetic acid (1 mL). Iron powder (56 mg) was added to the solution, and the mixture was stirred at 90° C. for four hours. The reaction mixture was returned to room temperature, and water (2 mL) was added to the reaction mixture. The precipitated solid was collected by filtration and washed with water. The resulting solid was dissolved in ethanol (1 mL) at 90° C. The solution was ice-cooled, and the precipitated solid was collected by filtration. The resulting solid was washed with MTBE to give the title compound (16 mg).

$^1$H-NMR (400 MHz, CDCl$_3$) δ (ppm): 1.43 (t, J=7.0 Hz, 3H), 2.03 (s, 3H), 2.21 (s, 3H), 2.55-2.67 (m, 1H), 2.76-2.87 (m, 1H), 4.07-4.17 (m, 2H), 4.23-4.47 (m, 4H), 5.62-5.70 (m, 1H), 6.53 (s, 1H), 7.12 (dd, J=8.2 Hz, 1.6 Hz, 1H), 7.32 (d, J=1.6 Hz, 1H), 8.10 (d, J=8.6 Hz, 1H), 8.31 (s, 1H), 11.02 (brs, 1H).

ESI-MS m/z 405 [M+H]$^+$

Example 63

Synthesis of (S)-7-(2-methoxy-3,5-dimethylpyridin-4-yl)-1-(tetrahydrofuran-3-yl)-1H-pyrazolo[4,3-c]quinolin-4(5H)-one

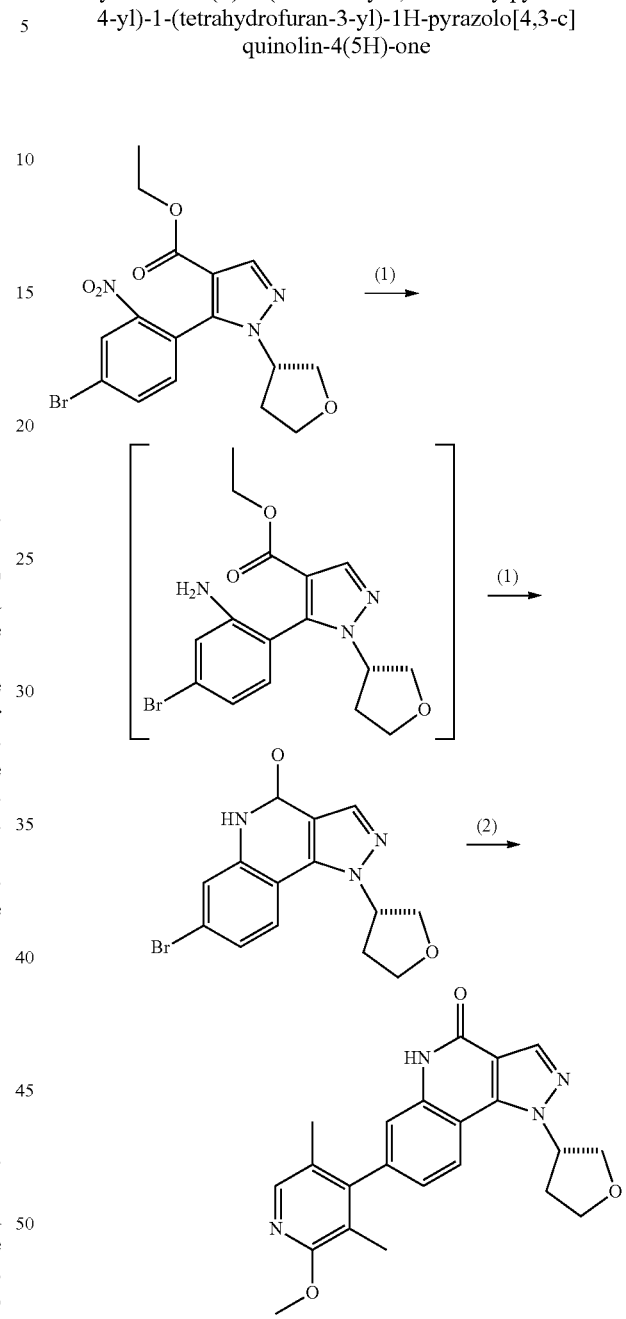

(1) Synthesis of (S)-7-bromo-1-(tetrahydrofuran-3-yl)-1H-pyrazolo[4,3-c]quinolin-4(5H)-one Sodium hydrosulfite (265 mg) was added to a solution of ethyl 5-(4-bromo-2-nitrophenyl)-1-[(S)-tetrahydrofuran-3-yl]-1H-pyrazole-4-carboxylate obtained in Preparation Example 7(1) (100 mg) in THF (1 mL) and water (0.5 mL) at 0° C. The mixture was stirred at room temperature for 46 horns. The reaction mixture was cooled at 0° C., and 5 N hydrochloric acid (0.25 mL) was then added. The mixture was stirred at room temperature for three hours. After cooling at 0° C., a 5 N aqueous sodium hydroxide solution (0.25 mL) was added to the reaction mixture. The mixture was extracted with isopropyl acetate. The organic layer was washed with water and brine and then concentrated under reduced pressure. Ethyl 5-(2-amino-4-bromophenyl)-1-[(S)-tetrahydrofuran-3-yl]-1H-pyrazolo-4-carboxylate (71 mg) was obtained as a crude purified product. This was used for the next step without further purification. Ethyl 5-(2-amino-4-bromophenyl)-1-[(S)-tetrahydrofuran-3-yl]-1H-pyrazolo-4-carboxylate (50 mg) obtained as a crude purified product was added to acetic acid (1 mL). The mixture was stirred at 60° C. for two hours. After cooling the reaction mixture to room temperature, water (1 mL) was added, and the mixture was stifled at room temperature for two hours. The precipitated solid was collected by filtration. The solid was washed with ethanol (1 mL) and then dried under reduced pressure. The title compound (42 mg) was obtained.

$^1$H-NMR (400 MHz, DMSO-$d_6$) δ (ppm): 2.41-2.56 (m, 2H), 3.89-4.03 (m, 2H), 4.10-4.19 (m, 2H), 5.78 (m, 1H), 7.41-7.44 (m, 1H), 7.64-7.65 (m, 1H), 8.16-8.18 (m, 2H), 11.53 (s, 1H).

ESI-MS m/z 336 [M+H]$^+$ (2) Synthesis of (S)-7-(2-methoxy-3,5-dimethylpyridin-4-yl)-1-(tetrahydrofuran-3-yl)-1H-pyrazolo[4,3-c]quinolin-4(5H)-one (S)-7-bromo-1-(tetrahydrofuran-3-yl)-1H-pyrazolo[4,3-c]quinolin-4(5H)-one (100 mg), (2-methoxy-3,5-dimethylpyridin-4-yl)boronic acid (65 mg) obtained in Preparation Example 29 (4) and cesium carbonate (293 mg) were added to a mixed solution of DMF (5 mL) and water (1 mL) at room temperature. PdCl$_2$(PPh$_3$)$_2$ (10.5 mg) was added to the mixture in a nitrogen gas stream. The mixture was stirred at 80° C. for one hour and at 100° C. for 4.5 hours. After cooling the reaction mixture to room temperature, water (5 mL) was added, and the mixture was extracted with isopropyl acetate. The organic layer was washed with water and brine and then concentrated under reduced pressure. A crude purified product (64.7 mg) was obtained as the title compound. The instrumental data of this compound were identical to those of the (-)-form of Example 25.

Pharmacological Test Examples

A PDE9 Inhibitory Activity Test Example

1) Preparation of a Human Recombinant PDE9 Protein

An hsPDE9A 1cDNA fragment was amplified by being based on a base sequence (Accession No.: AF048837) of the hsPDE9A1 registered on GenBank data base, and by using the following sequences (Hokkaido System Science Co., Ltd.) as a primer and Human hippocampus cDNA library (Clontech Laboratories, Inc.) as a template DNA, and using Pfu50 DNA polymerase (Invitrogen Corp.), and by a polymerase chain reaction (PCR) of the following condition.

```
An hPDE9-1 primer:
                                    (SEQ No. 1)
AGGATGGGATCCGGCTCCTCCA An hPDE9A-3 primer:
                                    (SEQ No. 2)
CAGGCACAGTCTCCTTCACTG
```

The condition of PCR: [96° C., 5 min]×1 cycle, [(96° C., 10 sec), (57° C., 5 sec), (72° C., 2 min)]×30 cycles The obtained hsPDE9A 1 cDNA fragment was incorporated in a TOPO-TA cloning vector (Invitrogen Corp.), and the base sequence was checked; and thereafter, the resultant was transfected in a pcDNA 3.1/myc His-tag vector (Invitrogen Corp.) to thereby make a human PDE9 expression vector for mammal cells. The human PDE9 expression vector for mammal cells was transfected with transient expression to an HEK293 cell by using a LIPOFETAMINE 2000 Reagent (Gibco). It was confirmed by Western blot method that the PDE9A expressed in the HEK293 cell, and then, the human PDE9A 1cDNA fragment was transfected in a pYNG vector (Katakura Industries Co., Ltd.) to thereby make an expression vector for insect cells. A supernatant of homogenized silk worm in which a large amount of PDE9 was expressed was purified by an equilibrated Ni column using a buffer A (20 mmol/L Tris-HCl, pH: 8.0, 1 mmol/L DTT, 10 mmol/L imidazole). After 1 hour of mixing of the supernatant and the Ni column, cleaning was carried out using a buffer B (20 mmol/L Tris-HCl, pH: 8.0, 1 mmol/L Du), and elution was carried out using a buffer C (20 mmol/L Tris-HCl, pH: 8.0, 1 mmol/L DTT, 100 mmol/L imidazole). An elution fraction was preparatively collected to thereby obtain a PDE9 enzyme solution.

2) Measurement of PDE9 Inhibitory Action

To 100 µL of a buffer D (40 mmol/L Tris-HCl, pH: 7.4, 10 mmol/L MgCl$_2$, 1 mM DTT, 2 µM cGMP) solution containing [$^3$H]-cGMP (0.5 pa/mL), 10 µL of a compound solution for evaluation (a solution in which a compound was dissolved in DMSO and diluted so that the DMSO concentration became 5%) and 90 µL of a solution prepared by diluting the PDE9 enzyme solution prepared in the above with a buffer E (40 mmol/L Tris-HCl, pH: 7.4, 10 mmol/L MgCl$_2$, 1 mM DTT, 1 mmol/L EGTA) were added under ice cooling. The resultant mixed solution was incubated at 30° C. for 10 min, and thereafter heated for 2 min in boiled water to stop the enzyme reaction of the PDE9. Then, the resultant was returned to room temperature; 50 µL of 5'-Nucleotidase (Biomol GmbH, 10 units/mL) was added thereto; and the resultant was incubated at 30° C. for 10 min to thereby convert [$^3$H]-5'-GMP formed in the previous reaction to [$^3$H]-guanosine. 500 µL of an anion exchange resin (Bio-Rad AG1-X2 resin, mesh size: 200-400, H$_2$O:resin=2:1) was added to the resultant reaction liquid, and allowed to stand for 10 min, and thereafter centrifuged (2,000 rpm, 10 min); and a supernatant in which the [$^3$H]-guanosine was present was transferred to a LumaPlate (PerkinElmer, Inc.), and the radioactivity was measured by a TopCount NXT microplate scintillation and luminescence counter (PerkinElmer, Inc.).

The inhibition percentage of the evaluation compound was calculated using the following expression, taking the radioactivity of a control containing no evaluation compound to be (A), the radioactivity of a blank containing no enzyme to be (B), and the radioactivity of the evaluation compound to be (C).

Inhibition percentage=$100-\{[(C)-(B)]/[(A)-(B)]\}\times 100(\%)$

The IC$_{50}$ value for PDE9 of the evaluation compound was determined from inhibition percentage for various concentrations. The IC$_{50}$ value in each evaluation compound is shown in Table 10.

TABLE 10

| Example | (+/−) or (R/S) | PDE9 IC$_{50}$ (µM) |
|---|---|---|
| 1 | | 0.0243 |
| 2 | | 0.025 |
| 3 | | 0.014 |
| 4 | | 0.00437 |
| 6 | | 0.00686 |
| 7 | | 0.0092 |
| 8 | | 0.0252 |
| 9 | | 0.0217 |
| 10 | | 0.0208 |
| 11 | | 0.0113 |
| 12 | | 0.0197 |
| 13 | | 0.0367 |
| 14 | | 0.0212 |
| 15 | | 0.00887 |
| 16 | | 0.00632 |
| 17 | | 0.00608 |
| 18 | | 0.0093 |
| 19 | | 0.013 |
| 20 | | 0.0289 |
| 21 | | 0.0539 |
| 22 | | 0.0523 |
| 23 | | 0.00951 |
| 24 | | 0.0187 |
| 25 | (−)S | 0.00943 |
| 25 | (+)R | 0.041 |
| 28 | (−) | 0.00836 |
| 28 | (+) | 0.0296 |
| 29 | (−) | 0.0307 |
| 29 | (+) | 0.137 |
| 30 | (−) | 0.0708 |
| 30 | (+) | 0.225 |
| 31 | (−) | 0.00742 |
| 31 | (+) | 0.0201 |
| 32 | (−) | 0.0122 |
| 32 | (+) | 0.0707 |
| 33 | (−) | 0.0279 |
| 33 | (+) | 0.113 |
| 34 | (−) | 0.00336 |
| 34 | (+) | 0.00388 |
| 35 | (−) | 0.00296 |
| 35 | (+) | 0.00262 |
| 36 | (−) | 0.0081 |
| 36 | (+) | 0.00898 |
| 37 | (−) | 0.0101 |
| 37 | (+) | 0.0109 |
| 38 | (−) | 0.0124 |
| 38 | (+) | 0.0171 |
| 39 | (−) | 0.00408 |
| 39 | (+) | 0.00507 |
| 40 | | 0.00321 |
| 41 | (−) | 0.0121 |
| 41 | (+) | 0.00591 |
| 42 | (−) | 0.022 |
| 42 | (+) | 0.00881 |
| 43 | | 0.0105 |
| 44 | | 0.0121 |
| 45 | | 0.00333 |
| 46 | | 0.0181 |
| 47 | | 0.00567 |
| 48 | | 0.00835 |
| 49 | | 0.0122 |
| 50 | | 0.00651 |
| 51 | | 0.00487 |
| 52 | | 0.00477 |
| 53 | | 0.0101 |
| 54 | | 0.00871 |
| 55 | | 0.0175 |
| 56 | | 0.0101 |
| 57 | | 0.0439 |
| 58 | | 0.0117 |
| 59 | | 0.0715 |
| 60 | | 0.0311 |
| 61 | | 0.0775 |
| 62 | | 0.0111 |

3) Effect on Rodent Cerebrospinal Fluid cGMP

The test compound was administered to ICR male mice (Charles River Laboratories Japan, Inc.), Sprague-Dawley male rats (SD) (Charles River Laboratories Japan, Inc.) or Long-Evans male rats (LE) (Institute for Animal Reproduction), and the cerebrospinal fluid was then collected under pentobarbital anesthesia and stored at −20° C. cGMP in the cerebrospinal fluid was measured in accordance with the acetylation EIA procedure of cGMP EIA kit (GE Healthcare) or the non-acetylation procedure of cGMP EIA kit (Cayman) The result was an increase (C) in the amount of cGMP of the test compound-administered group (B) relative to the amount of cGMP of the vehicle-administered group (A), and was calculated using the following formula $$cGMP\ \text{increase}(C) = [(B)-(A)]/(A) \times 100 (\%)$$

The results are shown in the following table.

TABLE 11

| Example | (+/−) or (R/S) | % CSF cGMP increase from vehicle control | species | dose (mg/kg, p.o.) | sampling time (hr) |
|---|---|---|---|---|---|
| 2 | | 110 | mouse | 10 | 0.5 |
| 3 | | 186 | rat(SD) | 10 | 2 |
| 4 | | 246 | rat(LE) | 30 | 1 |
| 6 | | 120 | rat(SD) | 10 | 1 |
| 12 | | 91 | rat(SD) | 3 | 1 |
| 15 | | 203 | rat(LE) | 30 | 1 |
| 18 | | 123 | rat(SD) | 3 | 1 |
| 24 | | 149 | rat(SD) | 10 | 1 |
| 26 | S | 274 | rat(LE) | 10 | 1 |
| 28 | (−) | 257 | rat(SD) | 3 | 1 |
| 29 | (−) | 238 | rat(LE) | 30 | 1 |
| 32 | (−) | 72 | rat(SD) | 10 | 1 |
| 43 | | 292 | rat(LE) | 10 | 1 |
| 51 | | 189 | rat(LE) | 10 | 1 |
| 53 | | 202 | rat(LE) | 10 | 1 |
| 54 | | 282 | rat(LE) | 10 | 1 |
| 55 | | 323 | rat(LE) | 10 | 1 |
| 62 | | 155 | rat(LE) | 3 | 1 |

4) Effect on Rodent Hippocampal cGMP

The test compound was administered to Sprague-Dawley male rats (Charles River Laboratories Japan, Inc.) or Long-Evans male rats (Institute for Animal Reproduction) and then the animals were sacrificed with microwave under pentobarbital anesthesia, and the hippocampus was extracted. After measuring the wet weight, the hippocampus was frozen with liquid nitrogen and stored at −80° C. In the measurement of cGMP in the hippocampus, a 0.5 M perchloric acid/1 mM EDTA solution was added at 5% (w/v) based on the wet weight, and the mixture was homogenized. After the homogenization, the homogenate was centrifuged (10000 rpm, 15 min), and the supernatant was collected. The collected supernatant was neutralized with a 2 M potassium bicarbonate solution and centrifuged (13000 rpm, 10 min). The cGMP concentration in the supernatant was measured in accordance with the non-acetylation EIA procedure of cGMP EIA kit (GE Healthcare). The result was an increase (C) in the amount of cGMP of the test compound-administered group (B) relative to the amount of cGMP of the vehicle-administered group (A), and was calculated using the following formula.

$$cGMP\ \text{increase}(C) = [(B)-(A)]/(A) \times 100 (\%)$$

The results are shown in the following table.

TABLE 12

| Example | (+/−) or (R/S) | % hippocampal cGMP increase from vehicle control | species | dose (mg/kg, p.o.) | sampling time (hr) |
|---|---|---|---|---|---|
| 3 | | 32 | rat(SD) | 10 | 4 |
| 4 | | 25 | rat(LE) | 30 | 1 |
| 15 | | 33 | rat(LE) | 30 | 1 |
| 26 | S | 58 | rat(LE) | 10 | 1 |
| 29 | (−) | 34 | rat(LE) | 30 | 1 |
| 43 | | 33 | rat(LE) | 10 | 1 |
| 51 | | 17 | rat(LE) | 10 | 1 |
| 53 | | 27 | rat(LE) | 10 | 1 |
| 54 | | 23 | rat(LE) | 10 | 1 |
| 55 | | 17 | rat(LE) | 10 | 1 |

What is claimed is:

1. A compound represented by the formula (I) or a pharmacologically acceptable salt thereof:

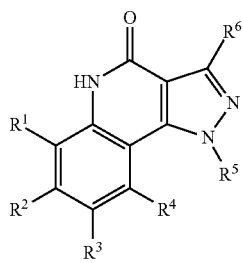

(I)

wherein
R$^1$ is a hydrogen atom;
R$^2$ is an aromatic ring group selected from the group consisting of a phenyl group, a pyridinyl group, and a pyrimidinyl group, where the two atoms on the aromatic ring which are adjacent to the carbon atom attached to the pyrazolo[4,3-c]quinoline ring each independently has a substituent selected from Group A1, and the other atoms on the aromatic ring independently optionally have a substituent selected from Group B1;
R$^3$ is a hydrogen atom, or a fluorine atom;
R$^4$ is a hydrogen atom;
R$^5$ is an oxepanyl group, a dioxepanyl group, a tetrahydropyranyl group, or a tetrahydrofuranyl group optionally substituted with a methoxy group;
R$^6$ is a hydrogen atom;
Group A1 consists of a halogen atom, a C1-6 alkyl group optionally substituted with 1 to 3 halogen atoms, and a C1-6 alkoxy group; and
Group B1 consists of a halogen atom, a cyano group, a C1-6 alkyl group optionally substituted with 1 to 3 halogen atoms, a C1-6 alkoxy-C1-6 alkyl group, a C1-6 alkoxy group optionally substituted with 1 to 3 halogen atoms, and a tetrahydropyranyl group, with the proviso that when R$^2$ is a 3-pyridinyl group, the substituent at the 4-position is a halogen atom, or a C1-6 alkyl group optionally substituted with 1 to 3 halogen atoms.

2. The compound or the pharmacologically acceptable salt thereof according to claim 1, wherein
R$^2$ is an aromatic ring group selected from the group consisting of a phenyl group, a 3-pyridinyl group, a 4-pyridinyl group, and a 5-pyrimidinyl group, where the two atoms on the aromatic ring which are adjacent to the carbon atom attached to the pyrazolo[4,3-c]quinoline ring each independently has a substituent selected from Group A2, and the other atoms on the aromatic ring independently optionally have a substituent selected from Group B2;
R$^5$ is a 4-oxepanyl group, a 1,4-dioxepan-6-yl group, a 3,4,5,6-tetrahydro-2H-3-pyranyl group, a 3,4,5,6-tetrahydro-2H-4-pyranyl group, or a 3-tetrahydrofuranyl group;
Group A2 consists of a chlorine atom, a methyl group optionally substituted with 1 to 2 fluorine atoms, an ethyl group, a methoxy group, and an ethoxy group; and
Group B2 consists of a fluorine atom, a chlorine atom, a cyano group, a methyl group optionally substituted with 1 to 3 fluorine atoms, an ethyl group, a methoxymethyl group, a methoxy group optionally substituted with 1 to 3 fluorine atoms, an ethoxy group, an isopropyloxy group, and a 3,4,5,6-tetrahydro-2H-4-pyranyl group.

3. The compound or the pharmacologically acceptable salt thereof according to claim 2, wherein $R^3$ is a fluorine atom.

4. The compound or the pharmacologically acceptable salt thereof according to claim 1, wherein
$R^3$ is a hydrogen atom; and
$R^5$ is a tetrahydropyranyl group, or a tetrahydrofuranyl group optionally substituted with a methoxy group.

5. The compound or the pharmacologically acceptable salt thereof according to claim 2, wherein
$R^3$ is a hydrogen atom; and
$R^5$ is a 3,4,5,6-tetrahydro-2H-3-pyranyl group, a 3,4,5,6-tetrahydro-2H-4-pyranyl group, or a 3-tetrahydrofuranyl group.

6. The compound or the pharmacologically acceptable salt thereof according to claim 1, wherein
$R^2$ is an aromatic ring group selected from the group consisting of a phenyl group, a 3-pyridinyl group, and a 4-pyridinyl group, where the two atoms on the aromatic ring which are adjacent to the carbon atom attached to the pyrazolo[4,3-c]quinoline ring each independently has a substituent selected from Group A3, and the other atoms on the aromatic ring independently optionally have a substituent selected from Group B3;
$R^3$ is a hydrogen atom;
$R^4$ is a hydrogen atom;
$R^5$ is a 3,4,5,6-tetrahydro-2H-4-pyranyl group, or a 3-tetrahydrofuranyl group;
Group A3 consists of a methyl group, and a methoxy group; and
Group B3 consists of a methyl group, a methoxy group, and a methoxymethyl group.

7. A compound selected from the group consisting of:
1) 7-(6-methoxy-2,4-dimethylpyridin-3-yl)-1-(tetrahydro-2H-pyran-4-yl)-1H-pyrazolo[4,3-c]quinolin-4(5H)-one,
2) 7-(2-methoxy-4,6-dimethylpyridin-3-yl)-1-(tetrahydro-2H-pyran-4-yl)-1H-pyrazolo[4,3-c]quinolin-4(5H)-one,
3) (S)-7-(6-isopropyloxy-2,4-dimethylpyridin-3-yl)-1-(tetrahydrofuran-3-yl)-1H-pyrazolo[4,3-c]quinolin-4(5H)-one,
4) 8-fluoro-7-(2-methoxy-4,6-dimethylpyridin-3-yl)-1-(tetrahydro-2H-pyran-4-yl)-1H-pyrazolo[4,3-c]quinolin-4(5H)-one,
5) 1-(1,4-dioxepan-6-yl)-7-(2-methoxy-3,5-dimethylpyridin-4-yl)-1H-pyrazolo[4,3-c]quinolin-4(5H)-one,
6) 1-(1,4-dioxepan-6-yl)-7-(2-methoxy-4,6-dimethylpyridin-3-yl)-1H-pyrazolo[4,3-c]quinolin-4(5H)-one,
7) (S)-8-fluoro-7-(2-methoxy-3,5-dimethylpyridin-4-yl)-1-(tetrahydrofuran-3-yl)-1H-pyrazolo[4,3-c]quinolin-4(5H)-one,
8) 7-(2-methoxy-3,5-dimethylpyridin-4-yl)-1-(tetrahydro-2H-pyran-4-yl)-1H-pyrazolo[4,3-c]quinolin-4(5H)-one,
9) (−)-7-(2-methoxy-4,6-dimethylpyridin-3-yl)-1-(tetrahydrofuran-3-yl)-1H-pyrazolo[4,3-c]quinolin-4(5H)-one,
10) (−)-7-(6-methoxy-2,4-dimethylpyridin-3-yl)-1-(tetrahydrofuran-3-yl)-1H-pyrazolo[4,3-c]quinolin-4(5H)-one,
11) (S)-8-fluoro-7-(2-methoxy-4,6-dimethylpyridin-3-yl)-1-(tetrahydrofuran-3-yl)-1H-pyrazolo[4,3-c]quinolin-4(5H)-one,
12) (S)-7-(6-ethoxy-2,4-dimethylpyridin-3-yl)-1-(tetrahydrofuran-3-yl)-1H-pyrazolo[4,3-c]quinolin-4(5H)-one,
13) (S)-8-fluoro-7-(6-methoxy-2,4-dimethylpyridin-3-yl)-1-(tetrahydrofuran-3-yl)-1H-pyrazolo[4,3-c]quinolin-4(5H)-one, and
14) (S)-7-(2-methoxy-3,5-dimethylpyridin-4-yl)-1-(tetrahydrofuran-3-yl)-1H-pyrazolo[4,3-c]quinolin-4(5H)-one, or a pharmacologically acceptable salt of any of the aforementioned.

8. 7-(6-isopropyloxy-2,4-dimethylpyridin-3-yl)-1-(tetrahydrofuran-3-yl)-1H-pyrazolo[4,3-c]quinolin-4(5H)-one or a pharmacologically acceptable salt thereof.

9. (S)-7-(6-isopropyloxy-2,4-dimethylpyridin-3-yl)-1-(tetrahydrofuran-3-yl)-1H-pyrazolo[4,3-c]quinolin-4(5H)-one or a pharmacologically acceptable salt thereof

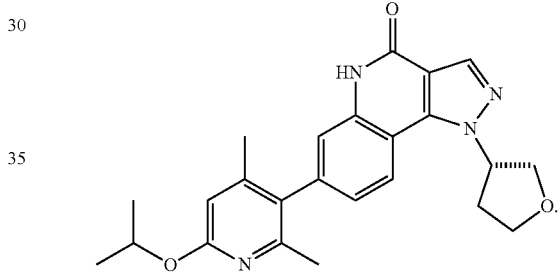

10. 8-fluoro-7-(2-methoxy-3,5-dimethylpyridin-4-yl)-1-(tetrahydrofuran-3-yl)-1H-pyrazolo[4,3-c]quinolin-4(5H)-one or a pharmacologically acceptable salt thereof.

11. (S)-8-fluoro-7-(2-methoxy-3,5-dimethylpyridin-4-yl)-1-(tetrahydrofuran-3-yl)-1H-pyrazolo[4,3-c]quinolin-4(5H)-one or a pharmacologically acceptable salt thereof:

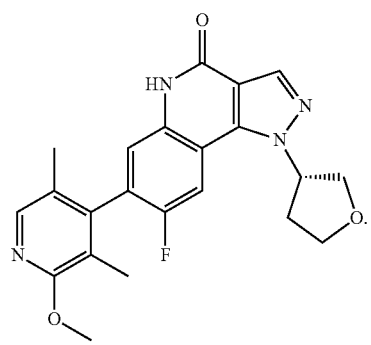 [SMILES: COc1ncc(C)c(-c2cc3[nH]c(=O)c4cnn([C@H]5CCOC5)c4c3cc2F)c1C]

12. 7-(2-methoxy-3,5-dimethylpyridin-4-yl)-1-(tetrahydrofuran-3-yl)-1H-pyrazolo[4,3-c]quinolin-4(5H)-one or a pharmacologically acceptable salt thereof.

13. (S)-7-(2-methoxy-3,5-dimethylpyridin-4-yl)-1-(tetrahydrofuran-3-yl)-1H-pyrazolo[4,3-c]quinolin-4(5H)-one or a pharmacologically acceptable salt thereof:

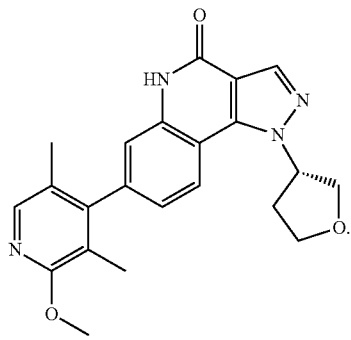 [SMILES: COc1ncc(C)c(-c2ccc3c(c2)[nH]c(=O)c2cnn([C@H]4CCOC4)c23)c1C]

14. 1-(1,4-dioxepan-6-yl)-7-(2-methoxy-3,5-dimethylpyridin-4-yl)-1H-pyrazolo[4,3-c]quinolin-4(5H)-one or a pharmacologically acceptable salt thereof:

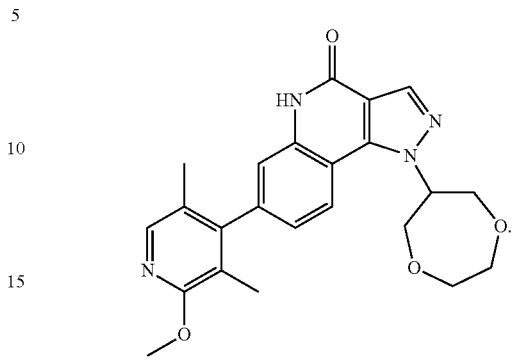

15. A pharmaceutical composition comprising the compound or the pharmacologically acceptable salt thereof according to claim 1 as an active ingredient.

* * * * *